(12) United States Patent
Wishka et al.

(10) Patent No.: US 7,067,515 B2
(45) Date of Patent: Jun. 27, 2006

(54) QUINUCLIDINES-SUBSTITUTED-MULTI-CYCLIC-HETEROARYLS FOR THE TREATMENT OF DISEASE

(75) Inventors: Donn G. Wishka, Kalamazoo, MI (US); Steven Charles Reitz, Toledo, OH (US); David W. Piotrowski, Portage, MI (US); Vincent E. Groppi, Jr., Kalamazoo, MI (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/163,564

(22) Filed: Jun. 6, 2002

(65) Prior Publication Data

US 2003/0045540 A1  Mar. 6, 2003

Related U.S. Application Data

(60) Provisional application No. 60/297,708, filed on Jun. 12, 2001, provisional application No. 60/297,709, filed on Jun. 12, 2001, provisional application No. 60/297,710, filed on Jun. 12, 2001, provisional application No. 60/297,711, filed on Jun. 12, 2001, provisional application No. 60/297,712, filed on Jun. 12, 2001, provisional application No. 60/328,596, filed on Oct. 11, 2001, provisional application No. 60/373,495, filed on Apr. 18, 2002.

(51) Int. Cl.
*C07D 453/02* (2006.01)
*A61K 31/439* (2006.01)

(52) U.S. Cl. ............... 514/228.2; 514/233.8; 514/253.04; 514/301; 514/302; 514/305; 544/61; 544/127; 544/362; 546/114; 546/115; 546/116; 546/133

(58) Field of Classification Search ........ 546/114, 546/115, 116, 133; 544/61, 127, 362; 514/228.2, 514/253.04, 301, 302, 305, 233.8
See application file for complete search history.

(56) References Cited

U.S. PATENT DOCUMENTS

| | | | |
|---|---|---|---|
| 4,612,319 A | 9/1986 | King | 514/305 |
| 4,721,720 A | 1/1988 | Wootton et al. | 514/304 |
| 4,797,406 A | 1/1989 | Richardson et al. | 514/299 |
| 4,798,829 A | 1/1989 | King et al. | 514/214 |
| 4,803,199 A | 2/1989 | Donatsch et al. | 514/214 |
| 4,822,795 A | 4/1989 | King | 514/214 |
| 4,835,162 A | 5/1989 | Abood | 514/305 |
| 4,845,092 A | 7/1989 | Sanger et al. | 514/216 |
| 4,863,919 A | 9/1989 | Smith | 514/214 |
| 4,863,921 A | 9/1989 | Youssefyeh et al. | 514/230 |
| 4,888,353 A | 12/1989 | Lednicer et al. | 514/422 |
| 4,910,193 A | 3/1990 | Buchheit | 514/216 |
| 4,920,127 A | 4/1990 | King et al. | 514/278 |
| 4,920,219 A | 4/1990 | Pelletier et al. | 540/523 |
| 4,920,227 A | 4/1990 | Pelletier et al. | 546/133 |
| 4,921,982 A | 5/1990 | Cohen et al. | 549/462 |
| 4,924,010 A | 5/1990 | Youssefyeh et al. | 549/355 |
| 4,933,445 A | 6/1990 | Pelletier et al. | 540/552 |
| 4,935,511 A | 6/1990 | Youssefyeh et al. | 540/552 |
| 4,937,247 A | 6/1990 | King | 514/299 |
| 4,973,594 A | 11/1990 | Tyers | 514/299 |
| 4,983,600 A | 1/1991 | Ward et al. | 514/214 |
| 4,985,437 A | 1/1991 | Tyers | 514/304 |
| 5,001,133 A | 3/1991 | Richardson et al. | 514/304 |
| 5,039,680 A | 8/1991 | Imperato et al. | 514/304 |

(Continued)

FOREIGN PATENT DOCUMENTS

DE  3810552 A1  3/1988

(Continued)

OTHER PUBLICATIONS

Layzer, Degenerative Diseases of the Nervous System, Cecil Textbook of Medicine, 20th Edition, vol. 2, pp. 2050-2057, 1996.*

(Continued)

*Primary Examiner*—Deepak Rao
(74) *Attorney, Agent, or Firm*—Steve T. Zelson; Eileen M. Ebel

(57) ABSTRACT

The invention provides compounds of Formula I:

Formula I

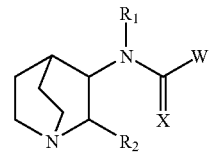

where in W is

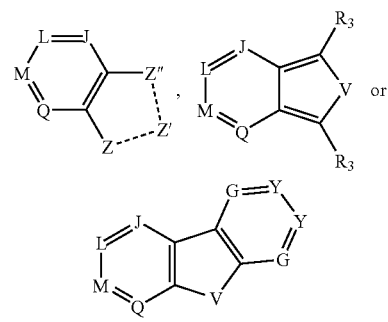

These compounds may be in the form of pharmaceutical salts or compositions, racemic mixtures, or pure enantiomers thereof. The compounds of Formula I are useful to treat diseases or conditions in which α7 is known to be involved.

64 Claims, No Drawings

U.S. PATENT DOCUMENTS

| | | | |
|---|---|---|---|
| 5,049,556 A | 9/1991 | King et al. | 514/183 |
| 5,063,231 A | 11/1991 | Sanger et al. | 512/214 |
| 5,114,947 A | 5/1992 | Imondi | 514/282 |
| 5,175,173 A | 12/1992 | Sun | 514/305 |
| 5,183,822 A | 2/1993 | Van Wijngaarden et al. | 514/305 |
| 5,217,975 A | 6/1993 | Wadsworth et al. | 514/299 |
| 5,246,942 A | 9/1993 | Youssefyeh et al. | 514/305 |
| 5,260,303 A | 11/1993 | Becker et al. | 514/300 |
| 5,272,154 A | 12/1993 | Dixon et al. | 514/299 |
| 5,273,972 A | 12/1993 | Jagdmann et al. | 514/210 |
| 5,300,512 A | 4/1994 | Flynn et al. | 514/305 |
| 5,322,951 A | 6/1994 | King et al. | 548/312 |
| 5,342,845 A | 8/1994 | Chokai et al. | 514/305 |
| 5,352,685 A | 10/1994 | Maruyama et al. | 514/301 |
| 5,362,734 A | 11/1994 | Ward et al. | 514/294 |
| 5,362,740 A | 11/1994 | Bedeschi et al. | 514/299 |
| 5,434,161 A | 7/1995 | Becker | 514/300 |
| 5,510,478 A | 4/1996 | Sabb | 540/585 |
| 5,543,426 A | 8/1996 | Dixon et al. | 514/410 |
| 5,556,851 A | 9/1996 | Maruyama et al. | 514/214 |
| 5,561,149 A | 10/1996 | Azria et al. | 514/397 |
| 5,599,937 A | 2/1997 | Glas et al. | 546/133 |
| 5,750,536 A | 5/1998 | Mantovanini et al. | 514/300 |
| 5,977,144 A | 11/1999 | Meyer et al. | 514/334 |
| 6,054,464 A | 4/2000 | Macor et al. | 514/299 |
| 2002/0016334 A1 | 2/2002 | Wadsworth et al. | 514/303 |
| 2003/0153595 A1* | 8/2003 | Walker et al. | 514/301 |

FOREIGN PATENT DOCUMENTS

| | | |
|---|---|---|
| EP | 0030254 | 8/1980 |
| EP | 0322016 A1 | 12/1988 |
| EP | 0457243 A1 | 5/1991 |
| EP | 0483 836 A1 | 10/1991 |
| EP | 0485962 A2 | 11/1991 |
| EP | 0496064 A1 | 12/1991 |
| EP | 0512 350 A2 | 4/1992 |
| EP | 0635508 A1 | 4/1992 |
| EP | 0 560 348 A1 | 3/1993 |
| JP | 2002-30084 | 1/2002 |
| WO | WO 90/14347 | 5/1990 |
| WO | WO 91/09593 | 12/1990 |
| WO | WO 91/17161 | 4/1991 |
| WO | WO 92/10494 | 12/1991 |
| WO | WO 93/06108 | 9/1992 |
| WO | WO 9309116 | 5/1993 |
| WO | WO 95/04742 | 8/1994 |
| WO | WO 95/27490 | 4/1995 |
| WO | WO 96/33186 | 4/1996 |
| WO | WO 97/35860 | 3/1997 |
| WO | WO 99/20633 | 10/1998 |
| WO | WO 00/73431 A2 | 5/2000 |
| WO | WO 01/36417 A1 | 11/2000 |
| WO | WO 01/60821 A1 | 2/2001 |
| WO | WO 01/76576 A2 | 3/2001 |
| WO | WO 03/055878 A1 | 7/2003 |
| WO | WO 03/078431 A1 | 9/2003 |
| WO | WO 03/087102 A1 | 10/2003 |
| WO | WO 03/087103 A1 | 10/2003 |
| WO | WO 03/087104 A1 | 10/2003 |

OTHER PUBLICATIONS

Damasio, Alzheimer's Disease and Relared Dementias, Cecil Textbook of Medicine, 20$^{th}$ Edition, vol. 2, pp. 1992-1996, 1996.*

Bitner et al., PubMed Abstract (Brain Res 938(1-2):45-54), May 2002.*

Mega, PubMed Abstract (Int J Neuropsychopharmacol, 3(7):3-12), Jul. 2000.*

W.R. Kem, *The brain α7 nicotine receptor may be an important therapeutic target for the treatment of Alzheimer's disease: studies with DMXBA (GTS-21)*, Behavioural Brain Research 113 (2000) pp. 169-181.

J.E.Macor, et al. *The 5-HT Antagonist Tropiestron (ICS 205-930) is a Potent and Selective α7 Nicotinic Receptor Partial Agonist,* Biorganic & Medicianl Chemistry Letters 11 (2001). pp. 319-321.

A Orjales, et al., *Benzimidazole-2-carboxylic acid amides and esters: a new structural class of 5-HT3 ligands,* Eur. J. Med. Chem. 34(1999) pp. 415-422.

* cited by examiner

QUINUCLIDINES-SUBSTITUTED-MULTI-CYCLIC-HETEROARYLS FOR THE TREATMENT OF DISEASE

CROSS REFERENCE TO RELATED APPLICATIONS

This application claims the benefit of U.S. provisional application Ser. No. 60/297,708 filed on 12 Jun. 2001, under 35 USC 119(e)(i); U.S. provisional application Ser. No. 60/297,709 filed on 12 Jun. 2001, under 35 USC 119(e)(i); U.S. provisional application Ser. No. 60/297,710 filed on 12 Jun. 2001, under 35 USC 119(e)(i); U.S. provisional application Ser. No. 60/297,711 filed on 12 Jun. 2001, under 35 USC 119(e)(i); U.S. provisional application Ser. No. 60/297,712 filed on 12 Jun. 2001, under 35 USC 119(e)(i); U.S. provisional application Ser. No. 60/328,596 filed on 11 Oct. 2001, under 35 USC 119(e)(i); and U.S. provisional application Ser. No. 60/373,495 filed on 18 Apr. 2002, under 35 USC 119(e)(i), which are incorporated herein by reference in their entirety.

FIELD OF INVENTION

Nicotinic acetylcholine receptors (nAChRs) play a large role in central nervous system (CNS) activity. Particularly, they are known to be involved in cognition, learning, mood, emotion, and neuroprotection. There are several types of nicotinic acetylcholine receptors, and each one appears to have a different role in regulating CNS function. Nicotine affects all such receptors, and has a variety of activities. Unfortunately, net all of the activities are desirable. In fact, one of the least desirable properties of nicotine is its addictive nature and the low ratio between efficacy and safety. The present invention relates to molecules that have a greater effect upon the α7 nAChRs as compared to other closely related members of this large ligand-gated receptor family. Thus, the invention provides compounds that are active drug molecules with fewer side effects.

BACKGROUND OF THE INVENTION

Cell surface receptors are, in general, excellent and validated drug targets. nAChRs comprise a large family of ligand-gated ion channels that control neuronal activity and brain function. These receptors have a pentameric structure. In mammals, this gene family is composed of nine alpha and four beta subunits that co-assemble to form multiple subtypes of receptors that have a distinctive pharmacology. Acetylcholine is the endogenous regulator of all of the subtypes, while nicotine non-selectively activates all nAChRs.

The α7 nAChR is one receptor system that has proved to be a difficult target for testing. Native α7 nAChR is not routinely able to be stably expressed in most mammalian cell lines (Cooper and Millar, Nature, 366(6454), p. 360–4, 1997). Another feature that makes functional assays of α7 nAChR challenging is that the receptor is rapidly (100 milliseconds) inactivated. This rapid inactivation greatly limits the functional assays that can be used to measure channel activity.

Recently, Eisele et al. has indicated that a chimeric receptor formed between the N-terminal ligand binding domain of the α7 nAChR (Eisele et al., Nature, 366(6454), p 479–83, 1993), and the pore forming C-terminal domain of the 5-HT$_3$ receptor expressed well in Xenopus oocytes while retaining nicotinic agonist sensitivity. Eisele et al. used the N-terminus of the avian (chick) form of the α7 nAChR receptor and the C-terminus of the mouse form of the 5-HT$_3$ gene. However, under physiological conditions the α7 nAChR is a calcium channel while the 5-HT$_3$R is a sodium and potassium channel. Indeed, Eisele et al. teaches that the chicken α7 nAChR/mouse 5-HT$_3$R behaves quite differently than the native α7 nAChR with the pore element not conducting calcium but actually being blocked by calcium ions. WO 00/73431 A2 reports on assay conditions under which the 5-HT$_3$R can be made to conduct calcium. This assay may be used to screen for agonist activity at this receptor.

WO 00/73431 A2 discloses two binding assays to directly measure the affinity and selectivity of compounds at the α7 nAChR and the 5-HT$_3$R. The combined use of these functional and binding assays may be used to identify compounds that are selective agonists of the α7 nAChR.

SUMMARY OF THE INVENTION

The present invention discloses compounds of the Formula I:

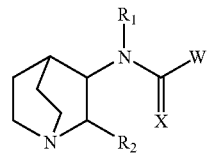

Formula I wherein W is

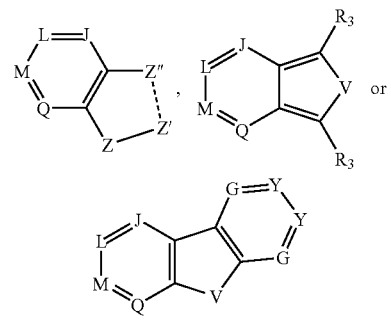

provided that the bond between the —C(=X)— group and the W group may be attached at any available carbon atom within the W group as provided in $R_3$, $R_6$, and $R_{15}$;

X is O, or S;

Each $R_1$ is H, alkyl, cycloalkyl, halogenated alkyl, substituted phenyl, or substituted naphthyl;

$R_2$ is H, alkyl, halogenated alkyl, substituted alkyl, cycloalkyl, or aryl;

Z---Z'---Z" is selected from N($R_4$)—C($R_3$)=C($R_3$), N=C($R_3$)—C($R_{15}$)$_2$, C($R_3$)=C($R_3$)—N($R_4$), C($R_3$)$_2$—N($R_4$)—C($R_3$)$_2$, C($R_{15}$)$_2$—C($R_3$)=N, N($R_4$)—C($R_3$)$_2$—C($R_3$)$_2$, C($R_3$)$_2$—C($R_3$)$_2$—N($R_4$), O—C($R_3$)=C($R_3$), O—C($R_3$)$_2$—C($R_3$)$_2$, C($R_3$)$_2$—O—C($R_3$)$_2$, C($R_3$)=C($R_3$)—O, C($R_3$)$_2$—C($R_3$)$_2$—O, S—C($R_3$)=C($R_3$), S—C($R_3$)$_2$—C($R_3$)$_2$, C($R_3$)$_2$—S—C($R_3$)$_2$, C($R_3$)=C($R_3$)—S, or C($R_3$)$_2$—C($R_3$)$_2$—S;

Each $R_3$ is independently a bond to the core molecule provided that only one $R_3$ and no $R_6$ or $R_{15}$ is also said bond, H, F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —NO$_2$, —OR$_1$, —C(O)N(R$_{10}$)$_2$, —NR$_1$COR$_{16}$, —N(R$_{10}$)$_2$, —SR$_1$, —S(O)$_2$R$_1$, —C(O)R$_{16}$, —CO$_2$R$_1$, aryl, R$_7$, or R$_9$;

J, L, M, and Q are N or C(R$_6$) provided that only one of J, L, M, or Q, is N and the others are C(R$_6$), further provided that when the core molecule is attached to the pyridinyl moiety at M, Q is C(H), and further provided that there is only one attachment to the core molecule;

G and Y are C(R$_6$), provided that when the molecule is attached to the phenyl moiety at Y, G is CH;

R$_4$ is H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, R$_7$, or R$_9$;

Each R$_5$ is independently H, C$_{1-3}$ alkyl, or C$_{2-4}$ alkenyl;

Each R$_6$ is independently H, F, Br, I, Cl, —CN, —CF$_3$, —OR$_5$, —SR$_5$, or —N(R$_5$)$_2$, or a bond to the core molecule provided that only one R$_6$ and no R$_3$ or R$_{15}$ is said bond, V is selected from O, S, or N(R$_4$);

R$_7$ is 5-membered heteroaromatic mono-cyclic moieties containing within the ring 1–3 heteroatoms independently selected from the group consisting of —O—, =N—, —N(R$_{19}$)—, and —S—, and having 0–1 substituent selected from R$_{20}$ and further having 0–3 substituents independently selected from F, Cl, Br, or I, or R$_7$ is a 9-membered fused-ring moiety having a 6-membered ring fused to a 5-membered ring and having the formula

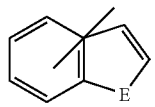

wherein E is O, S, or NR$_{19}$,

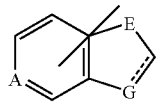

wherein E and G are independently selected from CR$_{18}$, O, S, N, or NR$_{19}$, and A is CR$_{18}$ or N, or

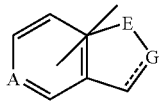

wherein E and G are independently selected from CR$_{18}$, O, S, N, or NR$_{19}$, and A is CR$_{18}$ or N, each 9-membered fused-ring moiety having 0–1 substituent selected from R$_{20}$ and further having 0–3 substituent(s) independently selected from F, Cl, Br, or I, and having a bond directly or indirectly attached to the core molecule where valency allows in either the 6-membered or the 5-membered ring of the fused-ring moiety;

Each R$_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, R$_7$, R$_9$, phenyl, or substituted phenyl;

R$_9$ is 6-membered heteroaromatic mono-cyclic moieties containing within the ring 1–3 heteroatoms selected from =N— and having 0–1 substituent selected from R$_{20}$ and 0–3 substituent(s) independently selected from F, Cl, Br, or I, or R$_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from R$_{20}$ and 0–3 substituent(s) independently selected from F, Cl, Br, or I and having a bond directly or indirectly attached to the core molecule where valency allows;

Each R$_{10}$ is independently H, alkyl, cycloalkyl, heterocycloalkyl, alkyl substituted with 1 substituent selected from R$_{13}$, cycloalkyl substituted with 1 substituent selected from R$_{13}$, heterocycloalkyl substituted with 1 substituent selected from R$_{13}$, halogenated alkyl, halogenated cycloalkyl, halogenated heterocycloalkyl, phenyl, or substituted phenyl;

Each R$_{11}$ is independently H, alkyl, cycloalkyl, heterocyclo-alkyl, halogenated alkyl, halogenated cycloalkyl, or halogenated heterocycloalkyl;

R$_{13}$ is —OR$_{11}$, —SR$_{11}$, —NR$_{11}$R$_{11}$, —C(O)R$_{11}$, —C(O)NR$_{11}$R$_{11}$, —CN, —CF$_3$, —NR$_{11}$C(O)R$_{11}$, —S(O)$_2$NR$_{11}$R$_{11}$, —NR$_{11}$S(O)$_2$R$_{11}$, or —NO$_2$;

Each R$_{15}$ is independently a bond to the core molecule provided that only one R$_{15}$ and no R$_6$ or R$_3$ is also said bond, H, F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —NO$_2$, —OR$_1$, —C(O)N(R$_{10}$)$_2$, —NR$_1$COR$_{16}$, —N(R$_{10}$)$_2$, —SR$_1$, —CO$_2$R$_1$, aryl, R$_7$, or R$_9$;

R$_{16}$ is H, alkyl, substituted alkyl, cycloalkyl, halogenated alkyl, heterocycloalkyl, substituted heterocycloalkyl, substituted phenyl, or substituted naphthyl;

Each R$_{18}$ is independently H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O)R$_{11}$, —S(O)$_2$NR$_{11}$R$_{11}$, —NR$_{11}$S(O)$_2$R$_{11}$, F, Cl, Br, I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —OR$_{11}$, —SR$_{11}$, —NR$_{11}$R$_{11}$, —C(O)R$_{11}$, —NO$_2$, —C(O)NR$_{11}$R$_{11}$, —CN, —NR$_{11}$C(O) R$_{11}$, —S(O)$_2$NR$_{11}$R$_{11}$, or —NR$_{11}$S(O)$_2$R$_{11}$, and further provided that the fused-ring moiety has 0–3 substituent(s) selected from F, Cl, Br, or I;

R$_{19}$ is H, alkyl, halogenated alkyl, substituted alkyl, cycloalkyl, halogenated cycloalkyl, substituted cycloalkyl, phenyl, —SO$_2$R$_8$, or phenyl having 1 substituent selected from R$_{20}$ and further having 0–3 substituents independently selected from F, Cl, Br, or I;

R$_{20}$ is alkyl, cycloalkyl, heterocycloalkyl, halogenated alkyl, halogenated cycloalkyl, halogenated heterocycloalkyl, —OR$_{11}$, —SR$_{11}$, —NR$_{11}$R$_{11}$, —C(O)R$_{11}$, —C(O)NR$_{11}$R$_{11}$, —CN, —NR$_{11}$C(O)R$_{11}$, —S(O)$_2$NR$_{11}$R$_{11}$, —NR$_{11}$S(O)$_2$R$_{11}$, —NO$_2$, alkyl substituted with 1–4 substituent(s) independently selected from F, Cl, Br, I, or R$_{13}$, cycloalkyl substituted with 1–4 substituent(s) independently selected from F, Cl, Br, I, or R$_{13}$, or heterocycloalkyl substituted with 1–4 substituent(s) independently selected from F, Cl, Br, I, or R$_{13}$;

or pharmaceutical composition, pharmaceutically acceptable salt, racemic mixture, or pure enantiomer thereof.

The compounds of Formula I are use to treat any one or more than one, or combination of cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulemia and anorexia nervosa, withdrawal symptoms associated with smoking cessation and dependant drug cessation, Gilles de la Tourette's Syndrome, glaucoma, neurodegeneration associated with glaucoma, or symptoms associated with pain.

DETAILED DESCRIPTION OF THE INVENTION

Surprisingly, we have found that compounds of Formula I:

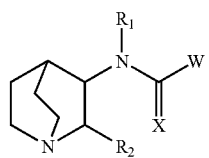

Formula I wherein W is

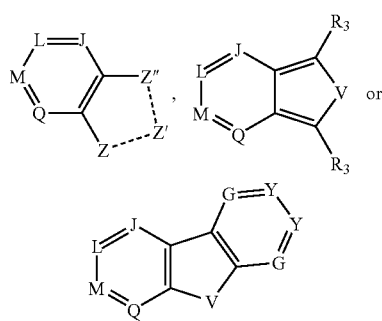

provided that the bond between the —C(=X)— group and the W group may be attached at any available carbon atom within the W group as provided in R$_3$, R$_6$, and R$_{15}$;

X is O, or S;

Each R$_1$ is H, alkyl, cycloalkyl, halogenated alkyl, substituted phenyl, or substituted naphthyl;

Alkyl is both straight- and branched-chain moieties having from 1–6 carbon atoms;

Halogenated alkyl is an alkyl moiety having from 1–6 carbon atoms and having 1 to (2n+1) substituent(s) independently selected from F, Cl, Br, or I where n is the maximum number of carbon atoms in the moiety;

Cycloalkyl is a cyclic alkyl moiety having from 3–6 carbon atoms;

Substituted phenyl is a phenyl either having 1–4 substituents independently selected from F, Cl, Br, or I, or having 1 substituent selected from R$_{12}$ and 0–3 substituents independently selected from F, Cl, Br, or I;

Substituted naphthyl is a naphthalene moiety either having 1–4 substituents independently selected from F, Cl, Br, or I, or having 1 substituent selected from R$_{12}$ and 0–3 substituents independently selected from F, Cl, Br, or I, where the substitution can be independently on either only one ring or both rings of said naphthalene moiety;

R$_2$ is H, alkyl, halogenated alkyl, substituted alkyl, cycloalkyl, or aryl;

Substituted alkyl is an alkyl moiety from 1–6 carbon atoms and having 0–3 substituents independently selected from F, Cl, Br, or I and further having 1 substituent selected from R$_7$, R$_9$, —OR$_{10}$, —SR$_{10}$, —NR$_{10}$R$_{10}$, —C(O)R$_{10}$, —C(O)NR$_{10}$R$_{10}$, —CN, —NR$_{10}$C(O)R$_{10}$, —S(O)$_2$NR$_{10}$R$_{10}$, —NR$_{10}$S(O)$_2$R$_{10}$, —NO$_2$, phenyl, or phenyl having 1 substituent selected from R$_{20}$ and further having 0–3 substituents independently selected from F, Cl, Br, or I;

Aryl is phenyl, substituted phenyl, naphthyl, or substituted naphthyl;

Z---Z'---Z'' is selected from N(R$_4$)—C(R$_3$)=C(R$_3$), N=C(R$_3$)—C(R$_{15}$)$_2$, C(R$_3$)=C(R$_3$)—N(R$_4$), C(R$_3$)$_2$—N(R$_4$)—C(R$_3$)$_2$, C(R$_{15}$)$_2$—C(R$_3$)=N, N(R$_4$)—C(R$_3$)$_2$—C(R$_3$)$_2$, C(R$_3$)$_2$—C(R$_3$)$_2$—N(R$_4$), O—C(R$_3$)=C(R$_3$), O—C(R$_3$)$_2$—C(R$_3$)$_2$, C(R$_3$)$_2$—O—C(R$_3$)$_2$, C(R$_3$)=C(R$_3$)—O, C(R$_3$)—C(R$_3$)$_2$—O, S—C(R$_3$)=C(R$_3$), S—C(R$_3$)$_2$—C(R$_3$)$_2$, C(R$_3$)$_2$—S—C(R$_3$)$_2$, C(R$_3$)=C(R$_3$)—S, or C(R$_3$)$_2$—C(R$_3$)$_2$—S;

Each R$_3$ is independently a bond to the core molecule provided that only one R$_3$ and no R$_6$ or R$_{15}$ is also said bond, H, F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —NO$_2$, —OR$_1$, —C(O)N(R$_{10}$)$_2$, —NR$_1$COR$_{16}$, —N(R$_{10}$)$_2$, —SR$_1$, —S(O)$_2$R$_1$, —C(O)R$_{16}$, —CO$_2$R$_1$, aryl, R$_7$, or R$_9$;

Lactam heterocycloalkyl is a cyclic moiety having from 4–7 atoms with one atom being only nitrogen with the bond to the lactam heterocycloalkyl thru said atom being only nitrogen and having a =O on a carbon adjacent to said nitrogen, and having up to 1 additional ring atom being oxygen, sulfur, or nitrogen and further having 0–2 substituents selected from F, Cl, Br, I, or R$_{14}$ where valency allows;

Alkenyl is straight- and branched-chain moieties having from 2–6 carbon atoms and having at least one carbon-carbon double bond;

Halogenated alkenyl is an unsaturated alkenyl moiety having from 2–6 carbon atoms and having 1 to (2n–1) substituent(s) independently selected from F, Cl, Br, or I where n is the maximum number of carbon atoms in the moiety;

Substituted alkenyl is an unsaturated alkenyl moiety having from 2–6 carbon atoms and having 0–3 substituents independently selected from —F, or —Cl, and further having 1 substituent selected from R$_7$, R$_9$, —OR$_{10}$, —SR$_{10}$, —NR$_{10}$R$_{10}$, —C(O)R$_{10}$, —C(O)NR$_{10}$R$_{10}$, —NR$_{10}$C(O)

$R_{10}$, —S(O)$_2$NR$_{10}$R$_{10}$, —NR$_{10}$S(O)$_2$R$_{10}$, —CN, phenyl, or phenyl having 1 substituent selected from R$_{20}$ and further having 0–3 substituents independently selected from F, Cl, Br, or I;

Alkynyl is straight- and branched-chained moieties having from 2–6 carbon atoms and having at least one carbon-carbon triple bond;

Halogenated alkynyl is an unsaturated alkynyl moiety having from 3–6 carbon atoms and having 1 to (2n–3) substituent(s) independently selected from F, Cl, Br, or I where n is the maximum number of carbon atoms in the moiety;

Substituted alkynyl is an unsaturated alkynyl moiety having from 3–6 carbon atoms and having 0–3 substituents independently selected from —F, or —Cl, and further having 1 substituent selected from R$_7$, R$_9$, —OR$_{10}$, —SR$_{10}$, —NR$_{10}$R$_{10}$, —C(O)R$_{10}$, —C(O)NR$_{10}$R$_{10}$, —NR$_{10}$C(O)R$_{10}$, —S(O)$_2$NR$_{10}$R$_{10}$, —NR$_{10}$S(O)$_2$R$_{10}$, —CN, phenyl, or phenyl having 1 substituent selected from R$_{20}$ and further having 0–3 substituents independently selected from F, Cl, Br, or I;

Halogenated cycloalkyl is a cyclic moiety having from 3–6 carbon atoms and having 1–4 substituents independently selected from F, or Cl;

Substituted cycloalkyl is a cyclic moiety having from 3–6 carbon atoms and having 0–3 substituents independently selected from F, or Cl, and further having 1 substituent selected from —OR$_{10}$, —SR$_{10}$, —NR$_{10}$R$_{10}$, —C(O)R$_{10}$, —CN, —C(O)NR$_{10}$R$_{10}$, —NR$_{10}$C(O)R$_{10}$, —S(O)$_2$NR$_{10}$R$_{10}$, —NR$_{10}$S(O)$_2$R$_{10}$, —NO$_2$, phenyl, or phenyl having 1 substituent selected from R$_{20}$ and further having 0–3 substituents independently selected from F, Cl, Br, or I;

Heterocycloalkyl is a cyclic moiety having 4–7 atoms with 1–2 atoms within the ring being —S—, —N(R$_{19}$)—, or —O—;

Halogenated heterocycloalkyl is a cyclic moiety having from 4–7 atoms with 1–2 atoms within the ring being —S—, —N(R$_{19}$)—, or —O—, and having 1–4 substituents independently selected from F, or Cl;

Substituted heterocycloalkyl is a cyclic moiety having from 4–7 atoms with 1–2 atoms within the ring being —S—, —N(R$_{19}$)—, or —O— and having 0–3 substituents independently selected from F, or Cl, and further having 1 substituent selected from —OR$_{10}$, —SR$_{10}$, —NR$_{10}$R$_{10}$, —C(O)R$_{10}$, —C(O)NR$_{10}$R$_{10}$, —CN, —NR$_{10}$C(O)R$_{10}$, —NO$_2$, —S(O)$_2$NR$_{10}$R$_{10}$, —NR$_{10}$S(O)$_2$R$_{10}$, phenyl, or phenyl having 1 substituent selected from R$_{20}$ and further having 0–3 substituents independently selected from F, Cl, Br, or I;

J, L, M, and Q are N or C(R$_6$) provided that only one of J, L, M, or Q, is N and the others are C(R$_6$), further provided that when the core molecule is attached to the pyridinyl moiety at M, Q is C(H), and further provided that there is only one attachment to the core molecule;

G and Y are C(R$_6$), provided that when the molecule is attached to the phenyl moiety at Y, G is CH;

R$_4$ is H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, R$_7$, or R$_9$;

Each R$_5$ is independently H, C$_{1-3}$ alkyl, or C$_{2-4}$ alkenyl;

C$_{1-3}$ alkyl is both straight- and branched-chain moieties having from 1–3 carbon atoms;

C$_{2-4}$ alkenyl straight- and branched-chain moieties having from 2–4 carbon atoms and having at least one carbon-carbon double bond;

Each R$_6$ is independently H, F, Br, I, Cl, —CN, —CF$_3$, —OR$_5$, —SR$_5$, or —N(R$_5$)$_2$, or a bond to the core molecule provided that only one R$_6$ and no R$_3$ or R$_{15}$ is said bond, V is selected from O, S, or N(R$_4$);

R$_7$ is 5-membered heteroaromatic mono-cyclic moieties containing within the ring 1–3 heteroatoms independently selected from the group consisting of —O—, =N—, —N(R$_{19}$)—, and —S—, and having 0–1 substituent selected from R$_{20}$ and further having 0–3 substituents independently selected from F, Cl, Br, or I, or R$_7$ is a 9-membered fused-ring moiety having a 6-membered ring fused to a 5-membered ring and having the formula

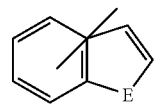

wherein E is O, S, or NR$_{19}$,

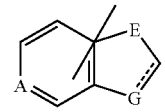

wherein E and G are independently selected from CR$_{18}$, O, S, N, or NR$_{19}$, and A is CR$_{18}$ or N, or

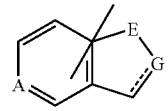

wherein E and G are independently selected from CR$_{18}$, O, S, N, or NR$_{19}$, and A is CR$_{18}$ or N, each 9-membered fused-ring moiety having 0–1 substituent selected from R$_{20}$ and further having 0–3 substituent(s) independently selected from F, Cl, Br, or I, and having a bond directly or indirectly attached to the core molecule where valency allows in either the 6-membered or the 5-membered ring of the fused-ring moiety;

Each R$_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, R$_7$, R$_9$, phenyl, or substituted phenyl;

R$_9$ is 6-membered heteroaromatic mono-cyclic moieties containing within the ring 1–3 heteroatoms selected from =N— and having 0–1 substituent selected from R$_{20}$ and 0–3 substituent(s) independently selected from F, Cl, Br, or I, or R$_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from R$_{20}$ and 0–3 substituent(s) independently selected from F, Cl, Br, or I and having a bond directly or indirectly attached to the core molecule where valency allows;

Each R$_{10}$ is independently H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, or substituted phenyl;

Each $R_{11}$ is independently H, alkyl, cycloalkyl, heterocyclo-alkyl, halogenated alkyl, halogenated cycloalkyl, or halogenated heterocycloalkyl;

$R_{12}$ is —$OR_{11}$, —$SR_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$;

$R_{13}$ is —$OR_{11}$, —$SR_{11}$, —$NR_{11}R_{11}$, —$C(O)R_{11}$, —$C(O)NR_{11}R_{11}$, —CN, —$CF_3$, —$NR_{11}C(O)R_{11}$, —$S(O)_2NR_{11}R_{11}$, —$NR_{11}S(O)_2R_{11}$, or —$NO_2$;

$R_{14}$ is alkyl, substituted alkyl, halogenated alkyl, —$OR_{11}$, —CN, —$NO_2$, —$NR_{10}R_{10}$;

Each $R_{15}$ is independently a bond to the core molecule provided that only one $R_{15}$ and no $R_6$ or $R_3$ is also said bond, H, F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —$NO_2$, —$OR_1$, —$C(O)N(R_{10})_2$, —$NR_1COR_{16}$, —$N(R_{10})_2$, —$SR_1$, —$CO_2R_1$, aryl, $R_7$, or $R_9$;

$R_{16}$ is H, alkyl, substituted alkyl, cycloalkyl, halogenated alkyl, heterocycloalkyl, substituted heterocycloalkyl, substituted phenyl, or substituted naphthyl;

Each $R_{18}$ is independently H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, —$NR_{11}S(O)_2R_{11}$, F, Cl, Br, I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, and further provided that the fused-ring moiety has 0–3 substituent(s) selected from F, Cl, Br, or I;

$R_{19}$ is H, alkyl, halogenated alkyl, substituted alkyl, cycloalkyl, halogenated cycloalkyl, substituted cycloalkyl, phenyl, —$SO_2R_8$, or phenyl having 1 substituent selected from $R_{20}$ and further having 0–3 substituents independently selected from F, Cl, Br, or I;

$R_{20}$ is alkyl, cycloalkyl, heterocycloalkyl, halogenated alkyl, halogenated cycloalkyl, halogenated heterocycloalkyl, —$OR_{11}$, —$SR_{11}$, —$NR_{11}R_{11}$, —$C(O)R_{11}$, —$C(O)NR_{11}R_{11}$, —CN, —$NR_{11}C(O)R_{11}$, —$S(O)_2NR_{11}R_{11}$, —$NR_{11}S(O)_2R_{11}$, —$NO_2$, alkyl substituted with 1–4 substituent(s) independently selected from F, Cl, Br, I, or $R_{13}$, cycloalkyl substituted with 1–4 substituent(s) independently selected from F, Cl, Br, I, or $R_{13}$, or heterocycloalkyl substituted with 1–4 substituent(s) independently selected from F, Cl, Br, I, or $R_{13}$;

or pharmaceutical composition, pharmaceutically acceptable salt, racemic mixture, or pure enantiomer thereof useful to treat any one or more than one, or combination of cognitive and attention deficit symptoms of Alzheimer's, neurodegeneration associated with diseases such as Alzheimer's disease, pre-senile dementia (mild cognitive impairment), senile dementia, schizophrenia, psychosis, attention deficit disorder, attention deficit hyperactivity disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulemia and anorexia nervosa, withdrawal symptoms associated with smoking cessation and dependant drug cessation, Gilles de la Tourette's Syndrome, glaucoma, neurodegeneration associated with glaucoma, or symptoms associated with pain.

In another aspect, the invention includes methods of treating a mammal suffering from schizophrenia or psychosis by administering compounds of Formula I in conjunction with antipsychotic drugs. The compounds of Formula I and the antipsychotic drugs can be administered simultaneously or at separate intervals. When administered simultaneously the compounds of Formula I and the antipsychotic drugs can be incorporated into a single pharmaceutical composition. Alternatively, two separate compositions, i.e., one containing compounds of Formula I and the other containing antipsychotic drugs, can be administered simultaneously.

The present invention also includes the intermediates, the processes to make them and the compounds of the present invention, pharmaceutical compositions containing the active compounds, and methods to treat the identified diseases.

A group of compounds of Formula I includes compounds wherein X is O. Another group of compounds of Formula I includes compounds wherein $R_1$ is H. Another group of compounds of Formula I includes compounds wherein $R_1$ is alkyl, cycloalkyl, halogenated alkyl, or aryl. Another group of compounds of Formula I includes compounds wherein the R configuration occurs at the C3 position of the quinuclidine ring. Another group of compounds of Formula I includes compounds wherein the S configuration occurs at the C3 position of the quinuclidine ring.

Another group of compounds of Formula I includes compounds wherein $R_2$ is H. Another group of compounds of Formula I includes compounds wherein $R_2$ is alkyl, halogenated alkyl, or substituted alkyl. Another group of compounds of Formula I includes compounds wherein $R_2$ is alkyl. Another group of compounds of Formula I includes compounds wherein $R_2$ is methyl. Another group of compounds of Formula I includes compounds wherein $R_2$ is alkyl, halogenated alkyl, substituted alkyl, cycloalkyl, or aryl. Another group of compounds of Formula I includes compounds where $R_2$ is other than H and wherein the stereochemistry is S at C2 and R at C3.

Another group of compounds of Formula I includes compounds wherein Z---Z'---Z" is selected from any one or more or combination of the following: $N(R_4)$—$C(R_3)$=$C(R_3)$, N=$C(R_3)$—$C(R_{15})_2$, $C(R_3)$=$C(R_3)$—$N(R_4)$, $C(R_3)_2$—$N(R_4)$—$C(R_3)_2$, $C(R_{15})_2$—$C(R_3)$=N, $N(R_4)$—$C(R_3)_2$—$C(R_3)_2$, $C(R_3)_2$—$C(R_3)_2$—$N(R_4)$, O—$C(R_3)$=$C(R_3)$, O—$C(R_3)_2$—$C(R_3)_2$, $C(R_3)_2$—O—$C(R_3)_2$, $C(R_3)$=$C(R_3)$—O, $C(R_3)_2$—$C(R_3)_2$—O, S—$C(R_3)$=$C(R_3)$, S—$C(R_3)_2$—$C(R_3)_2$, $C(R_3)_2$—S—$C(R_3)_2$, $C(R_3)$=$C(R_3)$—S, or $C(R_3)_2$—$C(R_3)_2$—S.

Another group of compounds of Formula I includes compounds wherein Z---Z'---Z" is selected from any one or more or combination of the following: $N(R_4)$—$C(R_3)$=C (R$_3$), C(R$_3$)=C(R$_3$)—N(R$_4$), N(R$_4$)—C(R$_3$)$_2$—C(R$_3$)$_2$, (R$_3$)$_2$—C(R$_3$)$_2$—N(R$_4$), O—C(R$_3$)=C(R$_3$), O—C(R$_3$)$_2$—C(R$_3$)$_2$, C(R$_3$)=C(R$_3$)—O, C(R$_3$)$_2$—C(R$_3$)$_2$—O, S—C(R$_3$)=C(R$_3$), S—C(R$_3$)$_2$—C(R$_3$)$_2$, C(R$_3$)=C(R$_3$)—S, or C(R$_3$)$_2$—C(R$_3$)$_2$—S.

Another group of compounds of Formula I includes compounds wherein M is N, J and Q are C(R$_6$), and L is a bond to the core molecule. Another group of compounds of Formula I includes compounds wherein L is N, J and Q are C(R$_6$), and M is a bond to the core molecule. Another group of compounds of Formula I includes compounds wherein J is N, M and Q are C(R$_6$), and L is a bond to the core molecule. Another group of compounds of Formula I includes compounds wherein one R$_3$ on Z' is the bond to the core molecule.

Another group of compounds of Formula I includes compounds wherein each R$_3$ is independently any one of the following: a bond to the core molecule provided that only one R$_3$ and no R$_6$ or R$_{15}$ is also said bond, H, F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —NO$_2$, —OR$_1$, —C(O)N(R$_{10}$)$_2$, —NR$_1$COR$_{16}$, —N(R$_{10}$)$_2$, —SR$_1$, —S(O)$_2$R$_1$, —C(O)R$_{16}$, —CO$_2$R$_1$, aryl, R$_7$, or R$_9$. Another group of compounds of Formula I includes compounds wherein each R$_3$ is independently H, F, Br, Cl, I, alkyl, substituted alkyl, halogenated alkyl, alkenyl, substituted alkenyl, halogenated alkenyl, alkynyl, substituted alkynyl, halogenated alkynyl, or a bond to the core molecule. For the compounds of the present invention, when R$_2$ is H, Q is N with J, L, and M being CH, and Z---Z'---Z" is NH—CR$_3$=CR$_3$, the R$_3$ for Z" cannot be a bond to the core molecule when the R$_3$ for Z' is H. Another group of compounds of Formula I includes compounds wherein R$_3$ is a bond to the core molecule provided that only one R$_3$ and no R$_6$ or R$_{15}$ is also said bond, H F, Br, Cl, —CN, —NO$_2$, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —OR$_1$, —NR$_1$COR$_{16}$, —N(R$_{10}$)$_2$, —SR$_1$, or aryl. One of ordinary skill in the art will recognize where the optional substitution is allowed by comparing the listed moieties with W and identifying where R$_3$, R$_4$, R$_6$ or R$_{15}$ would allow for substitution or be the bond to the core molecule.

Another group of compounds of Formula I includes compounds wherein R$_4$ is any one of the following: H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, R$_7$, or R$_9$. Another group of compounds of Formula I includes compounds wherein R$_4$ is any one of the following: H, alkyl, halogenated alkyl, substituted alkyl, cycloalkyl, halogenated cycloalkyl, or substituted cycloalkyl. Another group of compounds of Formula I includes compounds wherein R$_4$ is any one of the following: H, alkyl, halogenated alkyl, substituted alkyl, heterocycloalkyl, or substituted heterocycloalkyl.

Another group of compounds of Formula I includes compounds wherein each R$_6$ is independently any one of the following: a bond to the core molecule provided that only one R$_6$ and no R$_3$ or R$_{15}$ is said bond, H, F, Br, I, Cl, —CN, —CF$_3$, —OR$_5$, —SR$_5$, or —N(R$_5$)$_2$. Another group of compounds of Formula I includes compounds wherein each R$_6$ is independently any one of the following: a bond to the core molecule provided that only one R$_6$ and no R$_3$ or R$_{15}$ is said bond, H, F, Br, I, Cl, —CN, —CF$_3$, —OR$_5$, —SR$_5$, or —N(R$_5$)$_2$.

Another group of compounds of Formula I includes compounds wherein each R$_{15}$ is independently selected from any one of the following: a bond to the core molecule provided that only one R$_{15}$ and no R$_6$ or R$_3$ is also said bond, H, F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —NO$_2$, —OR$_1$, —C(O)N(R$_{10}$)$_2$, —NR$_1$COR$_{16}$, —N(R$_{10}$)$_2$, —SR$_1$, —CO$_2$R$_1$, aryl, R$_7$, or R$_9$.

Another group of compounds of Formula I includes compounds wherein each R$_{15}$ is independently selected from any one of the following: a bond to the core molecule provided that only one R$_{15}$ and no R$_6$ or R$_3$ is also said bond, H, F, Br, Cl, —CN, —NO$_2$, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —OR$_1$, —NR$_1$COR$_{16}$, —N(R$_{10}$)$_2$, —SR$_1$, or aryl. Another group of compounds of Formula I includes compounds wherein each R$_{15}$ is independently a bond to the core molecule provided that only one R$_{15}$ and no R$_6$ or R$_3$ is also said bond, H, F, Br, Cl, I, alkyl, substituted alkyl, halogenated alkyl, alkenyl, substituted alkenyl, halogenated alkenyl, alkynyl, substituted alkynyl, or halogenated alkynyl.

Another group of compounds of Formula I includes compounds wherein W is

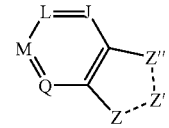

Another group of compounds of Formula I includes compounds wherein W is

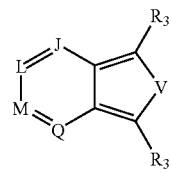

Another group of compounds of Formula I includes compounds wherein W is

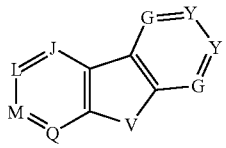

Another group of compounds of Formula I includes compounds wherein W includes any one or more or combination of the following: thieno[2,3-b]pyridin-2-yl, thieno[2,3-b]pyridin-5-yl, thieno[2,3-b]pyridin-6-yl, thieno[2,3-c]pyridin-2-yl, furo[3,2-c]pyridin-2-yl, thieno[3,2-b]pyridin- 2-yl, furo[2,3-b]pyridin-2-yl, benzothieno[2,3-c]pyridin-3-yl, thieno[3,2-b]pyridin-5-yl, thieno[3,2-b]pyridin-6-yl, furo[2,3-c]pyridin-5-yl, benzothieno[3,2-c]pyridin-3-yl, thieno[3,2-c]pyridin-2-yl, 2,3-dihydrofuro[2,3-c]pyridin-5-yl, thieno[2,3-c]pyridin-5-yl, furo[2,3-c]pyridin-2-yl, thieno[3,2-c]pyridin-6-yl, thieno[3,4-c]pyridin-6-yl, 1H-pyrrolo[2,3-c]pyridin-5-yl, furo[3,2-c]pyridin-6-yl, or benzofuro[3,2-c]pyridin-3-yl optionally substituted with F, Br, Cl, —CN, —CF$_3$, —NO$_2$, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, halogenated heterocycloalkyl, lactam heterocycloalkyl, —OR$_1$, —OR$_5$, —NR$_1$COR$_{16}$, —N(R$_{10}$)$_2$, —N(R$_5$)$_2$, —SR$_1$, —SR$_5$, or aryl. One of ordinary skill in the art will recognize where the optional substitution is allowed by comparing the listed moieties with W and identifying where R$_3$, R$_4$, R$_6$ or R$_{15}$ would allow for substitution or be the bond to the core molecule.

Another group of compounds of Formula I includes compounds wherein a carbon atom of sufficient valency of W is optionally substituted with any one or more or combination of the following: F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —CF$_3$, —NO$_2$, —OR$_1$, —OR$_5$, —C(O)N(R$_{10}$)$_2$, —NR$_1$COR$_{16}$, —N(R$_{10}$)$_2$, —N(R$_5$)$_2$, —SR$_1$, —SR$_5$, —S(O)$_2$R$_1$, —C(O)R$_{16}$, —CO$_2$R$_1$, aryl, R$_7$, or R$_9$. One of ordinary skill in the art will recognize where the optional substitution is allowed by comparing the listed moieties with W and identifying where R$_3$, R$_4$, R$_6$ or R$_{15}$ would allow for substitution or be the bond to the core molecule.

The compounds of Formula I have optically active center(s) on the quinuclidine ring. Although it is desirable that the stereochemical purity be as high as possible, absolute purity is not required. This invention involves racemic mixtures and compositions of varying degrees of stereochemical purities. It is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions.

Another group of compounds of Formula I includes any one or more or combination of the following: N-[(3R)-1-azabicyclo[2.2.2]oct-3-yl]-2,3-dihydrofuro[2,3-c]pyridine-5-carboxamide; N-[(3R)-1-azabicyclo[2.2.2]oct-3-yl]furo[3,2-c]pyridine-2-carboxamide; N-[(3R)-1-azabicyclo[2.2.2]oct-3-yl]-7-chlorofuro[2,3-c]pyridine-5-carboxamide; N-[(3R)-1-azabicyclo[2.2.2]oct-3-yl]furo[2,3-c]pyridine-5-carboxamide; N-[(3R)-1-azabicyclo[2.2.2]oct-3-yl]-3,3-dimethyl-2,3-dihydrofuro[2,3-c]pyridine-5-carboxamide; N-[(3R)-1-azabicyclo[2.2.2]oct-3-yl]-2-methylfuro[2,3-c]pyridine-5-carboxamide; N-[(3R)-1-azabicyclo[2.2.2]oct-3-yl]furo[2,3-c]pyridine-2-carboxamide; N-[(3R)-1-azabicyclo[2.2.2]oct-3-yl]furo[2,3-b]pyridine-2-carboxamide; N-[(3R)-1-azabicyclo[2.2.2]oct-3-yl]-3-methylfuro[2,3-c]pyridine-5-carboxamide; N-[(3R)-1-azabicyclo[2.2.2]oct-3-yl]-3-ethylfuro[2,3-c]pyridine-5-carboxamide; N-[(3R)-1-azabicyclo[2.2.2]oct-3-yl]-3-isopropylfuro[2,3-c]pyridine-5-carboxamide; N-[(3R)-1-azabicyclo[2.2.2]oct-3-yl]-7-(methylsulfanyl)furo[2,3-c]pyridine-5-carboxamide; N-((3R)-1-azabicyclo[2.2.2]oct-3-yl)thieno[2,3-b]pyridine-2-carboxamide; N-[(3R)-1-azabicyclo[2.2.2]oct-3-yl]thieno[2,3-b]pyridine-5-carboxamide; N-[(3R)-1-azabicyclo[2.2.2]oct-3-yl]thieno[2,3-b]pyridine-6-carboxamide; N-[(3R)-1-azabicyclo[2.2.2]oct-3-yl]thieno[2,3-c]pyridine-2-carboxamide; N-[(3R)-1-azabicyclo[2.2.2]oct-3-yl]thieno[3,2-b]pyridine-2-carboxamide; N-[(3R)-1-azabicyclo[2.2.2]oct-3-yl]thieno[3,2-b]pyridine-5-carboxamide; N-[(3R)-1-azabicyclo[2.2.2]oct-3-yl]thieno[3,2-b]pyridine-6-carboxamide; N-[(3R)-1-azabicyclo[2.2.2]oct-3-yl]thieno[3,2-c]pyridine-2-carboxamide; N-[(3R)-1-azabicyclo[2.2.2]oct-3-yl]thieno[2,3-c]pyridine-5-carboxamide; N-[(3R)-1-azabicyclo[2.2.2]oct-3-yl]thieno[3,2-c]pyridine-6-carboxamide; N-[(3R)-1-azabicyclo[2.2.2]oct-3-yl]-1H-pyrrolo[2,3-c]pyridine-5-carboxamide; N-((3R)-1-azabicyclo[2.2.2]oct-3-yl)-1-methyl-1H-pyrrolo[2,3-c]pyridine-5-carboxamide; N-[(3R)-1-azabicyclo[2.2.2]oct-3-yl]benzothieno[3,2-c]pyridine-3-carboxamide; N-[(3R)-1-azabicyclo[2.2.2]oct-3-yl]benzothieno[2,3-c]pyridine-3-carboxamide; N-[(3R)-1-azabicyclo[2.2.2]oct-3-yl]-3-chlorofuro[2,3-c]pyridine-5-carboxamide; N-[(3R)-1-azabicyclo[2.2.2]oct-3-yl]-3-bromofuro[2,3-c]pyridine-5-carboxamide; N-[(3R)-1-azabicyclo[2.2.2]oct-3-yl]furo[3,2-c]pyridine-6-carboxamide; N-[(3R)-1-azabicyclo[2.2.2]oct-3-yl]-3-bromothieno[2,3-c]pyridine-5-carboxamide; N-[(3R)-1-azabicyclo[2.2.2]oct-3-yl]benzofuro[3,2-c]pyridine-3-carboxamide; N-[(3R)-1-azabicyclo[2.2.2]oct-3-yl]-3-bromothieno[2,3-c]pyridine-5-carboxamide; N-[(3R)-1-azabicyclo[2.2.2]oct-3-yl]thieno[3,4-c]pyridine-6-carboxamide; or a pharmaceutical composition or a pharmaceutically acceptable salt thereof.

Another group of compounds of Formula I includes any one or more or combination of the following: N-[(2S,3R)-2-methyl-1-azabicyclo[2.2.2]oct-3-yl]-2,3-dihydrofuro[2,3-c]pyridine-5-carboxamide; N-[(2S,3R)-2-methyl-1-azabicyclo[2.2.2]oct-3-yl]furo[3,2-c]pyridine-2-carboxamide; N-[(2S,3R)-2-methyl-1-azabicyclo[2.2.2]oct-3-yl]-7-chlorofuro[2,3-c]pyridine-5-carboxamide; N-[(2S,3R)-2-methyl-1-azabicyclo[2.2.2]oct-3-yl]furo[2,3-c]pyridine-5-carboxamide; N-[(2S,3R)-2-methyl-1-azabicyclo[2.2.2]oct-3-yl]-3,3-dimethyl-2,3-dihydrofuro[2,3-c]pyridine-5-carboxamide; N-[(2S,3R)-2-methyl-1-azabicyclo[2.2.2]oct-3-yl]-2-methylfuro[2,3-c]pyridine-5-carboxamide; N-[(2S,3R)-2-methyl-1-azabicyclo[2.2.2]oct-3-yl]furo[2,3-c]pyridine-2-carboxamide; N-[(2S,3R)-2-methyl-1-azabicyclo[2.2.2]oct-3-yl]furo[2,3-b]pyridine-2-carboxamide; N-[(2S,3R)-2-methyl-1-azabicyclo[2.2.2]oct-3-yl]-3-methylfuro[2,3-c]pyridine-5-carboxamide; N-[(2S,3R)-2-methyl-1-azabicyclo[2.2.2]oct-3-yl]-3-ethylfuro[2,3-c]pyridine-5-carboxamide; N-[(2S,3R)-2-methyl-1-azabicyclo[2.2.2]oct-3-yl]-3-isopropylfuro[2,3-c]pyridine-5-carboxamide; N-[(2S,3R)-2-methyl-1-azabicyclo[2.2.2]oct-3-yl]-7-(methylsulfanyl)furo[2,3-c]pyridine-5-carboxamide; N-((2S,3R)-2-methyl-1-azabicyclo[2.2.2]oct-3-yl)thieno[2,3-b]pyridine-2-carboxamide; N-[(2S,3R)-2-methyl-1-azabicyclo[2.2.2]oct-3-yl]thieno[2,3-b]pyridine-5-carboxamide; N-[(2S,3R)-2-methyl-1-azabicyclo[2.2.2]oct-3-yl]thieno[2,3-b]pyridine-6-carboxamide; N-[(2S,3R)-2-methyl-1-azabicyclo[2.2.2]oct-3-yl]thieno[2,3-c]pyridine-2-carboxamide; N-[(2S,3R)-2-methyl-1-azabicyclo[2.2.2]oct-3-yl]thieno[3,2-b]pyridine-2-carboxamide; N-[(2S,3R)-2-methyl-1-azabicyclo[2.2.2]oct-3-yl]thieno[3,2-b]pyridine-5-carboxamide; N-[(2S,3R)-2-methyl-1-azabicyclo[2.2.2]oct-3-yl]thieno[3,2-b]pyridine-6-carboxamide; N-[(2S,3R)-2-methyl-1-azabicyclo[2.2.2]oct-3-yl]thieno[3,2-c]pyridine-2-carboxamide; N-[(2S,3R)-2-methyl-1-azabicyclo[2.2.2]oct-3-yl]thieno[2,3-c]pyridine-5-carboxamide; N-[(2S,3R)-2-methyl-1-azabicyclo[2.2.2]oct-3-yl]thieno[3,2-c]pyridine-6- carboxamide; N-[(2S,3R)-2-methyl-1-azabicyclo[2.2.2]oct-3-yl]-1H-pyrrolo[2,3-c]pyridine-5-carboxamide; N-((2S,3R)-2-methyl-1-azabicyclo[2.2.2]oct-3-yl)-1-methyl-1H-pyrrolo[2,3-c]pyridine-5-carboxamide; N-[(2S,3R)-2-methyl-1-azabicyclo[2.2.2]oct-3-yl]benzothieno[3,2-c]pyridine-3-carboxamide; N-[(2S,3R)-2-methyl-1-azabicyclo[2.2.2]oct-3-yl]benzothieno[2,3-c]pyridine-3-carboxamide; N-[(2S,3R)-2-methyl-1-azabicyclo[2.2.2]oct-3-yl]-3-chlorofuro[2,3-c]pyridine-5-carboxamide; N-[(2S,3R)-2-methyl-1-azabicyclo[2.2.2]oct-3-yl]-3-bromofuro[2,3-c]pyridine-5-carboxamide; N-[(2S,3R)-2-methyl-1-azabicyclo[2.2.2]oct-3-yl]furo[3,2-c]pyridine-6-carboxamide; N-[(2S,3R)-2-methyl-1-azabicyclo[2.2.2]oct-3-yl]-3-bromothieno[2,3-c]pyridine-5-carboxamide; N-[(2S,3R)-2-methyl-1-azabicyclo[2.2.2]oct-3-yl]benzofuro[3,2-c]pyridine-3-carboxamide; N-[(2S,3R)-2-methyl-1-azabicyclo[2.2.2]oct-3-yl]-3-ethynylfuro[2,3-c]pyridine-5-carboxamide; N-[(2S,3R)-2-methyl-1-azabicyclo[2.2.2]oct-3-yl]thieno[3,4-c]pyridine-6-carboxamide; or a pharmaceutical composition or a pharmaceutically acceptable salt thereof.

Another group of compounds of Formula I includes any one or more or combination of the following: N-[(3R)-1-azabicyclo[2.2.2]oct-3-yl]furo[3,2-c]pyridine-2-carboxamide; N-[(3R)-1-azabicyclo[2.2.2]oct-3-yl]furo[2,3-c]pyridine-5-carboxamide; N-[(3R)-1-azabicyclo[2.2.2]oct-3-yl]-2-methylfuro[2,3-c]pyridine-5-carboxamide; N-[(3R)-1-azabicyclo[2.2.2]oct-3-yl]-3-methylfuro[2,3-c]pyridine-5-carboxamide; N-[(3R)-1-azabicyclo[2.2.2]oct-3-yl]-3-ethylfuro[2,3-c]pyridine-5-carboxamide; N-[(3R)-1-azabicyclo[2.2.2]oct-3-yl]-3-isopropylfuro[2,3-c]pyridine-5-carboxamide; N-[(3R)-1-azabicyclo[2.2.2]oct-3-yl]thieno[2,3-b]pyridine-6-carboxamide; N-[(3R)-1-azabicyclo[2.2.2]oct-3-yl]thieno[2,3-c]pyridine-2-carboxamide; N-[(3R)-1-azabicyclo[2.2.2]oct-3-yl]thieno[2,3-c]pyridine-5-carboxamide; N-[(3R)-1-azabicyclo[2.2.2]oct-3-yl]thieno[3,2-c]pyridine-6-carboxamide; N-[(3R)-1-azabicyclo[2.2.2]oct-3-yl]benzothieno[2,3-c]pyridine-3-carboxamide; N-[(3R)-1-azabicyclo[2.2.2]oct-3-yl]-3-chlorofuro[2,3-c]pyridine-5-carboxamide; N-[(3R)-1-azabicyclo[2.2.2]oct-3-yl]-3-bromofuro[2,3-c]pyridine-5-carboxamide; N-[(3R)-1-azabicyclo[2.2.2]oct-3-yl]furo[3,2-c]pyridine-6-carboxamide; N-[(3R)-1-azabicyclo[2.2.2]oct-3-yl]-3-bromothieno[2,3-c]pyridine-5-carboxamide; N-[(3R)-1-azabicyclo[2.2.2]oct-3-yl]benzofuro[3,2-c]pyridine-3-carboxamide; N-[(3R)-1-azabicyclo[2.2.2]oct-3-yl]-3-ethynylfuro[2,3-c]pyridine-5-carboxamide; N-[(3R)-1-azabicyclo[2.2.2]oct-3-yl]thieno[3,4-c]pyridine-6-carboxamide; N-[(2S,3R)-2-methyl-1-azabicyclo[2.2.2]oct-3-yl]furo[3,2-c]pyridine-2-carboxamide; N-[(2S,3R)-2-methyl-1-azabicyclo[2.2.2]oct-3-yl]furo[2,3-c]pyridine-5-carboxamide; N-[(2S,3R)-2-methyl-1-azabicyclo[2.2.2]oct-3-yl]-2-methylfuro[2,3-c]pyridine-5-carboxamide; N-[(2S,3R)-2-methyl-1-azabicyclo[2.2.2]oct-3-yl]-3-methylfuro[2,3-c]pyridine-5-carboxamide; N-[(2S,3R)-2-methyl-1-azabicyclo[2.2.2]oct-3-yl]-3-ethylfuro[2,3-c]pyridine-5-carboxamide; N-[(2S,3R)-2-methyl-1-azabicyclo[2.2.2]oct-3-yl]-3-isopropylfuro[2,3-c]pyridine-5-carboxamide; N-[(2S,3R)-2-methyl-1-azabicyclo[2.2.2]oct-3-yl]thieno[2,3-b]pyridine-6-carboxamide; N-[(2S,3R)-2-methyl-1-azabicyclo[2.2.2]oct-3-yl]thieno[2,3-c]pyridine-2-carboxamide; N-[(2S,3R)-2-methyl-1-azabicyclo[2.2.2]oct-3-yl]thieno[2,3-c]pyridine-5-carboxamide; N-[(2S,3R)-2-methyl-1-azabicyclo[2.2.2]oct-3-yl]thieno[3,2-c]pyridine-6-carboxamide; N-[(2S,3R)-2-methyl-1-azabicyclo[2.2.2]oct-3-yl]benzothieno[2,3-c]pyridine-3-carboxamide; N-[(2S,3R)-2-methyl-1-azabicyclo[2.2.2]oct-3-yl]-3-chlorofuro[2,3-c]pyridine-5-carboxamide; N-[(2S,3R)-2-methyl-1-azabicyclo[2.2.2]oct-3-yl]-3-bromofuro[2,3-c]pyridine-5-carboxamide; N-[(2S,3R)-2-methyl-1-azabicyclo[2.2.2]oct-3-yl]furo[3,2-c]pyridine-6-carboxamide; N-[(2S,3R)-2-methyl-1-azabicyclo[2.2.2]oct-3-yl]-3-bromothieno[2,3-c]pyridine-5-carboxamide; N-[(2S,3R)-2-methyl-1-azabicyclo[2.2.2]oct-3-yl]benzofuro[3,2-c]pyridine-3-carboxamide; N-[(2S,3R)-2-methyl-1-azabicyclo[2.2.2]oct-3-yl]-3-ethynylfuro[2,3-c]pyridine-5-carboxamide; N-[(2S,3R)-2-methyl-1-azabicyclo[2.2.2]oct-3-yl]thieno[3,4-c]pyridine-6-carboxamide; or a pharmaceutical composition or a pharmaceutically acceptable salt thereof.

Another group of compounds of Formula I includes any one or more or combination of the following: N-[(3S)-1-azabicyclo[2.2.2]oct-3-yl]-2,3-dihydrofuro[2,3-c]pyridine-5-carboxamide; N-[(3S)-1-azabicyclo[2.2.2]oct-3-yl]furo[3,2-c]pyridine-2-carboxamide; N-[(3S)-1-azabicyclo[2.2.2]oct-3-yl]-7-chlorofuro[2,3-c]pyridine-5-carboxamide; N-[(3S)-1-azabicyclo[2.2.2]oct-3-yl]furo[2,3-c]pyridine-5-carboxamide; N-[(3S)-1-azabicyclo[2.2.2]oct-3-yl]-3,3-dimethyl-2,3-dihydrofuro[2,3-c]pyridine-5-carboxamide; N-[(3S)-1-azabicyclo[2.2.2]oct-3-yl]-2-methylfuro[2,3-c]pyridine-5-carboxamide; N-[(3S)-1-azabicyclo[2.2.2]oct-3-yl]furo[2,3-c]pyridine-2-carboxamide; N-[(3S)-1-azabicyclo[2.2.2]oct-3-yl]furo[2,3-b]pyridine-2-carboxamide; N-[(3S)-1-azabicyclo[2.2.2]oct-3-yl]-3-methylfuro[2,3-c]pyridine-5-carboxamide; N-[(3S)-1-azabicyclo[2.2.2]oct-3-yl]-3-methylfuro[2,3-c]pyridine-5-carboxamide; N-[(3S)-1-azabicyclo[2.2.2]oct-3-yl]furo[2,3-b]pyridine-2-carboxamide; N-[(3S)-1-azabicyclo[2.2.2]oct-3-yl]-3-methylfuro[2,3-c]pyridine-5-carboxamide; N-((3S)-1-azabicyclo[2.2.2]oct-3-yl)thieno[2,3-b]pyridine-2-carboxamide; N-[(3S)-1-azabicyclo[2.2.2]oct-3-yl]thieno[2,3-b]pyridine-5-carboxamide; N-[(3S)-1-azabicyclo[2.2.2]oct-3-yl]thieno[2,3-b]pyridine-6-carboxamide; N-[(3S)-1-azabicyclo[2.2.2]oct-3-yl]thieno[2,3-c]pyridine-2-carboxamide; N-[(3S)-1-azabicyclo[2.2.2]oct-3-yl]thieno[3,2-b]pyridine-2-carboxamide; N-[(3S)-1-azabicyclo[2.2.2]oct-3-yl]thieno[3,2-b]pyridine-5-carboxamide; N-[(3S)-1-azabicyclo[2.2.2]oct-3-yl]thieno[3,2-b]pyridine-6-carboxamide; N-[(3S)-1-azabicyclo[2.2.2]oct-3-yl]thieno[3,2-c]pyridine-2-carboxamide; N-[(3S)-1-azabicyclo[2.2.2]oct-3-yl]thieno[2,3-c]pyridine-5-carboxamide; N-[(3S)-1-azabicyclo[2.2.2]oct-3-yl]thieno[3,2-c]pyridine-6-carboxamide; N-[(3S)-1-azabicyclo[2.2.2]oct-3-yl]-1H-pyrrolo[2,3-c]pyridine-5-carboxamide; N-((3S)-1-azabicyclo[2.2.2]oct-3-yl)-1-methyl-1H-pyrrolo[2,3-c]pyridine-5-carboxamide; N-[(3S)-1-azabicyclo[2.2.2]oct-3-yl]benzothieno[3,2-c]pyridine-3-carboxamide; N-[(3S)-1-azabicyclo[2.2.2]oct-3-yl]benzothieno[2,3-c]pyridine-3-carboxamide; N-[(3S)-1-azabicyclo[2.2.2]oct-3-yl]-3-chlorofuro[2,3-c]pyridine-5-carboxamide; N-[(3S)-1-azabicyclo[2.2.2]oct-3-yl]-3-bromofuro[2,3-c]pyridine-5-carboxamide; N-[(3S)-1-azabicyclo[2.2.2]oct-3-yl]furo[3,2-c]pyridine-6-carboxamide; N-[(3S)-1-azabicyclo[2.2.2]oct-3-yl]-3-bromothieno[2,3-c]pyridine-5-carboxamide; N-[(3S)-1-azabicyclo[2.2.2]oct-3-yl]benzofuro[3,2-c]pyridine-3-carboxamide; N-[(3S)-1-azabicyclo[2.2.2]oct-3-yl]-3-ethynylfuro[2,3-c]pyridine-5-carboxamide; N-[(3S)-1-azabicyclo[2.2.2]oct-3-yl]thieno[3,4-c]pyridine-6-carboxamide; or a pharmaceutical composition or a pharmaceutically acceptable salt thereof.

Another group of compounds of Formula I includes any one or more or combination of the following compounds: N-[(3S)-1-azabicyclo[2.2.2]oct-3-yl]furo[3,2-c]pyridine-2-carboxamide; N-[(3S)-1-azabicyclo[2.2.2]oct-3-yl]furo[2,3-c]pyridine-5-carboxamide; N-[(3S)-1-azabicyclo[2.2.2]oct- 3-yl]-2-methylfuro[2,3-c]pyridine-5-carboxamide; N-[(3S)-1-azabicyclo[2.2.2]oct-3-yl]-3-methylfuro[2,3-c]pyridine-5-carboxamide; N-[(3S)-1-azabicyclo[2.2.2]pyridine-5-carboxamide; N-[(3S)-1-azabicyclo[2.2.2]oct-3-yl]-3-isopropylfuro[2,3-c]pyridine-5-carboxamide; N-[(3S)-1-azabicyclo[2.2.2]oct-3-yl]thieno[2,3-b]pyridine-6-carboxamide; N-[(3S)-1-azabicyclo[2.2.2]oct-3-yl]thieno[2,3-c]pyridine-2-carboxamide; N-[(3S)-1-azabicyclo[2.2.2]oct-3-yl]thieno[2,3-c]pyridine-5-carboxamide; N-[(3S)-1-azabicyclo[2.2.2]oct-3-yl]thieno[3,2-c]pyridine-6-carboxamide; N-[(3S)-1-azabicyclo[2.2.2]oct-3-yl]benzothieno[2,3-c]pyridine-3-carboxamide; N-[(3S)-1-azabicyclo[2.2.2]oct-3-yl]-3-chlorofuro[2,3-c]pyridine-5-carboxamide; N-[(3S)-1-azabicyclo[2.2.2]oct-3-yl]-3-bromofuro[2,3-c]pyridine-5-carboxamide; N-[(3S)-1-azabicyclo[2.2.2]oct-3-yl]furo[3,2-c]pyridine-6-carboxamide; N-[(3S)-1-azabicyclo[2.2.2]oct-3-yl]-3-bromothieno[2,3-c]pyridine-5-carboxamide; N-[(3S)-1-azabicyclo[2.2.2]oct-3-yl]benzofuro[3,2-c]pyridine-3-carboxamide; N-[(3S)-1-azabicyclo[2.2.2]oct-3-yl]-3-ethynylfuro[2,3-c]pyridine-5-carboxamide; or N-[(3S)-1-azabicyclo[2.2.2]oct-3-yl]thieno[3,4-c]pyridine-6-carboxamide.

Another group of compounds of Formula I includes any one or more or combination of the following compounds: N-[(3R)-1-azabicyclo[2.2.2]oct-3-yl]-2-vinylfuro[3,2-c]pyridine-6-carboxamide; 4-methyl-N-[(3R)-1-azabicyclo[2.2.2]oct-3-yl]furo[3,2-c]pyridine-6-carboxamide; 4-methylthio-N-[(3R)-1-azabicyclo[2.2.2]oct-3-yl]furo[3,2-c]pyridine-6-carboxamide; 4-methoxy-N-[(3R)-1-azabicyclo[2.2.2]oct-3-yl]furo[3,2-c]pyridine-6-carboxamide; 4-chloro-N-[(3R)-1-azabicyclo[2.2.2]oct-3-yl]furo[3,2-c]pyridine-6-carboxamide; N-[(3R)-1-azabicyclo[2.2.2]oct-3-yl]-2-ethynylfuro[3,2-c]pyridine-6-carboxamide; N-[(3R)-1-azabicyclo[2.2.2]oct-3-yl]-2-prop-1-ynylfuro[3,2-c]pyridine-6-carboxamide; N-[(3R)-1-azabicyclo[2.2.2]oct-3-yl]-2-(3-hydroxyprop-1-ynyl)furo[3,2-c]pyridine-6-carboxamide; methyl 3-(6-{[(3R)-1-azabicyclo[2.2.2]oct-3-ylamino]carbonyl}furo[3,2-c]pyridin-2-yl)prop-2-ynoate; 3-(6-{[(3R)-1-azabicyclo[2.2.2]oct-3-ylamino]carbonyl}furo[3,2-c]pyridin-2-yl)prop-2-ynoic acid; 2-(3-amino-3-oxoprop-1-ynyl)-N-[(3R)-1-azabicyclo[2.2.2]oct-3-yl]furo[3,2-c]pyridine-6-carboxamide; N-[(3R)-1-azabicyclo[2.2.2]oct-3-yl]-2-cyanofuro[3,2-c]pyridine-6-carboxamide; N-[(3R)-1-azabicyclo[2.2.2]oct-3-yl]-2-chlorofuro[3,2-c]pyridine-6-carboxamide; N-[(3R)-1-azabicyclo[2.2.2]oct-3-yl]-2-fluorofuro[3,2-c]pyridine-6-carboxamide; N-[(3R)-1-azabicyclo[2.2.2]oct-3-yl]-2-iodofuro[3,2-c]pyridine-6-carboxamide; N-[(3R)-1-azabicyclo[2.2.2]oct-3-yl]-2-trifluoromethylfuro[3,2-c]pyridine-6-carboxamide; N-[(3R)-1-azabicyclo[2.2.2]oct-3-yl]-2-mercaptofuro[3,2-c]pyridine-6-carboxamide; N-[(3R)-1-azabicyclo[2.2.2]oct-3-yl]-2-(methylthio)furo[3,2-c]pyridine-6-carboxamide; N-[(3R)-1-azabicyclo[2.2.2]oct-3-yl]-2-(methylamino)furo[3,2-c]pyridine-6-carboxamide; N-[(3R)-1-azabicyclo[2.2.2]oct-3-yl]-2-(formylamino)furo[3,2-c]pyridine-6-carboxamide; N-[(3R)-1-azabicyclo[2.2.2]oct-3-yl]-2-[formyl(methyl)amino]furo[3,2-c]pyridine-6-carboxamide; 2-(acetylamino)-N-[(3R)-1-azabicyclo[2.2.2]oct-3-yl]furo[3,2-c]pyridine-6-carboxamide; 2-(acetyl(methyl)amino)-N-[(3R)-1-azabicyclo[2.2.2]oct-3-yl]furo[3,2-c]pyridine-6-carboxamide; N-[(3R)-1-azabicyclo[2.2.2]oct-3-yl]-2-[(trifluoroacetyl)amino]furo[3,2-c]pyridine-6-carboxamide; N-[(3R)-1-azabicyclo[2.2.2]oct-3-yl]-2-(benzoylamino)furo[3,2-c]pyridine-6-carboxamide; N-[(3R)-1-azabicyclo[2.2.2]oct-3-yl]-2-(diethylamino)furo[3,2-c]pyridine-6-carboxamide; N-[(3R)-1-azabicyclo[2.2.2]oct-3-yl]-2-(diisopropylamino)furo[3,2-c]pyridine-6-carboxamide; N-[(3R)-1-azabicyclo[2.2.2]oct-3-yl]-2-(pyrrolidin-1-yl)furo[3,2-c]pyridine-6-carboxamide; N-[(3R)-1-azabicyclo[2.2.2]oct-3-yl]-2-(2-oxopyrrolidin-1yl)furo[3,2-c]pyridine-6-carboxamide; N-[(3R)-1-azabicyclo[2.2.2]oct-3-yl]-2-(piperidin-1-yl)furo[3,2-c]pyridine-6-carboxamide; N-[(3R)-1-azabicyclo[2.2.2]oct-3-yl]-2-(2-oxopiperidin-yl)furo[3,2-c]pyridine-6-carboxamide; N-[(3R)-1-azabicyclo[2.2.2]oct-3-yl]-2-(morpholin-4-yl)furo[3,2-c]pyridine-6-carboxamide; N-[(3R)-1-azabicyclo[2.2.2]oct-3-yl]-2-(3-oxomorpholin-4yl)furo[3,2-c]pyridine-6-carboxamide; N-[(3R)-1-azabicyclo[2.2.2]oct-3-yl]-2-(thiomorpholin-4yl)furo[3,2-c]pyridine-6-carboxamide; N-[(3R)-1-azabicyclo[2.2.2]oct-3-yl]-2-(3-oxothiomorpholin-4yl)furo[3,2-c]pyridine-6-carboxamide; N-[(3R)-1-azabicyclo[2.2.2]oct-3-yl]-2-(piperazin-1-yl)furo[3,2-c]pyridine-6-carboxamide; N-[(3R)-1-azabicyclo[2.2.2]oct-3-yl]-2-(2-oxopiperazin-1yl)furo[3,2-c]pyridine-6-carboxamide; N-[(3R)-1-azabicyclo[2.2.2]oct-3-yl]-2-(4-methylpiperazin-1-yl)furo[3,2-c]pyridine-6-carboxamide; N-[(3R)-1-azabicyclo[2.2.2]oct-3-yl]-2-(4-methyl-2-oxopiperazin-1yl)furo[3,2-c]pyridine-6-carboxamide; N-[(3R)-1-azabicyclo[2.2.2]oct-3-yl]-2-(3-oxopiperazin-1yl)furo[3,2-c]pyridine-6-carboxamide; N-[(3R)-1-azabicyclo[2.2.2]oct-3-yl]-2-(4-methyl-3-oxopiperazin-1yl)furo[3,2-c]pyridine-6-carboxamide; N-[(3R)-1-azabicyclo[2.2.2]oct-3-yl]-2-(cyclopropylamino)furo[3,2-c]pyridine-6-carboxamide; N-[(3R)-1-azabicyclo[2.2.2]oct-3-yl]-2-[dimethylamino]furo[3,2-c]pyridine-6-carboxamide; N-[(3R)-1-azabicyclo[2.2.2]oct-3-yl]-2-(1H-pyrrole-1yl)furo[3,2-c]pyridine-6-carboxamide; N-[(3R)-1-azabicyclo[2.2.2]oct-3-yl]-2-(1H-imidazol-1-yl)furo[3,2-c]pyridine-6-carboxamide; N-[(3R)-1-azabicyclo[2.2.2]oct-3-yl]-2-(1H-1,2,4-triazol-1-yl)furo[3,2-c]pyridine-6-carboxamide; N-[(3R)-1-azabicyclo[2.2.2]oct-3-yl]-2-(1H-1,2,3-triazol-1-yl)furo[3,2-c]pyridine-6-carboxamide; N-6-[(3R)-1-azabicyclo[2.2.2]oct-3-yl]furo[3,2-c]pyridine-2,6-dicarboxamide; N-[(3R)-1-azabicyclo[2.2.2]oct-3-yl]-2-(pyrrolidin-1-ylcarbonyl)furo[3,2-c]pyridine-6-carboxamide; N-[(3R)-1-azabicyclo[2.2.2]oct-3-yl]-2-(piperidin-1-ylcarbonyl)furo[3,2-c]pyridine-6-carboxamide; N-[(3R)-1-azabicyclo[2.2.2]oct-3-yl]-2-(piperazin-1-ylcarbonyl)furo[3,2-c]pyridine-6-carboxamide; N-[(3R)-1-azabicyclo[2.2.2]oct-3-yl]-2-[(4-methylpiperazin-1-yl)carbonyl]furo[3,2-c]pyridine-6-carboxamide; N-[(3R)-1-azabicyclo[2.2.2]oct-3-yl]-2-(morpholin-4-ylcarbonyl)furo[3,2-c]pyridine-6-carboxamide; N-[(3R)-1-azabicyclo[2.2.2]oct-3-yl]-2-(thiomorpholin-4-ylcarbonyl)furo[3,2-c]pyridine-6-carboxamide; N-[(3R)-1-azabicyclo[2.2.2]oct-3-yl]-2-(aziridin-1-ylcarbonyl)furo[3,2-c]pyridine-6-carboxamide; N-[(3R)-1-azabicyclo[2.2.2]oct-3-yl]-2-(azetidin-1-ylcarbonyl)furo[3,2-c]pyridine-6-carboxamide; N-[(3R)-1-azabicyclo[2.2.2]oct-3-yl]-2-formylfuro[3,2-c]pyridine-6-carboxamide; 2-acetyl-N-[(3R)-1-azabicyclo[2.2.2]oct-3-yl]furo[3,2-c]pyridine-6-carboxamide; N-[(3R)-1-azabicyclo[2.2.2]oct-3-yl]-2-(trifluoroacetyl)furo[3,2-c]pyridine-6-carboxamide; N-[(3R)-1-azabicyclo[2.2.2]oct-3-yl]-2-[(phenyl)sulfonyl]furo[3,2-c]pyridine-6-carboxamide; N-[(3R)-1-azabicyclo[2.2.2]oct-3-yl]-2-(methylsulfonyl)furo[3,2-c]pyridine-6-carboxamide; 6-{[(3R)-1-azabicyclo[2.2.2]oct-3-ylamino]carbonyl}furo[3,2-c]pyridine-2-carboxylic acid; methyl 6-{[(3R)-1-azabicyclo[2.2.2]oct-3-ylamino]carbonyl}furo[3,2-c]pyridine-2-carboxylate; isopropyl 6-{[(3R)-1-azabicyclo[2.2.2]oct-3-ylamino]carbonyl}furo[3,2-c]pyridine-2-carboxylate; 2,2,2-trifluoroethyl 6-{[(3R)-1-azabicyclo[2.2.2]oct-3-ylamino]

carbonyl}furo[3,2-c]pyridine-2-carboxylate; 4-methyl-N-[(2S,3R)-2-methyl-1-azabicyclo[2.2.2]oct-3-yl]furo[3,2-c]pyridine-6-carboxamide; 4-methylthio-N-[(2S,3R)-2-methyl-1-azabicyclo[2.2.2]oct-3-yl]furo[3,2-c]pyridine-6-carboxamide; 4-methoxy-N-[(2S,3R)-2-methyl-1-azabicyclo[2.2.2]oct-3-yl]furo[3,2-c]pyridine-6-carboxamide; 4-chloro-N-[(2S,3R)-2-methyl-1-azabicyclo[2.2.2]oct-3-yl]furo[3,2-c]pyridine-6-carboxamide; N-[(2S,3R)-2-methyl-1-azabicyclo[2.2.2]oct-3-yl]-2-vinylfuro[3,2-c]pyridine-6-carboxamide; N-[(2S,3R)-2-methyl-1-azabicyclo[2.2.2]oct-3-yl]-2-ethynylfuro[3,2-c]pyridine-6-carboxamide; N-[(2S,3R)-2-methyl-1-azabicyclo[2.2.2]oct-3-yl]-2-prop-1-ynylfuro[3,2-c]pyridine-6-carboxamide; N-[(2S,3R)-2-methyl-1-azabicyclo[2.2.2]oct-3-yl]-2-(3-hydroxyprop-1-ynyl)furo[3,2-c]pyridine-6-carboxamide; methyl 3-(6-{[(2S,3R)-2-methyl-1-azabicyclo[2.2.2]oct-3-ylamino]carbonyl}furo[3,2-c]pyridin-2-yl)prop-2-ynoate; 3-(6-{[(2S,3R)-2-methyl-1-azabicyclo[2.2.2]oct-3-ylamino]carbonyl}furo[3,2-c]pyridin-2-yl)prop-2-ynoic acid; 2-(3-amino-3-oxoprop-1-ynyl)-N-[(2S,3R)-2-methyl-1-azabicyclo[2.2.2]oct-3-yl]furo[3,2-c]pyridine-6-carboxamide; N-[(2S,3R)-2-methyl-1-azabicyclo[2.2.2]oct-3-yl]-2-cyanofuro[3,2-c]pyridine-6-carboxamide; N-[(2S,3R)-2-methyl-1-azabicyclo[2.2.2]oct-3-yl]-2-fluorofuro[3,2-c]pyridine-6-carboxamide; N-[(2S,3R)-2-methyl-1-azabicyclo[2.2.2]oct-3-yl]-2-chlorofuro[3,2-c]pyridine-6-carboxamide; N-[(2S,3R)-2-methyl-1-azabicyclo[2.2.2]oct-3-yl]-2-bromofuro[3,2-c]pyridine-6-carboxamide; N-[(2S,3R)-2-methyl-1-azabicyclo[2.2.2]oct-3-yl]-2-iodofuro[3,2-c]pyridine-6-carboxamide; N-[(2S,3R)-2-methyl-1-azabicyclo[2.2.2]oct-3-yl]-2-trifluoromethyl furo[3,2-c]pyridine-6-carboxamide; N-[(2S,3R)-2-methyl-1-azabicyclo[2.2.2]oct-3-yl]-2-mercaptofuro[3,2-c]pyridine-6-carboxamide; N-[(2S,3R)-2-methyl-1-azabicyclo[2.2.2]oct-3-yl]-2-(methylthio)furo[3,2-c]pyridine-6-carboxamide; N-[(2S,3R)-2-methyl-1-azabicyclo[2.2.2]oct-3-yl]-2-(methylamino)furo[3,2-c]pyridine-6-carboxamide; N-[(2S,3R)-2-methyl-1-azabicyclo[2.2.2]oct-3-yl]-2-(formylamino)furo[3,2-c]pyridine-6-carboxamide; N-[(2S,3R)-2-methyl-1-azabicyclo[2.2.2]oct-3-yl]-2-[formyl(methyl)amino]furo[3,2-c]pyridine-6-carboxamide; 2-(acetylamino)-N-[(2S,3R)-2-methyl-1-azabicyclo[2.2.2]oct-3-yl]furo[3,2-c]pyridine-6-carboxamide; 2-(acetyl(methyl)amino)-N-[(2S,3R)-2-methyl-1-azabicyclo[2.2.2]oct-3-yl]furo[3,2-c]pyridine-6-carboxamide; N-[(2S,3R)-2-methyl-1-azabicyclo[2.2.2]oct-3-yl]-2-[(trifluoroacetyl)amino]furo[3,2-c]pyridine-6-carboxamide; N-[(2S,3R)-2-methyl-1-azabicyclo[2.2.2]oct-3-yl]-2-(benzoylamino)furo[3,2-c]pyridine-6-carboxamide; N-[(2S,3R)-2-methyl-1-azabicyclo[2.2.2]oct-3-yl]-2-(diethylamino)furo[3,2-c]pyridine-6-carboxamide; N-[(2S,3R)-2-methyl-1-azabicyclo[2.2.2]oct-3-yl]-2-(diisopropylamino)furo[3,2-c]pyridine-6-carboxamide; N-[(2S,3R)-2-methyl-1-azabicyclo[2.2.2]oct-3-yl]-2-(pyrrolidin-1-yl)furo[3,2-c]pyridine-6-carboxamide; N-[(2S,3R)-2-methyl-1-azabicyclo[2.2.2]oct-3-yl]-2-(2-oxopyrrolidin-1ylfuro[3,2-c]pyridine-6-carboxamide; N-[(2S,3R)-2-methyl-1-azabicyclo[2.2.2]oct-3-yl]-2-(piperidin-1-yl)furo[3,2-c]pyridine-6-carboxamide; N-[(2S,3R)-2-methyl-1-azabicyclo[2.2.2]oct-3-yl]-2-(2-oxopiperidin-1yl)furo[3,2-c]pyridine-6-carboxamide; N-[(2S,3R)-2-methyl-1-azabicyclo[2.2.2]oct-3-yl]-2-(morpholin-4-yl)furo[3,2-c]pyridine-6-carboxamide; N-[(2S,3R)-2-methyl-1-azabicyclo[2.2.2]oct-3-yl]-2-(3-oxomorpholin-4yl)furo[3,2-c]pyridine-6-carboxamide; N-[(2S,3R)-2-methyl-1-azabicyclo[2.2.2]oct-3-yl]-2-(thiomorpholin-4yl)furo[3,2-c]pyridine-6-carboxamide; N-[(2S,3R)-2-methyl-1-azabicyclo[2.2.2]oct-3-yl]-2-(3-oxothiomorpholin-4yl)furo[3,2-c]pyridine-6-carboxamide; N-[(2S,3R)-2-methyl-1-azabicyclo[2.2.2]oct-3-yl]-2-(piperazin-1-yl)furo[3,2-c]pyridine-6-carboxamide; N-[(2S,3R)-2-methyl-1-azabicyclo[2.2.2]oct-3-yl]-2-(2-oxopiperazin-1yl)furo[3,2-c]pyridine-6-carboxamide; N-[(2S,3R)-2-methyl-1-azabicyclo[2.2.2]oct-3-yl]-2-(4-methylpiperazin-1-yl)furo[3,2-c]pyridine-6-carboxamide; N-[(2S,3R)-2-methyl-1-azabicyclo[2.2.2]oct-3-yl]-2-(4-methyl-2-oxopiperazin-1yl)furo[3,2-c]pyridine-6-carboxamide; N-[(2S,3R)-2-methyl-1-azabicyclo[2.2.2]oct-3-yl]-2-(3-oxopiperazin-1yl)furo[3,2-c]pyridine-6-carboxamide; N-[(2S,3R)-2-methyl-1-azabicyclo[2.2.2]oct-3-yl]-2-(4-methyl-3-oxopiperazin-1yl)furo[3,2-c]pyridine-6-carboxamide; N-[(2S,3R)-2-methyl-1-azabicyclo[2.2.2]oct-3-yl]-2-(cyclopropylamino)furo[3,2-c]pyridine-6-carboxamide; N-[(2S,3R)-2-methyl-1-azabicyclo[2.2.2]oct-3-yl]-2-[dimethylamino]furo[3,2-c]pyridine-6-carboxamide; N-[(2S,3R)-2-methyl-1-azabicyclo[2.2.2]oct-3-yl]-2-(1H-pyrrole-1yl)furo[3,2-c]pyridine-6-carboxamide; N-[(2S,3R)-2-methyl-1-azabicyclo[2.2.2]oct-3-yl]-2-(1H-imidazol-1-yl)furo[3,2-c]pyridine-6-carboxamide; N-[(2S,3R)-2-methyl-1-azabicyclo[2.2.2]oct-3-yl]-2-(1H-1,2,4-triazol-1-yl)furo[3,2-c]pyridine-6-carboxamide; N-[(2S,3R)-2-methyl-1-azabicyclo[2.2.2]oct-3-yl]-2-(1H-1,2,3-triazol-1-yl)furo[3,2-c]pyridine-6-carboxamide; N-6-[(2S,3R)-2-methyl-1-azabicyclo[2.2.2]oct-3-yl]furo[3,2-c]pyridine-2,6-dicarboxamide; N-[(2S,3R)-2-methyl-1-azabicyclo[2.2.2]oct-3-yl]-2-(pyrrolidin-1-ylcarbonyl)furo[3,2-c]pyridine-6-carboxamide; N-[(2S,3R)-2-methyl-1-azabicyclo[2.2.2]oct-3-yl]-2-(piperidin-1-ylcarbonyl)furo[3,2-c]pyridine-6-carboxamide; N-[(2S,3R)-2-methyl-1-azabicyclo[2.2.2]oct-3-yl]-2-(piperazin-1-ylcarbonyl)furo[3,2-c]pyridine-6-carboxamide; N-[(2S,3R)-2-methyl-1-azabicyclo[2.2.2]oct-3-yl]-2-[(4-methylpiperazin-1-yl)carbonyl]furo[3,2-c]pyridine-6-carboxamide; N-[(2S,3R)-2-methyl-1-azabicyclo[2.2.2]oct-3-yl]-2-(morpholin-4-ylcarbonyl)furo[3,2-c]pyridine-6-carboxamide; N-[(2S,3R)-2-methyl-1-azabicyclo[2.2.2]oct-3-yl]-2-(thiomorpholin-4-ylcarbonyl)furo[3,2-c]pyridine-6-carboxamide; N-[(2S,3R)-2-methyl-1-azabicyclo[2.2.2]oct-3-yl]-2-(aziridin-1-ylcarbonyl)furo[3,2-c]pyridine-6-carboxamide; N-[(2S,3R)-2-methyl-1-azabicyclo[2.2.2]oct-3-yl]-2-(azetidin-1-ylcarbonyl)furo[3,2-c]pyridine-6-carboxamide; N-[(2S,3R)-2-methyl-1-azabicyclo[2.2.2]oct-3-yl]-2-formylfuro[3,2-c]pyridine-6-carboxamide; 2-acetyl-N-[(2S,3R)-2-methyl-1-azabicyclo[2.2.2]oct-3-yl]furo[3,2-c]pyridine-6-carboxamide; N-[(2S,3R)-2-methyl-1-azabicyclo[2.2.2]oct-3-yl]-2-(trifluoroacetyl)furo[3,2-c]pyridine-6-carboxamide; N-[(2S,3R)-2-methyl-1-azabicyclo[2.2.2]oct-3-yl]-2-[(phenyl)sulfonyl]furo[3,2-c]pyridine-6-carboxamide; N-[(2S,3R)-2-methyl-1-azabicyclo[2.2.2]oct-3-yl]-2-(methylsulfonyl)furo[3,2-c]pyridine-6-carboxamide; 6-{[(2S,3R)-2-methyl-1-azabicyclo[2.2.2]oct-3-ylamino]carbonyl}furo[3,2-c]pyridine-2-carboxylic acid; methyl 6-{[(2S,3R)-2-methyl-1-azabicyclo[2.2.2]oct-3-ylamino]carbonyl}furo[3,2-c]pyridine-2-carboxylate; isopropyl 6-{[(2S,3R)-2-methyl-1-azabicyclo[2.2.2]oct-3-ylamino]carbonyl}furo[3,2-c]pyridine-2-carboxylate; 2,2,2-trifluoroethyl 6-{[(2S,3R)-2-methyl-1-azabicyclo[2.2.2]oct-3-ylamino]carbonyl}furo[3,2-c]pyridine-2-carboxylate;

N-[(3R)-1-azabicyclo[2.2.2]oct-3-yl]-2-vinylthieno[3,2-c]pyridine-6-carboxamide; 4-methyl-N-[(3R)-1-azabicyclo[2.2.2]oct-3-yl]thieno[3,2-c]pyridine-6-carboxamide; 4-methylthio-N-[(3R)-1-azabicyclo[2.2.2]oct-3-yl]thieno[3,2-c]pyridine-6-carboxamide; 4-methoxy-N-[(3R)-1-azabicyclo[2.2.2]oct-3-yl]thieno[3,2-c]pyridine-6-carboxamide;

4-chloro-N-[(3R)-1-azabicyclo[2.2.2]oct-3-yl]thieno[3,2-c]pyridine-6-carboxamide; N-[(3R)-1-azabicyclo[2.2.2]oct-3-yl]-2-ethynylthieno[3,2-c]pyridine-6-carboxamide; N-[(3R)-1-azabicyclo[2.2.2]oct-3-yl]-2-prop-1-ynylthieno[3,2-c]pyridine-6-carboxamide; N-[(3R)-1-azabicyclo[2.2.2]oct-3-yl]-2-(3-hydroxyprop-1-ynyl)thieno[3,2-c]pyridine-6-carboxamide; methyl 3-(6-{[(3R)-1-azabicyclo[2.2.2]oct-3-ylamino]carbonyl}thieno[3,2-c]pyridin-2-yl)prop-2-ynoate; 3-(6-{[(3R)-1-azabicyclo[2.2.2]oct-3-ylamino]carbonyl}thieno[3,2-c]pyridin-2-yl)prop-2-ynoic acid; 2-(3-amino-3-oxoprop-1-ynyl)-N-[(3R)-1-azabicyclo[2.2.2]oct-3-yl]thieno[3,2-c]pyridine-6-carboxamide; N-[(3R)-1-azabicyclo[2.2.2]oct-3-yl]-2-cyanothieno[3,2-c]pyridine-6-carboxamide; N-[(3R)-1-azabicyclo[2.2.2]oct-3-yl]-2-chlorothieno[3,2-c]pyridine-6-carboxamide; N-[(3R)-1-azabicyclo[2.2.2]oct-3-yl]-2-fluorothieno[3,2-c]pyridine-6-carboxamide; N-[(3R)-1-azabicyclo[2.2.2]oct-3-yl]-2-iodothieno[3,2-c]pyridine-6-carboxamide; N-[(3R)-1-azabicyclo[2.2.2]oct-3-yl]-2-trifluoromethylthieno[3,2-c]pyridine-6-carboxamide; N-[(3R)-1-azabicyclo[2.2.2]oct-3-yl]-2-mercaptothieno[3,2-c]pyridine-6-carboxamide; N-[(3R)-1-azabicyclo[2.2.2]oct-3-yl]-2-(methylthio)thieno[3,2-c]pyridine-6-carboxamide; N-[(3R)-1-azabicyclo[2.2.2]oct-3-yl]-2-(methylamino)thieno[3,2-c]pyridine-6-carboxamide; N-[(3R)-1-azabicyclo[2.2.2]oct-3-yl]-2-(formylamino)thieno[3,2-c]pyridine-6-carboxamide; N-[(3R)-1-azabicyclo[2.2.2]oct-3-yl]-2-[formyl(methyl)amino]thieno[3,2-c]pyridine-6-carboxamide; 2-(acetylamino)-N-[(3R)-1-azabicyclo[2.2.2]oct-3-yl]thieno[3,2-c]pyridine-6-carboxamide; 2-(acetyl(methyl)amino)-N-[(3R)-1-azabicyclo[2.2.2]oct-3-yl]thieno[3,2-c]pyridine-6-carboxamide; N-[(3R)-1-azabicyclo[2.2.2]oct-3-yl]-2-[(trifluoroacetyl)amino]thieno[3,2-c]pyridine-6-carboxamide; N-[(3R)-1-azabicyclo[2.2.2]oct-3-yl]-2-(benzoylamino)thieno[3,2-c]pyridine-6-carboxamide; N-[(3R)-1-azabicyclo[2.2.2]oct-3-yl]-2-(diethylamino)thieno[3,2-c]pyridine-6-carboxamide; N-[(3R)-1-azabicyclo[2.2.2]oct-3-yl]-2-(diisopropylamino)thieno[3,2-c]pyridine-6-carboxamide; N-[(3R)-1-azabicyclo[2.2.2]oct-3-yl]-2-(pyrrolidin-1-yl)thieno[3,2-c]pyridine-6-carboxamide; N-[(3R)-1-azabicyclo[2.2.2]oct-3-yl]-2-(2-oxopyrrolidin-1yl)thieno[3,2-c]pyridine-6-carboxamide; N-[(3R)-1-azabicyclo[2.2.2]oct-3-yl]-2-(piperidin-1-yl)thieno[3,2-c]pyridine-6-carboxamide; N-[(3R)-1-azabicyclo[2.2.2]oct-3-yl]-2-(2-oxopiperidin-1yl)thieno[3,2-c]pyridine-6-carboxamide; N-[(3R)-1-azabicyclo[2.2.2]oct-3-yl]-2-(morpholin-4-yl)thieno[3,2-c]pyridine-6-carboxamide; N-[(3R)-1-azabicyclo[2.2.2]oct-3-yl]-2-(3-oxomorpholin-4yl)thieno[3,2-c]pyridine-6-carboxamide; N-[(3R)-1-azabicyclo[2.2.2]oct-3-yl]-2-(thiomorpholin-4yl)thieno[3,2-c]pyridine-6-carboxamide; N-[(3R)-1-azabicyclo[2.2.2]oct-3-yl]-2-(3-oxothiomorpholin-4yl)thieno[3,2-c]pyridine-6-carboxamide; N-[(3R)-1-azabicyclo[2.2.2]oct-3-yl]-2-(piperazin-1-yl)thieno[3,2-c]pyridine-6-carboxamide; N-[(3R)-1-azabicyclo[2.2.2]oct-3-yl]-2-(2-oxopiperazin-1yl)thieno[3,2-c]pyridine-6-carboxamide; N-[(3R)-1-azabicyclo[2.2.2]oct-3-yl]-2-(4-methylpiperazin-1-yl)thieno[3,2-c]pyridine-6-carboxamide; N-[(3R)-1-azabicyclo[2.2.2]oct-3-yl]-2-(4-methyl-2-oxopiperazin-1yl)thieno[3,2-c]pyridine-6-carboxamide; N-[(3R)-1-azabicyclo[2.2.2]oct-3-yl]-2-(3-oxopiperazin-1yl)thieno[3,2-c]pyridine-6-carboxamide; N-[(3R)-1-azabicyclo[2.2.2]oct-3-yl]-2-(4-methyl-3-oxopiperazin-1yl)thieno[3,2-c]pyridine-6-carboxamide; N-[(3R)-1-azabicyclo[2.2.2]oct-3-yl]-2-(cyclopropylamino)thieno[3,2-c]pyridine-6-carboxamide; N-[(3R)-1-azabicyclo[2.2.2]oct-3-yl]-2-[dimethylamino]thieno[3,2-c]pyridine-6-carboxamide; N-[(3R)-1-azabicyclo[2.2.2]oct-3-yl]-2-(1H-pyrrole-1yl)thieno[3,2-c]pyridine-6-carboxamide; N-[(3R)-1-azabicyclo[2.2.2]oct-3-yl]-2-(1H-imidazol-1-yl)thieno[3,2-c]pyridine-6-carboxamide; N-[(3R)-1-azabicyclo[2.2.2]oct-3-yl]-2-(1H-1,2,4-triazol-1-yl)thieno[3,2-c]pyridine-6-carboxamide; N-[(3R)-1-azabicyclo[2.2.2]oct-3-yl]-2-(1H-1,2,3-triazol-1-yl)thieno[3,2-c]pyridine-6-carboxamide; N-6-[(3R)-1-azabicyclo[2.2.2]oct-3-yl]thieno[3,2-c]pyridine-2,6-dicarboxamide; N-[(3R)-1-azabicyclo[2.2.2]oct-3-yl]-2-(pyrrolidin-1-ylcarbonyl)thieno[3,2-c]pyridine-6-carboxamide; N-[(3R)-1-azabicyclo[2.2.2]oct-3-yl]-2-(piperidin-1-ylcarbonyl)thieno[3,2-c]pyridine-6-carboxamide; N-[(3R)-1-azabicyclo[2.2.2]oct-3-yl]-2-(piperazin-1-ylcarbonyl)thieno[3,2-c]pyridine-6-carboxamide; N-[(3R)-1-azabicyclo[2.2.2]oct-3-yl]-2-[(4-methylpiperazin-1-yl)carbonyl]thieno[3,2-c]pyridine-6-carboxamide; N-[(3R)-1-azabicyclo[2.2.2]oct-3-yl]-2-(morpholin-4-ylcarbonyl)thieno[3,2-c]pyridine-6-carboxamide; N-[(3R)-1-azabicyclo[2.2.2]oct-3-yl]-2-(thiomorpholin-4-ylcarbonyl)thieno[3,2-c]pyridine-6-carboxamide; N-[(3R)-1-azabicyclo[2.2.2]oct-3-yl]-2-(aziridin-1-ylcarbonyl)thieno[3,2-c]pyridine-6-carboxamide; N-[(3R)-1-azabicyclo[2.2.2]oct-3-yl]-2-(azetidin-1-ylcarbonyl)thieno[3,2-c]pyridine-6-carboxamide; N-[(3R)-1-azabicyclo[2.2.2]oct-3-yl]-2-formylthieno[3,2-c]pyridine-6-carboxamide; 2-acetyl-N-[(3R)-1-azabicyclo[2.2.2]oct-3-yl]thieno[3,2-c]pyridine-6-carboxamide; N-[(3R)-1-azabicyclo[2.2.2]oct-3-yl]-2-(trifluoroacetyl)thieno[3,2-c]pyridine-6-carboxamide; N-[(3R)-1-azabicyclo[2.2.2]oct-3-yl]-2-[(phenyl)sulfonyl]thieno[3,2-c]pyridine-6-carboxamide; N-[(3R)-1-azabicyclo[2.2.2]oct-3-yl]-2-(methylsulfonyl)thieno[3,2-c]pyridine-6-carboxamide; 6-{[(3R)-1-azabicyclo[2.2.2]oct-3-ylamino]carbonyl}theino[3,2-c]pyridine-2-carboxylic acid; methyl 6-{[(3R)-1-azabicyclo[2.2.2]oct-3-ylamino]carbonyl}thieno[3,2-c]pyridine-2-carboxylate; isopropyl 6-{[(3R)-1-azabicyclo[2.2.2]oct-3-ylamino]carbonyl}thieno[3,2-c]pyridine-2-carboxylate; 2,2,2-trifluoroethyl 6-{[(3R)-1-azabicyclo[2.2.2]oct-3-ylamino]carbonyl}thieno[3,2-c]pyridine-2-carboxylate; 4-methyl-N-[(2S,3R)-2-methyl-1-azabicyclo[2.2.2]oct-3-yl]thieno[3,2-c]pyridine-6-carboxamide; 4-methylthio-N-[(2S,3R)-2-methyl-1-azabicyclo[2.2.2]oct-3-yl]thieno[3,2-c]pyridine-6-carboxamide; 4-methoxy-N-[(2S,3R)-2-methyl-1-azabicyclo[2.2.2]oct-3-yl]thieno[3,2-c]pyridine-6-carboxamide; 4-chloro-N-[(2S,3R)-2-methyl-1-azabicyclo[2.2.2]oct-3-yl]thieno[3,2-c]pyridine-6-carboxamide; N-[(2S,3R)-2-methyl-1-azabicyclo[2.2.2]oct-3-yl]-2-vinylthieno[3,2-c]pyridine-6-carboxamide; N-[(2S,3R)-2-methyl-1-azabicyclo[2.2.2]oct-3-yl]-2-ethynylthieno[3,2-c]pyridine-6-carboxamide; N-[(2S,3R)-2-methyl-1-azabicyclo[2.2.2]oct-3-yl]-2-prop-1-ynylthieno[3,2-c]pyridine-6-carboxamide; N-[(2S,3R)-2-methyl-1-azabicyclo[2.2.2]oct-3-yl]-2-(3-hydroxyprop-1-ynyl)thieno[3,2-c]pyridine-6-carboxamide; methyl 3-(6-{[(2S,3R)-2-methyl-1-azabicyclo[2.2.2]oct-3-ylamino]carbonyl}thieno[3,2-c]pyridin-2-yl)prop-2-ynoate; 3-(6-{[(2S,3R)-2-methyl-1-azabicyclo[2.2.2]oct-3-ylamino]carbonyl}thieno[3,2-c]pyridin-2-yl)prop-2-ynoic acid; 2-(3-amino-3-oxoprop-1-ynyl)-N-[(2S,3R)-2-methyl-1-azabicyclo[2.2.2]oct-3-yl]thieno[3,2-c]pyridine-6-carboxamide; N-[(2S,3R)-2-methyl-1-azabicyclo[2.2.2]oct-3-yl]-2-cyanothieno[3,2-c]pyridine-6-carboxamide; N-[(2S,3R)-2-methyl-1-azabicyclo[2.2.2]oct-3-yl]-2-fluorothieno[3,2-c]pyridine-6-carboxamide; N-[(2S,3R)-2-methyl-1-azabicyclo[2.2.2]oct-3-yl]-2-chlorothieno[3,2-c]pyridine-6-carboxamide; N-[(2S,3R)-2-methyl-1-azabicyclo[2.2.2]oct-3-yl]-2-bromothieno[3,2-c]pyridine-6-carboxamide; N-[(2S,3R)-2-methyl-1-azabicyclo[2.2.2]oct- 3-yl]-2-iodothieno[3,2-c]pyridine-6-carboxamide; N-[(2S, 3R)-2-methyl-1-azabicyclo[2.2.2]oct-3-yl]-2-trifluoromethylthieno[3,2-c]pyridine-6-carboxamide; N-[(2S,3R)-2-methyl-1-azabicyclo[2.2.2]oct-3-yl]-2-mercaptothieno[3,2-c]pyridine-6-carboxamide; N-[(2S,3R)-2-methyl-1-azabicyclo[2.2.2]oct-3-yl]-2-(methylthio)thieno[3,2-c]pyridine-6-carboxamide; N-[(2S,3R)-2-methyl-1-azabicyclo[2.2.2]oct-3-yl]-2-(methylamino)thieno[3,2-c]pyridine-6-carboxamide; N-[(2S,3R)-2-methyl-1-azabicyclo[2.2.2]oct-3-yl]-2-(formylamino)thieno[3,2-c]pyridine-6-carboxamide; N-[(2S,3R)-2-methyl-1-azabicyclo[2.2.2]oct-3-yl]-2-[formyl(methyl)amino]thieno[3,2-c]pyridine-6-carboxamide; 2-(acetylamino)-N-[(2S,3R)-2-methyl-1-azabicyclo[2.2.2]oct-3-yl]thieno[3,2-c]pyridine-6-carboxamide; 2-(acetyl(methyl)amino)-N-[(2S,3R)-2-methyl-1-azabicyclo[2.2.2]oct-3-yl]thieno[3,2-c]pyridine-6-carboxamide; N-[(2S,3R)-2-methyl-1-azabicyclo[2.2.2]oct-3-yl]-2-[(trifluoroacetyl)amino]thieno[3,2-c]pyridine-6-carboxamide; N-[(2S,3R)-2-methyl-1-azabicyclo[2.2.2]oct-3-yl]-2-(benzoylamino)thieno[3,2-c]pyridine-6-carboxamide; N-[(2S,3R)-2-methyl-1-azabicyclo[2.2.2]oct-3-yl]-2-(diethylamino)thieno[3,2-c]pyridine-6-carboxamide; N-[(2S,3R)-2-methyl-1-azabicyclo[2.2.2]oct-3-yl]-2-(diisopropylamino)thieno[3,2-c]pyridine-6-carboxamide; N-[(2S,3R)-2-methyl-1-azabicyclo[2.2.2]oct-3-yl]-2-(pyrrolidin-1-yl)thieno[3,2-c]pyridine-6-carboxamide; N-[(2S,3R)-2-methyl-1-azabicyclo[2.2.2]oct-3-yl]-2-(2-oxopyrrolidin-1yl)thieno[3,2-c]pyridine-6-carboxamide; N-[(2S,3R)-2-methyl-1-azabicyclo[2.2.2]oct-3-yl]-2-(piperidin-1-yl)thieno[3,2-c]pyridine-6-carboxamide; N-[(2S,3R)-2-methyl-1-azabicyclo[2.2.2]oct-3-yl]-2-(2-oxopiperidin-1yl)thieno[3,2-c]pyridine-6-carboxamide; N-[(2S,3R)-2-methyl-1-azabicyclo[2.2.2]oct-3-yl]-2-(morpholin-4-yl)thieno[3,2-c]pyridine-6-carboxamide; N-[(2S,3R)-2-methyl-1-azabicyclo[2.2.2]oct-3-yl]-2-(3-oxomorpholin-4yl)thieno[3,2-c]pyridine-6-carboxamide; N-[(2S,3R)-2-methyl-1-azabicyclo[2.2.2]oct-3-yl]-2-(thiomorpholin-4yl)thieno[3,2-c]pyridine-6-carboxamide; N-[(2S,3R)-2-methyl-1-azabicyclo[2.2.2]oct-3-yl]-2-(3-oxothiomorpholin-4yl)thieno[3,2-c]pyridine-6-carboxamide; N-[(2S,3R)-2-methyl-1-azabicyclo[2.2.2]oct-3-yl]-2-(piperazin-1-yl)thieno[3,2-c]pyridine-6-carboxamide; N-[(2S,3R)-2-methyl-1-azabicyclo[2.2.2]oct-3-yl]-2-(2-oxopiperazin-1yl)thieno[3,2-c]pyridine-6-carboxamide; N-[(2S,3R)-2-methyl-1-azabicyclo[2.2.2]oct-3-yl]-2-(4-methylpiperazin-1-yl)thieno[3,2-c]pyridine-6-carboxamide; N-[(2S,3R)-2-methyl-1-azabicyclo[2.2.2]oct-3-yl]-2-(4-methyl-2-oxopiperazin-1yl)thieno[3.2-c]pyridine-6-carboxamide; N-[(2S,3R)-2-methyl-1-azabicyclo[2.2.2]oct-3-yl]-2-(3-oxopiperazin-1yl)thieno[3,2-c]pyridine-6-carboxamide; N-[(2S,3R)-2-methyl-1-azabicyclo[2.2.2]oct-3-yl]-2-(4-methyl-3-oxopiperazin-1yl)thieno[3,2-c]pyridine-6-carboxamide; N-[(2S,3R)-2-methyl-1-azabicyclo[2.2.2]oct-3-yl]-2-(cyclopropylamino)thieno[3,2-c]pyridine-6-carboxamide; N-[(2S,3R)-2-methyl-1-azabicyclo[2.2.2]oct-3-yl]-2-[dimethylamino]thieno[3,2-c]pyridine-6-carboxamide; N-[(2S,3R)-2-methyl-1-azabicyclo[2.2.2]oct-3-yl]-2-(1H-pyrrole-1yl)thieno[3,2-c]pyridine-6-carboxamide; N-[(2S,3R)-2-methyl-1-azabicyclo[2.2.2]oct-3-yl]-2-(1H-imidazol-1-yl)thieno[3,2-c]pyridine-6-carboxamide; N-[(2S,3R)-2-methyl-1-azabicyclo[2.2.2]oct-3-yl]-2-(1H-1,2,4-triazol-1-yl)thieno[3,2-c]pyridine-6-carboxamide; N-[(2S,3R)-2-methyl-1-azabicyclo[2.2.2]oct-3-yl]-2-(1H-1,2,3-triazol-1-yl)thieno[3,2-c]pyridine-6-carboxamide; N-6-[(2S,3R)-2-methyl-1-azabicyclo[2.2.2]oct-3-yl]thieno[3,2-c]pyridine-2,6-dicarboxamide; N-[(2S,3R)-2-methyl-1-azabicyclo[2.2.2]oct-3-yl]-2-(pyrrolidin-1-ylcarbonyl)thieno[3,2-c]pyridine-6-carboxamide; N-[(2S,3R)-2-methyl-1-azabicyclo[2.2.2]oct-3-yl]-2-(piperidin-1-ylcarbonyl)thieno[3,2-c]pyridine-6-carboxamide; N-[(2S,3R)-2-methyl-1-azabicyclo[2.2.2]oct-3-yl]-2-(piperazin-1-ylcarbonyl)thieno[3,2-c]pyridine-6-carboxamide; N-[(2S,3R)-2-methyl-1-azabicyclo[2.2.2]oct-3-yl]-2-[(4-methylpiperazin-1-yl)carbonyl]thieno[3,2-c]pyridine-6-carboxamide; N-[(2S,3R)-2-methyl-1-azabicyclo[2.2.2]oct-3-yl]-2-(morpholin-4-ylcarbonyl)thieno[3,2-c]pyridine-6-carboxamide; N-[(2S,3R)-2-methyl-1-azabicyclo[2.2.2]oct-3-yl]-2-(thiomorpholin-4-ylcarbonyl)thieno[3,2-c]pyridine-6-carboxamide; N-[(2S,3R)-2-methyl-1-azabicyclo[2.2.2]oct-3-yl]-2-(aziridin-1-ylcarbonyl)thieno[3,2-c]pyridine-6-carboxamide; N-[(2S,3R)-2-methyl-1-azabicyclo[2.2.2]oct-3-yl]-2-(azetidin-1-ylcarbonyl)thieno[3,2-c]pyridine-6-carboxamide; N-[(2S,3R)-2-methyl-1-azabicyclo[2.2.2]oct-3-yl]-2-formylthieno[3,2-c]pyridine-6-carboxamide; 2-acetyl-N-[(2S,3R)-2-methyl-1-azabicyclo[2.2.2]oct-3-yl]thieno[3,2-c]pyridine-6-carboxamide; N-[(2S,3R)-2-methyl-1-azabicyclo[2.2.2]oct-3-yl]-2-(trifluoroacetyl)thieno[3,2-c]pyridine-6-carboxamide; N-[(2S,3R)-2-methyl-1-azabicyclo[2.2.2]oct-3-yl]-2-[(phenyl)sulfonyl]thieno[3,2-c]pyridine-6-carboxamide; N-[(2S,3R)-2-methyl-1-azabicyclo[2.2.2]oct-3-yl]-2-(methylsulfonyl)thieno[3,2-c]pyridine-6-carboxamide; 6-{[(2S,3R)-2-methyl-1-azabicyclo[2.2.2]oct-3-ylamino]carbonyl}thieno[3,2-c]pyridine-2-carboxylic acid; methyl 6-{[(2S,3R)-2-methyl-1-azabicyclo[2.2.2]oct-3-ylamino]carbonyl}thieno[3,2-c]pyridine-2-carboxylate; isopropyl 6-{[(2S,3R)-2-methyl-1-azabicyclo[2.2.2]oct-3-ylamino]carbonyl}thieno[3,2-c]pyridine-2-carboxylate; 2,2,2-trifluoroethyl 6-{[(2S,3R)-2-methyl-1-azabicyclo[2.2.2]oct-3-ylamino]carbonyl}thieno[3,2-c]pyridine-2-carboxylate;

N-[(3R)-1-azabicyclo[2.2.2]oct-3-yl]-3-vinylfuro[2,3-c]pyridine-5-carboxamide; 7-methyl-N-[(3R)-1-azabicyclo[2.2.2]oct-3-yl]furo[2,3-c]pyridine-5-carboxamide; 7-methoxy-N-[(3R)-1-azabicyclo[2.2.2]oct-3-yl]furo[2,3-c]pyridine-5-carboxamide; N-[(3R)-1-azabicyclo[2.2.2]oct-3-yl]-3-ethynylfuro[2,3-c]pyridine-5-carboxamide; N-[(3R)-1-azabicyclo[2.2.2]oct-3-yl]-3-prop-1-ynylfuro[2,3-c]pyridine-5-carboxamide; N-[(3R)-1-azabicyclo[2.2.2]oct-3-yl]-3-(3-hydroxyprop-1-ynyl)furo[2,3-c]pyridine-5-carboxamide; methyl 3-(5-{[(3R)-1-azabicyclo[2.2.2]oct-3-ylamino]carbonyl}furo[2,3-c]pyridin-3-yl)prop-2-ynoate; 3-(5-{[(3R)-1-azabicyclo[2.2.2]oct-3-ylamino]carbonyl}furo[2,3-c]pyridin-3-yl)prop-2-ynoic acid; 3-(3-amino-3-oxoprop-1-ynyl)-N-[(3R)-1-azabicyclo[2.2.2]oct-3-yl]furo[2,3-c]pyridine-5-carboxamide; N-[(3R)-1-azabicyclo[2.2.2]oct-3-yl]-3-cyanofuro[2,3-c]pyridine-5-carboxamide; N-[(3R)-1-azabicyclo[2.2.2]oct-3-yl]-3-fluorofuro[2,3-c]pyridine-5-carboxamide; N-[(3R)-1-azabicyclo[2.2.2]oct-3-yl]-3-iodofuro[2,3-c]pyridine-5-carboxamide; N-[(3R)-1-azabicyclo[2.2.2]oct-3-yl]-3-trifluoromethylfuro[2,3-c]pyridine-5-carboxamide; N-[(3R)-1-azabicyclo[2.2.2]oct-3-yl]-3-mercaptofuro[2,3-c]pyridine-5-carboxamide; N-[(3R)-1-azabicyclo[2.2.2]oct-3-yl]-3-(methylthio)furo[2,3-c]pyridine-5-carboxamide; N-[(3R)-1-azabicyclo[2.2.2]oct-3-yl]-3-(methylamino)furo[2,3-c]pyridine-5-carboxamide; N-[(3R)-1-azabicyclo[2.2.2]oct-3-yl]-3-(formylamino)furo[2,3-c]pyridine-5-carboxamide; N-[(3R)-1-azabicyclo[2.2.2]oct-3-yl]-3-[formyl(methyl)amino]furo[2,3-c]pyridine-5-carboxamide; 3-(acetylamino)-N-[(3R)-1-azabicyclo[2.2.2]oct-3-yl]furo[2,3-c]pyridine-5-carboxamide; 3-(acetyl(methyl)amino)-N-[(3R)-1-azabicyclo[2.2.2]oct-3-yl]furo[2,3-c]pyridine-5- carboxamide; N-[(3R)-1-azabicyclo[2.2.2]oct-3-yl]-3-[(trifluoroacetyl)amino]furo[2,3-c]pyridine-5-carboxamide; N-[(3R)-1-azabicyclo[2.2.2]oct-3-yl]-3-(benzoylamino)furo[2,3-c]pyridine-5-carboxamide; N-[(3R)-1-azabicyclo[2.2.2]oct-3-yl]-3-(diethylamino)furo[2,3-c]pyridine-5-carboxamide; N-[(3R)-1-azabicyclo[2.2.2]oct-3-yl]-3-(diisopropylamino)furo[2,3-c]pyridine-5-carboxamide; N-[(3R)-1-azabicyclo[2.2.2]oct-3-yl]-3-(pyrrolidin-1-yl)furo[2,3-c]pyridine-5-carboxamide; N-[(3R)-1-azabicyclo[2.2.2]oct-3-yl]-3-(2-oxopyrrolidin-1ylfuro[2,3-c]pyridine-5-carboxamide; N-[(3R)-1-azabicyclo[2.2.2]oct-3-yl]-3-(piperidin-1-yl)furo[2,3-c]pyridine-5-carboxamide; N-[(3R)-1-azabicyclo[2.2.2]oct-3-yl]-3-(2-oxopiperidin-1yl)furo[2,3-c]pyridine-5-carboxamide; N-[(3R)-1-azabicyclo[2.2.2]oct-3-yl]-3-(morpholin-4-yl)furo[2,3-c]pyridine-5-carboxamide; N-[(3R)-1-azabicyclo[2.2.2]oct-3-yl]-3-(3-oxomorpholin-4yl)furo[2,3-c]pyridine-5-carboxamide; N-[(3R)-1-azabicyclo[2.2.2]oct-3-yl]-3-(thiomorpholin-4yl)furo[2,3-c]pyridine-5-carboxamide; N-[(3R)-1-azabicyclo[2.2.2]oct-3-yl]-3-(3-oxothiomorpholin-4yl)furo[2,3-c]pyridine-5-carboxamide; N-[(3R)-1-azabicyclo[2.2.2]oct-3-yl]-3-(piperazin-1-yl)furo[2,3-c]pyridine-5-carboxamide; N-[(3R)-1-azabicyclo[2.2.2]oct-3-yl]-3-(2-oxopiperazin-1yl)furo[2,3-c]pyridine-5-carboxamide; N-[(3R)-1-azabicyclo[2.2.2]oct-3-yl]-3-(4-methylpiperazin-1-yl)furo[2,3-c]pyridine-5-carboxamide; N-[(3R)-1-azabicyclo[2.2.2]oct-3-yl]-3-(4-methyl-2-oxopiperazin-1yl)furo[2,3-c]pyridine-5-carboxamide; N-[(3R)-1-azabicyclo[2.2.2]oct-3-yl]-3-(3-oxopiperazin-1yl)furo[2,3-c]pyridine-5-carboxamide; N-[(3R)-1-azabicyclo[2.2.2]oct-3-yl]-3-(4-methyl-3-oxopiperazin-1yl)furo[2,3-c]pyridine-5-carboxamide; N-[(3R)-1-azabicyclo[2.2.2]oct-3-yl]-3-(cyclopropylamino)furo[2,3-c]pyridine-5-carboxamide; N-[(3R)-1-azabicyclo[2.2.2]oct-3-yl]-3-[dimethylamino]furo[2,3-c]pyridine-5-carboxamide; N-[(3R)-1-azabicyclo[2.2.2]oct-3-yl]-3-(1H-pyrrole-1yl)furo[2,3-c]pyridine-5-carboxamide; N-[(3R)-1-azabicyclo[2.2.2]oct-3-yl]-3-(1H-imidazol-1-yl)furo[2,3-c]pyridine-5-carboxamide; N-[(3R)-1-azabicyclo[2.2.2]oct-3-yl]-3-(1H-1,2,4-triazol-1-yl)furo[2,3-c]pyridine-5-carboxamide; N-[(3R)-1-azabicyclo[2.2.2]oct-3-yl]-3-(1H-1,2,3-triazol-1-yl)furo[2,3-c]pyridine-5-carboxamide; N-5-[(3R)-1-azabicyclo[2.2.2]oct-3-yl]furo[2,3-c]pyridine-3,5-dicarboxamide; N-[(3R)-1-azabicyclo[2.2.2]oct-3-yl]-3-(pyrrolidin-1-ylcarbonyl)furo[2,3-c]pyridine-5-carboxamide; N-[(3R)-1-azabicyclo[2.2.2]oct-3-yl]-3-(piperidin-1-ylcarbonyl)furo[2,3-c]pyridine-5-carboxamide; N-[(3R)-1-azabicyclo[2.2.2]oct-3-yl]-3-(piperazin-1-ylcarbonyl)furo[2,3-c]pyridine-5-carboxamide; N-[(3R)-1-azabicyclo[2.2.2]oct-3-yl]-3-[(4-methylpiperazin-1-yl)carbonyl]furo[2,3-c]pyridine-5-carboxamide; N-[(3R)-1-azabicyclo[2.2.2]oct-3-yl]-3-(morpholin-4-ylcarbonyl)furo[2,3-c]pyridine-5-carboxamide; N-[(3R)-1-azabicyclo[2.2.2]oct-3-yl]-3-(thiomorpholin-4-ylcarbonyl)furo[2,3-c]pyridine-5-carboxamide; N-[(3R)-1-azabicyclo[2.2.2]oct-3-yl]-3-(aziridin-1-ylcarbonyl)furo[2,3-c]pyridine-5-carboxamide; N-[(3R)-1-azabicyclo[2.2.2]oct-3-yl]-3-(azetidin-1-ylcarbonyl)furo[2,3-c]pyridine-5-carboxamide; N-[(3R)-1-azabicyclo[2.2.2]oct-3-yl]-3-formylfuro[2,3-c]pyridine-5-carboxamide; 3-acetyl-N-[(3R)-1-azabicyclo[2.2.2]oct-3-yl]furo[2,3-c]pyridine-5-carboxamide; N-[(3R)-1-azabicyclo[2.2.2]oct-3-yl]-3-(trifluoroacetyl)furo[2,3-c]pyridine-5-carboxamide; N-[(3R)-1-azabicyclo[2.2.2]oct-3-yl]-3-[(phenyl)sulfonyl]furo[2,3-c]pyridine-5-carboxamide; N-[(3R)-1-azabicyclo[2.2.2]oct-3-yl]-3-(methylsulfonyl)furo[2,3-c]pyridine-5-carboxamide; 5-{[(3R)-1-azabicyclo[2.2.2]oct-3-ylamino]carbonyl}furo[2,3-c]pyridine-3-carboxylic acid; methyl 5-{[(3R)-1-azabicyclo[2.2.2]oct-3-ylamino]carbonyl}furo[2,3-c]pyridine-3-carboxylate; isopropyl 5-{[(3R)-1-azabicyclo[2.2.2]oct-3-ylamino]carbonyl}furo[2,3-c]pyridine-3-carboxylate; 2,2,2-trifluoroethyl 5-{[(3R)-1-azabicyclo[2.2.2]oct-3-ylamino]carbonyl}furo[2,3-c]pyridine-3-carboxylate; N-[(2S,3R)-2-methyl-1-azabicyclo[2.2.2]oct-3-yl]-3-vinylfuro[2,3-c]pyridine-5-carboxamide; 7-methyl-N-[(2S,3R)-2-methyl-1-azabicyclo[2.2.2]oct-3-yl]furo[2,3-c]pyridine-5-carboxamide; 7-methoxy-N-[(2S,3R)-2-methyl-1-azabicyclo[2.2.2]oct-3-yl]furo[2,3-c]pyridine-5-carboxamide; N-[(2S,3R)-2-methyl-1-azabicyclo[2.2.2]oct-3-yl]-3-ethynylfuro[2,3-c]pyridine-5-carboxamide; N-[(2S,3R)-2-methyl-1-azabicyclo[2.2.2]oct-3-yl]-3-prop-1-ynylfuro[2,3-c]pyridine-5-carboxamide; N-[(2S,3R)-2-methyl-1-azabicyclo[2.2.2]oct-3-yl]-3-(3-hydroxyprop-1-ynyl)furo[2,3-c]pyridine-5-carboxamide; methyl 3-(5-{[(2S,3R)-2-methyl-1-azabicyclo[2.2.2]oct-3-yl amino]carbonyl}furo[2,3-c]pyridin-3-yl)prop-2-ynoate; 3-(5-{[(2S,3R)-2-methyl-1-azabicyclo[2.2.2]oct-3-ylamino]carbonyl}furo[2,3-c]pyridin-3-yl)prop-2-ynoic acid; 3-(3-amino-3-oxoprop-1-ynyl)-N-[(2S,3R)-2-methyl-1-azabicyclo[2.2.2]oct-3-yl]furo[2,3-c]pyridine-5-carboxamide; N-[(2S,3R)-2-methyl-1-azabicyclo[2.2.2]oct-3-yl]-3-cyanofuro[2,3-c]pyridine-5-carboxamide; N-[(2S,3R)-2-methyl-1-azabicyclo[2.2.2]oct-3-yl]-3-fluorofuro[2,3-c]pyridine-5-carboxamide; N-[(2S,3R)-2-methyl-1-azabicyclo[2.2.2]oct-3-yl]-3-chlorofuro[2,3-c]pyridine-5-carboxamide; N-[(2S,3R)-2-methyl-1-azabicyclo[2.2.2]oct-3-yl]-3-bromofuro[2,3-c]pyridine-5-carboxamide; N-[(2S,3R)-2-methyl-1-azabicyclo[2.2.2]oct-3-yl]-3-iodofuro[2,3-c]pyridine-5-carboxamide; N-[(2S,3R)-2-methyl-1-azabicyclo[2.2.2]oct-3-yl]-3-trifluoromethylfuro[2,3-c]pyridine-5-carboxamide; N-[(2S,3R)-2-methyl-1-azabicyclo[2.2.2]oct-3-yl]-3-mercaptofuro[2,3-c]pyridine-5-carboxamide; N-[(2S,3R)-2-methyl-1-azabicyclo[2.2.2]oct-3-yl]-3-(methylthio)furo[2,3-c]pyridine-5-carboxamide; N-[(2S,3R)-2-methyl-1-azabicyclo[2.2.2]oct-3-yl]-3-(methylamino)furo[2,3-c]pyridine-5-carboxamide; N-[(2S,3R)-2-methyl-1-azabicyclo[2.2.2]oct-3-yl]-3-(formylamino)furo[2,3-c]pyridine-5-carboxamide; N-[(2S,3R)-2-methyl-1-azabicyclo[2.2.2]oct-3-yl]-3-[formyl(methyl)amino]furo[2,3-c]pyridine-5-carboxamide; 3-(acetylamino)-N-[(2S,3R)-2-methyl-1-azabicyclo[2.2.2]oct-3-yl]furo[2,3-c]pyridine-5-carboxamide; 3-(acetyl(methyl)amino)-N-[(2S,3R)-2-methyl-1-azabicyclo[2.2.2]oct-3-yl]furo[2,3-c]pyridine-5-carboxamide; N-[(2S,3R)-2-methyl-1-azabicyclo[2.2.2]oct-3-yl]-3-[(trifluoroacetyl)amino]furo[2,3-c]pyridine-5-carboxamide; N-[(2S,3R)-2-methyl-1-azabicyclo[2.2.2]oct-3-yl]-3-(benzoylamino)furo[2,3-c]pyridine-5-carboxamide; N-[(2S,3R)-2-methyl-1-azabicyclo[2.2.2]oct-3-yl]-3-(diethylamino)furo[2,3-c]pyridine-5-carboxamide; N-[(2S,3R)-2-methyl-1-azabicyclo[2.2.2]oct-3-yl]-3-(diisopropylamino)furo[2,3-c]pyridine-5-carboxamide; N-[(2S,3R)-2-methyl-1-azabicyclo[2.2.2]oct-3-yl]-3-(pyrrolidin-1-yl)furo[2,3-c]pyridine-5-carboxamide; N-[(2S,3R)-2-methyl-1-azabicyclo[2.2.2]oct-3-yl]-3-(2-oxopyrrolidin-1ylfuro[2,3-c]pyridine-5-carboxamide; N-[(2S,3R)-2-methyl-1-azabicyclo[2.2.2]oct-3-yl]-3-(piperidin-1-yl)furo[2,3-c]pyridine-5-carboxamide; N-[(2S,3R)-2-methyl-1-azabicyclo[2.2.2]oct-3-yl]-3-(2-oxopiperidin-1yl)furo[2,3-c]pyridine-5-carboxamide; N-[(2S,3R)-2-methyl-1-azabicyclo[2.2.2]oct-3-yl]-3-(morpholin-4-yl)furo[2,3-c]pyridine-5-carboxamide; N-[(2S,3R)-2-methyl-1-azabicyclo[2.2.2]oct-3-yl]-3-(3-oxomorpholin-4yl)furo[2,3-c]pyridine-5-carboxamide; N-[(2S,3R)-2-methyl-1-azabicyclo[2.2.2]oct-3-yl]-3-(thiomorpholin-4yl)furo[2,3-c]

pyridine-5-carboxamide; N-[(2S,3R)-2-methyl-1-azabicyclo[2.2.2]oct-3-yl]-3-(3-oxothiomorpholin-4yl)furo[2,3-c]pyridine-5-carboxamide; N-[(2S,3R)-2-methyl-1-azabicyclo[2.2.2]oct-3-yl]-3-(piperazin-1-yl)furo[2,3-c]pyridine-5-carboxamide; N-[(2S,3R)-2-methyl-1-azabicyclo[2.2.2]oct-3-yl]-3-(2-oxopiperazin-1yl)furo[2,3-c]pyridine-5-carboxamide; N-[(2S,3R)-2-methyl-1-azabicyclo[2.2.2]oct-3-yl]-3-(4-methylpiperazin-1-yl)furo[2,3-c]pyridine-5-carboxamide; N-[(2S,3R)-2-methyl-1-azabicyclo[2.2.2]oct-3-yl]-3-(4-methyl-2-oxopiperazin-1yl)furo[2,3-c]pyridine-5-carboxamide; N-[(2S,3R)-2-methyl-1-azabicyclo[2.2.2]oct-3-yl]-3-(3-oxopiperazin-1yl)furo[2,3-c]pyridine-5-carboxamide; N-[(2S,3R)-2-methyl-1-azabicyclo[2.2.2]oct-3-yl]-3-(4-methyl-3-oxopiperazin-1yl)furo[2,3-c]pyridine-5-carboxamide; N-[(2S,3R)-2-methyl-1-azabicyclo[2.2.2]oct-3-yl]-3-(cyclopropylamino)furo[2,3-c]pyridine-5-carboxamide; N-[(2S,3R)-2-methyl-1-azabicyclo[2.2.2]oct-3-yl]-3-[dimethylamino]furo[2,3-c]pyridine-5-carboxamide; N-[(2S,3R)-2-methyl-1-azabicyclo[2.2.2]oct-3-yl]-3-(1H-pyrrole-1yl)furo[2,3-c]pyridine-5-carboxamide; N-[(2S,3R)-2-methyl-1-azabicyclo[2.2.2]oct-3-yl]-3-(1H-imidazol-1-yl)furo[2,3-c]pyridine-5-carboxamide; N-[(2S,3R)-2-methyl-1-azabicyclo[2.2.2]oct-3-yl]-3-(1H-1,2,4-triazol-1-yl)furo[2,3-c]pyridine-5-carboxamide; N-[(2S,3R)-2-methyl-1-azabicyclo[2.2.2]oct-3-yl]-3-(1H-1,2,3-triazol-1-yl)furo[2,3-c]pyridine-5-carboxamide; N-5-[(2S,3R)-2-methyl-1-azabicyclo[2.2.2]oct-3-yl]furo[2,3-c]pyridine-3,5-dicarboxamide; N-[(2S,3R)-2-methyl-1-azabicyclo[2.2.2]oct-3-yl]-3-(pyrrolidin-1-ylcarbonyl)furo[2,3-c]pyridine-5-carboxamide; N-[(2S,3R)-2-methyl-1-azabicyclo[2.2.2]oct-3-yl]-3-(piperidin-1-ylcarbonyl)furo[2,3-c]pyridine-5-carboxamide; N-[(2S,3R)-2-methyl-1-azabicyclo[2.2.2]oct-3-yl]-3-(piperazin-1-ylcarbonyl)furo[2,3-c]pyridine-5-carboxamide; N-[(2S,3R)-2-methyl-1-azabicyclo[2.2.2]oct-3-yl]-3-[(4-methylpiperazin-1-yl)carbonyl]furo[2,3-c]pyridine-5-carboxamide; N-[(2S,3R)-2-methyl-1-azabicyclo[2.2.2]oct-3-yl]-3-(morpholin-4-ylcarbonyl)furo[2,3-c]pyridine-5-carboxamide; N-[(2S,3R)-2-methyl-1-azabicyclo[2.2.2]oct-3-yl]-3-(thiomorpholin-4-ylcarbonyl)furo[2,3-c]pyridine-5-carboxamide; N-[(2S,3R)-2-methyl-1-azabicyclo[2.2.2]oct-3-yl]-3-(aziridin-1-ylcarbonyl)furo[2,3-c]pyridine-5-carboxamide; N-[(2S,3R)-2-methyl-1-azabicyclo[2.2.2]oct-3-yl]-3-(azetidin-1-ylcarbonyl)furo[2,3-c]pyridine-5-carboxamide; N-[(2S,3R)-2-methyl-1-azabicyclo[2.2.2]oct-3-yl]-3-formylfuro[2,3-c]pyridine-5-carboxamide; 3-acetyl-N-[(2S,3R)-2-methyl-1-azabicyclo[2.2.2]oct-3-yl]furo[2,3-c]pyridine-5-carboxamide; N-[(2S,3R)-2-methyl-1-azabicyclo[2.2.2]oct-3-yl]-3-(trifluoroacetyl)furo[2,3-c]pyridine-5-carboxamide; N-[(2S,3R)-2-methyl-1-azabicyclo[2.2.2]oct-3-yl]-3-[(phenyl)sulfonyl]furo[2,3-c]pyridine-5-carboxamide; N-[(2S,3R)-2-methyl-1-azabicyclo[2.2.2]oct-3-yl]-3-(methylsulfonyl)furo[2,3-c]pyridine-5-carboxamide; 5-{[(2S,3R)-2-methyl-1-azabicyclo[2.2.2]oct-3-ylamino]carbonyl}furo[2,3-c]pyridine-3-carboxylic acid; methyl 5-{[(2S,3R)-2-methyl-1-azabicyclo[2.2.2]oct-3-ylamino]carbonyl}furo[2,3-c]pyridine-3-carboxylate; isopropyl 5-{[(2S,3R)-2-methyl-1-azabicyclo[2.2.2]oct-3-ylamino]carbonyl}furo[2,3-c]pyridine-3-carboxylate; 2,2,2-trifluoroethyl 5-{[(2S,3R)-2-methyl-1-azabicyclo[2.2.2]oct-3-ylamino]carbonyl}furo[2,3-c]pyridine-3-carboxylate; N-[(3R)-1-azabicyclo[2.2.2]oct-3-yl]furo[3,4-c]pyridine-6-carboxamide; N-[(2S,3R)-2-methyl-1-azabicyclo[2.2.2]oct-3-yl]furo[3,4-c]pyridine-6-carboxamide; 7-methyl-N-[(3R)-1-azabicyclo[2.2.2]oct-3-yl]thieno[2,3-c]pyridine-5-carboxamide; 7-methylthio-N-[(3R)-1-azabicyclo[2.2.2]oct-3-yl]thieno[2,3-c]pyridine-5-carboxamide; 7-methoxy-N-[(3R)-1-azabicyclo[2.2.2]oct-3-yl]thieno[2,3-c]pyridine-5-carboxamide; 7-chloro-N-[(3R)-1-azabicyclo[2.2.2]oct-3-yl]thieno[2,3-c]pyridine-5-carboxamide; N-[(3R)--1-azabicyclo[2.2.2]oct-3-yl]-3-vinylthieno[2,3-c]pyridine-5-carboxamide; N-[(3R)-1-azabicyclo[2.2.2]oct-3-yl]-3-ethynylthieno[2,3-c]pyridine-5-carboxamine; N-[(3R)-1-azabicyclo[2.2.2]oct-3-yl]-3-prop-1-ynylthieno[2,3-c]pyridine-5-carboxamide; N-[(3R)-1-azabicyclo[2.2.2]oct-3-yl]-3-(3-hydroxyprop-1-ynyl)thieno[2,3-c]pyridine-5-carboxamide; methyl 3-(5-{[(3R)-1-azabicyclo[2.2.2]oct-3-ylamino]carbonyl}thieno[2,3-c]pyridin-3-yl)prop-2-ynoate; 3-(5-{[(3R)-1-azabicyclo[2.2.2]oct-3-ylamino]carbonyl}thieno[2,3-c]pyridin-3-yl)prop-2-ynoic acid; 3-(3-amino-3-oxoprop-1-ynyl)-N-[(3R)-1-azabicyclo[2.2.2]oct-3-yl]thieno[2,3-c]pyridine-5-carboxamide; N-[(3R)-1-azabicyclo[2.2.2]oct-3-yl]-3-cyanothieno[2,3-c]pyridine-5-carboxamide; N-[(3R)-1-azabicyclo[2.2.2]oct-3-yl]-3-chlorothieno[2,3-c]pyridine-5-carboxamide; N-[(3R)-1-azabicyclo[2.2.2]oct-3-yl]-3-fluorothieno[2,3-c]pyridine-5-carboxamide; N-[(3R)-1-azabicyclo[2.2.2]oct-3-yl]-3-iodothieno[2,3-c]pyridine-5-carboxamide; N-[(3R)-1-azabicyclo[2.2.2]oct-3-yl]-3-trifluoromethylthieno[2,3-c]pyridine-5-carboxamide; N-[(3R)-1-azabicyclo[2.2.2]oct-3-yl]-3-mercaptothieno[2,3-c]pyridine-5-carboxamide; N-[(3R)-1-azabicyclo[2.2.2]oct-3-yl]-3-(methylthio)thieno[2,3-c]pyridine-5-carboxamide; N-[(3R)-1-azabicyclo[2.2.2]oct-3-yl]-3-(methylamino)thieno[2,3-c]pyridine-5-carboxamide; N-[(3R)-1-azabicyclo[2.2.2]oct-3-yl]-3-(formylamino)thieno[2,3-c]pyridine-5-carboxamide; N-[(3R)-1-azabicyclo[2.2.2]oct-3-yl]-3-[formyl(methyl)amino]thieno[2,3-c]pyridine-5-carboxamide; 3-(acetylamino)-N-[(3R)-1-azabicyclo[2.2.2]oct-3-yl]thieno[2,3-c]pyridine-5-carboxamide; 3-(acetyl(methyl)amino)-N-[(3R)-1-azabicyclo[2.2.2]oct-3-yl]thieno[2,3-c]pyridine-5-carboxamide; N-[(3R)-1-azabicyclo[2.2.2]oct-3-yl]-3-[(trifluoroacetyl)amino]thieno[2,3-c]pyridine-5-carboxamide; N-[(3R)-1-azabicyclo[2.2.2]oct-3-yl]-3-(benzoylamino)thieno[2,3-c]pyridine-5-carboxamide: N-[(3R)-1-azabicyclo[2.2.2]oct-3-yl]-3-(diethylamino)thieno[2,3-c]pyridine-5-carboxamide; N-[(3R)-1-azabicyclo[2.2.2]oct-3-yl]-3-(diisopropylamino)thieno[2.3-c]pyridine-5-carboxamide; N-[(3R)-1-azabicyclo[2.2.2]oct-3-yl]-3-(pyrrolidin-1-yl)thieno[2,3-c]pyridine-5-carboxamide; N-[(3R)-1-azabicyclo[2.2.2]oct-3-yl]-3-(2-oxopyrrolidin-1ylthieno[2,3-c]pyridine-5-carboxamide; N-[(3R)-1-azabicyclo[2.2.2]oct-3-yl]-3-(piperidin-1-yl)thieno[2,3-c]pyridine-5-carboxamide: N-[(3R)-1-azabicyclo[2.2.2]oct-3-yl]-3-(2-oxopiperidin-1yl)thieno[2,3-c]pyridine-5-carboxamide; N-[(3R)-1-azabicyclo[2.2.2]oct-3-yl]-3-(morpholin-4-yl)thieno[2,3-c]pyridine-5-carboxamide; N-[(3R)-1-azabicyclo[2.2.2]oct-3-yl]-3-(3-oxomorpholin-4yl)thieno[2,3-c]pyridine-5-carboxamide; N-[(3R)-1-azabicyclo[2.2.2]oct-3-yl]-3-(thiomorpholin-4yl)thieno[2,3-c]pyridine-5-carboxamide; N-[(3R)-1-azabicyclo[2.2.2]oct-3-yl]-3-(3-oxothiomorpholin-4yl)thieno[2,3-c]pyridine-5-carboxamide; N-[(3R)-1-azabicyclo[2.2.2]oct-3-yl]-3-(piperazin-1-yl)thieno[2,3-c]pyridine-5-carboxamide; N-[(3R)-1-azabicyclo[2.2.2]oct-3-yl]-3-(2-oxopiperazin-1yl)thieno[2,3-c]pyridine-5-carboxamide; N-[(3R)-1-azabicyclo[2.2.2]oct-3-yl]-3-(4-methylpiperazin-1-yl)thieno[2,3-c]pyridine-5-carboxamide; N-[(3R)-1-azabicyclo[2.2.2]oct-3-yl]-3-(4-methyl-2-oxopiperazin-1yl)thieno[2,3-c]pyridine-5-carboxamide; N-[(3R)-1-azabicyclo[2.2.2]oct-3-yl]-3-(3-oxopiperazin-1yl)thieno[2,3-c]pyridine-5-carboxamide; N-[(3R)-1-azabicyclo[2.2.2]oct-3-yl]-3-(4-methyl-3-oxopiperazin-1yl)thieno[2,3-c]pyridine-5-carboxamide; N-[(3R)-1-azabicyclo[2.2.2]oct-3-yl]-3-

(cyclopropylamino)thieno[2,3-c]pyridine-5-carboxamide; N-[(3R)-1-azabicyclo[2.2.2]oct-3-yl]-3-[dimethylamino]thieno[2,3-c]pyridine-5-carboxamide; N-[(3R)-1-azabicyclo[2.2.2]oct-3-yl]-3-(1H-pyrrole-1yl)thieno[2,3-c]pyridine-5-carboxamide; N-[(3R)-1-azabicyclo[2.2.2]oct-3-yl]-3-(1H-imidazol-1-yl)thieno[2,3-c]pyridine-5-carboxamide; N-[(3R)-1-azabicyclo[2.2.2]oct-3-yl]-3-(1H-1,2,4-triazol-1-yl)thieno[2,3-c]pyridine-5-carboxamide; N-[(3R)-1-azabicyclo[2.2.2]oct-3-yl]-3-(1H-1,2,3-triazol-1-yl)thieno[2,3-c]pyridine-5-carboxamide; N-5-[(3R)-1-azabicyclo[2.2.2]oct-3-yl]thieno[2,3-c]pyridine-3,5-dicarboxamide; N-[(3R)-1-azabicyclo[2.2.2]oct-3-yl]-3-(pyrrolidin-1-ylcarbonyl)thieno[2,3-c]pyridine-5-carboxamide; N-[(3R)-1-azabicyclo[2.2.2]oct-3-yl]-3-(piperidin-1-ylcarbonyl)thieno[2,3-c]pyridine-5-carboxamide; N-[(3R)-1-azabicyclo[2.2.2]oct-3-yl]-3-(piperazin-1-ylcarbonyl)thieno[2,3-c]pyridine-5-carboxamide; N-[(3R)-1-azabicyclo[2.2.2]oct-3-yl]-3-[(4-methylpiperazin-1-yl)carbonyl]thieno[2,3-c]pyridine-5-carboxamide; N-[(3R)-1-azabicyclo[2.2.2]oct-3-yl]-3-(morpholin-4-ylcarbonyl)thieno[2,3-c]pyridine-5-carboxamide; N-[(3R)-1-azabicyclo[2.2.2]oct-3-yl]-3-(thiomorpholin-4-ylcarbonyl)thieno[2,3-c]pyridine-5-carboxamide; N-[(3R)-1-azabicyclo[2.2.2]oct-3-yl]-3-(aziridin-1-ylcarbonyl)thieno[2,3-c]pyridine-5-carboxamide; N-[(3R)-1-azabicyclo[2.2.2]oct-3-yl]-3-(azetidin-1-ylcarbonyl)thieno[2,3-c]pyridine-5-carboxamide; N-[(3R)-1-azabicyclo[2.2.2]oct-3-yl]-3-formylthieno[2,3-c]pyridine-5-carboxamide; 3-acetyl-N-[(3R)-1-azabicyclo[2.2.2]oct-3-yl]thieno[2,3-c]pyridine-5-carboxamide; N-[(3R)-1-azabicyclo[2.2.2]oct-3-yl]-3-(trifluoroacetyl)thieno[2,3-c]pyridine-5-carboxamide; N-[(3R)-1-azabicyclo[2.2.2]oct-3-yl]-3-[(phenyl)sulfonyl]thieno[2,3-c]pyridine-5-carboxamide; N-[(3R)-1-azabicyclo[2.2.2]oct-3-yl]-3-(methylsulfonyl)thieno[2,3-c]pyridine-5-carboxamide; 5-{[(3R)-1-azabicyclo[2.2.2]oct-3-ylamino]carbonyl}theino[2,3-c]pyridine-3-carboxylic acid; methyl 5-{[(3R)-1-azabicyclo[2.2.2]oct-3-ylamino]carbonyl}thieno[2,3-c]pyridine-3-carboxylate; isopropyl 5-{[(3R)-1-azabicyclo[2.2.2]oct-3-ylamino]carbonyl}thieno[2,3-c]pyridine-3-carboxylate; 2,2,2-trifluoroethyl 5-{[(3R)-1-azabicyclo[2.2.2]oct-3-ylamino]carbonyl}thieno[2,3-c]pyridine-3-carboxylate; 7-methyl-N-[(2S,3R)-2-methyl-1-azabicyclo[2.2.2]oct-3-yl]thieno[2,3-c]pyridine-5-carboxamide; 7-methylthio-N-[(2S,3R)-2-methyl-1-azabicyclo[2.2.2]oct-3-yl]thieno[2,3-c]pyridine-5-carboxamide; 7-methoxy-N-[(2S,3R)-2-methyl-1-azabicyclo[2.2.2]oct-3-yl]thieno[2,3-c]pyridine-5-carboxamide; 7-chloro-N-[(2S,3R)-2-methyl-1-azabicyclo[2.2.2]oct-3-yl]thieno[2,3-c]pyridine-5-carboxamide; N-[(2S,3R)-2-methyl-1-azabicyclo[2.2.2]oct-3-yl]-3-vinylthieno[2,3-c]pyridine-5-carboxamide; N-[(2S,3R)-2-methyl-1-azabicyclo[2.2.2]oct-3-yl]-3-ethynylthieno[2,3-c]pyridine-5-carboxamide; N-[(2S,3R)-2-methyl-1-azabicyclo[2.2.2]oct-3-yl]-3-prop-1-ynylthieno[2,3-c]pyridine-5-carboxamide; N-[(2S,3R)-2-methyl-1-azabicyclo[2.2.2]oct-3-yl]-3-(3-hydroxyprop-1-ynyl)thieno[2,3-c]pyridine-5-carboxamide; methyl 3-(5-{[(2S,3R)-2-methyl-1-azabicyclo[2.2.2]oct-3-yl amino]carbonyl}thieno[2,3-c]pyridin-3-yl)prop-2-ynoate; 3-(5-{[(2S,3R)-2-methyl-1-azabicyclo[2.2.2]oct-3-ylamino]carbonyl}thieno[2,3-c]pyridin-3-yl)prop-2-ynoic acid; 3-(3-amino-3-oxoprop-1-ynyl)-N-[(2S,3R)-2-methyl-1-azabicyclo[2.2.2]oct-3-yl]thieno[2,3-c]pyridine-5-carboxamide; N-[(2S,3R)-2-methyl-1-azabicyclo[2.2.2]oct-3-yl]-3-cyanothieno[2,3-c]pyridine-5-carboxamide; N-[(2S,3R)-2-methyl-1-azabicyclo[2.2.2]oct-3-yl]-3-fluorothieno[2,3-c]pyridine-5-carboxamide; N-[(2S,3R)-2-methyl-1-azabicyclo[2.2.2]oct-3-yl]-3-chlorothieno[2,3-c]pyridine-5-carboxamide; N-[(2S,3R)-2-methyl-1-azabicyclo[2.2.2]oct-3-yl]-3-bromothieno[2,3-c]pyridine-5-carboxamide; N-[(2S,3R)-2-methyl-1-azabicyclo[2.2.2]oct-3-yl]-3-iodothieno[2,3-c]pyridine-5-carboxamide; N-[(2S,3R)-2-methyl-1-azabicyclo[2.2.2]oct-3-yl]-3-trifluoromethylthieno[2,3-c]pyridine-5-carboxamide; N-[(2S,3R)-2-methyl-1-azabicyclo[2.2.2]oct-3-yl]-3-mercaptothieno[2,3-c]pyridine-5-carboxamide; N-[(2S,3R)-2-methyl-1-azabicyclo[2.2.2]oct-3-yl]-3-(methylthio)thieno[2,3-c]pyridine-5-carboxamide; N-[(2S,3R)-2-methyl-1-azabicyclo[2.2.2]oct-3-yl]-3-(methylamino)thieno[2,3-c]pyridine-5-carboxamide; N-[(2S,3R)-2-methyl-1-azabicyclo[2.2.2]oct-3-yl]-3-(formylamino)thieno[2,3-c]pyridine-5-carboxamide; N-[(2S,3R)-2-methyl-1-azabicyclo[2.2.2]oct-3-yl]-3-[formyl(methyl)amino]thieno[2,3-c]pyridine-5-carboxamide; 3-(acetylamino)-N-[(2S,3R)-2-methyl-1-azabicyclo[2.2.2]oct-3-yl]thieno[2,3-c]pyridine-5-carboxamide; 3-(acetyl(methyl)amino)-N-[(2S,3R)-2-methyl-1-azabicyclo[2.2.2]oct-3-yl]thieno[2,3-c]pyridine-5-carboxamide; N-[(2S,3R)-2-methyl-1-azabicyclo[2.2.2]oct-3-yl]-3-[(trifluoroacetyl)amino]thieno[2,3-c]pyridine-5-carboxamide; N-[(2S,3R)-2-methyl-1-azabicyclo[2.2.2]oct-3-yl]-3-(benzoylamino)thieno[2,3-c]pyridine-5-carboxamide; N-[(2S,3R)-2-methyl-1-azabicyclo[2.2.2]oct-3-yl]-3-(diethylamino)thieno[2,3-c]pyridine-5-carboxamide; N-[(2S,3R)-2-methyl-1-azabicyclo[2.2.2]oct-3-yl]-3-(diisopropylamino)thieno[2,3-c]pyridine-5-carboxamide; N-[(2S,3R)-2-methyl-1-azabicyclo[2.2.2]oct-3-yl]-3-(pyrrolidin-1-yl)thieno[2,3-c]pyridine-5-carboxamide; N-[(2S,3R)-2-methyl-1-azabicyclo[2.2.2]oct-3-yl]-3-(2-oxopyrrolidin-1ylthieno[2,3-c]pyridine-5-carboxamide; N-[(2S,3R)-2-methyl-1-azabicyclo[2.2.2]oct-3-yl]-3-(piperidin-1-yl)thieno[2,3-c]pyridine-5-carboxamide; N-[(2S,3R)-2-methyl-1-azabicyclo[2.2.2]oct-3-yl]-3-(2-oxopiperidin-1yl)thieno[2,3-c]pyridine-5-carboxamide; N-[(2S,3R)-2-methyl-1-azabicyclo[2.2.2]oct-3-yl]-3-(morpholin-4-yl)thieno[2,3-c]pyridine-5-carboxamide; N-[(2S,3R)-2-methyl-1-azabicyclo[2.2.2]oct-3-yl]-3-(3-oxomorpholin-4yl)thieno[2,3-c]pyridine-5-carboxamide; N-[(2S,3R)-2-methyl-1-azabicyclo[2.2.2]oct-3-yl]-3-(thiomorpholin-4yl)thieno[2,3-c]pyridine-5-carboxamide; N-[(2S,3R)-2-methyl-1-azabicyclo[2.2.2]oct-3-yl]-3-(3-oxothiomorpholin-4yl)thieno[2,3-c]pyridine-5-carboxamide; N-[(2S,3R)-2-methyl-1-azabicyclo[2.2.2]oct-3-yl]-3-(piperazin-1-yl)thieno[2,3-c]pyridine-5-carboxamide; N-[(2S,3R)-2-methyl-1-azabicyclo[2.2.2]oct-3-yl]-3-(2-oxopiperazin-1yl)thieno[2,3-c]pyridine-5-carboxamide; N-[(2S,3R)-2-methyl-1-azabicyclo[2.2.2]oct-3-yl]-3-(4-methylpiperazin-1-yl)thieno[2,3-c]pyridine-5-carboxamide; N-[(2S,3R)-2-methyl-1-azabicyclo[2.2.2]oct-3-yl]-3-(4-methyl-2-oxopiperazin-1yl)thieno[2,3-c]pyridine-5-carboxamide; N-[(2S,3R)-2-methyl-1-azabicyclo[2.2.2]oct-3-yl]-3-(3-oxopiperazin-1yl)thieno[2,3-c]pyridine-5-carboxamide; N-[(2S,3R)-2-methyl-1-azabicyclo[2.2.2]oct-3-yl]-3-(4-methyl-3-oxopiperazin-1yl)thieno[2,3-c]pyridine-5-carboxamide; N-[(2S,3R)-2-methyl-1-azabicyclo[2.2.2]oct-3-yl]-3-(cyclopropylamino)thieno[2,3-c]pyridine-5-carboxamide; N-[(2S,3R)-2-methyl-1-azabicyclo[2.2.2]oct-3-yl]-3-[dimethylamino]thieno[2,3-c]pyridine-5-carboxamide; N-[(2S,3R)-2-methyl-1-azabicyclo[2.2.2]oct-3-yl]-3-(1H-pyrrole-1yl)thieno[2,3-c]pyridine-5-carboxamide; N-[(2S,3R)-2-methyl-1-azabicyclo[2.2.2]oct-3-yl]-3-(1H-imidazol-1-yl)thieno[2,3-c]pyridine-5-carboxamide; N-[(2S,3R)-2-methyl-1-azabicyclo[2.2.2]oct-3-yl]-3-(1H-1,2,4-triazol-1-yl)thieno[2,3-c]pyridine-5-carboxamide; N-[(2S,3R)-2-methyl-1-azabicyclo[2.2.2]oct-3-yl]-3-(1H-1,2,3-triazol-1- yl)thieno[2,3-c]pyridine-5-carboxamide; N-5-[(2S,3R)-2-methyl-1-azabicyclo[2.2.2]oct-3-yl]thieno[2,3-c]pyridine-3,5-dicarboxamide; N-[(2S,3R)-2-methyl-1-azabicyclo[2.2.2]oct-3-yl]-3-(pyrrolidin-1-ylcarbonyl)thieno[2,3-c]pyridine-5-carboxamide; N-[(2S,3R)-2-methyl-1-azabicyclo[2.2.2]oct-3-yl]-3-(piperidin-1-ylcarbonyl)thieno[2,3-c]pyridine-5-carboxamide; N-[(2S,3R)-2-methyl-1-azabicyclo[2.2.2]oct-3-yl]-3-(piperazin-1-ylcarbonyl)thieno[2,3-c]pyridine-5-carboxamide; N-[(2S,3R)-2-methyl-1-azabicyclo[2.2.2]oct-3-yl]-3-[(4-methylpiperazin-1-yl)carbonyl]thieno[2,3-c]pyridine-5-carboxamide; N-[(2S,3R)-2-methyl-1-azabicyclo[2.2.2]oct-3-yl]-3-(morpholin-4-ylcarbonyl)thieno[2,3-c]pyridine-5-carboxamide; N-[(2S,3R)-2-methyl-1-azabicyclo[2.2.2]oct-3-yl]-3-(thiomorpholin-4-ylcarbonyl)thieno[2,3-c]pyridine-5-carboxamide; N-[(2S,3R)-2-methyl-1-azabicyclo[2.2.2]oct-3-yl]-3-(aziridin-1-ylcarbonyl)thieno[2,3-c]pyridine-5-carboxamide; N-[(2S,3R)-2-methyl-1-azabicyclo[2.2.2]oct-3-yl]-3-(azetidin-1-ylcarbonyl)thieno[2,3-c]pyridine-5-carboxamide; N-[(2S,3R)-2-methyl-1-azabicyclo[2.2.2]oct-3-yl]-3-formylthieno[2,3-c]pyridine-5-carboxamide; 3-acetyl-N-[(2S,3R)-2-methyl-1-azabicyclo[2.2.2]oct-3-yl]thieno[2,3-c]pyridine-5-carboxamide; N-[(2S,3R)-2-methyl-1-azabicyclo[2.2.2]oct-3-yl]-3-(trifluoroacetyl)thieno[2,3-c]pyridine-5-carboxamide; N-[(2S,3R)-2-methyl-1-azabicyclo[2.2.2]oct-3-yl]-3-[(phenyl)sulfonyl]thieno[2,3-c]pyridine-5-carboxamide; N-[(2S,3R)-2-methyl-1-azabicyclo[2.2.2]oct-3-yl]-3-(methylsulfonyl)thieno[2,3-c]pyridine-5-carboxamide; 5-{[(2S,3R)-2-methyl-1-azabicyclo[2.2.2]oct-3-ylamino]carbonyl}thieno[2,3-c]pyridine-3-carboxylic acid; methyl 5-{[(2S,3R)-2-methyl-1-azabicyclo[2.2.2]oct-3-ylamino]carbonyl}thieno[2,3-c]pyridine-3-carboxylate; isopropyl 5-{[(2S,3R)-2-methyl-1-azabicyclo[2.2.2]oct-3-ylamino]carbonyl}thieno[2,3-c]pyridine-3-carboxylate; 2,2,2-trifluoroethyl 5-{[(2S,3R)-2-methyl-1-azabicyclo[2.2.2]oct-3-ylamino]carbonyl}thieno[2,3-c]pyridine-3-carboxylate; N-[(3R)-1-azabicyclo[2.2.2]oct-3-yl]-3-(phenylethynyl)furo[2,3-c]pyridine-5-carboxamide; N-[(3R)-1-azabicyclo[2.2.2]oct-3-yl]-3-(3,3,3-trifluoroprop-1-ynyl)furo[2,3-c]pyridine-5-carboxamide; N-[(3R)-1-azabicyclo[2.2.2]oct-3-yl]-3-(3,3-difluoroprop-1-ynyl)furo[2,3-c]pyridine-5-carboxamide; N-[(3R)-1-azabicyclo[2.2.2]oct-3-yl]-3-(3-pyrrolidin-1-ylprop-1-ynyl)furo[2,3-c]pyridine-5-carboxamide; N-[(3R)-1-azabicyclo[2.2.2]oct-3-yl]-3-(3-morpholin-4-ylprop-1-ynyl)furo[2,3-c]pyridine-5-carboxamide; N-[(3R)-1-azabicyclo[2.2.2]oct-3-yl]-3-(3-piperazin-1-ylprop-1-ynyl)furo[2,3-c]pyridine-5-carboxamide; N-[(3R)-1-azabicyclo[2.2.2]oct-3-yl]-3-[3-(4-methylpiperazin-1-yl)prop-1-ynyl]furo[2,3-c]pyridine-5-carboxamide; N-[(3R)-1-azabicyclo[2.2.2]oct-3-yl]-3-[3-(1H-pyrazol-1-yl)prop-1-ynyl]furo[2,3-c]pyridine-5-carboxamide; N-[(3R)-1-azabicyclo[2.2.2]oct-3-yl][1]benzofuro[2,3-c]pyridine-3-carboxamide; N-[(3R)-1-azabicyclo[2.2.2]oct-3yl]-2-(phenylethynyl)furo[3,2-c]pyridine-5-carboxamide; N-[(3R)-1-azabicyclo[2.2.2]oct-3yl]-2-(3,3,3-trifluoroprop-1-ynyl)furo[3,2-c]pyridine-5-carboxamide; N-[(3R)-1-azabicyclo[2.2.2]oct-3yl]-2-(3,3-difluoroprop-1-ynyl)furo[3,2-c]pyridine-5-carboxamide; N-[(3R)-1-azabicyclo[2.2.2]oct-3yl]-2-(3-pyrrolidin-1-yl-prop-1-ynyl)furo[3,2-c]pyridine-5-carboxamide; N-[(3R)-1-azabicyclo[2.2.2]oct-3yl]-2-(3-morpholin-4-ylprop-1-ynyl)furo[3,2-c]pyridine-5-carboxamide; N-[(3R)-1-azabicyclo[2.2.2]oct-3yl]-2-(3-piperazin-1-ylprop-1-ynyl)furo[3,2-c]pyridine-5-carboxamide; N-[(3R)-1-azabicyclo[2.2.2]oct-3yl]-2-[3-(4-methylpiperazin-1-yl)prop-1-ynyl]furo[3,2-c]pyridine-5-carboxamide; N-[(3R)-1-azabicyclo[2.2.2]oct-3yl]-2-[3-(1H-pyrazol-1-yl)prop-1-ynyl]furo[3,2-c]pyridine-5-carboxamide; N-[(3R)-1-azabicyclo[2.2.2]oct-3-yl]-3-(phenylethynyl)thieno[2,3-c]pyridine-5-carboxamide; N-[(3R)-1-azabicyclo[2.2.2]oct-3-yl]-3-(3,3,3-trifluoroprop-1-ynyl)thieno[2,3-c]pyridine-5-carboxamide; N-[(3R)-1-azabicyclo[2.2.2]oct-3-yl]-3-(3,3-difluoroprop-1-ynyl)thieno[2,3-c]pyridine-5-carboxamide; N-[(3R)-1-azabicyclo[2.2.2]oct-3-yl]-3-(3-pyrrolidin-1-ylprop-1-ynyl)thieno[2,3-c]pyridine-5-carboxamide; N-[(3R)-1-azabicyclo[2.2.2]oct-3-yl]-3-(3-morpholin-4-ylprop-1-ynyl)thieno[2,3-c]pyridine-5-carboxamide; N-[(3R)-1-azabicyclo[2.2.2]oct-3-yl]-3-(3-piperazin-1-ylprop-1-ynyl)thieno[2,3-c]pyridine-5-carboxamide; N-[(3R)-1-azabicyclo[2.2.2]oct-3-yl]-3-[3-(4-methylpiperazin-1-yl)prop-1-ynyl]thieno[2,3-c]pyridine-5-carboxamide; N-[(3R)-1-azabicyclo[2.2.2]oct-3-yl]-3-[3-(1H-pyrazol-1-yl)prop-1-ynyl]thieno[2,3-c]pyridine-5-carboxamide; N-[(3R)-1-azabicyclo[2.2.2]oct-3-yl][1]benzothieno[2,3-c]pyridine-3-carboxamide; N-[(3R)-1-azabicyclo[2.2.2]oct-3yl]-2-(phenylethynyl)thieno[3,2-c]pyridine-5-carboxamide; N-[(3R)-1-azabicyclo[2.2.2]oct-3yl]-2-(3,3,3-trifluoroprop-1-ynyl)thieno[3,2-c]pyridine-5-carboxamide; N-[(3R)-1-azabicyclo[2.2.2]oct-3yl]-2-(3,3-difluoroprop-1-ynyl)thieno[3,2-c]pyridine-5-carboxamide; N-[(3R)-1-azabicyclo[2.2.2]oct-3yl]-2-(3-pyrrolidin-1-yl-prop-1-ynyl)thieno[3,2-c]pyridine-5-carboxamide; N-[(3R)-1-azabicyclo[2.2.2]oct-3yl]-2-(3-morpholin-4-ylprop-1-ynyl)thieno[3,2-c]pyridine-5-carboxamide; N-[(3R)-1-azabicyclo[2.2.2]oct-3yl]-2-(3-piperazin-1-ylprop-1-ynyl)thieno[3,2-c]pyridine-5-carboxamide; N-[(3R)-1-azabicyclo[2.2.2]oct-3yl]-2-[3-(4-methylpiperazin-1-yl)prop-1-ynyl]thieno[3,2-c]pyridine-5-carboxamide; N-[(3R)-1-azabicyclo[2.2.2]oct-3yl]-2-[3-(1H-pyrazol-1-yl)prop-1-ynyl]thieno[3,2-c]pyridine-5-carboxamide;

N-[(2S,3R)-2-methyl-1-azabicyclo[2.2.2]oct-3-yl]-3-(phenylethynyl)furo[2,3-c]pyridine-5-carboxamide; N-[(2S,3R)-2-methyl-1-azabicyclo[2.2.2]oct-3-yl]-3-(3,3,3-trifluoroprop-1-ynyl)furo[2,3-c]pyridine-5-carboxamide; N-[(2S,3R)-2-methyl-1-azabicyclo[2.2.2]oct-3-yl]-3-(3,3-difluoroprop-1-ynyl)furo[2,3-c]pyridine-5-carboxamide; N-[(2S,3R)-2-methyl-1-azabicyclo[2.2.2]oct-3-yl]-3-(3-pyrrolidin-1-ylprop-1-ynyl)furo[2,3-c]pyridine-5-carboxamide; N-[(2S,3R)-2-methyl-1-azabicyclo[2.2.2]oct-3-yl]-3-(3-morpholin-4-ylprop-1-ynyl)furo[2,3-c]pyridine-5-carboxamide; N-[(2S,3R)-2-methyl-1-azabicyclo[2.2.2]oct-3-yl]-3-(3-piperazin-1-ylprop-1-ynyl)furo[2,3-c]pyridine-5-carboxamide; N-[(2S,3R)-2-methyl-1-azabicyclo[2.2.2]oct-3-yl]-3-[3-(4-methylpiperazin-1-yl)prop-1-ynyl]furo[2,3-c]pyridine-5-carboxamide; N-[(2S,3R)-2-methyl-1-azabicyclo[2.2.2]oct-3-yl]-3-[3-(1H-pyrazol-1-yl)prop-1-ynyl]furo[2,3-c]pyridine-5-carboxamide; N-[(2S,3R)-2-methyl-1-azabicyclo[2.2.2]oct-3-yl][1]benzofuro[2,3-c]pyridine-3-carboxamide; N-[(2S,3R)-2-methyl-1-azabicyclo[2.2.2]oct-3-yl]-2-(phenylethynyl)furo[3,2-c]pyridine-5-carboxamide; N-[(2S,3R)-2-methyl-1-azabicyclo[2.2.2]oct-3-yl]-2-(3,3,3-trifluoroprop-1-ynyl)furo[3,2-c]pyridine-5-carboxamide; N-[(2S,3R)-2-methyl-1-azabicyclo[2.2.2]oct-3-yl]-2-(3,3-difluoroprop-1-ynyl)furo[3,2-c]pyridine-5-carboxamide; N-[(2S,3R)-2-methyl-1-azabicyclo[2.2.2]oct-3-yl]-2-(3-pyrrolidin-1-ylprop-1-ynyl)furo[3,2-c]pyridine-5-carboxamide; N-[(2S,3R)-2-methyl-1-azabicyclo[2.2.2]oct-3-yl]-2-(3-morpholin-4-ylprop-1-ynyl)furo[3,2-c]pyridine-5-carboxamide; N-[(2S,3R)-2-methyl-1-azabicyclo[2.2.2]oct-3-yl]-2-(3-piperazin-1-ylprop-1-ynyl)furo[3,2-c]pyridine-5-carboxamide; N-[(2S,3R)-2-methyl-1-azabicyclo[2.2.2]oct-3-yl]-2-[3-(4-methylpiperazin-1-yl)prop-1-ynyl]furo[3,2-c]pyridine-5-carboxamide; N-[(2S,3R)-2-methyl-1-azabicyclo[2.2.2]oct- 3yl]-2-[3-(1H-pyrazol-1-yl)prop-1-ynyl]furo[3,2-c]pyridine-5-carboxamide; N-[(2S,3R)-2-methyl-1-azabicyclo[2.2.2]oct-3-yl]-3-(phenylethynyl)thieno[2,3-c]pyridine-5-carboxamide; N-[(2S,3R)-2-methyl-1-azabicyclo[2.2.2]oct-3-yl]-3-(3,3,3-trifluoroprop-1-ynyl)thieno[2,3-c]pyridine-5-carboxamide; N-[(2S,3R)-2-methyl-1-azabicyclo[2.2.2]oct-3-yl]-3-(3,3-difluoroprop-1-ynyl)thieno[2,3-c]pyridine-5-carboxamide; N-[(2S,3R)-2-methyl-1-azabicyclo[2.2.2]oct-3-yl]-3-(3-pyrrolidin-1-ylprop-1-ynyl)thieno[2,3-c]pyridine-5-carboxamide; N-[(2S,3R)-2-methyl-1-azabicyclo[2.2.2]oct-3-yl]-3-(3-morpholin-4-ylprop-1-ynyl)thieno[2,3-c]pyridine-5-carboxamide; N-[(2S,3R)-2-methyl-1-azabicyclo[2.2.2]oct-3-yl]-3-(3-piperazin-1-ylprop-1-ynyl)thieno[2,3-c]pyridine-5-carboxamide; N-[(2S,3R)-2-methyl-1-azabicyclo[2.2.2]oct-3-yl]-3-[3-(4-methylpiperazin-1-yl)prop-1-ynyl]thieno[2,3-c]pyridine-5-carboxamide; N-[(2S,3R)-2-methyl-1-azabicyclo[2.2.2]oct-3-yl]-3-[3-(1H-pyrazol-1-yl)prop-1-ynyl]thieno[2,3-c]pyridine-5-carboxamide; N-[(2S,3R)-2-methyl-1-azabicyclo[2.2.2]oct-3-yl][1]benzothieno[2,3-c]pyridine-3-carboxamide; N-[(2S,3R)-2-methyl-1-azabicyclo[2.2.2]oct-3yl]-2-(phenylethynyl)thieno[3,2-c]pyridine-5-carboxamide; N-[(2S,3R)-2-methyl-1-azabicyclo[2.2.2]oct-3yl]-2-(3,3,3-trifluoroprop-1-ynyl)thieno[3,2-c]pyridine-5-carboxamide; N-[(2S,3R)-2-methyl-1-azabicyclo[2.2.2]oct-3yl]-2-(3,3-difluoroprop-1-ynyl)thieno[3,2-c]pyridine-5-carboxamide; N-[(2S,3R)-2-methyl-1-azabicyclo[2.2.2]oct-3yl]-2-(3-pyrrolidin-1-ylprop-1-ynyl)thieno[3,2-c]pyridine-5-carboxamide; N-[(2S,3R)-2-methyl-1-azabicyclo[2.2.2]oct-3yl]-2-(3-morpholin-4-ylprop-1-ynyl)thieno[3,2-c]pyridine-5-carboxamide; N-[(2S,3R)-2-methyl-1-azabicyclo[2.2.2]oct-3yl]-2-(3-piperazin-1-ylprop-1-ynyl)thieno[3,2-c]pyridine-5-carboxamide; N-[(2S,3R)-2-methyl-1-azabicyclo[2.2.2]oct-3yl]-2-[3-(4-methylpiperazin-1-yl)prop-1-ynyl]thieno[3,2-c]pyridine-5-carboxamide; N-[(2S,3R)-2-methyl-1-azabicyclo[2.2.2]oct-3yl]-2-[3-(1H-pyrazol-1-yl)prop-1-ynyl]thieno[3,2-c]pyridine-5-carboxamide; or a pharmaceutical composition or pharmaceutically acceptable salt thereof.

Abbreviations which are well known to one of ordinary skill in the art may be used (e.g., "Ph" for phenyl, "Me" for methyl, "Et" for ethyl, "h" for hour or hours, min for minute or minutes, and "rt" or "RT" for room temperature).

All temperatures are in degrees Centigrade.

Room temperature is within the range of 15–25 degrees Celsius.

Pre-senile dementia is also known as mild cognitive impairment.

AChR refers to acetylcholine receptor.
nAChR refers to nicotinic acetyl choline receptor.
$5HT_3R$ refers to the serotonin-type 3 receptor.
α-btx refers to α-bungarotoxin.
FLIPR refers to a device marketed by Molecular Devices, Inc. designed to precisely measure cellular fluorescence in a high throughput whole-cell assay. (Schroeder et. al., *J. Biomolecular Screening*, 1(2), p 75–80, 1996).
TLC refers to thin-layer chromatography.
HPLC refers to high pressure liquid chromatography.
MeOH refers to methanol.
EtOH refers to ethanol.
IPA refers to isopropyl alcohol.
THF refers to tetrahydrofuran.
DMSO refers to dimethylsulfoxide.
DMF refers to dimethylformamide.
EtOAc refers to ethyl acetate.
TMS refers to tetramethylsilane.
TEA refers to triethylamine.
DIEA refers to diisopropylethylamine.
MLA refers to methyllycaconitine.
Ether refers to diethyl ether.
HATU refers to O-(7-azabenzotriazol-1-yl)-N,N,N',N'-tetramethyluronium hexafluorophosphate.
DBU refers to 1,8-diazabicyclo[5.4.0]undec-7-ene.
50% saturated 1:1 $NaCl/NaHCO_3$ means a solution made by making a solution of 1:1 saturated $NaCl/NaHCO_3$ and adding an equal volume of water.
Halogen is F, Cl, Br, or I.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-6}$ alkyl refers to alkyl of one to six carbon atoms.

The core molecule is the quinuclidinyl-(carboxamide-type moiety):

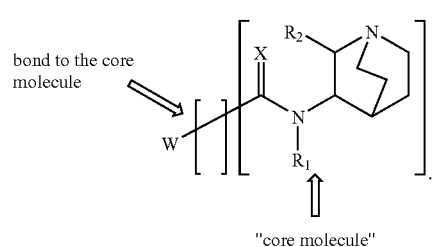

"core molecule"

Therefore, when speaking of the bond to the core molecule, the bond would be a bond of attachment between the C(=X) of the core molecule and the carbon atom of attachment of the W moiety.

Mammal denotes human and other mammals.
Brine refers to an aqueous saturated sodium chloride solution.
Equ means molar equivalents.
IR refers to infrared spectroscopy.
Lv refers to leaving groups within a molecule, including Cl, OH, or mixed anhydride.
Parr refers to the name of the company who sells the jars used for conducting reactions under pressure.
PSI means pound per square inch.
NMR refers to nuclear (proton) magnetic resonance spectroscopy, chemical shifts are reported in ppm (δ) downfield from TMS.
MS refers to mass spectrometry expressed as m/e or mass/charge unit. HRMS refers to high resolution mass spectrometry expressed as m/e or mass/charge unit. $M+H^+$ refers to the positive ion of a parent plus a hydrogen atom. $M-H^-$ refers to the negative ion of a parent minus a hydrogen atom. $M+Na^+$ refers to the positive ion of a parent plus a sodium atom. $M+K^+$ refers to the positive ion of a parent plus a potassium atom. EI refers to electron impact. ESI refers to electrospray ionization. CI refers to chemical ionization. FAB refers to fast atom bombardment.

Compounds of the present invention may be in the form of pharmaceutically acceptable salts. The term "pharmaceutically acceptable salts" refers to salts prepared from pharmaceutically acceptable non-toxic bases including inorganic bases and organic bases, and salts prepared from inorganic acids, and organic acids. Salts derived from inorganic bases include aluminum, ammonium, calcium, ferric, ferrous, lithium, magnesium, potassium, sodium, zinc, and the like.

Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and the like. Salts derived from inorganic acids include salts of hydrochloric acid, hydrobromic acid, hydroiodic acid, sulfuric acid, phosphoric acid, phosphorous acid and the like. Salts derived from pharmaceutically acceptable organic non-toxic acids include salts of $C_{1-6}$ alkyl carboxylic acids, di-carboxylic acids, and tri-carboxylic acids such as acetic acid, propionic acid, fumaric acid, succinic acid, tartaric acid, maleic acid, adipic acid, and citric acid, and aryl and alkyl sulfonic acids such as toluene sulfonic acids and the like.

By the term "effective amount" of a compound as provided herein is meant a non-toxic but sufficient amount of the compound(s) to provide the desired effect. As pointed out below, the exact amount required will vary from subject to subject, depending on the species, age, and general condition of the subject, the severity of the disease that is being treated, the particular compound(s) used, the mode of administration, and the like. Thus, it is not possible to specify an exact "effective amount." However, an appropriate effective amount may be determined by one of ordinary skill in the art using only routine experimentation.

The amount of therapeutically effective compound(s) that is administered and the dosage regimen for treating a disease condition with the compounds and/or compositions of this invention depends on a variety of factors, including the age, weight, sex and medical condition of the subject, the severity of the disease, the route and frequency of administration, and the particular compound(s) employed, and thus may vary widely. The compositions contain well know carriers and excipients in addition to a therapeutically effective amount of compounds of Formula I. The pharmaceutical compositions may contain active ingredient in the range of about 0.001 to 100 mg/kg/day for an adult, preferably in the range of about 0.1 to 50 mg/kg/day for an adult. A total daily dose of about 1 to 1000 mg of active ingredient may be appropriate for an adult. The daily dose can be administered in one to four doses per day.

In addition to the compound(s) of Formula I, the composition for therapeutic use may also comprise one or more non-toxic, pharmaceutically acceptable carrier materials or excipients. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose, or other methods known to those skilled in the art. For oral administration, the pharmaceutical composition may be in the form of, for example, a tablet, capsule, suspension or liquid. If desired, other active ingredients may be included in the composition.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, EtOH, corn oil, cottonseed oil, peanut oil, sesame oil, benzyl alcohol, sodium chloride, and/or various buffers. Other adjuvants and modes of administration are well and widely known in the pharmaceutical art.

The serotonin type 3 receptor ($5HT_3R$) is a member of a superfamily of ligand-gated ion channels, which includes the muscle and neuronal nAChR, the glycine receptor, and the γ-aminobutyric acid type A receptor. Like the other members of this receptor superfamily, the $5HT_3R$ exhibits a large degree of sequence homology with α7 nAChR but functionally the two ligand-gated ion channels are very different. For example, α7 nAChR is rapidly inactivated, is highly permeable to calcium and is activated by acetylcholine and nicotine. On the other hand, $5HT_3R$ is inactivated slowly, is relatively impermeable to calcium and is activated by serotonin. These experiments suggest that the α7 nAChR and $5HT_3R$ proteins have some degree of homology, but function very differently. Indeed the pharmacology of the channels is very different. For example, Ondansetron, a highly selective $5HT_3R$ antagonist, has little activity at the α7 nAChR. The converse is also true. For example, GTS-21, a highly selective α7 nAChR agonist, has little activity at the $5HT_3R$.

α7 nAChR is a ligand-gated $Ca^{++}$ channel formed by a homopentamer of α7 subunits. Previous studies have established that α-bungarotoxin (α-btx) binds selectively to this homopetameric, α7 nAChR subtype, and that α7 nAChR has a high affinity binding site for both α-btx and methyllycaconitine (MLA). α7 nAChR is expressed at high levels in the hippocampus, ventral tegmental area and ascending cholinergic projections from nucleus basilis to thalamocortical areas. α7 nAChR agonists increase neurotransmitter release, and increase cognition, arousal, attention, learning and memory.

Data from human and animal pharmacological studies establish that nicotinic cholinergic neuronal pathways control many important aspects of cognitive function including attention, learning and memory (Levin, E. D., *Psychopharmacology,* 108:417–31, 1992; Levin, E. D. and Simon B. B., Psychopharmacology, 138:217–30, 1998). For example, it is well known that nicotine increases cognition and attention in humans. ABT-418, a compound that activates α4β2 and α7 nAChR, improves cognition and attention in clinical trials of Alzheimer's disease and attention-deficit disorders (Potter, A. et. al., Psychopharmacology (Berl)., 142(4):334–42, March 1999; Wilens, T. E. et. al., Am. J. Psychiatry, 156 (12):1931–7, December 1999). It is also clear that nicotine and selective but weak α7 nAChR agonists increase cognition and attention in rodents and non-human primates.

Schizophrenia is a complex multifactorial illness caused by genetic and non-genetic risk factors that produce a constellation of positive and negative symptoms. The positive symptoms include delusions and hallucinations and the negative symptoms include deficits in affect, attention, cognition and information processing. No single biological element has emerged as a dominant pathogenic factor in this disease. Indeed, it is likely that schizophrenia is a syndrome that is produced by the combination of many low penetrance risk factors. Pharmacological studies established that dopamine receptor antagonists are efficacious in treating the overt psychotic features (positive symptoms) of schizophrenia such as hallucinations and delusions. Clozapine, an "a typical" antipsychotic drug, is novel because it is effective in treating both the positive and some of the negative symptoms of this disease. Clozapine's utility as a drug is greatly limited because continued use leads to an increased risk of agranulocytosis and seizure. No other antipsychotic drug is effective in treating the negative symptoms of schizophrenia. This is significant because the restoration of cognitive functioning is the best predictor of a successful clinical and functional outcome of schizophrenic patients (Green, M. F., Am J Psychiatry, 153:321–30, 1996). By extension, it is clear that better drugs are needed to treat the cognitive disorders of schizophrenia in order to restore a better state of mental health to patients with this disorder.

One aspect of the cognitive deficit of schizophrenia can be measured by using the auditory event-related potential (P50) test of sensory gating. In this test, electroencepholographic (EEG) recordings of neuronal activity of the hippocampus are used to measure the subject's response to a series of auditory "clicks" (Adler, L. E. et. al., Biol. Psychiatry, 46:8–18, 1999). Normal individuals respond to the first click with greater degree than to the second click. In general, schizophrenics and schizotypal patients respond to both clicks nearly the same (Cullum, C. M. et. al., Schizophr. Res., 10:131–41, 1993). These data reflect a schizophrenic's inability to "filter" or ignore unimportant information. The sensory gating deficit appears to be one of the key pathological features of this disease (Cadenhead, K. S. et. al., Am. J. Psychiatry, 157:55–9, 2000). Multiple studies show that nicotine normalizes the sensory deficit of schizophrenia (Adler, L. E. et. al., Am. J. Psychiatry, 150:1856–61, 1993). Pharmacological studies indicate that nicotine's effect on sensory gating is via the α7 nAChR (Adler, L. E. et. al., Schizophr. Bull., 24:189–202, 1998). Indeed, the biochemical data indicate that schizophrenics have 50% fewer of α7 nAChR receptors in the hippocampus, thus giving a rationale to partial loss of α7 nAChR functionality (Freedman, R. et. al., Biol. Psychiatry, 38:22–33, 1995). Interestingly, genetic data indicate that a polymorphism in the promoter region of the α7 nAChR gene is strongly associated with the sensory gating deficit in schizophrenia (Freedman, R. et. al., Proc. Nat'l Acad. Sci. USA, 94(2):587–92, 1997; Myles-Worsley, M. et. al., Am. J. Med. Genet, 88(5):544–50, 1999). To date, no mutation in the coding region of the α7 nAChR has been identified. Thus, schizophrenics express the same α7 nAChR as non-schizophrenics.

Selective α7 nAChR agonists may be found using a functional assay on FLIPR (see WO 00/73431 A2). FLIPR is designed to read the fluorescent signal from each well of a 96 or 384 well plate as fast as twice a second for up to 30 minutes. This assay may be used to accurately measure the functional pharmacology of α7 nAChR and $5HT_3R$. To conduct such an assay, one uses cell lines that expressed functional forms of the α7 nAChR using the α7/5-$HT_3$ channel as the drug target and cell lines that expressed functional $5HT_3R$. In both cases, the ligand-gated ion channel was expressed in SH-EP1 cells. Both ion channels can produce robust signal in the FLIPR assay.

The compounds of the present invention are α7 nAChR agonists and may be used to treat a wide variety of diseases. For example, they may be used in treating schizophrenia, or psychosis.

Schizophrenia is a disease having multiple aspects. Currently available drugs are generally aimed at controlling the positive aspects of schizophrenia, such as delusions. One drug, Clozapine, is aimed at a broader spectrum of symptoms associated with schizophrenia. This drug has many side effects and is thus not suitable for many patients. Thus, there is a need for a drug to treat the cognitive and attention deficits associated with schizophrenia. Similarly, there is a need for a drug to treat the cognitive and attention deficits associated with schizoaffective disorders, or similar symptoms found in the relatives of schizophrenic patients.

Psychosis is a mental disorder characterized by gross impairment in the patient's perception of reality. The patient may suffer from delusions, and hallucinations, and may be incoherent in speech. His behavior may be agitated and is often incomprehensible to those around him. In the past, the term psychosis has been applied to many conditions that do not meet the stricter definition given above. For example, mood disorders were named as psychoses.

There are a variety of antipsychotic drugs. The conventional antipsychotic drugs include Chlorpromazine, Fluphenazine, Haloperidol, Loxapine, Mesoridazine, Molindone, Perphenazine, Pimozide, Thioridazine, Thiothixene, and Trifluoperazine. These drugs all have an affinity for the dopamine 2 receptor.

These conventional antipsychotic drugs have several side effects, including sedation, weight gain, tremors, elevated prolactin levels, akathisia (motor restlessness), dystonia and muscle stiffness. These drugs may also cause tardive dyskinesia. Unfortunately, only about 70% of patients with schizophrenia respond to conventional antipsychotic drugs. For these patients, a typical antipsychotic drugs are available.

Atypical antipsychotic drugs generally are able to alleviate positive symptoms of psychosis while also improving negative symptoms of the psychosis to a greater degree than conventional antipsychotics. These drugs may improve neurocognitive deficits. Extrapyramidal (motor) side effects are not as likely to occur with the atypical antipsychotic drugs, and thus, these a typical antipsychotic drugs have a lower risk of producing tardive dyskinesia. Finally these a typical antipsychotic drugs cause little or no elevation of prolactin. Unfortunately, these drugs are not free of side effects. Although these drugs each produce different side effects, as a group the side effects include: agranulocytosis; increased risk of seizures, weight gain, somnolence, dizziness, tachycardia, decreased ejaculatory volume, and mild prolongation of QTc interval.

In a combination therapy to treat multiple symptoms of diseases such as schizophrenia, the compounds of Formula I and the anti-psychotic drugs can be administered simultaneously or at separate intervals. When administered simultaneously the compounds of Formula I and the anti-psychotic drugs can be incorporated into a single pharmaceutical composition, e.g., a pharmaceutical combination therapy composition. Alternatively, two separate compositions, i.e., one containing compounds of Formula I and the other containing anti-psychotic drugs, can be administered simultaneously. Examples of anti-psychotic drugs, in addition to those listed above, include, but are not limited to, Thorazine, Mellaril, Trilafon, Navane, Stelazine, Permitil, Prolixin, Risperdal, Zyprexa, Seroquel, ZELDOX, Acetophenazine, Carphenazine, Chlorprothixene, Droperidol, Loxapine, Mesoridazine, Molindone, Ondansetron, Pimozide, Prochlorperazine, and Promazine.

A pharmaceutical combination therapy composition can include therapeutically effective amounts of the compounds of Formula I, noted above, and a therapeutically effective amount of anti-psychotic drugs. These compositions may be formulated with common excipients, diluents or carriers, and compressed into tablets, or formulated elixirs or solutions for convenient oral administration or administered by intramuscular intravenous routes. The compounds can be administered rectally, topically, orally, sublingually, or parenterally and maybe formulated as sustained relief dosage forms and the like.

When separately administered, therapeutically effective amounts of compositions containing compounds of Formula I and anti-psychotic drugs are administered on a different schedule. One may be administered before the other as long as the time between the two administrations falls within a therapeutically effective interval. A therapeutically effective interval is a period of time beginning when one of either (a) the compounds of Formula I, or (b) the anti-psychotic drugs is administered to a human and ending at the limit of the beneficial effect in the treatment of schizophrenia or psychosis of the combination of (a) and (b). The methods of administration of the compounds of Formula I and the anti-psychotic drugs may vary. Thus, either agent or both agents may be administered rectally, topically, orally, sublingually, or parenterally.

As discussed, the compounds of the present invention are α7 nAChR agonists. Therefore, as another aspect of the present invention, the compounds of the present invention may be used to treat a variety of diseases including cognitive and attention deficit symptoms of Alzheimer's, neurodegeneration associated with diseases such as Alzheimer's disease, pre-senile dementia (also known as mild cognitive impairment), and senile dementia.

Alzheimer's disease has many aspects, including cognitive and attention deficits. Currently, these deficits are treated with cholinesterase inhibitors. These inhibitors slow the break down of acetylcholine, and thereby provide a general nonspecific increase in the activity of the cholinergic nervous system. Since the drugs are nonspecific, they have a wide variety of side effects. Thus, there is a need for a drug that stimulates a portion of the cholinergic pathways and thereby provides improvement in the cognitive and attention deficits associated with Alzheimer's disease without the side effects created by nonspecific stimulation of the cholinergic pathways.

Neurodegeneration is a common problem associated with diseases such as Alzheimer's disease. While the current drugs treat some of the symptoms of this disease, they do not control the underlying pathology of the disease. Accordingly, it would be desirable to provide a drug that can slow the progress of Alzheimer's disease.

Pre-senile dementia (mild cognitive impairmnent) concerns memory impairment rather than attention deficit problems and otherwise unimpaired cognitive functioning. Mild cognitive impairment is distinguished from senile dementia in that mild cognitive impairment involves a more persistent and troublesome problem of memory loss for the age of the patient. There currently is no medication specifically identified for treatment of mild cognitive impairment, due somewhat to the newness of identifying the disease. Therefore, there is a need for a drug to treat the memory problems associated with mild cognitive impairment.

Senile dementia is not a single disease state. However, the conditions classified under this name frequently include cognitive and attention deficits. Generally, these deficits are not treated. Accordingly, there is a need for a drug that provides improvement in the cognitive and attention deficits associated with senile dementia.

As discussed, the compounds of the present invention are α7 nAChR agonists. Therefore, yet other diseases to be treated with compounds of the present invention include treating the cognitive and attention deficits as well as the neurodegeneration associated with attention deficit disorder, attention deficit hyperactivity disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake including bulimia and anorexia nervosa, withdrawal symptoms associated with smoking cessation and dependant drug cessation, Gilles de la Tourette's Syndrome, glaucoma, or symptoms associated with pain.

Attention deficit disorder is generally treated with methylphenidate, an amphetamine-like molecule that has some potential for abuse. Accordingly, it would be desirable to provide a drug that treats attention deficit disorder while having fewer side effects than the currently used drug.

Attention deficit hyperactivity disorder, otherwise known as ADHD, is a neurobehavioral disorder affecting 3–5% of all American children. ADHD concerns cognitive alone or both cognitive and behavioral actions by interfering with a person's ability to stay on a task and to exercise age-appropriate inhibition. Several types of ADHD exist: a predominantly inattentive subtype, a predominantly hyperactive-impulsive subtype, and a combined subtype. Treatment may include medications such as methylphenidate, dextroamphetamine, or pemoline, which act to decrease impulsivity and hyperactivity and to increase attention. No "cure" for ADHD currently exists. Children with the disorder seldom outgrow it; therefore, there is a need for appropriate medicaments.

Mood and affective disorders fall within a large group of diseases, including monopolar depression and bi-polar mood disorder. These diseases are treated with three major classes of compounds. The first group is the heterocyclic antidepressant (HCA's). This group includes the well-known tricyclic antidepressants. The second group of compounds used to treat mood disorders is the monoamine oxidase inhibitors (MAOI's) that are used in particular types of diseases. The third drug is lithium. Common side effects from HCA's are sedation and weight gain. In elderly patients with organic brain disease, the side effects of HCA's can also include seizures and behavioral symptoms. The main side effects from using MAOI's occur from dietary and drug interactions. Benign side effects from the use of lithium include, but are not limited to, weight gain, nausea, diarrhea, polyuria, polydipsia, and tremor. Toxic side effects from lithium can include persistent headache, mental confusion, and may reach seizures and cardiac arrhythmias. Therefore, agents with less side effects or interactions with food or other medications would be useful.

Depression is a mood disorder of varying lengths of normally several months to more than two years and of varying degrees of feelings involving sadness, despair, and discouragement. The heterocyclic antidepressants (HCA's) are currently the largest class of antidepressants, but monoamine oxidase inhibitors (MAOI's) are used in particular types of depression. Common side effects from HCA's are sedation and weight gain. In elderly patients with organic brain disease, the side effects from HCA's can also include seizures and behavioral symptoms. The main side effects from using MAOI's occur from dietary and drug interactions. Therefore, agents with fewer side effects would be useful.

Borderline personality disorder, although not as well known as bipolar disorder, is more common. People having borderline personality disorder suffer from a disorder of emotion regulation. Pharmaceutical agents are used to treat specific symptoms, such as depression or thinking distortions.

Acquired immune deficiency syndrome (AIDS) results from an infection with the human immunodeficiency virus (HIV). This virus attacks selected cells and impairs the proper function of the immune, nervous, and other systems. HIV infection can cause other problems such as, but not limited to, difficulties in thinking, otherwise known as AIDS dementia complex. Therefore, there is a need to drugs to relieve the confusion and mental decline of persons with AIDS.

Amyotrophic lateral sclerosis, also known as Lou Gehrig's disease, belongs to a class of disorders known as motor neuron diseases wherein specific nerve cells in the brain and spinal cord gradually degenerate to negatively affect the control of voluntary movement. Currently, there is no cure for amyotrophic lateral sclerosis although patients may receive treatment from some of their symptoms and although Riluzole has been shown to prolong the survival of patients. Therefore, there is a need for a pharmaceutical agent to treat this disease.

Traumatic brain injury occurs when the brain is damaged from a sudden physical assault on the head. Symptoms of the traumatic brain injury include confusion and other cognitive problems. Therefore, there is a need to address the symptoms of confusion and other cognitive problems.

Brain tumors are abnormal growths of tissue found inside of the skull. Symptoms of brain tumors include behavioral and cognitive problems. Surgery, radiation, and chemotherapy are used to treat the tumor, but other agents are necessary to address associated symptoms. Therefore, there is a need to address the symptoms of behavioral and cognitive problems.

Persons with Down's syndrome have in all or at least some of their cells an extra, critical portion of the number 21 chromosome. Adults who have Down's syndrome are known to be at risk for Alzheimer-type dementia. Currently, there is no proven treatment for Down's syndrome. Therefore, there is a need to address the dementia associated with Down's syndrome.

Genetically programmed degeneration of neurons in certain areas of the brain cause Huntington's disease. Early symptoms of Huntington's disease include mood swings, or trouble learning new things or remembering a fact. Most drugs used to treat the symptoms of Huntington's disease have side effects such as fatigue, restlessness, or hyperexcitability. Currently, there is no treatment to stop or reverse the progression of Huntington's disease. Therefore, there is a need of a pharmaceutical agent to address the symptoms with fewer side effects.

General anxiety disorder (GAD) occurs when a person worries about things such as family, health, or work when there is no reason to worry and is unable not to worry. About 3 to 4% of the U.S. population has GAD during the course of a year. GAD most often strikes people in childhood or adolescence, but can begin in adulthood, too. It affects women more often than men. Currently, treatment involves cognitive-behavioral therapy, relaxation techniques, and biofeedback to control muscle tension and medications such as benzodiazepines, imipramine, and buspirone. These drugs are effective but all have side-effect liabilities. Therefore, there is a need of a pharmaceutical agent to address the symptoms with fewer side effects.

Dementia with Lewy Bodies is a neurodegenerative disorder involving abnormal structures known as Lewy bodies found in certain areas of the brain. Symptoms of dementia with Lewy bodies include, but are not limited to, fluctuating cognitive impairment with episodic delirium. Currently, treatment concerns addressing the parkinsonian and psychiatric symptoms. However, medicine to control tremors or loss of muscle movement may actually accentuate the underlying disease of dementia with Lewy bodies. Therefore, there is a need of a pharmaceutical agent to treat dementia with Lewy bodies.

Age-related macular degeneration (AMD) is a common eye disease of the macula which is a tiny area in the retina that helps produce sharp, central vision required for "straight ahead" activities that include reading and driving. Persons with AMD lose their clear, central vision. AMD takes two forms: wet and dry. In dry AMD, there is a slow breakdown of light-sensing cells in the macula. There currently is no cure for dry AMD. In wet AMD, new, fragile blood vessels growing beneath the macula as dry AMD worsens and these vessels often leak blood and fluid to cause rapid damage to the macula quickly leading to the loss of central vision. Laser surgery can treat some cases of wet AMD. Therefore, there is a need of a pharmaceutical agent to address AMD.

Parkinson's disease is a neurological disorder characterized by tremor, hypokinesia, and muscular rigidity. Currently, there is no treatment to stop the progression of the disease. Therefore, there is a need of a pharmaceutical agent to address Parkinson's.

Tardive dyskinesia is associated with the use of conventional antipsychotic drugs. This disease is characterized by involuntary movements most often manifested by puckering of the lips and tongue and/or writhing of the arms or legs. The incidence of tardive dyskinesia is about 5% per year of drug exposure among patients taking conventional antipsychotic drugs. In about 2% of persons with the disease, tardive dyskinesia is severely disfiguring. Currently, there is no generalized treatment for tardive dyskinesia. Furthermore, the removal of the effect-causing drugs is not always an option due to underlying problems. Therefore, there is a need for a pharmaceutical agent to address the symptoms of tardive dyskinesia.

Pick's disease results from a slowly progressive deterioration of social skills and changes in personality with the resulting symptoms being impairment of intellect, memory, and language. Common symptoms include memory loss, lack of spontaneity, difficulty in thinking or concentrating, and speech disturbances. Currently, there is no specific treatment or cure for Pick's disease but some symptoms can be treated with cholinergic and serotonin-boosting antidepressants. In addition, antipsychotic medications may alleviate symptoms in FTD patients who are experiencing delusions or hallucinations. Therefore, there is a need for a pharmaceutical agent to treat the progressive deterioration of social skills and changes in personality and to address the symptoms with fewer side effects.

Post-traumatic stress disorder (PTSD) is a form of anxiety triggered by memories of a traumatic event that directly affected the patient or that the patient may have witnessed. The disorder commonly affects survivors of traumatic events including sexual assault, physical assault, war, torture, natural disasters, an automobile accident, an airplane crash, a hostage situation, or a death camp. The affliction also can affect rescue workers at an airplane crash or a mass shooting, someone who witnessed a tragic accident or someone who has unexpectedly lost a loved one. Treatment for PTSD includes cognitive-behavioral therapy, group psychotherapy, and medications such as Clonazepam, Lorazepam and selective serotonin-reuptake inhibitors such as Fluoxetine, Sertraline, Paroxetine, Citalopram and Fluvoxamine. These medications help control anxiety as well as depression. Various forms of exposure therapy (such as systemic desensitization and imaginal flooding) have all been used with PTSD patients. Exposure treatment for PTSD involves repeated reliving of the trauma, under controlled conditions, with the aim of facilitating the processing of the trauma. Therefore, there is a need for better pharmaceutical agents to treat Post traumatic stress disorder.

Dysregulation of food intake associated with eating disease, including bulemia nervosa and anorexia nervosa, involve neurophysiological pathways. Anorexia nervosa is hard to treat due to patients not entering or remaining in after entering programs. Currently, there is no effective treatment for persons suffering from severe anorexia nervosa. Cognitive behavioral therapy has helped patients suffering from bulemia nervosa; however, the response rate is only about 50% and current treatment does not adequately address emotional regulation. Therefore, there is a need for pharmaceutical agents to address neurophysiological problems underlying diseases of dysregulation of food intake.

Cigarette smoking has been recognized as a major public health problem for a long time. However, in spite of the public awareness of health hazard, the smoking habit remains extraordinarily persistent and difficult to break. There are many treatment methods available, and yet people continue to smoke. Administration of nicotine transdermally, or in a chewing gum base is common treatments. However, nicotine has a large number of actions in the body, and thus can have many side effects. It is clear that there is both a need and a demand of long standing for a convenient and relatively easy method for aiding smokers in reducing or eliminating cigarette consumption. A drug that could selectively stimulate only certain of the nicotinic receptors would be useful in smoke cessation programs.

Smoke cessation programs may involve oral dosing of the drug of choice. The drug may be in the form of tablets. However, it is preferred to administer the daily dose over the waking hours, by administration of a series of incremental doses during the day. The preferred method of such administration is a slowly dissolving lozenge, troche, or chewing gum, in which the drug is dispersed. Another drug in treating nicotine addiction is Zyban. This is not a nicotine replacement, as are the gum and patch. Rather, this works on other areas of the brain, and its effectiveness is to help control nicotine craving or thoughts about cigarette use in people trying to quit. Zyban is not very effective and effective drugs are needed to assist smokers in their desire to stop smoking. These drugs may be administered transdermally through the use of skin patches. In certain cases, the drugs may be administered by subcutaneous injection, especially if sustained release formulations are used.

Drug use and dependence is a complex phenomenon, which cannot be encapsulated within a single definition. Different drugs have different effects, and therefore different types of dependence. Drug dependence has two basic causes, that is, tolerance and physical dependence. Tolerance exists when the user must take progressively larger doses to produce the effect originally achieved with smaller doses. Physical dependence exists when the user has developed a state of physiologic adaptation to a drug, and there is a withdrawal (abstinence) syndrome when the drug is no longer taken. A withdrawal syndrome can occur either when the drug is discontinued or when an antagonist displaces the drug from its binding site on cell receptors, thereby counteracting its effect. Drug dependence does not always require physical dependence.

In addition drug dependence often involves psychological dependence, that is, a feeling of pleasure or satisfaction when taking the drug. These feelings lead the user to repeat the drug experience or to avoid the displeasure of being deprived of the drug. Drugs that produce strong physical dependence, such as nicotine, heroin and alcohol are often abused, and the pattern of dependence is difficult to break. Drugs that produce dependence act on the CNS and generally reduce anxiety and tension; produce elation, euphoria, or other pleasurable mood changes; provide the user feelings of increased mental and physical ability; or alter sensory perception in some pleasurable manner. Among the drugs that are commonly abused are ethyl alcohol, opioids, anxiolytics, hypnotics, cannabis (marijuana), cocaine, amphetamines, and hallucinogens. The current treatment for drug-addicted people often involves a combination of behavioral therapies and medications. Medications, such as methadone or LAAM (levo-alpha-acetyl-methadol), are effective in suppressing the withdrawal symptoms and drug craving associated with narcotic addiction, thus reducing illicit drug use and improving the chances of the individual remaining in treatment. The primary medically assisted withdrawal method for narcotic addiction is to switch the patient to a comparable drug that produces milder withdrawal symptoms, and then gradually taper off the substitute medication. The medication used most often is methadone, taken orally once a day. Patients are started on the lowest dose that prevents the more severe signs of withdrawal and then the dose is gradually reduced. Substitutes can be used also for withdrawal from sedatives. Patients can be switched to long-acting sedatives, such as diazepam or phenobarbital, which are then gradually reduced.

Gilles de la Tourette's Syndrome is an inherited neurological disorder. The disorder is characterized by uncontrollable vocal sounds called tics and involuntary movements. The symptoms generally manifest in an individual before the person is 18 years of age. The movement disorder may begin with simple tics that progress to multiple complex tics, including respiratory and vocal ones. Vocal tics may begin as grunting or barking noises and evolve into compulsive utterances. Coprolalia (involuntary scatologic utterances) occurs in 50% of patients. Severe tics and coprolalia may be physically and socially disabling. Tics tend to be more complex than myoclonus, but less flowing than choreic movements, from which they must be differentiated. The patient may voluntarily suppress them for seconds or minutes.

Currently simple tics are often treated with benzodiazepines. For simple and complex tics, Clonidine may be used. Long-term use of Clonidine does not cause tardive dyskinesia; its limiting adverse effect is hypotension. In more severe cases, antipsychotics, such as Haloperidol may be required, but side effects of dysphoria, parkinsonism, akathisia, and tardive dyskinesia may limit use of such antipsychotics. There is a need for safe and effective methods for treating this syndrome.

Glaucoma is within a group of diseases occurs from an increase in intraocular pressure causing pathological changes in the optical disk and negatively affects the field of vision. Medicaments to treat glaucoma either decrease the amount of fluid entering the eye or increase drainage of fluids from the eye in order to decrease intraocular pressure. However, current drugs have drawbacks such as not working over time or causing side effects so the eye-care professional has to either prescribe other drugs or modify the prescription of the drug being used. There is a need for safe and effective methods for treating problems manifesting into glaucoma.

Ischemic periods in glaucoma cause release of excitotoxic amino acids and stimulate inducible form of nitric oxide synthase (iNOS) leading to neurodegeneration. Alpha 7 nicotinic agonists may stimulate the release of inhibitory amino acids such as GABA which will dampen hyperexcitablity. Alpha 7 nicotinic agonists are also directly neuroprotective on neuronal cell bodies. Thus alpha 7 nicotinic agonists have the potential to be neuroprotective in glaucoma.

Persons afflicted with pain often have what is referred to as the "terrible triad" of suffering from the pain, resulting in sleeplessness and sadness, all of which are hard on the afflicted individual and that individual's family. Pain can manifest itself in various forms, including, but not limited to, headaches of all severity, back pain, neurogenic, and pain from other ailments such as arthritis and cancer from its existence or from therapy to irradicate it. Pain can be either chronic (persistent pain for months or years) or acute (short-lived, immediate pain to inform the person of possible injury and need of treatment). Persons suffering from pain respond differently to individual therapies with varying degrees of success. There is a need for safe and effective methods for treating pain.

Finally, the compounds of the present invention may be used in combination therapy with typical and a typical anti-psychotic drugs. All compounds within the present invention are useful for and may also be used in combination with each other to prepare pharmaceutical compositions. Such combination therapy lowers the effective dose of the anti-psychotic drug and thereby reduces the side effects of the anti-psychotic drugs. Some typical anti-psychotic drugs that may be used in the practice of the invention include Haldol. Some a typical anti-psychotic drugs include Ziprasidone, Olanzapine, Resperidone, and Quetiapine.

Compounds of Formula I can be prepared as shown in Scheme 1. The key step in the preparation of this class of compounds is the coupling of commercially-available 3-aminoquinuclidine with the requisite acid chloride (Lv=Cl), mixed anhydride (e.g., Lv=diphenyl phosphoryl, Bis(2-oxo-3-oxazolidinyl)phosphinyl, or acyloxy of the general formula of O—C(O)—$R_{Lv}$, where $R_{Lv}$ includes phenyl or t-butyl), or carboxylic acid (Lv=OH) in the presence of an activating agent. Suitable activating reagents are well known in the art, for examples see Kiso, Y., Yajima, H. "Peptides" pp. 39–91, San Diego, Calif., Academic Press, (1995), and include, but are not limited to, agents such as carbodiimides, phosphonium and uronium salts (such as uronium salt HATU).

Scheme 1

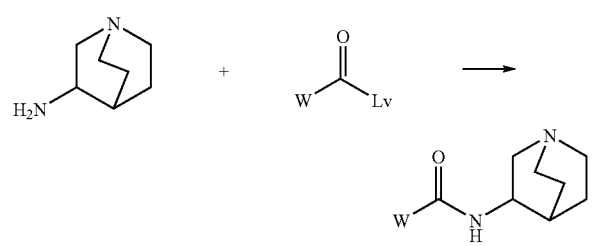

Preferably, the acid is converted into a mixed anhydride by treatment with bis (2-oxo-3-oxazolidinyl)phosphinic chloride in the presence of TEA with $CH_2Cl_2$ or $CHCl_3$ as the solvent. The resulting anhydride solution is directly reacted with 3-aminoquinuclidine added neat or using DMF or aqueous DMF as solvent. Likewise, treatment of a mixture of the acid and 3-aminoquinuclidine dihydrochloride with HATU in the presence of an appropriate tertiary amine such as diisopropylethyl amine in a solvent such as DMF leads to the desired amides. Alternatively, condensation of 3-aminoquinuclidine with an ester (W—C(O)—O-alkyl or W—C(O)—O-(electron-deficient aryl)) in an appropriate solvent such as ethanol at an elevated temperature will yield desired amides.

It will be apparent to those skilled in the art that the requisite carboxylic acids can be obtained through synthesis via literature procedures or through the slight modification thereof. Further, it will be apparent to those skilled in the art that one can functionalize W using the ester of W as an intermediate.

One of ordinary skill in the art will recognize that the methods described for the reaction of the unsubstituted 3-aminoquinuclidine ($R_2$=H) are equally applicable to substituted compounds ($R_2 \neq$H). Such compounds can be prepared by reduction of the oxime of the corresponding 3-quinuclidinone (see *J. Labelled Compds. Radiopharm.*, 53–60 (1995) and *J. Med. Chem.* 988–995, (1998)). The oximes can be prepared by treatment of the 3-quinuclidinones with hydroxylamine hydrochloride in the presence of a base. The 3-quinuclidinones, where $R_2$=substituted alkyl, or cycloalkyl can be prepared by known procedures (see *Tet. Lett.* 1015–1018, (1972), *J. Am. Chem. Soc.* 1278–1291 (1994), *J. Am. Chem. Soc.* 4548–4552 (1989), *Tetrahedron*, 1139–1146 (2000)). The 3-quinuclidinones, where $R_2$=aryl, can be prepared by palladium catalyzed arylation as described in *J. Am. Chem. Soc.* 1473–1478 (1999) and *J. Am. Chem. Soc.* 1360–1370 (2000).

There are a variety of methods for constructing thioamides. One can treat the corresponding amide with a reagent such as Lawesson's reagent (2,4-bis(4-methoxyphenyl)-1,3-dithia-2,4-diphosphetane-2,4-disulfide). See Lawesson et. al. in *Bull. Soc. Chim. Belg.*, 229 (1978)), or $P_4S_{10}$ (see *Chem. Rev.*, 45 (1961). Alternatively, one can react a dithiocarboxylic ester with the corresponding quinuclidine to form the same thioamide.

The following examples are provided as examples and are not intended to limit the scope of this invention to only those provided examples and named compounds. Although one stereoisomer of the quinuclidine may be used to make an example, e.g., 3R-aminoquinuclidine, the other stereoisomer, 3S-aminoquinuclidine, may be used making non-critical changes to the methods provided herein. Further, the naming of specific stereoisomers is for exemplification, and is not intended to limit in anyway the scope of the invention. Also, the salts made in the examples are only exemplary and are not intended to limit the invention. Any pharmaceutically acceptable salt can be made by one of ordinary skill in the art. The invention includes the following examples in pure stereoisomeric form or as racemic mixtures.

EXAMPLE 1

N-[(3R)-1-azabicyclo[2.2.2]oct-3-yl]-2,3-dihydrofuro[2,3-c]pyridine-5-carboxamide dihydrochloride

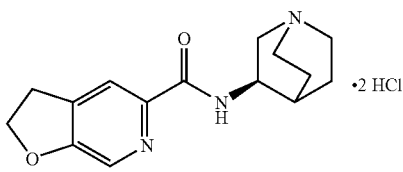

Preparation of the Acid:

2-Chloro-3-pyridinol (20.0 g, 0.154 mole), NaHCO$_3$ (19.5 g, 0.232 mole, 1.5 equ), and 150 mL of water are placed in a flask. The flask is placed in an oil bath at 90° C., and after 5 min, 37% aqueous formaldehyde (40.5 mL, 0.541 mole, 3.5 equ) is added in six unequal doses in the following order: 12 mL, 3×8 mL, then 2.2 mL all at 90-minute intervals and then the final 2.3 mL after the reaction had stirred for 15 h at 90° C. The reaction is stirred at 90° C. for another 4 h and then is cooled by placing the flask in an ice bath. The pH of the reaction is then adjusted to 1 using 6N HCl. The reaction is stirred for 1.5 h in an ice bath allowing an undesired solid to form. The undesired solid is removed by filtration, and the filtrate is extracted seven times with EtOAc. The combined organic extracts are concentrated in vacuo, toluene is added to the flask and removed in vacuo to azeotrope water, and then CH$_2$Cl$_2$ is added and removed in vacuo to obtain 2-chloro-6-(hydroxymethyl)-3-pyridinol (C1) as a pale yellow solid (81% yield) sufficiently pure for subsequent reaction. MS (EI) for C$_6$H$_6$ClNO$_2$, m/z: 159(M)$^+$.

C1 (11.6 g, 72.7 mmol) and NaHCO$_3$ (18.3 g, 218 mmol) are added to 200 mL water. The mixture is stirred until homogeneous, the flask is placed in an ice bath, iodine (19.4 g, 76.3 mmol) is added, and the reaction is stirred over the weekend at rt. The pH of the mixture is adjusted to 3 with 2N NaHSO$_4$, and the mixture is extracted with 4×50 mL EtOAc. The combined organic layer is dried over anhydrous MgSO$_4$, is filtered, and the filtrate is concentrated in vacuo to a yellow solid. The crude solid is washed with EtOAc to provide 2-chloro-6-(hydroxymethyl)-4-iodo-3-pyridinol (C2) as an off-white solid (62% yield), and the filtrate is concentrated to a small volume and is chromatographed over 250 g silica gel (230–400 mesh) eluting with 2.5:4.5:4:0.1 EtOAc/CH$_2$Cl$_2$/hexane/acetic acid. The fractions with the desired compound are combined and concentrated to afford additional pure C2 (12% yield). MS (EI) for C$_6$H$_5$ClINO$_2$, m/z: 285(M)$^+$.

C2 (13.9 g, 48.6 mmol) is combined with trimethylsilylacetylene (9.6 mL, 68 mmol), bis(triphenylphosphine)palladium dichloride (1.02 g, 1.46 mmol) and cuprous iodide (139 mg, 0.73 mmol) in 80 mL CHCl$_3$/40 mL THF under N$_2$. TEA (21 mL, 151 mmol) is added, and the reaction is stirred 3 h at rt and is diluted with 200 mL CHCl$_3$. The mixture is washed with 2×150 mL 5% HCl and the combined aqueous layers are extracted with 2×50 mL CHCl$_3$. The combined organic layer is washed with 100 mL 50% saturated NaCl, is dried over anhydrous MgSO$_4$, and is concentrated in vacuo to an amber oil. The crude material is chromatographed over 350 g silica gel (230–400 mesh), eluting with 35% EtOAc/hexane. The fractions with the desired compound are combined and concentrated to afford 2-chloro-6-(hydroxymethyl)-4-[(trimethylsilyl)ethynyl]-3-pyridinol (C3) as a golden solid (92% yield). MS (EI) for C$_{11}$H$_{14}$ClNO$_2$Si, m/z: 255(M)$^+$.

C3 (7.9 g, 31.2 mmol) and cuprous iodide (297 mg, 1.6 mmol) in 60 mL EtOH/60 mL TEA are added to a flask. The reaction is placed in an oil bath at 70° C. for 3.5 h, is cooled to room temperature, and concentrated in vacuo. The residue is partitioned between 100 mL 5% HCl and CH$_2$Cl$_2$ (4×50 mL). The combined organic layer is dried over anhydrous MgSO$_4$, filtered, and concentrated in vacuo to give 6.5 g of a crude amber solid. The crude material is chromatographed over 300 g silica gel (230–400 mesh) eluting with 30–40% EtOAc/hexane. Two sets of fractions with two different desired compounds are identified by TLC/UV. The two compounds eluted separately. The early-eluting pool of fractions is combined and concentrated to afford [7-chloro-2-(trimethylsilyl)furo[2,3-c]pyridin-5-yl]methanol (C5 as a white solid (46% yield). The later-eluting pool of fractions is combined and concentrated to provide (7-chlorofuro[2,3-c]pyridin-5-yl)methanol (C4) as a white solid (27% yield). MS (EI) for C$_8$H$_6$ClNO$_2$, m/z: 183 (M)$^+$ for C4. HRMS (FAB) calculated for C$_{11}$H$_{14}$ClNO$_2$Si m/z: 255.0482, found 255.0481 for C5.

Oxalyl chloride (3.1 mL, 35 mmol) is dissolved in 200 mL CH$_2$Cl$_2$ in dried flask under N$_2$. The flask is placed in a dry-ice/acetone bath at –78° C., DMSO (4.95 mL, 70 mmol) in 10 mL CH$_2$Cl$_2$ is added drop-wise, and the mixture is stirred for 20 min. C4 (5.5 g, 30 mmol) in 10 mL CH$_2$Cl$_2$ is added, and the reaction is stirred 30 min at –78° C. TEA (21.3 mL, 153 mmol) is then added. The reaction is stirred 30 min in the dry-ice/acetone bath at –78° C., an ice bath replaced the dry-ice/acetone bath, and the reaction is stirred 1 h and is washed with 100 mL 1:1 saturated NaCl/NaHCO$_3$. The organic layer is dried over anhydrous K$_2$CO$_3$, filtered, and then concentrated in vacuo to afford 7-chlorofuro[2,3-c]pyridine-5-carbaldehyde (C6) as a pale yellow solid (97% yield). MS (EI) for C$_8$H$_4$ClNO$_2$ m/z: 181 (M)$^+$.

C6 (3.0 g, 16.5 mmol) is dissolved in 40 mL DMSO. KH$_2$PO$_4$ (561 mg, 4.1 mmol) in 6.5 mL water is added and then NaClO$_2$ (2.6 g, 23.1 mmol) in 24 mL water is added, and the reaction is stirred overnight at rt. The reaction is diluted with 200 mL water, the pH is adjusted to 9 with 2N NaOH, and any remaining aldehyde is extracted into 3×50 mL ether. The pH of the aqueous layer is adjusted to 3 with 10% aqueous HCl and is extracted with 4×50 mL EtOAc. The combined organic layer is dried over anhydrous MgSO$_4$, filtered, and then concentrated in vacuo to a white solid. The solid is washed with ether and is dried to afford 7-chlorofuro[2,3-c]pyridine-5-carboxylic acid (C7) (55% yield). MS (CI) for C$_8$H$_4$ClNO$_3$, m/z: 198 (M+H)$^+$.

C7 (980 mg, 4.98 mmol) is dissolved in 75 mL MeOH containing 500 mg 20% palladium hydroxide on carbon in a 250 mL Parr shaker bottle. The reaction mixture is hydrogenated at 20 PSI for 24 h. The catalyst is removed by filtration and the filtrate is concentrated in vacuo to a white solid. The solid is dissolved in MeOH and is loaded onto 20 mL Dowex 50W-X2 ion exchange resin (hydrogen form) which had been prewashed with MeOH. The column is eluted with 50 mL MeOH followed by 150 mL 5% TEA in MeOH. The fractions with the desired compound are combined and concentrated to afford 2,3-dihydrofuro[2,3-c]pyridine-5-carboxylic acid (C8) (74% yield). HRMS (FAB) calculated for $C_8H_7NO_3+H$: 166.0504, found 166.0498 $(M+H)^+$.

Method A:

C8 (182 mg, 1.10 mmol) is suspended in 10 mL $CH_2Cl_2$ in a flask under $N_2$. TEA (153 μL, 1.10 mmol) is added and then bis (2-oxo-3-oxazolidinyl)phosphinic chloride (281 mg, 1.10 mmol) is added, and the mixture is stirred 30 min at rt. Solid (R)(+)-3-aminoquinuclidine free base (126 mg, 1.10 mmol) is added to the mixture, and the resulting mixture is stirred overnight at rt. The reaction is diluted with 10 mL saturated $NaHCO_3$, is stirred vigorously for 1 h, the layers are separated, and the aqueous layer is extracted with 3×10 mL $CH_2Cl_2$. The combined organic layer is concentrated to a pale oil which is dissolved in MeOH and passed over 15 mL Dowex 50W-X2 (hydrogen form) ion exchange resin eluting with MeOH followed by 5% TEA in MeOH. The fraction with the desired compound is concentrated in vacuo to give 150 mg of a pale oil. The crude oil is dissolved in 5 mL MeOH, 2 mL 1N methanolic HCl is added, and the solution is concentrated to a pale yellow solid. The solid is stirred with 5 mL isopropanol overnight. The solid is collected, washed with ether, and is dried to afford N-[(3R)-1-azabicyclo[2.2.2]oct-3-yl]-2,3-dihydrofuro[2,3-c]pyridine-5-carboxamide dihydrochloride (51% yield). HRMS (FAB) calculated for $C_{15}H_{19}N_3O_2+H$: 274.1555, found 274.1564 $(M+H)^+$.

EXAMPLE 2

N-[(3R)-1-azabicyclo[2.2.2]oct-3-yl]furo[3,2-c]pyridine-2-carboxamide

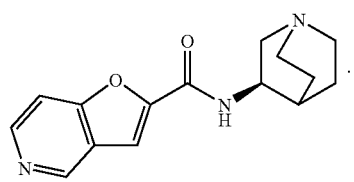

Preparation of the Acid:

4-Hydroxy-pyridine (23.8 g, 250 mmol) and $Na_2CO_3$ (7.4 g, 70 mmol) are added to 80 mL water. The reaction mixture is heated to reflux and a solution of iodine (23.2 g, 92 mmol) and potassium iodide (80 g, 482 mmol) in 250 mL water is slowly added drop-wise. The reaction is refluxed for 1 h after the addition. The mixture is filtered hot to remove a by-product, and the filtrate is cooled to rt, a solid is removed and dried to afford 3-iodo-4-pyridinol (C10) (32% yield). HRMS (FAB) calculated for $C_5H_4INO+H$: 221.9418, found 221.9416 $(M+H)^+$.

C10 (3.5 g, 15.8 mmol) is added to a suspension of triphenylphosphine (166 mg, 0.63 mmol) and palladium acetate (71 mg, 0.32 mmol) in 25 mL DMF in dry flask under $N_2$. Propioaldehyde diethyl acetal (2.3 mL, 15.8 mmol), cuprous iodide (120 mg, 0.63 mmol), and piperidine (1.6 mL, 16 mmol), are added successively, and the reaction is stirred 6 h at rt. The mixture is diluted with 125 mL EtOAc, is extracted with 4×50 mL 50% saturated 1:1 $NaCl/NaHCO_3$, and the organic layer is dried over anhydrous $Na_2SO_4$ and then filtered. The dried organic layer is concentrated in vacuo to a dark oil. The crude material is chromatographed over 40 g silica gel (Biotage), eluting with 50% EtOAc/hexane. The fractions with the desired compound are combined and concentrated to afford 2-(diethoxymethyl)furo[3,2-c]pyridine (C11) (64% yield). HRMS (FAB) calculated for $C_{12}H_{15}NO_3+H$: 222.1130, found 222.1123 $(M+H)^+$.

C11 (2.2 g, 10 mmol) and 10 mL formic acid are placed in a flask under $N_2$. Water (2 mL) is added, and the reaction is stirred 18 h at rt. The reaction is quenched into 100 mL saturated $NaHCO_3$, and the mixture is stirred vigorously for 30 min. The aqueous mixture is extracted with 4×25 mL EtOAc, the combined organic layer is dried over anhydrous $Na_2SO_4$, filtered, and concentrated in vacuo to afford furo[3,2-c]pyridine-2-carbaldehyde (C12) (88% yield). MS (EI) for $C_8H_5NO_2$, m/z: 147 $(M)^+$.

C12 (1.2 g, 8.2 mmol) is dissolved in 16 mL DMSO. $KH_2PO_4$ (312 mg, 2.3 mmol) in 3 mL water is added, and then $NaClO_2$ (1.3 g, 11.5 mmol) in 11 mL water is slowly added drop-wise to minimize exotherm. The reaction is stirred 6 h at rt, is diluted with 50 mL water, and the pH is adjusted to 9 with 2N NaOH. The mixture is extracted with 2×25 mL ether, the pH is adjusted to 3.5 with 10% HCl, the resulting white solid is collected, washed with water, and dried to afford furo[3,2-c]pyridine-2-carboxylic acid (C13) (67% yield). HRMS (FAB) calculated for $C_8H_5NO_3+H$: 164.0348, found 164.0346 $(M+H)^+$.

Coupling:

Example 2 is obtained (31% yield) using acid C13 according to Method A with non-critical changes. HRMS (FAB) calculated for $C_{15}H_{17}N_3O_2+H$: 272.1399, found 272.1389 $(M+H)^+$.

EXAMPLE 3

N-[(3R)-1-azabicyclo[2.2.2]oct-3-yl]-7-chlorofuro[2,3-c]pyridine-5-carboxamide hydrochloride

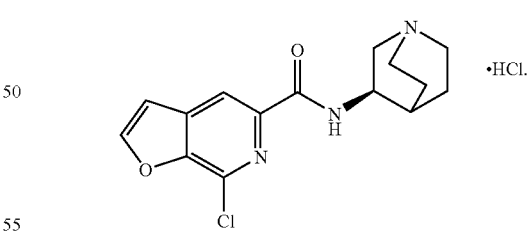

Method B:

Acid C7 (435 mg, 2.2 mmol) and TEA (307 μL, 2.2 mmol) in $CH_2Cl_2$ (10 mL) are stirred until dissolved, diphenylphosphoryl azide (431 μL, 2.0 mmol) is added, and the reaction is stirred for 20 min at rt. R-(+)-3-aminoquinuclidine (252 mg, 2.0 mmol) in $CH_2Cl_2$ (3 mL) is added, and the reaction is stirred for 18 h at rt. The solution is diluted with MeOH and loaded onto a column of AG 50W-X2 resin (hydrogen form). The column is rinsed with MeOH, and the product eluted with a 5% TEA/MeOH solution onto a column of AMBERJET 4400 OH resin. The eluted material is concentrated to an oil. The crude material is chromatographed over 25 g slurry-packed silica gel, eluting with 0.3% ammonium hydroxide/4% MeOH/CH$_2$Cl$_2$ followed by 0.5% ammonium hydroxide/5% MeOH/CH$_2$Cl$_2$, and finally 0.5% ammonium hydroxide/8% MeOH/CH$_2$Cl$_2$. The fractions with the desired compound are collected and concentrated to an oil. The oil is dissolved in a minimum amount of MeOH and 1N HCl in MeOH (5 mL) is added. The material is concentrated to dryness, dissolved in MeOH (1 mL) and isopropanol is added until a solid began to form. The resulting solid is collected under N$_2$ and dried in vacuo at 50° C. overnight to afford Example 3 as a white solid (56% yield). HRMS (FAB) calculated for C$_{15}$H$_{16}$ClN$_3$O$_2$+H: 306.1009, found 306.1020 (M+H)$^+$.

EXAMPLE 4

N-[(3R)-1-azabicyclo[2.2.2]oct-3-yl]furo[2,3-c]pyridine-5-carboxamide dihydrochloride

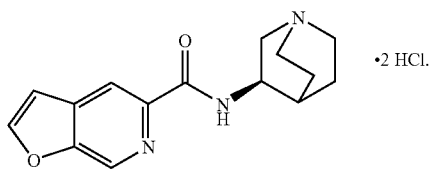

Preparation of the Acid:

C5 (1.05 g, 4.1 mmol) and 10% Pd/C catalyst (1.05 g) are placed in 20 mL absolute EtOH. Cyclohexene (4 mL, 40.1 mmol) is added, and the reaction is refluxed for 2.5 h, and then filtered through celite. The filter cake is washed with 1:1 EtOH/CH$_2$Cl$_2$, and the filtrate is concentrated to a pale yellow solid. The residue is partitioned between 40 mL saturated NaHCO$_3$ and extracted with CH$_2$Cl$_2$ (4×20 mL). The combined organic layer is dried over anhydrous MgSO$_4$, filtered, and then concentrated in vacuo to a pale oil (1.04 g). The pale oil is chromatographed over 50 g silica gel (230–400 mesh) eluting with 50–70% EtOAc/hexane. The fractions with the desired compound combined and concentrated to afford 5-hydroxymethyl-2-trimethylsilyl-furo[2,3-c]pyridine (C14) as a white solid (90% yield). MS (EI) for C$_{11}$H$_{15}$NO$_2$Si, m/z: 221 (M)$^+$.

C14 (770 mg, 3.48 mmol) is dissolved in 10 mL MeOH. 2N NaOH (3 mL, 6 mmol) is added, and the reaction is stirred for 1.5 h at rt. The solution is concentrated in vacuo to a residue. Water (20 mL) is added to the residue and extracted with 4×10 mL CH$_2$Cl$_2$. The combined organic layer is dried over K$_2$CO$_3$, filtered, and then concentrated in vacuo to afford furo[2,3-c]pyridin-5-yl methanol (C16) as a white solid (90% yield). Analysis calculated for C$_8$H$_7$NO$_2$: C, 64.42; H, 4.73; N, 9.39. Found: C, 64.60; H. 4.56; N, 9.44.

Oxalyl chloride (685 µL, 7.8 mmol) is dissolved in 30 mL CH$_2$Cl$_2$ in a dry flask under N$_2$. The flask is placed in a dry-ice/acetone bath, DMSO (1.11 mL, 15.6 mmol) in 5 mL CH$_2$Cl$_2$ is added drop-wise, and the mixture is stirred for 20 min. C16 (1.0 g, 6.7 mmol) in 10 mL CH$_2$Cl$_2$ is added, and the reaction is stirred 30 min at −78° C. TEA (4.7 mL, 33.5 mmol) is added, the reaction is allowed to warm to rt, is stirred 1 h, and is washed with 25 mL saturated NaHCO$_3$. The organic layer is dried over anhydrous K$_2$CO$_3$, filtered, and is concentrated in vacuo to an orange solid. The crude material is chromatographed over 50 g silica gel (230–400 mesh) eluting with 33% EtOAc/hexane. The fractions with the desired compound are combined and concentrated to provide furo[2,3-c]pyridine-5-carbaldehyde (C17) as a white solid (86% yield). MS (EI) for C$_8$H$_5$NO$_2$, m/z: 147 (M)$^+$.

C17 (850 mg, 5.8 mmol) is dissolved in 10 mL DMSO. KH$_2$PO$_4$ (221 mg, 1.6 mmol) in 3 mL water is added and then NaClO$_2$ (920 mg, 8.2 mmol) in 7 mL water is added, and the reaction is stirred 3 h at rt. The reaction is diluted with 25 mL water, the pH is adjusted to 10 with 2N NaOH, and the mixture is extracted with 3×20 mL ether. The combined ether layer is discarded. The pH of the aqueous layer is adjusted to 3.5 with 10% aqueous HCl and is extracted with 13×10 mL 10% MeOH/CH$_2$Cl$_2$. The MeOH/CH$_2$Cl$_2$ organic layer is dried over anhydrous Na$_2$SO$_4$, filtered, and concentrated in vacuo to a pale oil. The residual DMSO is removed under a stream of N$_2$ at rt to provide a white paste. The paste is dissolved in MeOH and is concentrated to dryness. The white solid is washed with ether and dried to afford crude furo[2,3-c]pyridine-5-carboxylic acid (C18) (94% yield). MS (ESI) for C$_8$H$_5$NO$_3$, 162.8 (M−H)$^−$.

Method C:

Acid C18 (1.96 g, 12.0 mmol), DIEA (6.27 mL, 36.0 mmol), and R-(+)-3-aminoquinuclidine dihydrochloride (2.42 g, 12.1 mmol) are added to DMF (60 mL), and the reaction is cooled in an ice bath. HATU (4.57 g, 12.0 mmol) is added, the solution allowed to warm to rt over 2.5 h, then concentrated in vacuo. The residue is stirred with saturated NaHCO$_3$ (30 mL) for 30 min, then extracted with CHCl$_3$ (10×50 mL). The combined organic layer is dried over Na$_2$SO$_4$ and is concentrated in vacuo. The crude material is chromatographed over 130 g slurry-packed silica gel, eluting with 0.5% ammonium hydroxide in 10% MeOH/CHCl$_3$. The appropriate fractions are combined and concentrated to a residue. The residue is dissolved in MeOH (26.5 ml), treated with 1M HCl in MeOH (32.5 ml) and the salt allowed to settle out of solution and is collected to give 2.86 g of a white solid. Trituration with hot methanol followed by cooling gives Example 4 as a white solid (56% yield). MS (EI) for C$_{15}$H$_{17}$N$_3$O$_2$, m/z: 271 (M)$^+$.

EXAMPLE 5

N-[(3R)-1-azabicyclo[2.2.2]oct-3-yl]-3,3-dimethyl-2,3-dihydrofuro[2,3-c]pyridine-5-carboxamide dihydrochloride

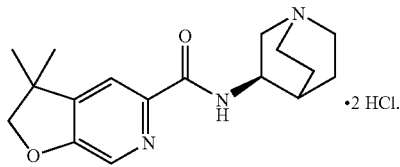

Preparation of the Acid:

C2 (6.3 g, 22 mmol) is dissolved in 30 mL DMF in a dry flask under N$_2$. The flask is placed in an ice bath, and 60% sodium hydride in mineral oil (880 mg, 22 mmol) is added. The reaction is stirred 30 min while the flask is kept in an ice bath. The ice bath is removed for 30 min and then the flask is placed back into the ice bath to cool the reaction. 3-Bromo-2-methylpropene (23.1 mmol) is added, and the reaction is stirred overnight at rt. The reaction is diluted with 150 mL EtOAc and is washed with 4×50 mL 50% saturated 1:1 NaCl/NaHCO$_3$. The organic layer is dried over anhydrous Na$_2$SO$_4$, filtered, and then concentrated in vacuo to a pale oil which is crystallized from hexanes to afford (6-chloro-4-iodo-5-[(2-methyl-2-propenyl)oxy]-2-pyridinyl)methanol (C19) (86% yield). HRMS (FAB) calculated for C$_{10}$H$_{11}$ClINO$_2$+H: 339.9603, found 339.9604 (M+H)$^+$.

C19 (6.3 g, 18.9 mmol), sodium formate (1.49 g, 21.8 mmol), TEA (8 mL, 57.2 mmol), palladium acetate (202 mg, 0.9 mmol) and tetra (n-butyl)ammonium chloride (5.25 g, 18.9 mmol) are added to 30 mL DMF in a dry flask under N$_2$. The reaction is warmed to 60° C. for 5 h, is poured into 150 mL EtOAc, and is washed with 4×50 mL 50% saturated 1:1 NaCl/NaHCO$_3$. The organic layer is dried over anhydrous Na$_2$SO$_4$, filtered, and concentrated in vacuo to a pale oil. The crude material is chromatographed over 40 g silica gel (Biotage), eluting with 30% EtOAc/hexane. The fractions with the desired compound are combined and concentrated to afford (7-chloro-3,3-dimethyl-2,3-dihydrofuro[2,3-c]pyridin-5-yl)methanol (C20) (54% yield). MS (EI) for C$_{10}$H$_{12}$ClNO$_2$, m/z: 213 (M)$^+$.

C20 (2.11 g, 9.9 mmol) and 600 mg 10% Pd/C catalyst are placed in 30 mL EtOH in a 250 mL Parr shaker bottle. 2N NaOH (5 mL, 10 mmol) is then added and the mixture is hydrogenated at 20 PSI for 2.5 h. The catalyst is removed by filtration, and the filtrate is concentrated in vacuo to an aqueous residue. Saturated NaHCO$_3$ (20 mL) is added to the residue and extracted with 4×20 mL CH$_2$Cl$_2$. The combined organic layer is dried over anhydrous K$_2$CO$_3$, filtered, and concentrated in vacuo to afford (3,3-dimethyl-2,3-dihydrofuro[2,3-c]pyridin-5-yl)methanol (C21) (92% yield). MS (EI) for C$_{10}$H$_{13}$NO$_2$, m/z: 179 (M)$^+$.

Oxalyl chloride (869 μL, 9.9 mmol) is dissolved in 50 mL CH$_2$Cl$_2$ in a dry flask under N$_2$. The flask is placed in a dry-ice/acetone bath at −78° C., DMSO (1.41 mL, 19.8 mmol) in 5 mL CH$_2$Cl$_2$ is added drop-wise, and the mixture is stirred for 20 min. 3,3-Dimethyl-2,3-dihydrofuro[2,3-c]pyridin-5-yl)methanol (C21) (1.53 g, 8.5 mmol) in 5 mL CH$_2$Cl$_2$ is then added, and the reaction is stirred 30 min at −78° C. TEA (5.9 mL, 42.5 mmol) is added and the reaction is stirred 20 min at −78° C. The dry-ice/acetone bath is removed, the reaction is stirred 1 h, and the reaction is washed with 25 mL saturated NaHCO$_3$. The organic layer is dried over anhydrous K$_2$CO$_3$, filtered, and then concentrated in vacuo to an orange solid. The crude material is chromatographed over 40 g silica gel (Biotage) eluting with 25% EtOAc/hexane. The fractions with the desired compound are combined and concentrated to afford 3,3-dimethyl-2,3-dihydrofuro[2,3-c]pyridine-5-carbaldehyde (C22) (92% yield). MS (EI) for C$_{10}$H$_{11}$NO$_2$, m/z: 177 (M)$^+$.

C22 (1.35 g, 7.62 mmol) is dissolved in 40 mL THF, 20 mL t-butanol, and 20 mL water. KH$_2$PO$_4$ (3.11 g, 22.9 mmol) and NaClO$_2$ (2.58 g, 22.9 mmol) are added, and the reaction is stirred over the weekend at rt. The reaction is concentrated in vacuo to a residue. The residue is partitioned between 20 mL water and CH$_2$Cl$_2$ (2×50 mL). The combined organic layer is dried over anhydrous Na$_2$SO$_4$, filtered, and then concentrated in vacuo to afford crude 3,3-dimethyl-2,3-dihydrofuro[2,3-c]pyridine-5-carboxylic acid (C23) (99% yield). HRMS (FAB) calculated for C$_{10}$H$_{11}$NO$_3$+H: 194.0817, found 194.0808 (M+H)$^+$.

Coupling:
Example 5 is obtained (21% yield) using acid C23 according to Method A with non-critical changes. HRMS (FAB) calculated for C$_{17}$H$_{23}$N$_3$O$_2$+H: 302.1868, found 302.1880 (M+H)$^+$.

EXAMPLE 6

N-[(3R)-1-azabicyclo[2.2.2]oct-3-yl]-2-methylfuro[2,3-c]pyridine-5-carboxamide dihydrochloride

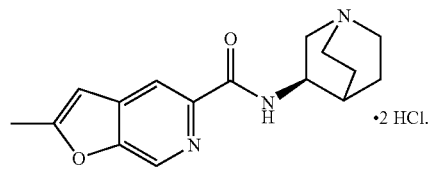

Preparation of the Acid:
C2 (4.6 g, 16 mmol). propargyl trimethylsilane (2 g, 17.8 mmol), bis(triphenylphosphine)palladium dichloride (156 mg, 0.21 mmol), cuprous iodide (122 mg, 0.64 mmol), and piperidine (3.52 mL, 26.6 mmol) are added to 25 mL DMF in a dry flask under N$_2$. The mixture is warmed to 45° C. for 7 h, is stirred overnight at rt, and is diluted with 150 mL EtOAc. The mixture is washed with 4×50 mL 50% saturated 1:1 NaCl/NaHCO$_3$. The organic layer is dried over anhydrous Na$_2$SO$_4$, filtered, and then concentrated in vacuo to an amber oil. The crude material is chromatographed over 40 g silica gel (230–400 mesh) eluting with 35% EtOAc/hexane. The fractions with the desired compound are combined and concentrated to afford (7-chloro-2-methylfuro[2,3-c]pyridin-5-yl)methanol (C24) (44% yield). MS (CI) for C$_9$H$_8$ClNO$_2$, m/z: 198 (M+H)$^+$.

C24 (2.0 g, 10.8 mmol) is added to 500 mg 10% Pd/C catalyst in 25 mL EtOH in a 250 mL Parr shaker bottle. 2N NaOH (6 mL, 12 mmol) is added, and the reaction is hydrogenated at 20 PSI for 6 h. The catalyst is removed by filtration, and the filtrate is concentrated in vacuo to an aqueous residue. The residue is partitioned between 50 mL 50% saturated NaCl and 30 mL CH$_2$Cl$_2$. The organic layer is dried over anhydrous K$_2$CO$_3$, filtered, and then concentrated in vacuo to afford(2-methylfuro[2,3-c]pyridin-5-yl)methanol (C25) (77% yield). MS (CI) for C$_9$H$_9$NO$_2$, m/z: 164 (M+H)$^+$.

Oxalyl chloride (784 μL, 8.9 mmol) is dissolved in 25 mL CH$_2$Cl$_2$ in a dry flask under N$_2$. The flask is placed in a dry-ice/acetone bath at −78° C., and DMSO (1.26 mL, 17.8 mmol) in 5 mL CH$_2$Cl$_2$ is added. The mixture is stirred for 20 min and C25 (1.53 g, 8.5 mmol) in 5 mL CH$_2$Cl$_2$ is added. The reaction is stirred 1 h, TEA (5.9 mL, 42.5 mmol) is added, and the reaction is stirred 30 min at −78° C. The flask is placed in an ice bath, and the reaction is stirred 1 h. The reaction is washed with 50 mL saturated NaHCO$_3$. The organic layer is dried over anhydrous K$_2$CO$_3$, filtered, and then concentrated in vacuo to a tan solid. The crude material is chromatographed over 40 g silica gel (Biotage) eluting with 25% EtOAc/hexane. The fractions with the desired compound are combined and concentrated to afford 2-methylfuro[2,3-c]pyridine-5-carbaldehyde (26) (99% yield). MS (EI) for C$_9$H$_7$NO$_2$, m/z: 161 (M)$^+$.

C26 (1.15 g, 7.1 mmol) is dissolved in 40 mL THF, 20 mL t-butanol, and 20 mL water. 2-Methyl-2-butene (6.5 mL, 57.4 mmol) is added, and then KH$_2$PO$_4$ (3.11 g, 22.9 mmol) and NaClO$_2$ (2.58 g, 22.9 mmol) are added. The reaction is stirred 6 h at rt. The reaction is concentrated in vacuo. Water (20 ml) is added to the residue, a white solid remained. The white solid is collected, washed with water and then with ether, and is dried to afford 2-methylfuro[2,3-c]pyridine-5-carboxylic acid (C27) (70% yield). MS (EI) for C$_9$H$_7$NO$_3$, m/z: 177 (M)$^+$.

Coupling:

Example 6 is obtained (54% yield) using acid C27 according to Method A with non-critical changes. HRMS (FAB) calculated for C$_{16}$H$_{19}$N$_3$O$_2$+H: 286.1555, found 286.1560 (M+H)$^+$.

EXAMPLE 7

N-[(3R)-1-azabicyclo[2.2.2]oct-3-yl]furo[2,3-c]pyridine-2-carboxamide dihydrochloride

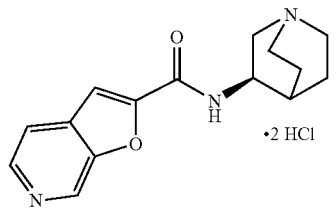

Preparation of the Acid:

Bromine (52 mL, 1.0 mole) is added drop-wise to a solution of NaOH (93 g, 2.32 mole) in 800 mL water in an ice bath. The resulting bromate solution is added drop-wise to a solution of 3-pyridinol (47.6 g, 0.5 mole) in 125 mL water containing NaOH (20 g, 0.5 mole) in a flask that is in an ice bath, and the reaction is stirred 1.5 h at 0–5° C. The pH is adjusted to 3 with 12N HCl, and the solid precipitate is collected, washed with water, and dried. The crude solid is dissolved in 400 mL EtOAc, and the solution is diluted with 1600 mL heptane, and is allowed to crystallize overnight. The solid is collected to give 2-bromo-3-pyridinol (C29). The mother liquor is concentrated in vacuo to a pale yellow solid. The crude solid is recrystallized from 1:1 EtOH/water to afford 2,6-dibromo-3-pyridinol (C28) (29% yield). HRMS (FAB) calculated for C$_5$H$_3$Br$_2$NO+H: 251.8661, found 251.8669 (M+H)$^+$.

C28 (15 g, 59 mmol), NaHCO$_3$ (18 g, 205 mmol), and iodine (18.6 g, 73 mmol) are added to 160 mL water. The reaction is stirred for 5 days at rt, the excess iodine is quenched with saturated sodium thiosulfate, and the pH is adjusted to 2 with 12N HCl. The white solid is collected, washed with water, and dried to give 22 g (97% crude) of 2,6-dibromo-4-iodo-3-pyridinol (C30).

C30 (14 g, 37 mmol), propioaldehyde diethyl acetal (5 g, 39 mmol), bis(triphenylphosphine)palladium diacetate (554 mg, 0.74 mmol), cuprous iodide (282 mg, 1.5 mmol), and piperidine (7.3 mL, 74 mmol) are added to 50 mL DMF in a dry flask under N$_2$. The mixture underwent a vigorous exotherm, is cooled in an ice bath, and the mixture is stirred 6 h at rt. The mixture is diluted with 250 mL EtOAc, is washed with 4×100 mL 50% saturated 1:1 NaCl/NaHCO$_3$, and the organic layer is dried over anhydrous MgSO$_4$, filtered, and is concentrated in vacuo to an amber oil. The crude material is chromatographed over 250 g silica gel (230–400 mesh) eluting with 5% EtOAc/hexane. The fractions with the desired compound are combined and concentrated to afford 5,7-dibromo-2-(diethoxymethyl)furo[2,3-c]pyridine (C31) (28% yield). HRMS (FAB) calculated for C$_{12}$H$_{13}$Br$_2$NO$_3$+H: 377.9341, found 377.9330 (M+H)$^+$.

C31 (2.5 g, 6.6 mmol) is added to 500 mg 10% Pd/C catalyst and 2N NaOH (6.6 mL, 13.2 mmol) in 50 mL EtOH in a 250 mL Parr shaker bottle. The mixture is hydrogenated at 20 PSI for 8 h, the catalyst is removed by filtration, and the filtrate is concentrated to a pale oil. The crude material is chromatographed over 40 g silica gel (Biotage) eluting with 40% EtOAc/hexane. The fractions with the desired compound are combined and concentrated to afford 2-(diethoxymethyl)furo[2,3-c]pyridine (C32) (68% yield).

C32 (950 mg, 4.29 mmol) is dissolved in 5 mL formic acid. Water (1 mL) is added, and the reaction is stirred overnight at rt. The reaction is warmed to 45° C. for 8 h. The reaction is concentrated in vacuo to give a residue. The residue is partitioned between 20 mL saturated NaHCO$_3$ and CH$_2$Cl$_2$ (4×10 mL). The combined organic layer is dried over anhydrous K$_2$CO$_3$, filtered and then concentrated in vacuo to afford furo[2,3-c]pyridine-2-carbaldehyde (C33) (95% yield). MS (EI) for C$_8$H$_5$NO$_2$, (EI) m/z: 147 (M)$^+$.

C33 (558 mg, 3.79 mmol) is dissolved in 25 mL THF, 12 mL t-butanol, and 12 mL water. KH$_2$PO$_4$ (1.03 g, 7.6 mmol) and NaClO$_2$ (1.28 g, 114 mmol) are added, and the reaction is stirred 3 h at rt. The reaction is concentrated in vacuo to a residue. Water (20 mL) is added, and the pH of the mixture is adjusted to 3 with 10% aqueous HCl. The mixture is stirred 20 min in an ice bath, the resultant white solid is collected, washed with water and dried to afford furo[2,3-c]pyridine-2-carboxylic acid (C34) (84% yield). HRMS (FAB) calculated for C$_8$H$_5$NO$_3$+H: 164.0348, found 164.0344 (M+H)$^+$.

Coupling:

Example 7 is obtained as a white solid with a yield of 18% using acid C34 according to Method A with non-critical changes. HRMS (FAB) calculated for C$_{15}$H$_{17}$N$_3$O$_2$+H: 272.1399, found 272.1402 (M+H)$^+$.

EXAMPLE 8

N-[(3R)-1-azabicyclo[2.2.2]oct-3-yl]furo[2,3-b]pyridine-2-carboxamide hydrochloride

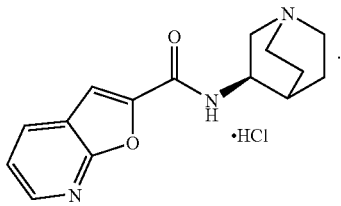

Preparation of the Acid:

Ethyl glycolate (35.5 mL, 375 mmol) is slowly added (over 20 min) to a slurry of NaOH (15.8 g, 394 mmol) in 1,2-dimethoxyethane (400 mL) in a dry flask under N$_2$ with the flask being in an ice bath. The mixture is allowed to warm to rt, is stirred for 30 min, and ethyl 2-chloronicotinate (27.84 g, 150 mmol) in 1,2-dimethoxyethane (50 mL) is added over 10 min. The reaction is warmed to 65° C. for 15 h in an oil bath. The mixture is concentrated to dryness, the residue is dissolved in water (500 mL), washed with hexane (500 mL), acidified to pH 3 with 5% HCl, and extracted with $CHCl_3$ (4×400 mL). The combined organic layer is dried over $MgSO_4$, filtered, and concentrated to a yellow solid. The solid is suspended in ether (200 mL) and heated on a steam bath until concentrated to a volume of 40 mL. The material is allowed to crystallize overnight, then filtered to afford ethyl 3-hydroxyfuro[2,3-b]pyridine-2-carboxylate as a pale orange solid (41% yield). Additional material is obtained by concentrating the filtrate. Recrystallization in ether a second time affords ethyl 3-hydroxyfuro[2,3-b]pyridine-2-carboxylate (C40) as a pale yellow solid (7.3% yield). MS (EI) for $C_{10}H_9NO_4$, m/z: 207 (M)$^+$.

C40 (207 mg, 1.0 mmol) is was added to TEA (139 µL, 1.0 mmol) in $CH_2Cl_2$ (5 mL) at rt and 2-[N,N-bis(trifluoromethylsulfonyl)amino]-5-chloropyridine (393 mg, 1.0 mmol) is added. The solution is stirred for 1 h at rt, diluted with EtOAc (25 mL) and washed with 50% saturated brine (2×15 mL). The organic layer is dried over $Na_2SO_4$, filtered, and concentrated to a yellow oil which solidified upon standing. The crude material is adsorbed onto silica gel (1.2 g) and chromatographed over 25 g slurry-packed silica gel, eluting with 20% EtOAc/hexane. The fractions with the desired compound are combined and concentrated to afford ethyl 3-([(trifluoromethyl)sulfonyl]oxy)furo[2,3-b]pyridine-2-carboxylate (C41) as a white crystalline solid (98% yield). Analysis calculated for $C_{11}H_8F_3NO_6S$: C, 38.94; H, 2.38; N, 4.13, found: C, 38.84; H, 2.29; N, 4.11.

C41 (1.36 g, 4.0 mmol) is added to 10% Pd/C catalyst (68 mg) and $NaHCO_3$ (336 mg, 4.0 mmol) in EtOH (100 mL)/water (5 mL) in a 250 mL Parr shaker bottle. The mixture is hydrogenated at 10 PSI for 5 h, filtered and concentrated to a residue. The residue is partitioned between 50% saturated $NaHCO_3$ (80 mL) and EtOAc (80 mL). The organic layer is dried over $Na_2SO_4$, filtered, and concentrated in vacuo to a colorless oil which solidified upon standing (793 mg). The crude material is chromatographed over 40 g slurry-packed silica gel, eluting with 25% EtOAc/hexane. The fractions with the desired compound are combined and concentrated to afford ethyl furo[2,3-b]pyridine-2-carboxylate (C42) as a white solid (90% yield). MS (EI) for $C_{10}H_9NO_3$, m/z: 191 (M)$^+$.

C42 (758 mg, 3.96 mmol) is dissolved in MeOH (20 mL) and lithium hydroxide monohydrate (366 mg, 8.7 mmol) in 6 mL water is added under $N_2$. The reaction is stirred at rt for 2 h, concentrated to near-dryness, diluted with water (5 mL) and acidified to pH 3 with 10% HCl. The resulting solid is collected by filtration, washed with additional water and dried to afford furo[2,3-b]pyridine-2-carboxylic acid (C43) as a white solid (97% yield). MS (EI) for $C_8H_5NO_3$, m/z: 163 (M)$^+$.

Coupling:

Example 8 is obtained as a white solid (29% yield) using acid C43 according to Method A with non-critical changes. MS (EI) for $C_{15}H_{17}N_3O_2$, m/z: 271 (M)$^+$.

EXAMPLE 9

N-[(3R)-1-azabicyclo[2.2.2]oct-3-yl]-3-methylfuro[2,3-c]pyridine-5-carboxamide

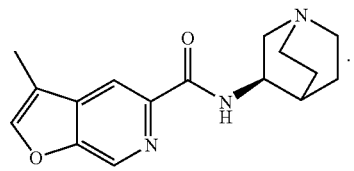

Method D:

C2 (7.14 g, 25.0 mmol) is dissolved in DMF (50 mL) in a dry flask under $N_2$, sodium hydride (60% dispersion in mineral oil) (1.0 g, 25.0 mmol) is added, and the reaction is stirred for 1 h at rt. Allyl bromide (2.38 mL, 27.5 mmol) is added, and the reaction mixture is stirred 48 h at rt. The mixture is diluted with EtOAc (50 mL) and washed 4×25 mL of a 50% saturated solution of 1:1 $NaCl/NaHCO_3$. The organic layer is dried over $MgSO_4$, filtered and concentrated in vacuo to a white solid. The solid is washed with hexane and dried to afford 3-(allyloxy)-2-chloro-6-(hydroxymethyl)-4-iodopyridine (C50) as a white solid (68% yield). MS (EI) for $C_9H_9ClINO_2$, m/z: 325 (M)$^+$.

C50 (5.51 g, 16.9 mmol) is suspended in benzene (30 mL) in a dry flask under $N_2$. Azo(bis)isobutyryl nitrite (289 mg, 1.8 mmol) is added, the mixture is rapidly heated to reflux, and tributyltin hydride (4.91 mL, 18.2 mmol) in benzene (10 mL) is added. The solution is refluxed for 1.5 h, allowed to cool to rt and concentrated in vacuo. The resulting residue is chromatographed over 125 g slurry-packed silica gel, eluting with a gradient of EtOAc/hexane (20%–60%). The fractions with the desired compound are combined and concentrated to a colorless oil that solidified upon standing to afford (7-chloro-3-methyl-2,3-dihydrofuro[2,3-c]pyridin-5-yl)methanol (C51) as a white solid (89% yield). MS (ESI) for $C_9H_{10}ClNO_2$+H, m/z: 200.1 (M+H)$^+$.

C51 (3.00 g, 15.0 mmol) is added to 20% palladium hydroxide on carbon (800 mg) and 2N NaOH (9.2 mL, 18.2 mmol) in a Parr shaker bottle. The mixture is hydrogenated at 20 PSI for 3 h, is filtered through celite and concentrated in vacuo to a residue. The resulting residue is partitioned between water (50 mL) and $CH_2Cl_2$ (4×30 mL). The combined organic layer is dried over $MgSO_4$, filtered, and concentrated to a colorless oil which solidified upon standing to afford 2.50 g (greater than 100% yield) of (3-methyl-2,3-dihydrofuro[2,3-c]pyridin-5-yl)methanol (C52) as a white crystalline solid. MS (EI) for $C_9H_{11}NO_2$, m/z: 165 (M)$^+$.

C52 (2.48 g, 15.03 mmol) is dissolved in pyridine (15 mL), acetic anhydride (4.18 mL, 45.09 mmol) is added, and stirred for 16 h at rt under $N_2$. The reaction is concentrated in vacuo, and the residue is diluted with EtOAc (75 mL), washed with 50% saturated $NaHCO_3$ (4×30 mL), and dried over $MgSO_4$. The organic layer is filtered and concentrated in vacuo to afford (3-methyl-2,3-dihydrofuro[2,3-c]pyridin-5-yl)methyl acetate (C53) as a colorless oil (92% yield). MS (EI) for $C_{11}H_{13}NO_3$, m/z: 207 (M)$^+$.

C53 (2.85 g, 13.8 mmol) is dissolved in dioxane (100 mL), 2,3,5,6-tertachlorobenzoquinone (3.72 g, 15.1 mmol) is added, and the reaction is heated to reflux for 17 h. The reaction is concentrated in vacuo. The resulting brown solid is washed with 1:1 EtOAc/ether (50 mL), and the insoluble material filtered off. The filtrate is concentrated to a brown solid, dissolved in MeOH (50 mL), treated with 2N NaOH (16 mL, 32 mmol), and stirred at rt for 1 h. The mixture is concentrated to dryness, dissolved in 1N NaOH (75 mL), and extracted with $CH_2Cl_2$ (4×50 mL). The combined organic layer is dried over $K_2CO_3$, filtered, and concentrated to a white solid (2.0 g). The crude material is adsorbed onto silica gel (4 g) and chromatographed over a standard 40 g Biotage column, eluting with 90% EtOAc/hexane. The fractions with the desired compound are collected and concentrated to afford (3-methylfuro[2,3-c]pyridin-5-yl)methanol (C54) as a white solid (84% yield). MS (EI) for $C_9H_9NO_2$, m/z: 163 (M)$^+$.

Oxalyl chloride (1.16 mL, 13.2 mmol) is added to $CH_2Cl_2$ (30 mL) in a dry flask under $N_2$ and in a dry-ice/acetone bath at −78° C. DMSO (18.80 mL, 26.5 mmol) is slowly added. The solution is stirred for 20 min, and C54 (1.88 g, 11.5 mmol) is added. The mixture is stirred for 1 h at −78° C., then 30 min at 0–5° C. The material is washed with saturated $NaHCO_3$ (75 mL), dried over $K_2CO_3$, filtered, and concentrated in vacuo to a yellow solid (3.23 g). The crude material is adsorbed onto silica gel (6 g) and chromatographed over a standard 40 g Biotage column, eluting with 25% EtOAc/hexane. The fractions with the desired compound are concentrated to afford 3-methylfuro[2,3-c]pyridine-5-carbaldehyde (C55) as a white solid (72% yield). MS (EI) for $C_9H_7NO_2$, m/z: 161 (M)$^+$.

C55 (1.33 g, 8.28 mmol) is dissolved in THF (50 mL), tert-butylalcohol (25 mL) and water (25 mL), under $N_2$, and $NaClO_2$ (2.81 g, 24.84 mmol) and $KH_2PO_4$ (2.25 g, 16.56 mmol) are added. The reaction mixture is stirred overnight at rt, concentrated to dryness, dissolved in 50% saturated brine (60 mL) and extracted with ether (3×). TLC of extracts indicated acid as well as residual aldehyde, so the organic and aqueous layers are combined and basified to pH 10 with ammonium hydroxide. The layers are separated and the residual aldehyde extracted with additional ether. The aqueous layer is acidified to pH 3 with concentrated HCl, then extracted with $CH_2Cl_2$ (4×). Large amounts of acid remained in the aqueous layer, so the aqueous layer is concentrated to dryness. The solid is triturated with $CHCl_3$ (4×), and then 10% MeOH/$CH_2Cl_2$ (4×) to extract much of the acid into the supernatant. The combined organic layer is dried over $Na_2SO_4$, filtered, and concentrated to a tan solid (1.69 g, greater than 100% isolated yield). The solid is diluted with $CHCl_3$ and refluxed for 3 h. The flask is removed from heat, allowed to cool slightly, then filtered. The filtrate is concentrated to a tan solid (1.02 g). The solid is triturated with ether, filtered and dried to afford 3-methylfuro[2,3-c]pyridine-5-carboxylic acid (C56) as a light tan solid (51% yield). MS (CI) for $C_9H_7NO_3$, m/z: 178 (M+H)$^+$.

Coupling:

Example 9 is obtained as an off-white solid (64% yield) using acid C56 according to Method A with non-critical changes. HRMS (FAB) calculated for $C_{16}H_{19}N_3O_2$+H: 286.1555, found 286.1562 (M+H)$^+$.

EXAMPLE 10

N-[(3R)-1-azabicyclo[2.2.2]oct-3-yl]-3-ethylfuro[2,3-c]pyridine-5-carboxamide dihydrochloride

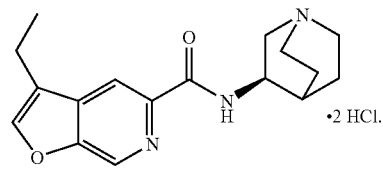

Using Method D with non-critical changes and starting with 1-chloro-2-butene and C2, the corresponding 3-ethylfuro[2,3-c]pyridine-5-carboxylic acid (C60) is prepared. HRMS (FAB) calculated for $C_{10}H_9NO_3$+H: 192.0661, found 192.0659 (M+H)$^+$.

Example 10 is obtained as an off-white solid (49% yield) using acid C60 according to Method A with non-critical. HRMS (FAB) calculated for $C_{17}H_{21}N_3O_2$+H: 300.1712, found 300.1716 (M+H)$^+$.

EXAMPLE 11

N-[(3R)-1-azabicyclo[2.2.2]oct-3-yl]-3-isopropyl-furo[2,3-c]pyridine-5-carboxamide

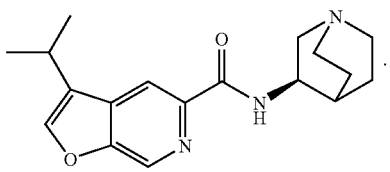

Using Method D with non-critical changes and starting with 1-chloro-3-methyl-2-butene and 2-chloro-6-(hydroxymethyl)-4-iodo-3-pyridinol (C2), the corresponding 3-isopropylfuro[2,3-c]pyridine-5-carboxylic acid (C70) is made. HRMS (FAB) calculated for $C_{11}H_{11}NO_3$+H: 206.0817, found 206.0817 (M+H)$^+$.

Example 11 is obtained as an off-white solid (56% yield) using acid C70 according to Method A with non-critical changes. HRMS (FAB) calculated for $C_{18}H_{23}N_3O_2$+H: 314.1868, found 314.1874 (M+H)$^+$.

EXAMPLE 12

N-[(3R)-1-azabicyclo[2.2.2]oct-3-yl]-7-(methylsulfanyl)furo[2,3-c]pyridine-5-carboxamide dihydrochloride

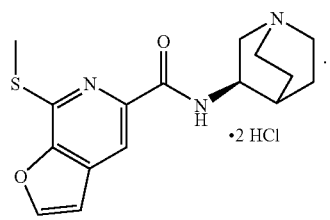

Example 3 (220 mg, 0.72 mmol) and sodium thiomethoxide (55 mg, 0.79 mmol) are added to DMF (3 mL) and stirred for 2 h at rt. The solution is diluted with MeOH and loaded onto a column of AG 50W-X2 resin (hydrogen form). The column is rinsed with MeOH, and the product eluted with a 5% TEA/MeOH solution onto a column of AMBERJET 4400 OH resin. The eluted material is concentrated to an oil (116 mg). The crude material is chromatographed over 5 g slurry-packed silica gel, eluting with 0.5% ammonium hydroxide/8% MeOH/CH$_2$Cl$_2$. The fractions with the desired compound are concentrated, dissolved in MeOH, and 1M methanolic HCl (1.15 mL) is added. The mixture is concentrated to dryness. The resulting residue is dissolved in a small amount of isopropyl alcohol, and ether is added drop-wise until a solid began to form. The mixture is stirred for 16 h. The resulting solid is filtered under N$_2$ to afford Example 12 as a white solid (23% yield). HRMS (FAB) calculated for C$_{16}$H$_{19}$N$_3$O$_2$S+H: 318.1276, found 318.1278 (M+H)$^+$.

EXAMPLE 13

N-((3R)-1-azabicyclo[2.2.2]oct-3-yl)thieno[2,3-b]pyridine-2-carboxamide dihydrochloride

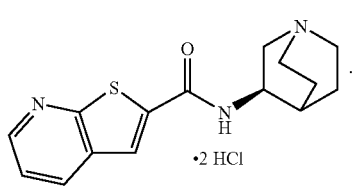

Preparation of the Acid:

THF (200 mL) in a dry flask under N$_2$ is chilled by placing the flask in a dry-ice/acetone bath at −78° C. Butyllithium (125 mL, 200 mmol) is added drop-wise, followed by the drop-wise addition of iodobenzene (11.19 mL, 100 mmol) in THF (10 mL). The solution is allowed to stir for 30 min at −78° C. Diisopropylamine (0.70 mL, 5 mmol) in THF (3 mL) and 2-chloropyridine (9.46 mL, 100 mmol) in THF (30 mL) are added successively in a drop-wise manner, and the solution is stirred for 1 h at −40° C. Formyl piperidine (11.1 mL, 100 mmol) in THF (25 mL) is added drop-wise, and the solution is stirred for 1 h at −40° C. The reaction is quenched with 40 mL 6N HCl, diluted with 250 mL ether, and a small amount of sodium thiosulfate solution is added to remove the iodine color. The solution is neutralized with saturated NaHCO$_3$, filtered, and extracted with ether (3×150 mL). The combined organic layer is dried over Na$_2$SO$_4$, filtered, and concentrated in vacuo. The crude material is chromatographed over 600 g slurry-packed silica, eluting with 20% EtOAc/hexane. The fractions with the desired compound are collected and concentrated to afford 2-chloronicotinaldehyde (C90) as a pale orange solid (54% yield). MS (EI) for C$_6$H$_4$ClNO, m/z: 141 (M)$^+$.

C90 (1.41 g, 10.01 mmol) is dissolved in DMF (10 mL) and water (1 mL) under N$_2$. K$_2$CO$_3$ (1.56 g, 11.27 mmol) and methyl thioglycolate (1.00 mL, 11.25 mmol) are added portionwise. The reaction is stirred at 35° C. for 24 h, quenched with cold water (75 mL), and placed in an ice bath to enhance precipitation. The precipitate is isolated by filtration, affording methyl-thieno[2,3-b]pyridine-2-carboxylate (C101) as an orange powder (40% yield). MS (EI) for C$_9$H$_7$NO$_2$S, m/z: 193 (M)$^+$.

C101 (0.700 g, 3.63 mmol) is dissolved in MeOH (15 mL) and 3 mL water. 2N NaOH (1.82 mL, 3.63 mmol) is added drop-wise, and the reaction is stirred at rt for 24 h. The reaction is concentrated in vacuo, and water (40 mL) is added to dissolve the residue. The resulting solution is acidified to pH 4 using concentrated HCl, and the precipitate is isolated by filtration, yielding thieno[2,3-b]pyridine-2-carboxylic acid (C102) as a white powder (85% yield). MS (EI) for C$_8$H$_5$NO$_2$S, m/z: 179 (M)$^+$.

Coupling:

Example 13 is obtained as a white salt (9% yield) using acid C102 according to Method A with non-critical changes. HRMS (FAB) calculated for C$_{15}$H$_{17}$N$_3$OS+H: 288.1170, found 288.1175 (M+H)$^+$.

EXAMPLE 14

N-[(3R)-1-azabicyclo[2.2.2]oct-3-yl]thieno[2,3-b]pyridine-5-carboxamide dihydrochloride

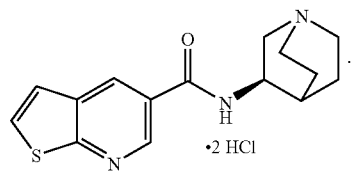

Preparation of the Acid:

2-Nitrothiophene (33.76 g, 261.4 mmol) is suspended in concentrated HCl (175 mL) and heated to 50° C. Stannous chloride (118.05 g, 523.2 mmol) is added portionwise, maintaining the reaction temperature between 45–50° C. with an ice bath, that is removed after the addition. The solution is allowed to cool slowly to 30° C. over an hour. The solution is then cooled in an ice bath and filtered. The cake is washed with concentrated HCl (20 mL), dried in a stream of air, and washed with ether (50 mL) to afford the hexachlorostannate salt of 2-aminothiophene as a brown solid (26% yield).

3,3-Dimethyl-2-formyl propionitrile sodium (3.33 g, 20.2 mmol) can readily be prepared from the method described by Bertz, S. H., et al., *J. Org. Chem.*, 47, 2216–2217 (1982). 3,3-Dimethyl-2-formyl propionitrile sodium is dissolved in MeOH (40 mL), and concentrated HCl (4 mL) and the hexachlorostannate salt of 2-aminothiophene (10.04 g, 19.1 mmol) in MeOH (130 mL) is slowly added drop-wise to the mixture. Following addition, the mixture is refluxed in an oil bath (80° C.) for 4 h, and then MeOH (10 mL) and concentrated HCl (10 mL) are added. The reaction continued refluxing for another 20 h. The solution is cooled to rt, and the reaction is concentrated in vacuo. The purple residue is dissolved in water (60 mL), and the slurry is filtered. The cake is pulverized and stirred vigorously with 5% MeOH/CHCl$_3$ (105 mL) while heating to 55° C. The mixture is cooled and filtered, and the organic layer is concentrated to a green oil. The crude material is chromatographed over 130 g slurry-packed silica, eluting with 30% EtOAc/hexane. The fractions with the desired compound are collected and concentrated to afford thieno[2,3-b]pyridine-5-carbonitrile (C105) as a pale yellow solid (24% yield). HRMS (FAB) calculated for C$_8$H$_4$N$_2$S+H: 161.0173, found 161.0173 (M+H)$^+$.

NaOH (0.138 g, 3.45 mmol) is added to a solution of C105 (0.503 g, 3.14 mmol) dissolved in 70% EtOH/H$_2$O (12 mL). The mixture is refluxed at 100° C. for 3 h. The reaction is concentrated in vacuo, and the residue is dissolved in water (8 mL) and neutralized with concentrated HCl. The slurry is filtered and rinsed with ether. An initial NMR of the isolated material indicated presence of the carboxamide intermediate, so the material is suspended in 1M NaOH (6 mL) and stirred over night. Water (10 mL) is added, the solution is extracted with ether (3×10 mL), and the mixture is neutralized with concentrated HCl. The slurry is filtered and rinsed with ether, affording of thieno[2,3-b]pyridine-5-carboxylic acid (C106) as an off-white solid (48% yield). MS (EI) for $C_8H_5NO_2S$, m/z: 179 (M)$^+$.

Coupling:

Example 14 is obtained as a white salt (18% yield) using acid C106 according to Method A with non-critical changes. HRMS (FAB) calculated for $C_{15}H_{17}N_3OS+H$: 288.1170, found 288.1180 (M+H)$^+$.

EXAMPLE 15

N-[(3R)-1-azabicyclo[2.2.2]oct-3-yl]thieno[2,3-b]pyridine-6-carboxamide dihydrochloride

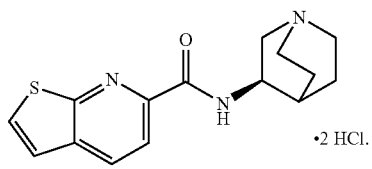

•2 HCl.

Preparation of the Acid:

2-Nitrothiophene (12.9 g, 99.9 mmol) is dissolved in concentrated HCl (200 mL) and stirred vigorously at 30° C. Granular tin (25 g, 210 mmol) is slowly added portionwise. When the tin is completely dissolved, zinc chloride (6.1 g, 44.7 mmol) in EtOH (70 mL) is added drop-wise, the mixture is heated to 85° C., and malondialdehyde diethyl acetal (24 mL, 100 mmol) in EtOH (30 mL) is added. The solution continued stirring at 85° C. for 1 h, and is quenched by pouring over ice (100 g). The mixture is adjusted to pH 10 with ammonium hydroxide, and the resulting slurry is carefully filtered through celite overnight. The liquor is extracted with $CHCl_3$ (3×300 mL), and the combined organic layer is dried over $MgSO_4$, filtered, and concentrated to a brown oil. The crude material is chromatographed over 250 g slurry-packed silica, eluting with 35% EtOAc/hexane. The fractions with the desired compound are collected and concentrated to give thieno[2,3-b]pyridine (C110) as an orange oil (26% yield). MS (EI) for $C_7H_5NS$, m/z: 135 (M)$^+$.

C110 (3.47 g, 25.7 mmol) is dissolved in acetic acid (12 mL) and heated to 85° C. 30% Hydrogen peroxide (9 mL) is added drop-wise and the solution is allowed to stir overnight. The reaction is allowed to cool to rt and quenched with paraformaldehyde until a peroxide test proved negative using starch-iodine paper. The solution is diluted with water (100 mL) and neutralized with $NaHCO_3$, then extracted repeatedly with $CHCl_3$ (12×80 mL, 6×50 mL). The combined organic layer is dried over $Na_2SO_4$, filtered, and concentrated to a brown solid. The crude material is chromatographed over 70 g slurry-packed silica eluting with 3.5% MeOH/$CH_2Cl_2$. The fractions with the desired compound are combined and concentrated to afford thieno[2,3-b]pyridine-7-oxide (C111) as a pale yellow solid (22% yield). MS (EI) for $C_7H_5NOS$ m/z: 151 (M)$^+$.

A 0.5M solution of C111 (5 mL, 2.5 mmol) in $CH_2Cl_2$ is diluted with 8 mL of $CH_2Cl_2$ under $N_2$. Dimethyl carbamyl chloride (0.27 mL, 2.9 mmol) is added drop-wise, followed by the addition of trimethylsilyl cyanide (0.388 mL, 2.9 mmol) via syringe. The reaction is allowed to stir for 9 days and is quenched with 10% $K_2CO_3$ (10 mL). The layers are allowed to separate, the organic layer is isolated and dried over $K_2CO_3$, filtered, and concentrated to a brown solid. The crude material is chromatographed over 25 g slurry-packed silica, eluting with 35% EtOAc/hexane. The fractions with the desired compound are collected and concentrated to produce thieno[2,3-b]pyridine-6-carbonitrile (C112) as a pale yellow solid (100% yield). Analysis calculated for $C_8H_4N_2S$: C, 59.98; H, 2.52; N, 17.49, found: C, 59.91; H, 2.57; N, 17.43.

NaOH (398 mg, 9.95 mmol) is added portionwise to a solution of C112 (674 mg, 4.2 mmol) in 70% EtOH/$H_2O$ (20 mL). The solution is refluxed at 100° C. for 24 h, and the reaction is concentrated in vacuo. The residue is dissolved in water (15 mL) and washed with ether (3×10 mL). Concentrated HCl is used to adjust the pH to 3.5, creating a precipitate. The slurry is filtered, giving thieno[2,3-b]pyridine-6-carboxylic acid (C113) as a white solid (45% yield). MS (EI) for $C_8H_5NO_2S$, m/z: 179(M)$^+$.

Coupling:

Example 15 is obtained as a yellow solid (43% yield) using acid C113 according to Method A with non-critical changes. MS (EI) for $C_{15}H_{17}N_3OS$, m/z: 287 (M)$^+$.

EXAMPLE 17

N-[(3R)-1-azabicyclo[2.2.2]oct-3-yl]thieno[2,3-c]pyridine-2-carboxamide dihydrochloride

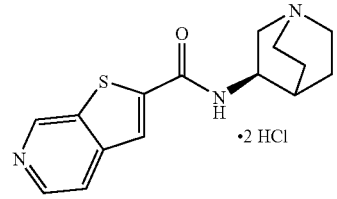

•2 HCl

Preparation of the Acid:

THF (200 mL) is chilled to −70° C. in a dry flask under $N_2$, and N-butyllithium (24.4 mL, 55.0 mmol) is added drop-wise. The reaction is placed in an ice bath and diisopropyl amine (7.71 mL, 55.0 mmol) in THF (20 mL) is added drop-wise. The solution is again chilled to −70° C., and 3-chloropyridine (4.75 mL, 50.0 mmol) in THF (20 mL) is added drop-wise. The reaction is allowed to stir for 4 h at −70° C. and ethyl formate (4.44 mL, 55.0 mmol) in THF (20 mL) is added. The reaction is stirred for an additional 3 h at −70° C. and quenched with $H_2O$ (500 mL). The layers are allowed to separate, and the aqueous layer is extracted with EtOAc (3×250 mL). The combined organic layer is dried over $MgSO_4$, filtered, and concentrated to a dark brown solid. The crude material is chromatographed over 250 g slurry-packed silica, eluting with 50% EtOAc/hexane. The fractions with the desired compound are collected and concentrated to give 3-chloroisonicotinaldehyde (C120) as an off-white solid (55% yield). MS (EI) for $C_6H_4ClNO$, m/z: 141 (M)$^+$.

C120 (2.12 g, 14.9 mmol) is dissolved in DMF (75 mL) with a small amount of $H_2O$ (7.5 mL). Methyl thioglycolate (1.67 mL, 18.7 mmol) and $K_2CO_3$ (2.59 g, 18.7 mmol) are added portionwise, and the mixture is stirred at 45° C. for 24 h. The reaction is quenched with cold $H_2O$ (200 mL) and extracted with EtOAc (3×150 mL). The combined organic layer is washed with 50% NaCl solution (3×150 mL), dried over $MgSO_4$, filtered, and concentrated to an orange solid. The crude material is chromatographed over 40 g slurry-packed silica, eluting with 50% EtOAc/hexane. The fractions with the desired compound are collected and concentrated, affording ethyl thieno[2,3-c]pyridine-2-carboxylate (C121) as a pale yellow solid (22% yield).

C121 (577 mg, 2.99 mmol) is combined with 2M NaOH (1.5 mL, 3.0 mmol) in MeOH (15 mL) and $H_2O$ (1.5 mL). The reaction is stirred at rt for 24 h. The reaction is concentrated in vacuo and the residue is dissolved in water (75 mL). Concentrated HCl is used to acidify the solution to pH 3. The slurry is filtered, washed with $H_2O$ and ether, and dried, affording thieno[2,3-c]pyridine-2-carboxylic acid (C122) as an off-white solid (38% yield). HRMS (FAB) calculated for $C_8H_5NO_2S+H$: 180.0119, found 180.0119 $(M+H)^+$.

Coupling:

Example 17 is obtained as a white solid (8% yield) using acid C122 according to Method A with non-critical changes. HRMS (FAB) calculated for $C_{15}H_{17}N_3OS+H$: 288.1170, found 288.1173 $(M+H)^+$.

EXAMPLE 18

N-[(3R)-1-azabicyclo[2.2.2]oct-3-yl]thieno[3,2-b]pyridine-2-carboxamide

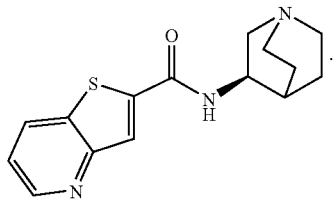

Preparation of the Acid:

3-Chloropyridine (9.5 mL. 99.9 mmol) is dissolved in acetic acid (35 mL) and heated to 98° C. 30% Hydrogen peroxide (28 mL) is added drop-wise, and the reaction stirred for 5 h at 98° C. The reaction is cooled and paraformaldehyde is added so that a negative peroxide test is achieved using starch-iodine paper. The solution is concentrated in vacuo and the crude paste is chromatographed over 600 g slurry-packed silica eluting with 4 L of 2% MeOH/$CH_2Cl_2$, 2 L of 4% MeOH/$CH_2Cl_2$, and finally 1 L of 10% MeOH/$CH_2Cl_2$. The fractions with the desired compound are collected and concentrated to afford 3-chloropyridine 1-oxide (C125) as a pale oil (100% yield).

A 2M solution of 3-chloropyridine 1-oxide (C125) (10 mL, 20 mmol) is combined with an additional 90 mL of $CH_2Cl_2$. Dimethylcarbamoyl chloride (2.03 mL, 22.0 mmol) is added drop-wise, followed by the addition of trimethyl silylcyanide (2.93 mL, 22.0 mmol) via syringe. The reaction stirred at rt for 10 days and is quenched with 10% $K_2CO_3$ (100 mL). The layers are allowed to separate, and the organic layer is dried over $K_2CO_3$, filtered, and concentrated to an orange solid. The crude material is chromatographed over 160 g slurry-packed silica eluting with 40% EtOAc/hexane. The fractions with the desired compound are collected and concentrated to yield 3-chloropyridine-2-carbonitrile (C126) as a white solid (59% yield). MS (EI) for $C_6H_3ClN_2$, m/z: 138 $(M)^+$.

C126 (1.01 g, 7.29 mmol) and $K_2CO_3$ (1.10 g, 7.96 mmol) are added to DMF (10 mL) and water (1 mL). Methyl thioglycolate (0.709 mL, 7.93 mmol) is added drop-wise, and the solution is heated to 40° C. and stirred for 3 h. The reaction is quenched with cold water (70 mL) and placed on ice to enhance precipitation. The slurry is filtered and the cake is dissolved in $CHCl_3$. This organic solution is dried over $MgSO_4$, filtered, and concentrated, affording methyl 3-aminothieno[3,2-b]pyridine-2-carboxylate (C127) as a yellow solid (84% yield). HRMS (FAB) calculated for $C_9H_8N_2O_2S+H$: 209.0385, found 209.0383 $(M+H)^+$.

C127 (0.919 g, 4.42 mmol) is dissolved in 50% hypophosphorous acid (35 mL) and chilled in an ice bath. Sodium nitrite (0.61 g, 8.84 mmol) is dissolved in a minimal amount of water and added drop-wise to the previous solution, and the reaction is stirred for 3 h in an ice bath. 3M NaOH is used to adjust the pH to 7.9, and the solution is extracted with EtOAc (3×100 mL). The combined organic layer is dried over $MgSO_4$, filtered, and concentrated to afford methyl thieno[3,2-b]pyridine-2-carboxylate (C128) as a yellow solid (44% yield). MS (EI) for $C_9H_7NO_2S$, m/z: 193 $(M)^+$.

2M NaOH (0.8 mL, 1.6 mmol) and C128 (300 mg, 1.55 mmol) are added to MeOH (8 mL) and water (1 mL) and stirred for 24 h. The reaction is concentrated in vacuo, and the residue is dissolved with water (5 mL). 5% HCl is used to adjust the pH to 3.5, creating a precipitate. The slurry is filtered and washed with ether, affording thieno[3,2-b]pyridine-2-carboxylic acid (C129) as a brown solid (67% yield). HRMS (FAB) calculated for $C_8H_5NO_2S+H$: 180.0119, found 180.0121 $(M+H)^+$.

Coupling:

Example 18 is obtained as a white solid (52% yield) using acid C129 according to Method A with non-critical changes. HRMS (FAB) calculated for $C_{15}H_{17}N_3OS+H$: 288.1170, found 288.1174 $(M+H)^+$.

EXAMPLE 19

N-[(3R)-1-azabicyclo[2.2.2]oct-3-yl]thieno[3,2-b]pyridine-5-carboxamide dihydrochloride

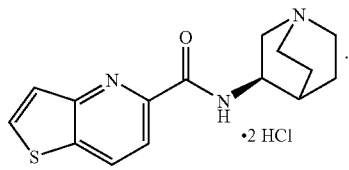

Example 19 is obtained as a white salt (37% yield) using thieno[3,2-b]pyridine-5-carboxylic acid according to Method A with non-critical changes. HRMS (FAB) calculated for $C_{15}H_{17}N_3OS+H$: 288.1170, found 288.1180 $(M+H)^+$.

EXAMPLE 20

N-[(3R)-1-azabicyclo[2.2.2]oct-3-yl]thieno[3,2-b]pyridine-6-carboxamide dihydrochloride

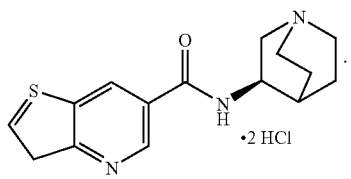

Preparation of the Acid:

Methyl 3-aminothiophene-2-carboxylate (1.52 g, 9.68 mmol) is dissolved in 2M NaOH (10 mL, 20 mmol) and refluxed in a 115° C. oil bath for 30 min. The mixture is cooled to rt, placed in an ice bath, and carefully acidified with concentrated HCl. The slurry is filtered and rinsed with water (25 mL). The cake is then dissolved in acetone (50 mL), dried over MgSO$_4$, filtered, and concentrated to a thick paste. The crude material is dissolved in 1-propanol (25 mL), and oxalic acid (0.90 g, 10.0 mmol) is added portion-wise. The mixture is heated at 38° C. for forty-five min, cooled to rt, and diluted with ether. The precipitate is isolated via filtration, and washed with ether, affording 3-amino-thiophene oxalate (C135) as a fluffy white solid (70% yield). HRMS (FAB) calculated for $C_4H_5NS+H$: 100.0221, found 100.0229 (M+H)$^+$.

3,3-Dimethyl-2-formyl propionitrile sodium (5.38 g, 32.6 mmol) is dissolved in MeOH (60 mL) with concentrated HCl (6 mL). C135 (6.16 g, 32.6 mmol) is suspended in MeOH (200 mL) and added drop-wise to the acidic solution. The mixture is refluxed at 80° C. for 5 h when an additional 20 mL concentrated HCl and 20 mL H$_2$O are added; the mixture continued refluxing for another 12 h. The mixture is concentrated in vacuo, and the residue is dissolved with cold H$_2$O (100 mL). The resulting precipitate is filtered off and dried, giving thieno[3,2-b]pyridine-6-carbonitrile (C136) as a brown solid (44% yield). HRMS (FAB) calculated for $C_8H_4N_2S+H$: 161.0173, found 161.0170 (M+H)$^+$.

C136 (1.99 g, 12.5 mmol) is dissolved in 70% EtOH/H$_2$O (20 mL), and NaOH (0.52 g, 13.0 mmol) is added portion-wise. The mixture is heated at 100° C. for 15 h and then allowed to cool to rt. The mixture is concentrated in vacuo. The residue is dissolved in cold H$_2$O (30 mL), and the solution is rinsed with ether (3×10 mL). The pH is adjusted to 3.5 with concentrated HCl to precipitate the desired product that is removed by filtration to give thieno[3,2-b]pyridine-6-carboxylic acid (C137) as a tan solid (77% yield). HRMS (FAB) calculated for $C_8H_5NO_2S+H$: 180.0119, found 180.0118 (M+H)$^+$.

Coupling:

Example 20 is obtained as a white salt (37% yield) using acid C137 according to Method A with non-critical changes. HRMS (FAB) calculated for $C_{15}H_{17}N_3OS+H$: 288.1170, found 288.1167 (M+H)$^+$.

EXAMPLE 21

N-[(3R)-1-azabicyclo[2.2.2]oct-3-yl]thieno[3,2-c]pyridine-2-carboxamide dihydrochloride

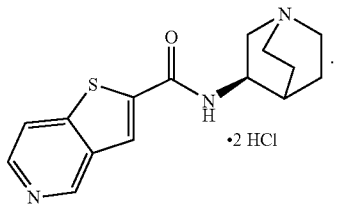

Preparation of the Acid:

4-Chloropyridine hydrochloride (15 g, 99.9 mmol) is free-based by stirring in 1000 mL 1:1 saturated NaHCO$_3$/ether for 1 h. The layers are allowed to separate, the aqueous layer is extracted with ether (2×175 mL), and the combined organic layer is dried over MgSO$_4$, filtered, and concentrated to an oil. THF (300 mL) is chilled to −70° C. in a dry flask. N-butyllithium (105.1 mL, 168.2 mmol) is added drop-wise, and the mixture is placed in an ice bath. Diisopropylamine (23.6 mL. 168.4 mmol) in THF (50 mL) is added drop-wise, the yellow solution is stirred for 30 min, and the reaction is cooled to −70° C. The free-based 4-chloropyridine oil (9.55 g, 84.1 mmol) is dissolved in THF (50 mL) and added drop-wise to the chilled yellow solution, that turned dark red after the addition. The reaction is stirred at −70° C. for 2 h. Ethyl formate (13.6 mL, 168.3 mmol) in THF (25 mL) is then added drop-wise to the dark solution at −70° C. After 2 hours, the reaction is warmed to −10° C. and quenched with water (450 mL). The layers are allowed to separate, and the aqueous layer is extracted with ether (3×200 mL). The combined organic layer is dried over MgSO$_4$, filtered, and concentrated in vacuo to an oil. The crude material is chromatographed over 320 g slurry-packed silica eluting with 30% EtOAc/hexane. The fractions with the desired compound are collected and concentrated to an orange oil which solidified under vacuum, affording 4-chloropyridine-3-carboxaldehyde (C140) as an orange solid (21% yield).

C140 (2.53 g, 17.9 mmol) is dissolved in DMF (20 mL) and water (2 mL). K$_2$CO$_3$ (2.97 g, 21.5 mmol) and methyl thioglycolate (1.92 mL, 21.5 mmol) are added portionwise. The reaction is stirred at 45° C. for 24 h, then quenched with cold water (100 mL), and the flask is placed on ice to enhance precipitation. The precipitate is isolated by filtration and dried, affording methyl thieno[3,2-c]pyridine-2-carboxylate (C141) as a white solid (92% yield). MS (EI) for $C_9H_7NO_2S$, m/z: 193 (M)$^+$.

C141 (2.65 g, 13.7 mmol) is dissolved in MeOH (70 mL) and water (5 mL). 2N NaOH (6.86 mL, 13.7 mmol) is added drop-wise, and the reaction is stirred at rt for 24 h. The reaction is concentrated in vacuo, and water (150 mL) is added to dissolve the residue. The resulting salt solution is acidified to pH 3.5 using concentrated HCl, and the precipitate is isolated by filtration and dried, affording thieno[3,2-c]pyridine-2-carboxylic acid (C142) as a white powder (57% yield). HRMS (FAB) calculated for $C_8H_5NO_2S+H$: 180.0119, found 180.0124 (M+H)$^+$.

Coupling:

Example 21 is obtained as a yellow salt (25% yield) using acid C142 according to Method A with non-critical changes. HRMS (FAB) calculated for $C_{15}H_{17}N_3OS+H$: 288.1170, found 288.1189 (M+H)$^+$.

EXAMPLE 22

N-[(3R)-1-azabicyclo[2.2.2]oct-3-yl]thieno[2,3-c]pyridine-5-carboxamide dihydrochloride

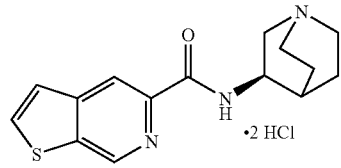

Preparation of the Acid:

Glyoxylic acid monohydrate (20.3 g, 221 mmol) and benzyl carbamate (30.6 g, 202 mmol) are added to ether (200 mL). The solution is allowed to stir for 24 h at rt. The resulting thick precipitate is filtered, and the residue is washed with ether, affording ([(benzyloxy)carbonyl]amino)(hydroxy)acetic acid (C150) as a white solid (47% yield). MS (CI) for $C_{10}H_{11}NO_5+H$ m/z: 226 (M+H)$^+$.

C150 (11.6 g, 51.5 mmol) is dissolved in absolute MeOH (120 mL) and chilled in an ice bath. Concentrated sulfuric acid (2.0 mL) is carefully added drop-wise. The ice bath is allowed to expire as the solution stirred for 2 days. The reaction is quenched by pouring onto a mixture of 500 g ice with saturated NaHCO$_3$ solution (400 mL). The solution is extracted with EtOAc (3×300 mL), and the combined organic layer is dried over MgSO$_4$, filtered, and concentrated to a pale oil that crystallized upon standing, giving methyl([(benzyloxy)carbonyl]amino)(methoxy)acetate (C151) as a white solid (94% yield). Analysis calculated for $C_{12}H_{15}NO_5$: C, 56.91; H, 5.97; N, 5.53, found: C, 56.99; H, 6.02; N, 5.60.

C151 (11.76 g, 46.4 mmol) is dissolved in toluene (50 mL) under N$_2$ and heated to 70° C. Phosphorous trichloride (23.2 mL, 46.4 mmol) is added drop-wise via syringe, and the solution is stirred for 18 h at 70° C. Trimethyl phosphite (5.47 mL, 46.4 mmol) is then added drop-wise, and stirring continued for an additional 2 h at 70° C. The mixture is concentrated in vacuo to an oil, and the crude material is dissolved in EtOAc (100 mL) and washed with saturated NaHCO$_3$ (3×50 mL). The organic layer is dried over Na$_2$SO$_4$, filtered, and concentrated to a volume of 30 mL. This remaining solution is stirred vigorously while hexane is added until a precipitate formed. The precipitated solid is removed by filtration, affording methyl ([(benzyloxy)carbonyl]amino)(dimethoxyphosphoryl)acetate (C152) as a white solid (84% yield). MS (EI) for $C_{13}H_{18}NO_7P$, m/z: 331 (M)$^+$.

C152 (12.65 g, 38.2 mmol) and acetic anhydride (9.02 mL, 95.5 mmol) in MeOH (100 mL) are added to a Parr flask. The solution is hydrogenated with 10% Pd/C catalyst (0.640 g) at 45 PSI for 3 h. The catalyst is filtered off, and the filtrate is concentrated in vacuo to an oil. The oil is placed under reduced pressure and solidified as the reduced pressure is applied. The white residue is dissolved in a small amount of EtOAc and stirred vigorously while pentane is added until a precipitate began to form. The precipitate is removed by filtration to give methyl (acetylamino)(dimethoxyphosphoryl)acetate (C153) as a white powder (87% yield). MS (CI) for $C_7H_{14}NO_6P$, m/z: 240 (M+H)$^+$.

2,3-Thiophene dicarboxaldehyde (1.40 g, 9.99 mmol) is dissolved in CH$_2$Cl$_2$ (100 mL) and the flask is placed in an ice bath. C153 (2.63 g, 11.0 mmol) is dissolved in CH$_2$Cl$_2$ (50 mL), DBU (1.65 mL, 11.0 mmol) is added, and this solution is added drop-wise to the chilled thiophene solution. The reaction mixture is stirred for 1 h while the flask is in an ice bath and then over night at rt. The reaction is concentrated in vacuo, and the crude material is chromatographed over 300 g slurry-packed silica eluting with 50% EtOAc/hexane. The fractions are collected in two different groups to obtain the desired compounds. Each group of fractions is combined and concentrated separately. Methyl thieno[2,3-c]pyridine-5-carboxylate (C154) elutes first and the appropriate fractions are concentrated to give a white solid (41% yield). The second group of appropriate fractions are collected and concentrated to give methyl thieno[3,2-c]pyridine-6-carboxylate (C155) as a yellow solid (38% yield). MS (EI) for C154 for $C_9H_7NO_2S$, m/z: 193 (M)$^+$. MS (EI) for C155 for $C_9H_7NO_2S$, m/z: 193 (M)$^+$.

C154 (736 mg, 3.8 mmol) is dissolved in MeOH (16 mL) with water (2 mL). 2M NaOH (2.0 mL, 4.0 mmol) is added drop-wise and the solution stirred at rt. After 2 days (complete disappearance of ester by TLC), the reaction is concentrated in vacuo. The residue is dissolved in water (12 mL), and the pH is adjusted to 3.5 with 10% HCl. The precipitated solid is removed by filtration, and the solid is rinsed with ether, affording thieno[2,3-c]pyridine-5-carboxylic acid (C156) as a white solid (58% yield). HRMS (FAB) calculated for $C_8H_5NO_2S+H$: 180.0119, found 180.0123 (M+H)$^+$.

Coupling:

Example 22 is obtained as a white salt (32% yield) using acid C156 according to Method A with non-critical changes. MS (EI) for $C_{15}H_{17}N_3OS$, m/z: 287 (M)$^+$.

EXAMPLE 23

N-[(3R)-1-azabicyclo[2.2.2]oct-3-yl]thieno[3,2-c]pyridine-6-carboxamide dihydrochloride

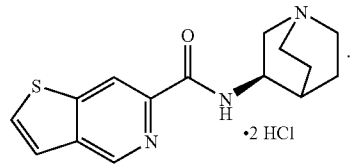

Preparing the Acid:

Methyl thieno[3,2-c]pyridine-6-carboxylate (C155) (678 mg, 3.5 mmol) is dissolved in MeOH (16 mL) and water (2 mL). 2M NaOH (1.8 mL, 3.6 mmol) is added drop-wise, and the solution stirred at rt. After 2 days (complete disappearance of ester by TLC), the solution is concentrated in vacuo. The residue is dissolved in water (12 mL), and the pH is adjusted to 3.5 with 10% HCl. The precipitated solid is removed by filtration, and the solid is rinsed with ether, affording thieno[3,2-c]pyridine-6-carboxylic acid (C160) as a white solid (43% yield). HRMS (FAB) calculated for $C_8H_5NO_2S+H$: 180.0119, found 180.0123 (M+H)$^+$.

Coupling:

Example 23 is obtained as a white salt (31% yield) using acid C160 according to Method A with non-critical changes. MS (EI) for $C_{15}H_{17}N_3OS$, m/z: 287 (M)⁺.

EXAMPLE 24

N-[(3R)-1-azabicyclo[2.2.2]oct-3-yl]-1H-pyrrolo[2,3-c]pyridine-5-carboxamide dihydrochloride

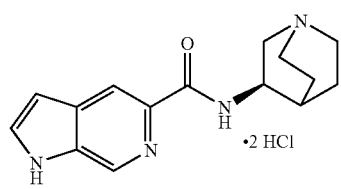

Preparation of the Acid:

2,4-Lutidine (51.4 mL, 0.445 mole) is added drop-wise to 250 mL fuming sulfuric acid in a flask under $N_2$ in an ice bath. The solution is treated portionwise with potassium nitrate (89.9 g, 0.889 mole) over a 15 min period. The reaction is stirred 1 h in an ice bath, 2 h at rt, is gradually warmed in a 100° C. oil bath for 5 h, and then in a 130° C. oil bath for 4 h. The mixture is cooled, is poured into 1000 mL ice, and the mixture is neutralized with $NaHCO_3$ (1,100 g, 13.1 mole). The precipitated $Na_2SO_4$ is removed by filtration, the solid is washed with 500 mL water and the filtrate is extracted with 4×500 mL ether. The combined organic layer is dried over anhydrous $MgSO_4$ and is concentrated in vacuo to a yellow oil (50 g). The crude oil is distilled under vacuum to provide three fractions: 16 g recovered 2,4-lutidine (85° C.), 16 g 2,4-dimethyl-3-nitropyridine (C169) contaminated with 25% 2,4-dimethyl-5-nitro-pyridine (135–145° C.), and 16 g 2,4-dimethyl-5-nitro-pyridine (C170) contaminated with 2,4-dimethyl-3-nitropyridine (145–153° C.). ¹H NMR of C169 (CDCl₃) δ 2.33 (s, 3H), 2.54 (s, 3H), 7.10 (d, J=5 Hz, 1H), 8.43 (d, J=5 Hz, 1H) ppm. ¹H NMR of C170 (CDCl₃) δ 2.61 (s, 3H), 2.62 (s, 3H), 7.16 (s, 1H), 9.05 (s, 1H) ppm.

C170/C169 (75:25) (5.64 g, 37 mmol) is combined with benzeneselenic anhydride (8.2 g, 22.8 mmol) in 300 mL dioxane in a flask under $N_2$. The reaction is warmed to reflux for 10 h, is cooled, and is concentrated to a dark yellow oil. The oil is chromatographed over 250 g silica gel (230–400 mesh) eluting with 15% EtOAc/hexane. The appropriate fractions are concentrated to afford 2-formyl-4-methyl-5-nitropyridine (C171) (66% yield). HRMS (EI) calculated for $C_7H_6N_2O_3$: 166.0378, found 166.0383 (M⁺).

C171 (1.15 g, 6.9 mmol), p-toluene sulfonic acid (41 mg, 0.22 mmol), and ethylene glycol (1.41 mL, 25 mmol) are added to 25 mL toluene in a flask equipped with a Dean-Starke trap. The reaction is warmed to reflux for 2 h, is cooled to rt, and is concentrated in vacuo to an oily residue. The crude oil is chromatographed over 40 g silica gel (Biotage), eluting with 20% EtOAc/hexane. The appropriate fractions are combined and concentrated to afford 2-(1,3-dioxolan-2-yl)-4-methyl-5-nitropyridine (C172) (90% yield). MS (EI) for $C_9H_{10}N_2O_4$, m/z: 210 (M)⁺.

C172 (1.3 g, 6.2 mmol) and DMF dimethyl acetal (1.12 mL, 8.4 mmol) are added to 15 mL DMF under $N_2$. The reaction is warmed to 90° C. for 3 h, is cooled, and reaction is concentrated in vacuo. The residue is combined with 1.25 g 5% Pd/BaSO₄ in 20 mL EtOH in a 250 mL Parr shaker bottle and the mixture is hydrogenated at ambient pressure until uptake ceased. The catalyst is removed by filtration, and the filtrate is combined with 500 mg 10% Pd/C catalyst in a 250 mL Parr shaker bottle. The mixture is hydrogenated at ambient pressure for 1 h. No additional hydrogen uptake is observed. The catalyst is removed by filtration, and the filtrate is concentrated in vacuo to a tan solid. The crude material is chromatographed over 50 g silica gel (230–400 mesh), eluting with 7% MeOH/CH₂Cl₂. The appropriate fractions are combined and concentrated to afford 5-(1,3-dioxolan-2-yl)-1H-pyrrolo[2,3-c]pyridine (C173) (69% yield). MS for $C_{10}H_{10}N_2O_2$, (EI) m/z: 190 (M)⁺.

C173 (800 mg, 4.21 mmol) is dissolved in 44 mL 10% aqueous acetonitrile. p-Toluene sulfonic acid (630 mg, 3.3 mmol) is added, and the mixture is heated to reflux for 5 h. The mixture is cooled to rt, is concentrated in vacuo, and the resultant residue is diluted with 15 mL saturated NaHCO₃. A pale yellow solid is collected, washed with water, and is dried to afford 1H-pyrrolo[2,3-c]pyridine-5-carbaldehyde (C174) (81% yield). HRMS (FAB) calculated for $C_8H_6N_2O+H$: 147.0558, found 147.0564 (M+H)⁺.

C174 (500 mg, 3.42 mmol) is dissolved in 1.5 mL formic acid. The solution is cooled to in an ice bath, 30% aqueous hydrogen peroxide (722 μL, 6.8 mmol) is added drop-wise, and the reaction is stirred 1 h in an ice bath, and allowed to stand overnight at 5° C. The mixture is diluted with water, the solid is collected, washed with water and is dried to give 522 mg of an off-white solid. The formate salt is added to 7 mL water, 3 mL 2N NaOH is added, and the pH is adjusted to 3 with 5% aqueous HCl. The precipitate is collected and is dried to afford 1H-pyrrolo[2,3-c]pyridine-5-carboxylic acid (C176) (67% yield). HRMS (FAB) calculated for $C_8H_6N_2O_2+H$: 163.0508, found 163.0507 (M+H)⁺.

Coupling:

Example 24 is obtained as a white solid (40% yield) using acid C176 using Method C with non-critical changes. HRMS (FAB) calculated for $C_{15}H_{18}N_4O+H$: 271.1559, found 271.1562 (M+H)⁺.

EXAMPLE 25

N-((3R)1-azabicyclo[2.2.2]oct-3-yl)-1-methyl-1H-pyrrolo[2,3-c]pyridine-5-carboxamide dihydrochloride

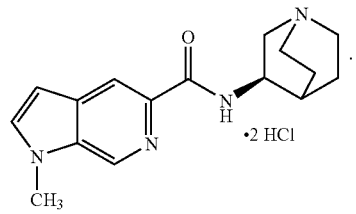

Preparation of the Acid:

C173 (1.05 g, 5.52 mmol) is dissolved in 20 mL THF in a dried flask under $N_2$. 60% Sodium hydride (243 mg, 6.07 mmol) is added, the reaction is stirred 30 min, methyl iodide (360 μL, 5.8 mmol) is added, and the reaction is stirred overnight at rt. The reaction is concentrated in vacuo and the residue is partitioned between 10 mL saturated NaCl and $CH_2Cl_2$ (4×10 mL). The combined organic layer is dried over anhydrous $K_2CO_3$ and is concentrated in vacuo to a tan paste. The crude material is chromatographed over 50 g silica gel (230–400 mesh) eluting with 5% $MeOH/CH_2Cl_2$. The appropriate fractions are combined and concentrated to afford 5-(1,3-dioxolan-2-yl)-1-methyl-1H-pyrrolo[2,3-c]pyridine (C175) (86% yield). HRMS (FAB) calculated for $C_{11}H_{12}N_2O_2$+H: 205.0977, found 205.0983.

C175 (920 mg, 4.5 mmol) is dissolved in 25 mL 10% aqueous acetonitrile in a flask. p-Toluene sulfonic acid (630 mg, 3.3 mmol) is added, and the mixture is heated to 90° C. for 8 h. The mixture is cooled to rt, concentrated in vacuo, and the residue is partitioned between 15 mL saturated $NaHCO_3$ and $CH_2Cl_2$ (4×10 mL). The combined organic layer is dried over anhydrous $K_2CO_3$ and is concentrated in vacuo to afford 1-methyl-pyrrolo[2,3-c]pyridine-5-carbaldehyde (C177) (99% yield). HRMS (FAB) calculated for $C_9H_8N_2O$+H: 161.0715, found 161.0711.

C177 (690 mg, 4.3 mmol) is dissolved in 2 mL formic acid. The solution is cooled in an ice bath, 30% aqueous hydrogen peroxide (970 μL, 8.6 mmol) is added drop-wise, and the reaction is stirred 1 h in an ice bath, and allow to stand overnight at 5° C. The mixture is concentrated to dryness, is suspended in water, and the pH is adjusted to 7 with 2N NaOH. The mixture is concentrated to dryness, is dissolved in MeOH, and is passed over 15 mL 50W-X2 ion exchange resin (hydrogen form) eluting with 200 mL MeOH followed by 200 mL 5% $Et_3N/MeOH$. The basic wash is concentrated to dryness to afford 1-methyl-pyrrolo[2,3-c]pyridine-5-carboxylic acid (C178) (78% yield). HRMS (FAB) calculated for $C_9H_8N_2O_2$+H: 177.0664, found 177.0672 (M+H)$^+$.

Coupling:

Example 25 is obtained as a yellow solid (54% yield) using acid C178 according to Method C with non-critical changes. HRMS (FAB) calculated for $C_{16}H_{20}N_4O$+H: 285.1715, found 285.1713 (M+H)$^+$.

EXAMPLE 26

N-[(3R)-1-azabicyclo[2.2.2]oct-3-yl]benzothieno[3,2-c]pyridine-3-carboxamide dihydrochloride

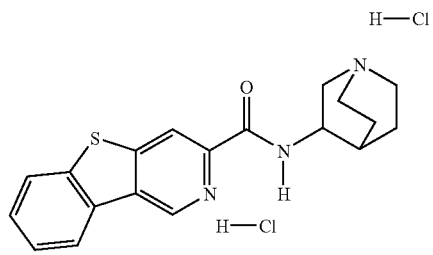

Preparation of the Acid:

N-Butyl lithium (150.6 ml, 241 mmol) is added dropwise to ether (100 ml) at −20° C. under $N_2$. 3-Bromothianaphthene (10.5 ml, 80.3 mmol) is dissolved in ether (50 ml) and also added dropwise to the chilled solution, stirring cold for 0.5 h. DMF (16.3 ml, 210 mmol) is dissolved in ether (75 ml) and added dropwise, and the solution stirred an additional 15 h at −20° C. The reaction is quenched onto ice (300 g) in 10% $H_2SO_4$ (200 ml) and stirred until both layers turned yellow in color. The resulting slurry is filtered, and the cake is allowed to dry in the air stream, affording 1-benzothiophene-2,3-dicarbaldehyde (C180) as a yellow solid (60% yield). HRMS (FAB) calculated for $C_{10}H_6O_2S$+H: 191.0167, found 191.0172 (M+H)$^+$.

C180 (1.91 g, 10.0 mmol) is dissolved in $CH_2Cl_2$ (100 ml) and chilled in an ice bath. C152 (2.63 g, 11.0 mmol) is dissolved in $CH_2Cl_2$ (50 ml) and added to DBU (1.65 ml, 11.0 mmol), stirring for 5 min. This solution is added dropwise to the chilled thiophene solution. The reaction mixture is stirred in the ice bath for 1 h and then over night at rt. The reaction is concentrated in vacuo and the crude material is chromatographed over 500 g slurry-packed silica eluting with 50% ethyl acetate/hexane.

Two groups of fractions are collected to give: (C183) methyl benzothieno[2,3-c]pyridine-3-carboxylate (200 mg, 8% yield) and (C181) methyl benzothieno[3,2-c]pyridine-3-carboxylate (1.75 g, 73%) as a white solid. Methyl benzothieno[2,3-c]pyridine-3-carboxylate: $^1$H NMR ($CDCl_3$) δ 4.12, 7.62 (t, J=7 Hz), 7.69 (t, J=8 Hz), 7.99 (d, J=8 Hz), 8.37 (d, J=8 Hz), 8.92, 9.30 ppm. Methyl benzothieno[3,2-c]pyridine-3-carboxylate: $^1$H NMR ($CDCl_3$) δ 4.10, 7.63, 7.96, 8.37, 8.72, 9.51 ppm. MS (EI) m/z: 243 (M$^+$).

C181 (1.43 g, 5.87 mmol) is dissolved in methanol (25 ml) with water (3 ml). 2M NaOH (3.0 ml, 6.0 mmol) is added dropwise and the solution stirred at rt. After 4 days (complete disappearance of ester by TLC), the reaction is concentrated in vacuo. The residue is dissolved in water (5 ml) and the pH is adjusted to 3.2 with 10% HCl. The solution stirred over night before precipitation is visible. The slurry is filtered and the cake is rinsed with ether, giving a 100% yield of benzothieno[3,2-c]pyridine-3-carboxylic acid (C182) as a white solid. HRMS (FAB) calculated for $C_{12}H_7NO_2S$+H 230.0276, found 230.0275 (M+H)$^+$.

Coupling:

Example 26 is obtained as a white salt (62% yield) using acid C182 according to Method A with non critical changes. HRMS (FAB) calculated for $C_{19}H_{19}N_3OS$+H: 338.1327, found 338.1328 (M+H)$^+$.

EXAMPLE 27

N-[(3R)-1-azabicyclo[2.2.2]oct-3-yl]benzothieno[2,3-c]pyridine-3-carboxamide dihydrochloride

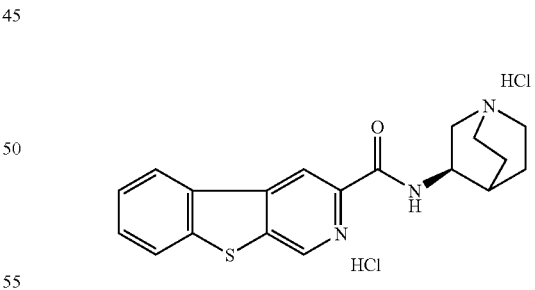

C183 (200 mg, 0.82 mmol) is dissolved in MeOH (4 ml) with water (0.5 ml). 2M NaOH (0.45 ml, 0.9 mmol) is added dropwise and the solution stirred at rt. The reaction is monitored by TLC and stopped when no ester could be seen. The volatiles are removed in vacuo, and the residue is dissolved in water (10 ml). The pH is adjusted to 3.5 with concentrated HCl, and the solution is allowed to stir over night. The slurry is then filtered and the cake is dried in an air stream, yielding 162 mg (86%) of benzothieno[2,3-c]pyridine-3-carboxylic acid as a tan solid. $^1$H NMR (DMSO-$d_6$) δ 7.62, 7.73, 8.21, 8.70, 9.05, 9.42 ppm.

Coupling:

Example 27 is obtained using benzothieno[2,3-c]pyridine-3-carboxylic acid according to Method C making non-critical changes to afford 115 mg (86% yield) as a pale yellow solid. HRMS (FAB) calcd for $C_{19}H_{19}N_3OS+H$: 338.1327, found 338.1325.

EXAMPLE 28

N-[(3R)-1-Azabicyclo[2.2.2]oct-3-yl]-3-chlorofuro[2,3-c]pyridine-5-carboxamide dihydrochloride

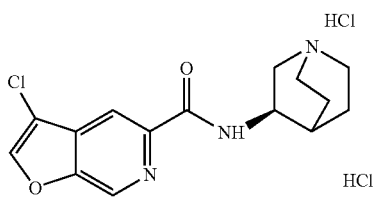

Preparation of the Acid:

Furo[2,3-c]pyridin-5-ylmethanol (7.70 g, 51.63 mmol) is dissolved in pyridine (45 mL), treated with acetic anhydride (14.36 mL, 154.9 mmol) and stirred for 18 h at rt. The pyridine is removed in vacuo and the resulting residue dissolved in EtOAc (200 mL), washed with 50% saturated sodium bicarbonate (4×90 mL), dried over $MgSO_4$ and concentrated in vacuo to afford 9.32 g (94%) of furo[2,3-c]pyridin-5-ylmethyl acetate as a yellow oil. MS (EI) m/z: 191 ($M^+$), 277, 148, 119, 118, 86, 84, 77, 63, 51, 50.

Furo[2,3-c]pyridin-5-ylmethyl acetate (956 mg, 5 mmol) is dissolved in $CH_2Cl_2$ (40 mL) and cooled to 0° C. Chlorine gas is bubbled through the solution for 15 min, the cooling bath is immediately removed and the mixture stirred for 2 h. The mixture is re-cooled to 0° C., saturated with chlorine gas, the cooling bath removed and the solution warmed to rt. The solution is layered with saturated $NaHCO_3$ (20 mL), stirred gently for 2 h then stirred vigorously for 15 min. The mixture is diluted with saturated $NaHCO_3$ (50 mL), extracted with $CH_2Cl_2$ (1×40 mL then 1×20 mL), dried over $K_2CO_3$ and concentrated to a volume of 20 mL under a stream of nitrogen. The solution is diluted with EtOH (35 mL), treated with $K_2CO_3$ (4.09 g, 29.6 mmol) and stirred for 18 h at rt. Water (7 mL) is added and the mixture stirred for 2 days. The mixture is concentrated to dryness, partitioned between 50% saturated NaCl (50 mL) and $CH_2Cl_2$ (4×50 mL), dried over $K_2CO_3$ and concentrated in vacuo to a brown solid (833 mg). The crude material is chromatographed over a standard 40 g Biotage column, eluting with 50% EtOAc/hexane. The appropriate fractions are combined and concentrated to afford 624 mg (68%) of (3-chlorofuro[2,3-c]pyridin-5-yl)methanol as a yellow oil. $^1H$ NMR (DMSO-$d_6$): δ 4.69, 5.56, 7.69, 8.55, 8.93 ppm.

Oxalyl chloride (231 μL, 2.6 mmol) is combined with $CH_2Cl_2$ (10 mL), cooled to −78° C., treated dropwise with DMSO (373 μL, 5.3 mmol) and stirred for 20 min. The cooled solution is treated dropwise with a solution of (3-chlorofuro[2,3-c]pyridin-5-yl)methanol (420 mg, 2.3 mmol) in THF (5 mL)/$CH_2Cl_2$ (5 mL), stirred for 1 h, then treated dropwise with $Et_3N$ (1.59 mL, 11.45 mmol). The mixture is stirred for 30 min at −78° C., then 30 min at 0° C. The mixture is washed with saturated $NaHCO_3$ (20 mL) and the organics dried over $K_2CO_3$ and concentrated in vacuo to a yellow solid (410 mg). The crude material is chromatographed over 20 g slurry-packed silica gel, eluting with 15% EtOAc/hexane. The appropriate fractions are combined and concentrated in vacuo to afford 322 mg (77%) of 3-chlorofuro[2,3-c]pyridine-5-carbaldehyde as a white solid. $^1H$ NMR ($CDCl_3$): δ 7.89, 8.33, 9.02, 10.18 ppm.

3-Chlorofuro[2,3-c]pyridine-5-carbaldehyde (317 mg, 1.74 mmol) is dissolved in THF (10 mL)/t-BuOH (5 mL)/$H_2O$ (5 mL), treated with a single portion of sodium chlorite (592 mg, 5.24 mmol) and $KH_2PO_4$ (473 mg, 3.48 mmol) and stirred at rt for 18 h. The reaction mixture is concentrated in vacuo to dryness, suspended in water (10 μL), acidified to pH 3.5 with concentrated HCl and stirred at rt for 2 h. The resulting solid is filtered, washed with water and dried in a vacuum oven at 40° C. for 18 h to afford 364 mg of 3-chlorofuro[2,3-c]pyridine-5-carboxylic acid as a white solid. MS (EI) m/z: 197 ($M^+$).

Coupling:

Example 28 is obtained using 3-chlorofuro[2,3-c]pyridine-5-carboxylic acid according to Method C making non-critical changes to afford 101 mg of a white solid. MS (EI) m/z: 305 ($M^+$).

EXAMPLE 29

N-[(3R)-1-Azabicyclo[2.2.2]oct-3-yl]-3-bromofuro[2,3-c]pyridine-5-carboxamide

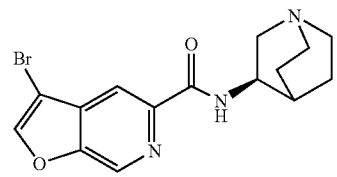

Preparation of Acid:

Furo[2,3-c]pyridin-5-ylmethyl acetate (5.17 g, 27.05 mmol) is dissolved in $CH_2Cl_2$ (130 mL), layered with saturated $NaHCO_3$ (220 mL), treated with $Br_2$ (8.36 mL, 162.3 mmol) and stirred very slowly for 4.5 h at rt. The mixture is stirred vigorously for 30 min, is diluted with $CH_2Cl_2$ (100 mL) and the layers separated. The aqueous layer is extracted with $CH_2Cl_2$ (2×100 mL) and the combined organics are concentrated to a small volume under a stream of nitrogen. The solution is diluted with EtOH (200 mL), treated with $K_2CO_3$ (22.13 g, 160.1 mmol) and stirred for 2.5 days at rt. The mixture is concentrated to dryness, partitioned between 50% saturated NaCl (200 mL) and $CH_2Cl_2$ (5×200 mL), dried over $Na_2SO_4$ and concentrated in vacuo to a yellow solid (6.07 g). The crude material is adsorbed onto silica gel (12 g) and chromatographed over 250 g slurry-packed silica gel, eluting with a gradient of 50% EtOAc/hexane to 100% EtOAc. The appropriate fractions are combined and concentrated in vacuo to afford 5.02 g (81%) of (3-bromofuro[2,3-c]pyridin-5-yl)methanol as a white solid. MS (EI) m/z: 227 ($M^+$).

Oxalyl chloride (1.77 mL, 20.1 mmol) is combined with $CH_2Cl_2$ (60 mL) in a dried flask under nitrogen, cooled to −78° C., treated dropwise with DMSO (2.86 mL, 40.25 mmol) and stirred for 20 min. The cooled solution is treated drop-wise with a solution of (3-bromofuro[2,3-c]pyridin-5-yl)methanol (4.0 mg, 17.5 mmol) in THF (50 mL), stirred for 1 h, then treated drop-wise with $Et_3N$ (12.2 mL, 87.5 mmol). The mixture is stirred for 30 min at −78° C., then 30 min at 0° C. The mixture is washed with saturated NaHCO$_3$ (120 mL) and the organics dried over K$_2$CO$_3$ and concentrated in vacuo to a dark yellow solid (3.91 g). The crude material is chromatographed over 150 g slurry-packed silica gel, eluting with 30% EtOAc/hexane. The appropriate fractions are combined and concentrated in vacuo to afford 3.93 g (99%) of 3-bromofuro[2,3-c]pyridine-5-carbaldehyde as a white solid. MS (EI) m/z: 225 (M$^+$).

3-Bromofuro[2,3-c]pyridine-5-carbaldehyde (3.26 g, 14.42 mmol) is dissolved in THF (100 mL)/t-BuOH (50 mL)/H$_2$O (50 mL), treated with a single portion of NaOCl$_2$ (4.89 g, 43.3 mmol) and KH$_2$PO$_4$ (3.92 g, 28.8 mmol) and stirred at rt for 18 h. The white solid is collected via filtration and the filtrate is concentrated in vacuo to dryness. The residue is suspended in water (25 mL), acidified to pH 2 with concentrated HCl and the resulting solid collected via filtration. The collected solids are dried in a vacuum oven at 50° C. for 18 h and combined to afford 3.52 g (99%) of 3-bromofuro[2,3-c]pyridine-5-carboxylic acid as a white solid. MS (EI) m/z: 241 (M$^+$).

Coupling:

Example 29 is obtained using 3-bromofuro[2,3-c]pyridine-5-carboxylic acid according to Method C making non-critical changes to afford 670 mg (96% yield) of a white solid. MS (EI) m/z: 335 (M$^+$).

EXAMPLE 30

N-[(3R)-1-Azabicyclo[2.2.2]oct-3-yl]furo[3,2-c]pyridine-6-carboxamide dihydrochloride

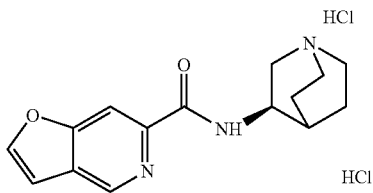

3-Bromofuran (8.99 mL, 100.0 mmol) is dissolved in DMF (8.5 mL), cooled to 0° C., treated dropwise with POCl$_3$ (9.79 mL, 105.0 mmol), stirred for 1 h at rt and then heated to 80° C. for 2 h. The mixture is cooled to rt, poured over ice (1 kg) and neutralized to pH 9 with solid K$_2$CO$_3$. The mixture is stirred for 1 h, extracted with Et$_2$O (3×500 mL), dried over K$_2$CO$_3$ and concentrated to a dark brown oil. The crude material is chromatographed over 600 g slurry-packed silica gel, eluting with 6% EtOAc/hexane (4 L), 8% EtOAc/hexane (2 L), 10% EtOAc/hexane (1 L), and finally 20% EtOAc/hexane. The appropriate fractions are combined and concentrated in vacuo to afford 14.22 g (81%) of 3-bromo-2-furaldehyde as a yellow oil. MS (EI) m/z: 174 (M$^+$).

3-Bromo-2-furaldehyde (14.22 g, 81.3 mmol) is combined with ethylene glycol (6.55 mL, 117.4 mmol) and para-toluene sulfonic acid monohydrate (772 mg, 4.06 mmol) in benzene (200 mL) and heated to reflux with a Dean-Stark trap for 5 h. Additional ethylene glycol (1.64 mL, 29.41 mmol) and benzene (150 mL) are added and the solution is heated for an additional 2 h. The mixture is cooled to rt, treated with saturated NaHCO$_3$ and stirred for 0.5 h. The layers are separated and the organics are dried over Na$_2$SO$_4$ and concentrated to a brown oil (18.8 g). The crude material is chromatographed over 700 g slurry-packed silica gel, eluting with 15% EtOAc/hexane. The appropriate fractions are combined and concentrated in vacuo to afford 16.45 g (92%) of 2-(3-bromo-2-furyl)-1,3-dioxolane as a yellow-orange oil. MS (EI) m/z: 218 (M$^+$).

2-(3-Bromo-2-furyl)-1,3-dioxolane (438 mg, 2.0 mmol) is dissolved in Et$_2$O (5 mL) in an oven-dried flask, under nitrogen, cooled to −78° C., treated dropwise with tert-butyllithium (2.59 mL, 4.4 mmol) and stirred for 1 h. DMF (178 μL, 2.3 mmol) in Et$_2$O (2 mL) is added dropwise, the mixture stirred for 4 h at −78° C., then treated with oxalic acid dihydrate (504 mg, 4.0 mmol) followed by water (2 mL). The cooling bath is removed and the mixture allowed to warm to rt over 1 h. The mixture is diluted with water (20 mL) and EtOAc (20 mL), the layers are separated and the aqueous layer extracted with EtOAc (1×20 mL). The organics are dried over Na$_2$SO$_4$ and concentrated to a yellow oil. The crude material is chromatographed over 12 g slurry-packed silica gel, eluting with 15% EtOAc/hexane. The appropriate fractions are combined and concentrated in vacuo to afford 228 mg (68%) of 2-(1,3-dioxolan-2-yl)-3-furaldehyde as a pale yellow oil. MS (EI) m/z: 168 (M$^+$).

2-(1,3-Dioxolan-2-yl)-3-furaldehyde (2.91 g, 17.31 mmol) is combined with formic acid (17 mL, 451 mmol) and water (4.25 mL) and stirred at rt for 18 h. The mixture is slowly transferred into a solution of NaHCO$_3$ (45 g, 541 mmol) in water (600 mL), then stirred for 0.5 h. EtOAc (200 mL) is added, the layers separated and the aqueous layer extracted with EtOAc (2×200 mL). The combined organics are dried over Na$_2$SO$_4$ and concentrated to a yellow oil (3.28 g). The crude material is chromatographed over 90 g slurry-packed silica gel, eluting with 20% EtOAc/hexane. The appropriate fractions are combined and concentrated to afford 2.45 g of furan-2,3-dicarbaldehyde slightly contaminated with ethylene glycol diformate as a yellow oil. $^1$H NMR (CDCl$_3$): δ 7.00, 7.67, 10.07, 10.49 ppm.

C153 (2.34 g, 9.8 mmol) is dissolved in CHCl$_3$ (40 mL), treated with DBU (1.46 mL, 9.8 mmol), stirred for 5 min then added drop-wise to a 0° C. solution of furan-2,3-dicarbaldehyde (1.65 g, 8.9 mmol) in CHCl$_3$ (80 mL). The mixture is stirred for 2.5 h as the cooling bath expired then 5.5 h at rt and finally 24 h at 50° C. The mixture is concentrated in vacuo to a yellow oily-solid (6.66 g). The crude material is chromatographed over a standard 100 g slurry-packed silica gel, eluting with 65% EtOAc/hexane. The appropriate fractions are combined and concentrated in vacuo to afford 1.30 g (82%) of methyl furo[3,2-c]pyridine-6-carboxylate as a yellow solid. MS (EI) m/z: 177 (M$^+$).

Methyl furo[3,2-c]pyridine-6-carboxylate (1.55 g, 8.74 mmol) is dissolved in MeOH (30 mL) and H$_2$O (15 mL), treated with 3 N NaOH (6.4 mL) and stirred at rt for 7 h. The mixture is concentrated to dryness, dissolved in H$_2$O (10 mL) and acidified to pH 2 with concentrated HCl. The solution is concentrated to dryness, suspended in a smaller amount of water (7 mL) and the resulting solid collected via filtration (lot A). The filtrate is concentrated, triturated with water (3 mL) and the resulting solid collected via filtration (lot B). The filtrate from lot B is concentrated and carried on without further purification as an acid/salt mixture (lot C). Both lots A and B are dried in a vacuum oven at 50° C. for 18 h to afford 690 mg (48%) for lot A, 591 mg (42%) for lot B and 130 mg (10%) of furo[3,2-c]pyridine-6-carboxylic acid as yellow solids. MS (CI) m/z: 164 (M+H$^+$).

Coupling:

Example 30 is obtained using furo[3,2-c]pyridine-6-carboxylic acid according to Method C to afford 163 mg (54%) of a pale yellow solid. MS (EI) m/z: 271 (M+).

EXAMPLE 31

N-[(3R)-1-azabicyclo[2.2.2]oct-3-yl]-3-bromothieno[2,3-c]pyridine-5-carboxamide

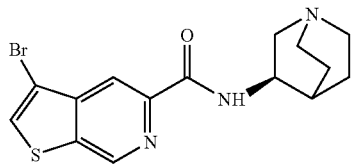

Preparation of the Acid:

C154 (630 mg, 3.3 mmole) is dissolved in 20 ml CH$_2$Cl$_2$. The solution is treated with Br$_2$ (1.1 ml, 20 mmole), is layered with 20 ml saturated NaHCO$_3$, and the two-phase mixture is agitated gently for 2 h. The reaction is stirred vigorously for 30 min, the layers are separated, and the organic layer is dried over anhydrous K$_2$CO$_3$. The organic layer is concentrated to a dark tan solid. The solid is dissolved in 20 ml 10% MeOH/CH$_2$Cl$_2$, is adsorbed onto 2 g silica gel (230–400 mesh), and chromatographed over 25 g silica gel (230–400 mesh) eluting with 65% EtOAc/hexane. The appropriate fractions are combined and concentrated to afford 635 mg (71%) of methyl-3-bromothieno[2,3-c]pyridine-5-carboxylate as a tan solid. $^1$H NMR (CDCl$_3$) δ 4.09, 7.82, 8.59, 9.25 ppm.

Methyl-3-bromothieno[2,3-c]pyridine-5-carboxylate (635 mg, 2.33 mmol) is combined with 25 ml MeOH. The mixture is treated with 2N NaOH (3 ml, 6 mmole) and 3 ml H$_2$O and the reaction is stirred 4 h at rt. The volatiles are removed in vacuo and the residue is combined with 5 ml H$_2$O. The pH of the mixture is adjusted to 3.5 with 10% aqueous HCl. The tan precipitate is collected, washed with water, and is dried in vacuo at 50° C. to afford 475 mg (79%) of 3-bromothieno[2,3-c]pyridine-5-carboxylic acid as a tan solid. MS (ESI): 257.9.

Coupling:

Example 31 is obtained using 3-bromothieno[2,3-c]pyridine-5-carboxylic acid according to Method C to afford 240 mg (91%) of an off-white solid. MS (EI) m/z: 365 (M+).

EXAMPLE 32

N-[(3R)-1-azabicyclo[2.2.2]oct-3-yl]benzofuro[3,2-c]pyridine-3-carboxamide

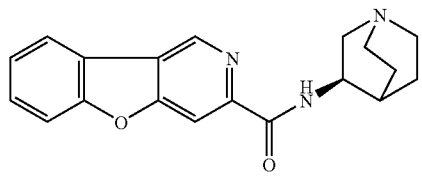

Benzofuran (11.02 ml, 100 mmol) and potassium acetate (1.96 g, 200 mmol) are dissolved in CHCl$_3$ (50 ml). Bromine (10.3 ml, 200 mmol) is dissolved in CHCl$_3$ (20 ml) and added dropwise. Following addition, the reaction is heated at 50° C. for 5 h. The mixture is cooled to rt and quenched onto 5% sodium bisulfite solution (100 ml). The layers are allowed to separate, and the organic is washed with 5% NaHCO$_3$ (1×100 ml), dried over Na$_2$SO$_4$, filtered, and concentrated to a green oil. The crude material is chromatographed over 1 kg slurry-packed silica eluting with 100% pentane. The appropriate fractions are combined and concentrated to give 15.86 g (57%) of 2,3-dibromobenzofuran as a pale oil. HRMS (EI) calcd for C$_8$H$_4$Br$_2$O: 273.8630, found 273.8624.

2,3-Dibromobenzofuran (1.37 g, 5.0 mmol) is dissolved in Et$_2$O (20 ml) in a dry flask under nitrogen and cooled to −78° C. t-Butyllithium (6.47 ml, 11.0 mmol) is added dropwise, and the chilled solution is stirred 1 h. DMF (0.45 ml, 5.75 mmol) is dissolved in Et$_2$O (5 ml) and also added dropwise, and the mixture is stirred at −78° C. for another 4 h. The reaction is warmed to rt, whereby oxalic acid dihydrate (1.26 g, 10.0 mmol) and water (5 ml) are added. The reaction continued stirring at rt for 2 days and is then diluted with water (25 ml) and EtOAc (35 ml). The layers are allowed to separate, and the aqueous is extracted with EtOAc (1×35 ml). The organics are combined, dried over Na$_2$SO$_4$, filtered, and concentrated to an orange oil that solidified upon standing. The crude material is chromatographed over 100 g slurry-packed silica, eluting with 20% EtOAc/hexane. The appropriate fractions are combined and concentrated to afford 628 mg (56%) of 3-bromo-1-benzofuran-2-carbaldehyde as a yellow crystalline solid. HRMS (FAB) calcd for C$_9$H$_5$BrO$_2$+H: 224.9552, found 224.9555.

3-bromo-1-benzofuran-2-carbaldehyde (5.49 g, 24.4 mmol) is combined with para-toluene sulfonic acid hydrate (232 mg, 1.2 mmol) and ethylene glycol (2.44 ml, 43.9 mmol) in benzene (75 ml). The reaction is refluxed with a Dean-Stark trap for 5 h. The mixture is cooled to rt and diluted with saturated NaHCO$_3$ solution (20 ml) and left to stir for an additional 12 h. The layers are allowed to separate, and the organic layer is dried over Na$_2$SO$_4$, filtered, and concentrated to afford 6.6 g (100%) of 3-bromo-2-(1,3-dioxolan-2-yl)-1-benzofuran as a dark brown oil. HRMS (FAB) calcd for C$_{11}$H$_9$BrO$_3$+H: 268.9814, found 268.9821.

3-Bromo-2-(1,3-dioxolan-2-yl)-1-benzofuran (6.6 g 24.5 mmol) is dissolved in Et$_2$O (100 ml) in a 3-neck, flame-dried, round-bottom flask under nitrogen and cooled to −78° C. tert-butyllithium (31.7 ml, 53.9 mmol) is added dropwise, and the chilled solution is stirred 1 h. DMF (2.18 ml, 28.2 mmol) is dissolved in Et$_2$O (25 ml) and also added dropwise, and the mixture is stirred at −78° C. for another 7 h. The reaction is warmed to rt, whereby oxalic acid dihydrate (6.18 g, 49.0 mmol) and water (25 ml) are added. The reaction continued stirring at rt overnight and is then diluted with water (125 ml) and EtOAc (175 ml). The layers are allowed to separate, and the aqueous is extracted with EtOAc (1×100 ml). The organics are combined, dried over sodium sulfate, filtered, and concentrated to a brown oil. The crude material is chromatographed over 350 g slurry-packed silica, eluting with 30% ethyl acetate/hexane. The appropriate fractions are combined and concentrated to afford 3.84 g (72%) of 2-(1,3-dioxolan-2-yl)-1-benzofuran-3-carbaldehyde as a yellow/orange oil. MS (EI) m/z: 218 (M+).

2-(1,3-Dioxolan-2-yl)-1-benzofuran-3-carbaldehyde (3.63 g, 16.6 mmol) is dissolved in formic acid (16.3 ml, 433 mmol) with water (4.1 ml). After 2 hours, additional formic acid (10 ml) and water (2.5 ml) are added to alleviate the slurry. The reaction stirred 12 h and is diluted with water (30 ml). The resulting slurry is filtered, dried in an air stream, affording 2.66 g (92%) of 1-benzofuran-2,3-dicarbaldehyde as an orange solid. MS (EI) m/z: 174 (M$^+$).

1-Benzofuran-2,3-dicarbaldehyde (174 mg, 1.0 mmol) is dissolved in $CH_2Cl_2$ (5 ml) and chilled to 0° C. C153 (263 mg, 1.1 mmol) is dissolved in $CH_2Cl_2$ (5 ml) and combined with DBU (0.16 ml, 1.1 mmol), stirring for 5 min. This solution is added dropwise to the chilled benzofuran solution. The reaction mixture is stirred cold for 1 h, 4 days at tr, and 2 days at 45° C. The volatiles are removed in vacuo and the crude material is chromatographed over 50 g slurry-packed silica eluting with 40% EtOAc/hexane. The appropriate fractions are combined and concentrated to give 180 mg (79%) of methyl benzofuro[3,2-c]pyridine-3-carboxylate as a yellow solid. HRMS (FAB) calcd for $C_{13}H_9NO_3$+ H: 228.0661, found 228.0654.

Methyl benzofuro[3,2-c]pyridine-3-carboxylate (2.02 g, 8.89 mmol) is dissolved in MeOH (50 ml) and water (10 ml). 2M NaOH (5.3 ml, 10.67 mmol) is added dropwise, and the reaction stirred overnight at rt. When the reaction is complete by TLC, the volatiles are removed in vacuo. The solid residue is suspended in water (40 ml) and the pH is adjusted to 3 with concentrated HCl. The white slurry is filtered, and the cake is dried first in a stream of air and then in a vacuum oven overnight, affording 1.84 g (97%) of benzofuro[3,2-c]pyridine-3-carboxylic acid as a pale yellow solid. $^1$H NMR (DMSO-d$_6$) δ 7.56 (t, J=8 Hz), 7.68 (t, J=7 Hz), 7.877 (d, J=8 Hz), 8.38 (m), 9.51 ppm.

Coupling:

Example 32 is obtained using benzofuro[3,2-c]pyridine-3-carboxylic acid according to Method C to afford 337 mg of a tan solid. MS (ESI+) for $C_{19}H_{19}N_3O_2$ m/z 322.1 (M+H)$^+$.

EXAMPLE 33

N-[(2S,3R)-2-methyl-1-azabicyclo[2.2.2]oct-3-yl] furo[2,3-c]pyridine-5-carboxamide dihydrochloride

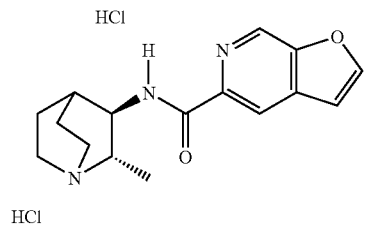

Preparation of (2S,3R)-2-methyl-1-azabicyclo[2.2.2]octan-3-amine dihydrochloride:

A mixture of 2-methylene-3-quinuclidinone dihydrate hydrochloride (27.18 g, 0.1296 mol, 1 eq) and $K_2CO_3$ (86.0 g, 0.6213 mol, 4.8 eq) is dissolved in 130 mL water and 250 mL $CH_2Cl_2$ and stirred vigorously. After 3 days, the layers are separated and the aqueous layer is extracted with $CH_2Cl_2$. The combined organic layers are dried (MgSO$_4$), filtered and concentrated to give 17.8 g (100%) of 2-methylenequinuclidin-3-one as a yellow oil. MS (ESI) for $C_8H_{11}NO$ m/z 138.1 (M$^+$).

2-Methylenequinuclidin-3-one (17.8 g, 0.1296 mol, 1 eq) is dissolved in 40 mL MeOH in a Parr hydrogenation bottle. A THF slurry of 10% Pd/C (0.57 g) is added. The mixture is hydrogenated for 45 min at 45 psi, recharging as needed. The mixture is filtered through a pad of Celite. The Celite is washed with excess MeOH. The solution is concentrated to give a solid and a yellow oil. The mixture is taken up in ether, filtered and concentrated to provide 16.2 g (90%) of 2-methylquinuclidin-3-one. MS (ESI) for $C_8H_{13}NO$ m/z 140.2 (M$^+$).

2-Methylquinuclidin-3-one (39.59 g, 0.2844 mol, 1 eq) and hydroxylamine hydrochloride (20.0 g, 0.2878 mol, 1.01 eq) are dissolved in 170 mL absolute EtOH. The mixture is heated under reflux until a clear solution develops (about 20 min), after which is immediately followed by formation of a white precipitate. The reaction is cooled and allowed to stand overnight. The mixture is cooled in an ice bath, the solids are filtered and dried (house vacuum) to provide 46.4 g of (3E/Z)-2-methyl-1-azabicyclo[2.2.2]octan-3-one oxime hydrochloride. A second crop of 2.4 g is also obtained. Overall yield is 48.8 g (90%). The 2-methyl-1-azabicyclo[2.2.2]octan-3-one oxime hydrochloride is a 4:1 mixture of oxime isomers. MS (ESI) for $C_8H_{14}N_2O$ m/z 154.8 (M$^+$). Partial $^1$H NMR (400 MHz, DMSO) δ 4.39 (0.2H), 4.29 (0.8H), 1.57 (0.6H), 1.47 (2.4H).

A solution of sodium n-propoxide (prepared from 5.5 g sodium (0.24 mol) and 100 mL n-propanol) is added dropwise to a suspension of (3E/Z)-2-methyl-1-azabicyclo[2.2.2]octan-3-one oxime hydrochloride (45.8 g, 0.24 mol, 1 eq) in 150 mL n-propanol. After complete addition, 250 mL of n-propanol is added, and the mixture is heated under reflux. Sodium (55.2 g, 2.40 mol, 10 eq) is added in portions to the refluxing mixture. The mixture is heated under reflux overnight. After about 14 h, the mixture is cooled, water is added and the layers are separated. The n-propanol layer is washed with brine and dried (MgSO$_4$). The combined aqueous layers are extracted with CHCl$_3$ and dried (MgSO$_4$). The combined, dried organic layers are treated with about 70 mL concentrated HCl. The solvent is removed in vacuo. Absolute EtOH is added, and the solvent is removed. The sequence is repeated 2–3 times with fresh EtOH until a white solid formed. Absolute EtOH is added, the solids are filtered and dried (vacuum oven, about 60° C.) to provide 36.5 g of trans 3-amino-2-methylquinuclidine dihydrochloride. MS (ESI) for $C_8H_{16}N_2$ m/z 141.3 (M$^+$). Additional material is obtained from the mother liquor: 7.8 g (2$^{nd}$ crop) and 1.5 g (3$^{rd}$ crop); this material is a mixture of both trans and cis isomers.

4-Chlorobenzoic acid (26.3 g, 0.1681 mol, 1.1 eq) and TEA (106 mL, 0.764 mol, 5 eq.) are dissolved in 300 mL THF. Diphenylphosphoryl chloride (32.0 mL, 0.1681 mol, 1.1 eq) is added dropwise. After 1 h, trans 2-methylquinuclidin-3-amine dihydrochloride (32.6 g, 0.1528 mol, 1 eq) is added. The mixture is allowed to stir at RT overnight. 1N NaOH (about 100 mL) is added, and the pH is adjusted to pH 11 with 50% NaOH and about 50 g $K_2CO_3$. The layers are separated. The aqueous layer is extracted with CHCl$_3$. The combined organic layers are dried (MgSO$_4$), filtered and concentrated. The residue is taken up in heptane and concentrated to give 35.1 g (82%) of 4-chloro-N-(2-methyl-1-azabicyclo[2.2.2]oct-3-yl)phenyl-2-carboxamide as a light yellow solid. The enantiomers are separated on a 5×50 cm Chiralcel OD column at 30° C., eluting with 15% IPA/heptane+0.1% DEA at 90 mL/min to provide 17.4 g of the eutomer at about 97% ee. The p-TsOH salt is prepared and recrystallized from EtOH/EtOAc. [α]$^{25}_D$=+3° (c 0.96, methanol). HRMS (FAB) calcd for $C_{15}H_{19}ClN_2O$+H 279.1264, found 279.1272.

A solution of 4-chloro-N-[(2S,3R)-2-methyl-1-azabicyclo[2.2.2]oct-3-yl]benzamide (17.2 g, 61.7 mmol) in absolute EtOH (70 mL) and concentrated HCl (70 mL) is heated under reflux for about 64 h. The reaction is monitored for disappearance of starting amide by reverse phase HPLC (ZORBAX Eclipse XDB-C8, 4.6 mm×15 cm, 80:12:8 $H_2O$/$CH_3CN$/IPA). The solvent is removed in vacuo. The residue is dissolved/suspended in EtOH and the solvent is removed (twice). The solid is suspended in boiling EtOH, filtered and dried (vacuum oven, about 60° C.) to provide 8.8 g (67%) of N-(2S,3R)-2-methyl-1-azabicyclo[2.2.2]octan-3-amine dihydrochloride as a white solid. MS (EI) m/z 141.2 ($M^+$).

Coupling:

Example 33 is prepared using C18 according to Method C to afford 0.79 g (73%) of the desired product. MS for $C_{16}H_{19}N_3O_2$ (ESI) $(M+H)^+$ m/z 286.2.

EXAMPLE 34

3-methyl-N-[(2S,3R)-2-methyl-1-azabicyclo[2.2.2]oct-3-yl]furo[2,3-c]pyridine-5-carboxamide dihydrochloride

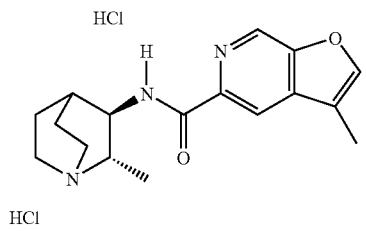

Example 34 is obtained using (2S,3R)-2-methyl-1-azabicyclo[2.2.2]octan-3-amine dihydrochloride and C56 according to Method C to afford 0.18 g (49%) of the desired product. HRMS (FAB) calculated for $C_{17}H_{21}N_3O_2$+H 300.1712, found 300.1701.

EXAMPLE 35

N-[(2S,3R)-2-methyl-1-azabicyclo[2.2.2]oct-3-yl]thieno[2,3-c]pyridine-5-carboxamide dihydrochloride

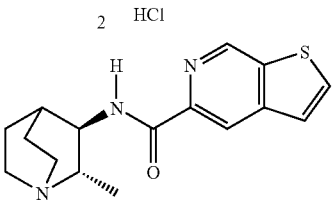

Coupling:

Example 35 is obtained using (2S,3R)-2-methyl-1-azabicyclo[2.2.2]octan-3-amine dihydrochloride and C156 according to Method C to afford 0.209 g (53%) of the desired product. HRMS (FAB) calculated for $C_{16}H_{19}N_3OS$+H 302.1327, found 302.1347.

EXAMPLE 36

N-[(2S,3R)-2-methyl-1-azabicyclo[2.2.2]oct-3-yl]thieno[3,2-c]pyridine-6-carboxamide dihydrochloride

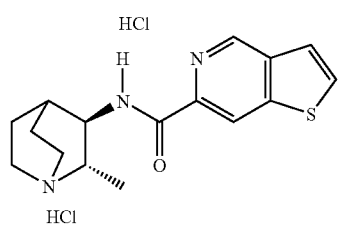

Coupling:

Example 36 is obtained using thieno[2,3-c]pyridine-6-carboxylic acid and (2S,3R)-2-methyl-1-azabicyclo[2.2.2]octan-3-amine dihydrochloride according to Method C to provide 0.166 g (44%) of the desired product. HRMS (FAB) calculated for $C_{16}H_{19}N_3OS$+H 302.1327, found 302.1323.

EXAMPLE 37

N-[(3R)-1-Azabicyclo[2.2.2]oct-3-yl]-3-ethynylfuro[2,3-c]pyridine-5-carboxamide

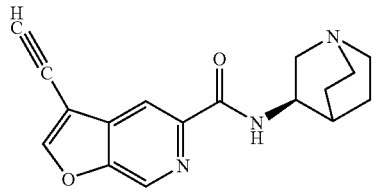

Example 29 (350 mg, 1 mmol) is combined with dichlorobis(benzonitrile)palladium (II) (57 mg, 0.15 mmol) and cuprous iodide (19 mg, 0.1 mmol) in a dry flask, and the flask is purged with $N_2$. Anhydrous dioxane (3 mL) is added, followed by tri-t-butylphosphine (10% wt. in hexane, 658 μL, 0.325 mmol), trimethylsilylacetylene (170 μL, 1.2 mmol) and finally DIEA (168 μL, 1.2 mmol). The mixture is stirred at rt under $N_2$ for 24 h, then concentrated in vacuo. The residue is partitioned between $CHCl_3$ and 50% saturated NaCl, and the organics are dried over $Na_2SO_4$ and concentrated in vacuo. The crude material is chromatographed over 17.5 g silica gel, eluting with 0.5% $NH_4OH$/8% MeOH/$CHCl_3$. The appropriate fractions are combined and concentrated to an oil. The oil is layered with $Et_2O$, capped and allowed to stand for 18 h. The resulting solid is placed under high vacuum to afford 176 mg (48%) of N-[(3R)-1-azabicyclo[2.2.2]oct-3-yl]-3-[(trimethylsilyl)ethynyl]furo[2,3-c]pyridine-5-carboxamide as a taupe-colored solid. HRMS (FAB) calcd for $C_{20}H_{25}N_3O_2Si$+$H_1$ 368.1794, found 368.1802.

N-[(3R)-1-azabicyclo[2.2.2]oct-3-yl]-3-[(trimethylsilyl)ethynyl]furo[2,3-c]pyridine-5-carboxamide (168 mg, 0.46 mmol) is dissolved in MeOH (10 mL), treated with $NaHCO_3$ (800 mg, 9.5 mmol) in $H_2O$ (10 mL) and stirred at rt for 3 h. The mixture is concentrated to dryness and partitioned between $CHCl_3$ and $H_2O$. The organics are dried over Na$_2$SO$_4$ and concentrated to a brown oil. The crude material is chromatographed over 6 g silica gel, eluting with 1% N$_4$OH/6% MeOH/CHCl$_3$. The appropriate fractions are combined and concentrated to afford 54 mg (40%) of Example 37 as a white solid. HRMS (FAB) calcd for C$_{17}$H$_{17}$N$_3$O$_2$+H$_1$ 296.1399, found 296.1388.

EXAMPLE 38

N-[(3S)-1-azabicyclo[2.2.2]oct-3-yl]furo[2,3-c]pyridine-5-carboxamide

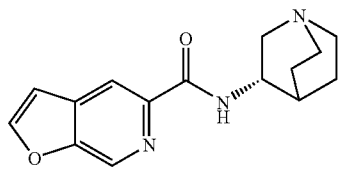

Example 38 is obtained (92% yield) as the free base by coupling acid C18 with (S)-(−)-3-aminoquinuclidine according to Method C with omission of the HCl treatment. HRMS (FAB) calculated for C$_{15}$H$_{17}$N$_3$O$_2$+H: 272.1399, found 272.1404 (M+H)$^+$.

EXAMPLE 39

N-[(+/−)1-azabicyclo[2.2.2]oct-3-yl]furo[2,3-c]pyridine-5-carboxamide

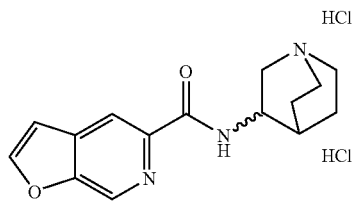

Example 39 is obtained (43% yield) by coupling acid C18 with (+/−)-3-aminoquinuclidine according to Method C with non-critical changes. MS (ESI) m/z: 272.1 (M+H)$^+$.

EXAMPLE 40

N-[(3R)-1-azabicyclo[2.2.2]oct-3-yl]thieno[3,4-c]pyridine-6-carboxamide methanesulfonate

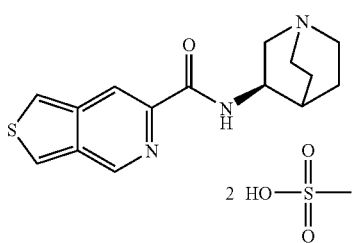

3,4-Dibromothiophene (12.5 ml, 113 mmol) is combined with CuCN (30.4 g, 339 mmol) in DMF (40 ml) in a dry flask under nitrogen utilizing an over-head stirrer. The reaction is allowed to reflux at 180° C. for 5 h. The dark mixture is then poured into a solution of FeCl$_3$ (113.6 g, 700 mmol) in 1.7M HCl (200 ml) and heated at 65° C. for 0.5 h, again using the over-head stirrer. The reaction is cooled to rt and extracted with CH$_2$Cl$_2$ (7×300 ml). Each extract is washed individually with 200 ml each 6M HCl (2×), water, saturated NaHCO$_3$, and water. The organics are then combined, dried over MgSO$_4$, filtered, and concentrated, affording 10.49 g (69%) of 3,4-dicyanothiophene as a fluffy tan solid. HRMS (EI) calcd for C$_6$H$_2$N$_2$S: 133.9939, found 133.9929 (M$^+$).

3,4-Dicyanothiophene (5.0 g, 37.2 mmol) is suspended in benzene (150 ml) in a dry flask under nitrogen utilizing an over-head stirrer. Diisobutyl aluminum hydride (1.0M in toluene) (82.0 ml, 82.0 mmol) is added dropwise, and the reaction stirred at rt for 2 h. The reaction is then carefully quenched with MeOH (5 ml) and poured onto 30% H$_2$SO$_4$ (60 ml) with ice (200 g). The slurry is stirred until all lumps are dissolved, and the layers are allowed to separate. The aqueous layer is extracted with Et$_2$O (4×200 ml), and the combined organics are dried over MgSO$_4$, filtered, and adsorbed onto silica. The crude material is chromatographed over 225 g slurry-packed silica, eluting with 40% EtOAc/hexane. The appropriate fractions are combined and concentrated to afford 1.88 g (36%) of 3,4-thiophene dicarboxaldehyde as a pale yellow solid. MS (EI) m/z: 140 (M$^+$).

3,4-Thiophene dicarboxaldehyde (1.0 g, 7.13 mmol) is dissolved in CH$_2$Cl$_2$ (40 ml) and chilled to 0° C. C153 (1.88 g, 7.85 mmol) is dissolved in CH$_2$Cl$_2$ (30 ml) and combined with DBU (1.1 ml, 7.85 mmol). This solution is added dropwise to the chilled thiophene solution after stirring for 5 min. The reaction mixture is stirred at 0° C. for 1 h and then overnight at rt. The volatiles are removed in vacuo and the crude material is chromatographed over 68 g slurry-packed silica eluting with 70% EtOAc/hexane. The appropriate fractions are combined and concentrated to yield 2.09 g of the carbinol intermediate as a white foam. The intermediate is dissolved in CHCl$_3$ (50 ml) and treated with DBU (1.32 ml, 8.8 mmol) and TFAA (1.24 ml, 8.8 mmol) in a drop-wise fashion. The reaction is stirred overnight at rt and is then quenched with saturated NaHCO$_3$ solution (50 ml). The layers are separated, and the aqueous layer is extracted with CHCl$_3$ (2×50 ml). The combined organics are dried over MgSO$_4$, filtered, and concentrated to a yellow oil. This oil is chromatographed over 50 g slurry-packed silica, eluting with 90% EtOAc/hexane. The appropriate fractions are combined and concentrated to afford 1.2 g (88%) of methyl thieno[3,4-c]pyridine-6-carboxylate as a yellow solid. MS (EI) m/z: 193 (M$^+$).

Methyl thieno[3,4-c]pyridine-6-carboxylate (250 mg, 1.3 mmol) is dissolved in MeOH (7 ml) and water (1 ml). 2M NaOH (0.72 ml, 1.43 mmol) is added drop-wise. The reaction is stirred overnight at rt and is monitored by TLC. The volatiles are removed in vacuo and the residue is dissolved in water (2 ml). 10% HCl is used to adjust the pH to 3, and the reaction again stirred overnight at rt. The aqueous solution is extracted repeatedly with EtOAc (20×10 ml). The combined organics are dried over MgSO$_4$, filtered, and concentrated to a yellow solid. The amount of isolated product via extraction is minimal (67 mg), so the aqueous layer is concentrated and found to contain the majority of product. Extraction of the solid aqueous residue with EtOAc provided 225 mg (97%) of thieno[3,4-c]pyridine-6-carboxylic acid as a yellow solid. MS (EI) m/z: 179 (M$^+$).

Thieno[3,4-c]pyridine-6-carboxylic acid (180 mg, 1.0 mmol) is dissolved in DMF (5 ml) with DIEA (0.52 ml, 3.0 mmol) and (3R)-aminoquinuclidine dihydrochloride (219 mg, 1.1 mmol) and chilled to 0° C. HATU (380 mg, 1.0 mmol) is added portion-wise and the reaction is stirred for 3 h, allowing the ice bath to expire. Volatiles are removed in vacuo, leaving a brown crude oil. The crude material is chromatographed over 25 g slurry-packed silica, eluting with 1% NH$_4$OH/10% MeOH/CH$_2$Cl$_2$. The appropriate fractions are collected and concentrated to a dark oil. The oil is dissolved in 1M HCl in MeOH (3 ml) and stirred overnight. A brown precipitate is formed, but upon isolation via filtration, the compound quickly degraded. The isolated salt is then free-based in MeOH with Amberjet 4400 OH Strongly Basic Anion Exchanger resin. The resin is filtered off, and the liquor concentrated to a glass. The residue is treated with EtOAc (1 ml), Et$_2$O (1 ml), and MeSO$_3$H (52 μl, 0.78 mmol), and stirred overnight at rt. The precipitate is isolated via filtration and handled carefully under nitrogen, affording 67 mg (14%) of Example 40 as a yellow solid. MS (EI) m/z: 287 (M$^+$).

Materials and Methods for Identifying Binding Constants:

Membrane Preparation. Male Sprague-Dawley rats (300–350 g) are sacrificed by decapitation and the brains (whole brain minus cerebellum) are dissected quickly, weighed and homogenized in 9 volumes/g wet weight of ice-cold 0.32M sucrose using a rotating pestle on setting 50 (10 up and down strokes). The homogenate is centrifuged at 1,000×g for 10 minutes at 4° C. The supernatant is collected and centrifuged at 20,000×g for 20 minutes at 4° C. The resulting pellet is resuspended to a protein concentration of 1–8 mg/mL. Aliquots of 5 mL homogenate are frozen at −80° C. until needed for the assay. On the day of the assay, aliquots are thawed at room temperature and diluted with Kreb's—20 mM Hepes buffer pH 7.0 (at room temperature) containing 4.16 mM NaHCO$_3$, 0.44 mM KH$_2$PO$_4$, 127 mM NaCl, 5.36 mM KCl, 1.26 mM CaCl$_2$, and 0.98 mM MgCl$_2$, so that 25–150 μg protein are added per test tube. Proteins are determined by the Bradford method (Bradford, M. M., *Anal. Biochem.*, 72, 248–254, 1976) using bovine serum albumin as the standard.

Binding Assay. For saturation studies, 0.4 mL homogenate are added to test tubes containing buffer and various concentrations of radioligand, and are incubated in a final volume of 0.5 mL for 1 hour at 25° C. Nonspecific binding was determined in tissues incubated in parallel in the presence of 1 μM MLA, added before the radioligand. In competition studies, drugs are added in increasing concentrations to the test tubes before addition of approximately 3.0 to 4.0 nM [$^3$H]-MLA. The incubations are terminated by rapid vacuum filtration through Whatman GF/B glass filter paper mounted on a 48 well Brandel cell harvester. Filters are pre-soaked in 50 mM Tris HCl pH 7.0–0.05% polyethylenimine. The filters are rapidly washed two times with 5 mL aliquots of cold 0.9% saline and then counted for radioactivity by liquid scintillation spectrometry.

Data Analysis. In competition binding studies, the inhibition constant (Ki) was calculated from the concentration dependent inhibition of [$^3$H]-MLA binding obtained from non-linear regression fitting program according to the Cheng-Prusoff equation (Cheng, Y. C. and Prussoff, W. H., *Biochem. Pharmacol.*, 22, p. 3099–3108, 1973). Hill coefficients were obtained using non-linear regression (Graph-Pad Prism sigmoidal dose-response with variable slope).

The aforementioned examples have the provided Ki values:

| Example # | Ki Value (nM) | Example # | Ki Value (nM) |
|---|---|---|---|
| Example 1 | 50–60 | Example 22 | 5 |
| Example 2 | 1301 | Example 23 | 5 |
| Example 3 | 2249 | Example 28 | 3 |
| Example 4 | 9–10 | Example 29 | 4 |
| Example 6 | 119 | Example 30 | 45 |
| Example 9 | 1–6 | Example 31 | 9 |
| Example 13 | 108 | Example 33 | 15 |
| Example 17 | 65 | Example 34 | 15 |
| Example 19 | 274 | Example 35 | 18 |
| Example 20 | 952 | Example 36 | 12 |
| Example 21 | 269 | Example 40 | 25 |

What is claimed is:

1. A compound of the Formula I:

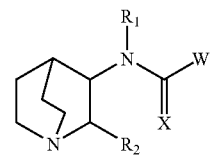

Formula I wherein W is

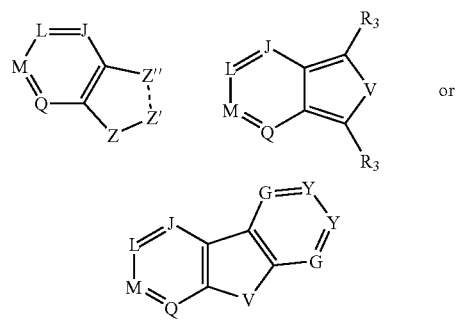

or provided that the bond between the —C(=X)— group and the W group may be attached at any available carbon atom within the W group as provided in R$_3$, R$_6$, and R$_{15}$;

X is O, or S;

Each R$_1$ is H, alkyl, cycloalkyl, halogenated alkyl, substituted phenyl, or substituted naphthyl;

R$_2$ is H, alkyl, halogenated alkyl, substituted alkyl, cycloalkyl, or aryl;

Z---Z'---Z" is selected from the group consisting of O—C(R$_3$)=C(R$_3$), O—C(R$_3$)$_2$—C(R$_3$)$_2$, C(R$_3$)$_2$—O—C(R$_3$)$_2$, C(R$_3$)=C(R$_3$)—O, C(R$_3$)$_2$—C(R$_3$)$_2$—O, S—C(R$_3$)=C(R$_3$), S—C(R$_3$)$_2$—C(R$_3$)$_2$, C(R$_3$)$_2$—S—C(R$_3$)$_2$, C(R$_3$)=C(R$_3$)—S and C(R$_3$)$_2$—C(R$_3$)$_2$—S;

Each R$_3$ is independently a bond to the core molecule provided that only one R$_3$ and no R$_6$ or R$_{15}$ is also said bond, H, F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —NO$_2$, —OR$_1$, —C(O)N(R$_{10}$)$_2$, —NR$_1$COR$_{16}$, —N(R$_{10}$)$_2$, —SR$_1$, —S(O)$_2$R$_1$, —C(O)R$_{16}$, —CO$_2$R$_1$, aryl, R$_7$, or R$_9$;

J, L, M, and Q are N or $C(R_6)$ provided that only one of J, L, M, or Q, is N and the others are $C(R_6)$, further provided that when the core molecule is attached to the pyridinyl moiety at M, Q is C(H), and further provided that there is only one attachment to the core molecule;

G and Y are $C(R_6)$, provided that when the molecule is attached to the phenyl moiety at Y, G is CH;

$R_4$ is H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, or $R_9$;

Each $R_5$ is independently $C_{1-3}$ alkyl or $C_{2-4}$ alkenyl;

Each $R_6$ is independently H, F, Br, I, Cl, —CN, —$CF_3$, —$OR_5$, —$SR_5$, or —$N(R_5)_2$, or a bond to the core molecule provided that only one $R_6$ and no $R_3$ or $R_{15}$ is said bond, V is selected from the group consisting of O, S, and $N(R_4)$;

$R_7$ is 5-membered heteroaromatic mono-cyclic moieties containing within the ring 1–3 heteroatoms independently selected from the group consisting of —O—, =N—, —$N(R_{19})$—, and —S—, and having 0–1 substituent selected from $R_{20}$ and further having 0–3 substituents independently selected from the group consisting of F, Cl, Br, and I, or $R_7$ is a 9-membered fused-ring moiety having a 6-membered ring fused to a 5-membered ring and having the formula

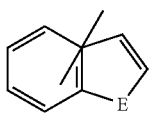

wherein E is O, S, or $NR_{19}$,

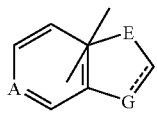

wherein E and G are independently selected from the group consisting of $CR_{18}$, O, S, N, and $NR_{19}$, and A is $CR_{18}$ or N, or

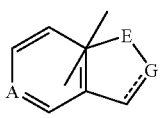

wherein E and G are independently selected from the group consisting of $CR_{18}$, O, S, N, and $NR_{19}$, and A is $CR_{18}$ or N, each 9-membered fused-ring moiety having 0–1 substituent selected from $R_{20}$ and further having 0–3 substituent(s) independently selected from the group consisting of F, Cl, Br, and I, and having a bond directly or indirectly attached to the core molecule where valency allows in either the 6-membered or the 5-membered ring of the fused-ring moiety;

Each $R_8$ is independently H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_9$ is 6-membered heteroaromatic mono-cyclic moieties containing within the ring 1–3 heteroatoms selected from =N— and having 0–1 substituent selected from $R_{20}$ and 0–3 substituent(s) independently selected from the group consisting of F, Cl, Br, and I, or $R_9$ is 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from $R_{20}$ and 0–3 substituent(s) independently selected from the group consisting of F, Cl, Br, and I and having a bond directly or indirectly attached to the core molecule where valency allows;

Each $R_{10}$ is independently H, alkyl, cycloalkyl, heterocycloalkyl, alkyl substituted with 1 substituent selected from the group consisting of $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, and substituted phenyl;

Each $R_{11}$ is independently H, alkyl, cycloalkyl, heterocyclo-alkyl, halogenated alkyl, halogenated cycloalkyl, or halogenated heterocycloalkyl;

$R_{13}$ is —$OR_{11}$, —$SR_{11}$, —$NR_{11}R_{11}$, —$C(O)R_{11}$, —$C(O)NR_{11}R_{11}$, —CN, —$CF_3$, —$NR_{11}C(O)R_{11}$, —$S(O)_2NR_{11}R_{11}$, —$NR_{11}S(O)_2R_{11}$, or —$NO_2$;

Each $R_{15}$ is independently a bond to the core molecule provided that only one $R_{15}$ and no $R_6$ or $R_3$ is also said bond, H, F, Br, Cl, I, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, lactam heterocycloalkyl, —CN, —$NO_2$, —$OR_1$, —$C(O)N(R_{10})_2$, —$NR_1COR_{16}$, —$N(R_{10})_2$, —$SR_1$, —$CO_2R_1$, aryl, $R_7$, or $R_9$;

$R_{16}$ is H, alkyl, substituted alkyl, cycloalkyl, halogenated alkyl, heterocycloalkyl, substituted heterocycloalkyl, substituted phenyl, or substituted naphthyl;

Each $R_{18}$ is independently H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, —$NR_{11}S(O)_2R_{11}$, F, Cl, Br, I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, and further provided that the fused-ring moiety has 0–3 substituent(s) selected from F, Cl, Br, or I;

$R_{19}$ is H, alkyl, halogenated alkyl, substituted alkyl, cycloalkyl, halogenated cycloalkyl, substituted cycloalkyl, phenyl, —$SO_2R_8$, or phenyl having 1 substituent selected from $R_{20}$ and further having 0–3 substituents independently selected from F, Cl, Br, or I;

$R_{20}$ is alkyl, cycloalkyl, heterocycloalkyl, halogenated alkyl, halogenated cycloalkyl, halogenated heterocycloalkyl, —OR₁₁, —SR₁₁, —NR₁₁R₁₁, —C(O)R₁₁, —C(O)NR₁₁R₁₁, —CN, —NR₁₁C(O)R₁₁, —S(O)₂NR₁₁R₁₁, —NR₁₁S(O)₂R₁₁, —NO₂, alkyl substituted with 1–4 substituent(s) independently selected from the group consisting of F, Cl, Br, I, and R₁₃, cycloalkyl substituted with 1–4 substituent(s) independently selected from the group consisting of F, Cl, Br, I, and R₁₃, or heterocycloalkyl substituted with 1–4 substituent(s) independently selected from the group consisting of F, Cl, Br, I, and R₁₃;

or pharmaceutically acceptable salt, or racemic mixture thereof.

2. The compound according to claim 1, wherein X is O.
3. The compound according to claim 2, wherein R₁ is H.
4. The compound according to claim 3, wherein W is

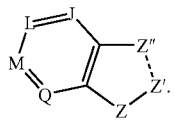

5. A compound of the Formula I:

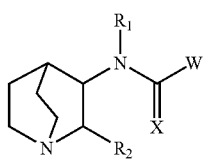

Formula I wherein
X is O, or S;
Each R₁ is H, alkyl, cycloalkyl, halogenated alkyl, substituted phenyl, or substituted naphthyl;
R₂ is H, alkyl, halogenated alkyl, substituted alkyl, cycloalkyl, or aryl; and W is thieno[2,3-b]pyridin-2-yl, thieno[2,3-b]pyridin-5-yl, thieno[2,3-b]pyridin-6-yl, thieno[2,3-c]pyridin-2-yl, furo[3,2-c]pyridin-2-yl, thieno[3,2-b]pyridin-2-yl, furo[2,3-b]pyridin-2-yl, thieno[3,2-b]pyridin-5-yl, thieno[3,2-b]pyridin-6-yl, furo[2,3-c]pyridin-5-yl, thieno[3,2-c]pyridin-2-yl, 2,3-dihydrofuro[2,3-c]pyridin-5-yl, thieno[2,3-c]pyridin-5-yl, furo[2,3-c]pyridin-2-yl, thieno[3,2-c]pyridin-6-yl, 1H-pyrrolo[2,3-c]pyridin-5-yl, or furo[3,2-c]pyridin-6-yl, any of which is optionally substituted with F, Br, Cl, —CN, —NO₂, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, halogenated heterocycloalkyl, lactam heterocycloalkyl, —OR₁, —NR₁COR₁₆, —N(R₁₀)₂, —SR₁, or aryl, with the proviso that R₁ in the OR₁ group may not be H, wherein each R₁₀ is independently H, alkyl, cycloalkyl, heterocycloalkyl, alkyl substituted with 1 substituent selected from the group consisting of R₁₃, cycloalkyl substituted with 1 substituent selected from R₁₃, heterocycloalkyl substituted with 1 substituent selected from R₁₃, halogenated alkyl, halogenated cycloalkyl, halogenated heterocycloalkyl, phenyl, and substituted phenyl;
R₁₃ is —OR₁₁, —SR₁₁, —NR₁₁R₁₁, —C(O)R₁₁, —C(O)NR₁₁R₁₁, —CN, —CF₃, —NR₁₁C(O)R₁₁, —S(O)₂NR₁₁R₁₁, —NR₁₁S(O)₂R₁₁, or —NO₂;

each R₁₁ is independently H, alkyl, cycloalkyl, heterocyclo-alkyl, halogenated alkyl, halogenated cycloalkyl, or halogenated heterocycloalkyl;
and R₁₆ is H, alkyl, substituted alkyl, cycloalkyl, halogenated alkyl, heterocycloalkyl, substituted heterocycloalkyl, substituted phenyl, or substituted naphthyl;

or a pharmaceutically acceptable salt, or racemic mixture thereof.

6. The compound according to claim 5, wherein R₂ is alkyl, halogenated alkyl, or substituted alkyl.
7. The compound according to claim 6, wherein R₂ is alkyl.
8. The compound according to claim 7, wherein R₂ is CH₃.
9. The compound according to claim 8, wherein the compound of Formula I has the R stereochemistry at C3 of quinuclidine.
10. The compound according to claim 9, wherein the compound is N-[(2S,3R)-2-methyl-1-azabicyclo[2.2.2]oct-3-yl]-2,3-dihydrofuro[2,3c-]pyridine-5-carboxamide;

N-[(2S,3R)-2-methyl-1-azabicyclo[2.2.2]oct-3-yl]furo[3,2-c]pyridine-2-carboxamide;

N-[(2S,3R)-2-methyl-1-azabicyclo[2.2.2]oct-3-yl]-7-chlorofuro[2,3-c]pyridine-5-carboxamide;

N-[(2S,3R)-2-methyl-1-azabicyclo[2.2.2]oct-3-yl]furo[2,3-c]pyridine-5-carboxamide;

N-[(2S,3R)-2-methyl-1-azabicyclo[2.2.2]oct-3-yl]-3,3-dimethyl-2,3-dihydrofuro[2,3-c]pyridine-5-carboxamide;

N-[(2S,3R)-2-methyl-1-azabicyclo[2.2.2]oct-3-yl]-2-methylfuro[2,3-c]pyridine-5-carboxamide;

N-[(2S,3R)-2-methyl-1-azabicyclo[2.2.2]oct-3-yl]furo[2,3-c]pyridine-2-carboxamide;

N-[(2S,3R)-2-methyl-1-azabicyclo[2.2.2]oct-3-yl]furo[2,3-b]pyridine-2-carboxamide;

N-[(2S,3R)-2-methyl-1-azabicyclo[2.2.2]oct-3-yl]-3-methylfuro[2,3-c]pyridine-5-carboxamide;

N-[(2S,3R)-2-methyl-1-azabicyclo[2.2.2]oct-3-yl]-3-ethylfuro[2,3-c]pyridine-5-carboxamide;

N-[(2S,3R)-2-methyl-1-azabicyclo[2.2.2]oct-3-yl]-3-isopropylfuro[2,3-c]pyridine-5-carboxamide;

N-[(2S,3R)-2-methyl-1-azabicyclo[2.2.2]oct-3-yl]-7-(methylsulfanyl)furo[2,3-c]pyridine-5-carboxamide;

N-((2S,3R)-2-methyl-1-azabicyclo[2.2.2]oct-3-yl)thieno[2,3-b]pyridine-2-carboxamide;

N-[(2S,3R)-2-methyl-1-azabicyclo[2.2.2]oct-3-yl]thieno[2,3-b]pyridine-5-carboxamide;

N-[(2S,3R)-2-methyl-1-azabicyclo[2.2.2]oct-3-yl]thieno[2,3-b]pyridine-6-carboxamide;

N-[(2S,3R)-2-methyl-1-azabicyclo[2.2.2]oct-3-yl]thieno[2,3-c]pyridine-2-carboxamide;

N-[(2S,3R)-2-methyl-1-azabicyclo[2.2.2]oct-3-yl]thieno[3,2-b]pyridine-2-carboxamide;

N-[(2S,3R)-2-methyl-1-azabicyclo[2.2.2]oct-3-yl]thieno[3,2-b]pyridine-5-carboxamide;

N-[(2S,3R)-2-methyl-1-azabicyclo[2.2.2]oct-3-yl]thieno[3,2-b]pyridine-6-carboxamide;

N-[(2S,3R)-2-methyl-1-azabicyclo[2.2.2]oct-3-yl]thieno[3,2-c]pyridine-2-carboxamide;

N-[(2S,3R)-2-methyl-1-azabicyclo[2.2.2]oct-3-yl]thieno[2,3-c]pyridine-5-carboxamide;

N-[(2S,3R)-2-methyl-1-azabicyclo[2.2.2]oct-3-yl]thieno[3,2-c]pyridine-6-carboxamide;

N-[(2S,3R)-2-methyl-1-azabicyclo[2.2.2]oct-3-yl]-1H-pyrrolo[2,3-c]pyridine-5-carboxamide;

N-((2S,3R)-2-methyl-1-azabicyclo[2.2.2]oct-3-yl)-1-methyl-1H-pyrrolo[2,3-c]pyridine-5-carboxamide;
N-[(2S,3R)-2-methyl-1-azabicyclo[2.2.2]oct-3-yl]-3-chlorofuro[2,3-c]pyridine-5-carboxamide;
N-[(2S,3R)-2-methyl-1-azabicyclo[2.2.2]oct-3-yl]-3-bromofuro[2,3-c]pyridine-5-carboxamide;
N-[(2S,3R)-2-methyl-1-azabicyclo[2.2.2]oct-3-yl]furo[3,2-c]pyridine-6-carboxamide;
N-[(2S,3R)-2-methyl-1-azabicyclo[2.2.2]oct-3-yl]-3-bromothieno[2,3-c]pyridine-5-carboxamide;
N-[(2S,3R)-2-methyl-1-azabicyclo[2.2.2]oct-3-yl]-3-ethynylfuro[2,3-c]pyridine-5-carboxamide; or a pharmaceutically acceptable salt thereof.

11. The compound according to claim 9, wherein the compound is
N-[(2S,3R)-2-methyl-1-azabicyclo[2.2.2]oct-3-yl]furo[3,2-c]pyridine-2-carboxamide;
N-[(2S,3R)-2-methyl-1-azabicyclo[2.2.2]oct-3-yl]furo[2,3-c]pyridine-5-carboxamide;
N-[(2S,3R)-2-methyl-1-azabicyclo[2.2.2]oct-3-yl]-2-methylfuro[2,3-c]pyridine-5-carboxamide;
N-[(2S,3R)-2-methyl-1-azabicyclo[2.2.2]oct-3-yl]-3-methylfuro[2,3-c]pyridine-5-carboxamide;
N-[(2S,3R)-2-methyl-1-azabicyclo[2.2.2]oct-3-yl]-3-ethylfuro[2,3-c]pyridine-5-carboxamide;
N-[(2S,3R)-2-methyl-1-azabicyclo[2.2.2]oct-3-yl]-3-isopropylfuro[2,3-c]pyridine-5-carboxamide;
N-[(2S,3R)-2-methyl-1-azabicyclo[2.2.2]oct-3-yl]thieno[2,3-b]pyridine-6-carboxamide;
N-[(2S,3R)-2-methyl-1-azabicyclo[2.2.2]oct-3-yl]thieno[2,3-c]pyridine-2-carboxamide;
N-[(2S,3R)-2-methyl-1-azabicyclo[2.2.2]oct-3-yl]thieno[2,3-c]pyridine-5-carboxamide;
N-[(2S,3R)-2-methyl-1-azabicyclo[2.2.2]oct-3-yl]thieno[3,2-c]pyridine-6-carboxamide;
N-[(2S,3R)-2-methyl-1-azabicyclo[2.2.2]oct-3-yl]-3-chlorofuro[2,3-c]pyridine-5-carboxamide;
N-[(2S,3R)-2-methyl-1-azabicyclo[2.2.2]oct-3-yl]-3-bromofuro[2,3-c]pyridine-5-carboxamide;
N-[(2S,3R)-2-methyl-1-azabicyclo[2.2.2]oct-3-yl]furo[3,2-c]pyridine-6-carboxamide;
N-[(2S,3R)-2-methyl-1-azabicyclo[2.2.2]oct-3-yl]-3-bromothieno[2,3-c]pyridine-5-carboxamide;
N-[(2S,3R)-2-methyl-1-azabicyclo[2.2.2]oct-3-yl]-3-ethynylfuro[2,3-c]pyridine-5-carboxamide; or a pharmaceutically acceptable salt thereof.

12. The compound according to claim 9, wherein the compound is
4-methyl-N-[(2S,3R)-2-methyl-1-azabicyclo[2.2.2]oct-3-yl]furo[3,2-c]pyridine-6-carboxamide;
4-methylthio-N-[(2S,3R)-2-methyl-1-azabicyclo[2.2.2]oct-3-yl]furo[3,2-c]pyridine-6-carboxamide;
4-methoxy-N-[(2S,3R)-2-methyl-1-azabicyclo[2.2.2]oct-3-yl]furo[3,2-c]pyridine-6-carboxamide;
4-chloro-N-[(2S,3R)-2-methyl-1-azabicyclo[2.2.2]oct-3-yl]furo[3,2-c]pyridine-6-carboxamide;
N-[(2S,3R)-2-methyl-1-azabicyclo[2.2.2]oct-3-yl]-2-vinylfuro[3,2-c]pyridine-6-carboxamide;
N-[(2S,3R)-2-methyl-1-azabicyclo[2.2.2]oct-3-yl]-2-ethynylfuro[3,2-c]pyridine-6-carboxamide;
N-[(2S,3R)-2-methyl-1-azabicyclo[2.2.2]oct-3-yl]-2-prop-1-ynylfuro[3,2-c]pyridine-6-carboxamide;
N-[(2S,3R)-2-methyl-1-azabicyclo[2.2.2]oct-3-yl]-2-(3-hydroxyprop-1-ynyl)furo[3,2-c]pyridine-6-carboxamide;
methyl 3-(6-{[(2S,3R)-2-methyl-1-azabicyclo[2.2.2]oct-3-ylamino]carbonyl}furo[3,2-c]pyridin-2-yl)prop-2-ynoate;
3-(6-{[(2S,3R)-2-methyl-1-azabicyclo[2.2.2]oct-3-ylamino]carbonyl}furo[3,2-c]pyridin-2-yl)prop-2-ynoic acid;
2-(3-amino-3-oxoprop-1-ynyl)-N-[(2S,3R)-2-methyl-1-azabicyclo[2.2.2]oct-3-yl]furo[3,2-c]pyridine-6-carboxamide;
N-[(2S,3R)-2-methyl-1-azabicyclo[2.2.2]oct-3-yl]-2-cyanofuro[3,2-c]pyridine-6-carboxamide;
N-[(2S,3R)-2-methyl-1-azabicyclo[2.2.2]oct-3-yl]-2-fluorofuro[3,2-c]pyridine-6-carboxamide;
N-[(2S,3R)-2-methyl-1-azabicyclo[2.2.2]oct-3-yl]-2-chlorofuro[3,2-c]pyridine-6-carboxamide;
N-[(2S,3R)-2-methyl-1-azabicyclo[2.2.2]oct-3-yl]-2-bromofuro[3,2-c]pyridine-6-carboxamide;
N-[(2S,3R)-2-methyl-1-azabicyclo[2.2.2]oct-3-yl]-2-iodofuro[3,2-c]pyridine-6-carboxamide;
N-[(2S,3R)-2-methyl-1-azabicyclo[2.2.2]oct-3-yl]-2-trifluoromethylfuro[3,2-c]pyridine-6-carboxamide;
N-[(2S,3R)-2-methyl-1-azabicyclo[2.2.2]oct-3-yl]-2-mercaptofuro[3,2-c]pyridine-6-carboxamide;
N-[(2S,3R)-2-methyl-1-azabicyclo[2.2.2]oct-3-yl]-2-(methylthio)furo[3,2-c]pyridine-6-carboxamide;
N-[(2S,3R)-2-methyl-1-azabicyclo[2.2.2]oct-3-yl]-2-(methylamino)furo[3,2-c]pyridine-6-carboxamide;
N-[(2S,3R)-2-methyl-1-azabicyclo[2.2.2]oct-3-yl]-2-(formylamino)furo[3,2-c]pyridine-6-carboxamide;
N-[(2S,3R)-2-methyl-1-azabicyclo[2.2.2]oct-3-yl]-2-[formyl(methyl)amino]furo[3,2-c]pyridine-6-carboxamide;
2-(acetylamino)-N-[(2S,3R)-2-methyl-1-azabicyclo[2.2.2]oct-3-yl]furo[3,2-c]pyridine-6-carboxamide;
2-(acetyl(methyl)amino)-N-[(2S,3R)-2-methyl-1-azabicyclo[2.2.2]oct-3-yl]furo[3,2-c]pyridine-6-carboxamide;
N-[(2S,3R)-2-methyl-1-azabicyclo[2.2.2]oct-3-yl]-2-[(trifluoroacetyl)amino]furo[3,2-c]pyridine-6-carboxamide;
N-[(2S,3R)-2-methyl-1-azabicyclo[2.2.2]oct-3-yl]-2-(benzoylamino)furo[3,2-c]pyridine-6-carboxamide;
N-[(2S,3R)-2-methyl-1-azabicyclo[2.2.2]oct-3-yl]-2-(diethylamino)furo[3,2-c]pyridine-6-carboxamide;
N-[(2S,3R)-2-methyl-1-azabicyclo[2.2.2]oct-3-yl]-2-(diisopropylamino)furo[3,2-c]pyridine-6-carboxamide;
N-[(2S,3R)-2-methyl-1-azabicyclo[2.2.2]oct-3-yl]-2-(pyrrolidin-1-yl)furo[3,2-c]pyridine-6-carboxamide;
N-[(2S,3R)-2-methyl-1-azabicyclo[2.2.2]oct-3-yl]-2-(2-oxopyrrolidin-1ylfuro[3,2-c]pyridine-6-carboxamide;
N-[(2S,3R)-2-methyl-1-azabicyclo[2.2.2]oct-3-yl]-2-(piperidin-1-yl)furo[3,2-c]pyridine-6-carboxamide;
N-[(2S,3R)-2-methyl-1-azabicyclo[2.2.2]oct-3-yl]-2-(2-oxopiperidin-1yl)furo[3,2-c]pyridine-6-carboxamide;
N-[(2S,3R)-2-methyl-1-azabicyclo[2.2.2]oct-3-yl]-2-(morpholin-4-yl)furo[3,2-c]pyridine-6-carboxamide;
N-[(2S,3R)-2-methyl-1-azabicyclo[2.2.2]oct-3-yl]-2-(3-oxomorpholin-4yl)furo[3,2-c]pyridine-6-carboxamide;
N-[(2S,3R)-2-methyl-1-azabicyclo[2.2.2]oct-3-yl]-2-(thiomorpholin-4yl)furo[3,2-c]pyridine-6-carboxamide;
N-[(2S,3R)-2-methyl-1-azabicyclo[2.2.2]oct-3-yl]-2-(3-oxothiomorpholin-4yl)furo[3,2-c]pyridine-6-carboxamide;
N-[(2S,3R)-2-methyl-1-azabicyclo[2.2.2]oct-3-yl]-2-(piperazin-1-yl)furo[3,2-c]pyridine-6-carboxamide;

N-[(2S,3R)-2-methyl-1-azabicyclo[2.2.2]oct-3-yl]-2-(2-oxopiperazin-1yl)furo[3,2-c]pyridine-6-carboxamide;
N-[(2S,3R)-2-methyl-1-azabicyclo[2.2.2]oct-3-yl]-2-(4-methylpiperazin-1-yl)furo[3,2-c]pyridine-6-carboxamide;
N-[(2S,3R)-2-methyl-1-azabicyclo[2.2.2]oct-3-yl]-2-(4-methyl-2-oxopiperazin-1yl)furo[3,2-c]pyridine-6-carboxamide;
N-[(2S,3R)-2-methyl-1-azabicyclo[2.2.2]oct-3-yl]-2-(3-oxopiperazin-1yl)furo[3,2-c]pyridine-6-carboxamide;
N-[(2S,3R)-2-methyl-1-azabicyclo[2.2.2]oct-3-yl]-2-(4-methyl-3-oxopiperazin-1yl)furo[3,2-c]pyridine-6-carboxamide;
N-[(2S,3R)-2-methyl-1-azabicyclo[2.2.2]oct-3-yl]-2-(cyclopropylamino)furo[3,2-c]pyridine-6-carboxamide;
N-[(2S,3R)-2-methyl-1-azabicyclo[2.2.2]oct-3-yl]-2-[dimethylamino]furo[3,2-c]pyridine-6-carboxamide;
N-[(2S,3R)-2-methyl-1-azabicyclo[2.2.2]oct-3-yl]-2-(1H-pyrrole-1yl)furo[3,2-c]pyridine-6-carboxamide;
N-[(2S,3R)-2-methyl-1-azabicyclo[2.2.2]oct-3-yl]-2-(1H-imidazol-1-yl)furo[3,2-c]pyridine-6-carboxamide;
N-[(2S,3R)-2-methyl-1-azabicyclo[2.2.2]oct-3-yl]-2-(1H-1,2,4-triazol-1-yl)furo[3,2-c]pyridine-6-carboxamide;
N-[(2S,3R)-2-methyl-1-azabicyclo[2.2.2]oct-3-yl]-2-(1H-1,2,3-triazol-1-yl)furo[3,2-c]pyridine-6-carboxamide;
N-6-[(2S,3R)-2-methyl-1-azabicyclo[2.2.2]oct-3-yl]furo[3,2-c]pyridine-2,6-dicarboxamide;
N-[(2S,3R)-2-methyl-1-azabicyclo[2.2.2]oct-3-yl]-2-(pyrrolidin-1-ylcarbonyl)furo[3,2-c]pyridine-6-carboxamide;
N-[(2S,3R)-2-methyl-1-azabicyclo[2.2.2]oct-3-yl]-2-(piperidin-1-ylcarbonyl)furo[3,2-c]pyridine-6-carboxamide;
N-[(2S,3R)-2-methyl-1-azabicyclo[2.2.2]oct-3-yl]-2-(piperazin-1-ylcarbonyl)furo[3,2-c]pyridine-6-carboxamide;
N-[(2S,3R)-2-methyl-1-azabicyclo[2.2.2]oct-3-yl]-2-[(4-methylpiperazin-1-yl)carbonyl]furo[3,2-c]pyridine-6-carboxamide;
N-[(2S,3R)-2-methyl-1-azabicyclo[2.2.2]oct-3-yl]-2-(morpholin-4-ylcarbonyl)furo[3,2-c]pyridine-6-carboxamide;
N-[(2S,3R)-2-methyl-1-azabicyclo[2.2.2]oct-3-yl]-2-(thiomorpholin-4-ylcarbonyl)furo[3,2-c]pyridine-6-carboxamide;
N-[(2S,3R)-2-methyl-1-azabicyclo[2.2.2]oct-3-yl]-2-(aziridin-1-ylcarbonyl)furo[3,2-c]pyridine-6-carboxamide;
N-[(2S,3R)-2-methyl-1-azabicyclo[2.2.2]oct-3-yl]-2-(azetidin-1-ylcarbonyl)furo[3,2-c]pyridine-6-carboxamide;
N-[(2S,3R)-2-methyl-1-azabicyclo[2.2.2]oct-3-yl]-2-formylfuro[3,2-c]pyridine-6-carboxamide;
2-acetyl-N-[(2S,3R)-2-methyl-1-azabicyclo[2.2.2]oct-3-yl]furo[3,2-c]pyridine-6-carboxamide;
N-[(2S,3R)-2-methyl-1-azabicyclo[2.2.2]oct-3-yl]-2-(trifluoroacetyl)furo[3,2-c]pyridine-6-carboxamide;
N-[(2S,3R)-2-methyl-1-azabicyclo[2.2.2]oct-3-yl]-2-[(phenyl)sulfonyl]furo[3,2-c]pyridine-6-carboxamide;
N-[(2S,3R)-2-methyl-1-azabicyclo[2.2.2]oct-3-yl]-2-(methylsulfonyl)furo[3,2-c]pyridine-6-carboxamide;
6-{[(2S,3R)-2-methyl-1-azabicyclo[2.2.2]oct-3-ylamino]carbonyl}furo[3,2-c]pyridine-2-carboxylic acid;
methyl 6-{[(2S,3R)-2-methyl-1-azabicyclo[2.2.2]oct-3-ylamino]carbonyl}furo[3,2-c]pyridine-2-carboxylate;
isopropyl 6-{[(2S,3R)-2-methyl-1-azabicyclo[2.2.2]oct-3-ylamino]carbonyl}furo[3,2-c]pyridine-2-carboxylate;
2,2,2-trifluoroethyl 6-{[(2S,3R)-2-methyl-1-azabicyclo[2.2.2]oct-3-ylamino]carbonyl}furo[3,2-c]pyridine-2-carboxylate;
4-methyl-N-[(2S,3R)-2-methyl-1-azabicyclo[2.2.2]oct-3-yl]thieno[3,2-c]pyridine-6-carboxamide;
4-methylthio-N-[(2S,3R)-2-methyl-1-azabicyclo[2.2.2]oct-3-yl]thieno[3,2-c]pyridine-6-carboxamide;
4-methoxy-N-[(2S,3R)-2-methyl-1-azabicyclo[2.2.2]oct-3-yl]thieno[3,2-c]pyridine-6-carboxamide;
4-chloro-N-[(2S,3R)-2-methyl-1-azabicyclo[2.2.2]oct-3-yl]thieno[3,2-c]pyridine-6-carboxamide;
N-[(2S,3R)-2-methyl-1-azabicyclo[2.2.2]oct-3-yl]-2-vinylthieno[3,2-c]pyridine-6-carboxamide;
N-[(2S,3R)-2-methyl-1-azabicyclo[2.2.2]oct-3-yl]-2-ethynylthieno[3,2-c]pyridine-6-carboxamide;
N-[(2S,3R)-2-methyl-1-azabicyclo[2.2.2]oct-3-yl]-2-prop-1-ynylthieno[3,2-c]pyridine-6-carboxamide;
N-[(2S,3R)-2-methyl-1-azabicyclo[2.2.2]oct-3-yl]-2-(3-hydroxyprop-1-ynyl)thieno[3,2-c]pyridine-6-carboxamide;
methyl 3-(6-{[(2S,3R)-2-methyl-1-azabicyclo[2.2.2]oct-3-ylamino]carbonyl}thieno[3,2-c]pyridine-2-yl)prop-2-ynoate;
3-(6-{[(2S,3R)-2-methyl-1-azabicyclo[2.2.2]oct-3-ylamino]carbonyl}thieno[3,2-c]pyridine-2-yl)prop-2-ynoic acid;
2-(3-amino-3-oxoprop-1-ynyl)-N-[(2S,3R)-2-methyl-1-azabicyclo[2.2.2]oct-3-yl]thieno[3,2-c]pyridine-6-carboxamide;
N-[(2S,3R)-2-methyl-1-azabicyclo[2.2.2]oct-3-yl]-2-cyanothieno[3,2-c]pyridine-6-carboxamide;
N-[(2S,3R)-2-methyl-1-azabicyclo[2.2.2]oct-3-yl]-2-fluorothieno[3,2-c]pyridine-6-carboxamide;
N-[(2S,3R)-2-methyl-1-azabicyclo[2.2.2]oct-3-yl]-2-chlorothieno[3,2-c]pyridine-6-carboxamide;
N-[(2S,3R)-2-methyl-1-azabicyclo[2.2.2]oct-3-yl]-2-bromothieno[3,2-c]pyridine-6-carboxamide;
N-[(2S,3R)-2-methyl-1-azabicyclo[2.2.2]oct-3-yl]-2-iodothieno[3,2-c]pyridine-6-carboxamide;
N-[(2S,3R)-2-methyl-1-azabicyclo[2.2.2]oct-3-yl]-2-trifluoromethylthieno[3,2-c]pyridine-6-carboxamide;
N-[(2S,3R)-2-methyl-1-azabicyclo[2.2.2]oct-3-yl]-2-mercaptothieno[3,2-c]pyridine-6-carboxamide;
N-[(2S,3R)-2-methyl-1-azabicyclo[2.2.2]oct-3-yl]-2-(methylthio)thieno[3,2-c]pyridine-6-carboxamide;
N-[(2S,3R)-2-methyl-1-azabicyclo[2.2.2]oct-3-yl]-2-(methylamino)thieno[3,2-c]pyridine-6-carboxamide;
N-[(2S,3R)-2-methyl-1-azabicyclo[2.2.2]oct-3-yl]-2-(formylamino)thieno[3,2-c]pyridine-6-carboxamide;
N-[(2S,3R)-2-methyl-1-azabicyclo[2.2.2]oct-3-yl]-2-[formyl(methyl)amino]thieno[3,2-c]pyridine-6-carboxamide;
2-(acetylamino)-N-[(2S,3R)-2-methyl-1-azabicyclo[2.2.2]oct-3-yl]thieno[3,2-c]pyridine-6-carboxamide;
2-(acetyl(methyl)amino)-N-[(2S,3R)-2-methyl-1-azabicyclo[2.2.2]oct-3-yl]thieno[3,2-c]pyridine-6-carboxamide;
N-[(2S,3R)-2-methyl-1-azabicyclo[2.2.2]oct-3-yl]-2-[(trifluoroacetyl)amino]thieno[3,2-c]pyridine-6-carboxamide;
N-[(2S,3R)-2-methyl-1-azabicyclo[2.2.2]oct-3-yl]-2-(benzoylamino)thieno[3,2-c]pyridine-6-carboxamide;
N-[(2S,3R)-2-methyl-1-azabicyclo[2.2.2]oct-3-yl]-2-(diethylamino)thieno[3,2-c]pyridine-6-carboxamide;

N-[(2S,3R)-2-methyl-1-azabicyclo[2.2.2]oct-3-yl]-2-(di-isopropylamino)thieno[3,2-c]pyridine-6-carboxamide;

N-[(2S,3R)-2-methyl-1-azabicyclo[2.2.2]oct-3-yl]-2-(pyrrolidin-1-yl)thieno[3,2-c]pyridine-6-carboxamide;

N-[(2S,3R)-2-methyl-1-azabicyclo[2.2.2]oct-3-yl]-2-(2-oxopyrrolidin-1ylthieno[3,2-c]pyridine-6-carboxamide;

N-[(2S,3R)-2-methyl-1-azabicyclo[2.2.2]oct-3-yl]-2-(piperidin-1-yl)thieno[3,2-c]pyridine-6-carboxamide;

N-[(2S,3R)-2-methyl-1-azabicyclo[2.2.2]oct-3-yl]-2-(2-oxopiperidin-1yl)thieno[3,2-c]pyridine-6-carboxamide;

N-[(2S,3R)-2-methyl-1-azabicyclo[2.2.2]oct-3-yl]-2-(morpholin-4-yl)thieno[3,2-c]pyridine-6-carboxamide;

N-[(2S,3R)-2-methyl-1-azabicyclo[2.2.2]oct-3-yl]-2-(3-oxomorpholin-4yl)thieno[3,2-c]pyridine-6-carboxamide;

N-[(2S,3R)-2-methyl-1-azabicyclo[2.2.2]oct-3-yl]-2-(thiomorpholin-4yl)thieno[3,2-c]pyridine-6-carboxamide;

N-[(2S,3R)-2-methyl-1-azabicyclo[2.2.2]oct-3-yl]-2-(3-oxothiomorpholin-4yl)thieno[3,2-c]pyridine-6-carboxamide;

N-[(2S,3R)-2-methyl-1-azabicyclo[2.2.2]oct-3-yl]-2-(piperazin-1-yl)thieno[3,2-c]pyridine-6-carboxamide;

N-[(2S,3R)-2-methyl-1-azabicyclo[2.2.2]oct-3-yl]-2-(2-oxopiperazin-1yl)thieno[3,2-c]pyridine-6-carboxamide;

N-[(2S,3R)-2-methyl-1-azabicyclo[2.2.2]oct-3-yl]-2-(4-methylpiperazin-1-yl)thieno[3,2-c]pyridine-6-carboxamide;

N-[(2S,3R)-2-methyl-1-azabicyclo[2.2.2]oct-3-yl]-2-(4-methyl-2-oxopiperazin-1yl)thieno[3,2-c]pyridine-6-carboxamide;

N-[(2S,3R)-2-methyl-1-azabicyclo[2.2.2]oct-3-yl]-2-(3-oxopiperazin-1yl)thieno[3,2-c]pyridine-6-carboxamide;

N-[(2S,3R)-2-methyl-1-azabicyclo[2.2.2]oct-3-yl]-2-(4-methyl-3-oxopiperazin-1yl)thieno[3,2-c]pyridine-6-carboxamide;

N-[(2S,3R)-2-methyl-1-azabicyclo[2.2.2]oct-3-yl]-2-(cyclopropylamino)thieno[3,2-c]pyridine-6-carboxamide;

N-[(2S,3R)-2-methyl-1-azabicyclo[2.2.2]oct-3-yl]-2-[dimethylamino]thieno[3,2-c]pyridine-6-carboxamide;

N-[(2S,3R)-2-methyl-1-azabicyclo[2.2.2]oct-3-yl]-2-(1H-pyrrole-1yl)thieno[3,2-c]pyridine-6-carboxamide;

N-[(2S,3R)-2-methyl-1-azabicyclo[2.2.2]oct-3-yl]-2-(1H-imidazol-1-yl)thieno[3,2-c]pyridine-6-carboxamide;

N-[(2S,3R)-2-methyl-1-azabicyclo[2.2.2]oct-3-yl]-2-(1H-1,2,4-triazol-1-yl)thieno[3,2-c]pyridine-6-carboxamide;

N-[(2S,3R)-2-methyl-1-azabicyclo[2.2.2]oct-3-yl]-2-(1H-1,2,3-triazol-1-yl)thieno[3,2-c]pyridine-6-carboxamide;

N-6-[(2S,3R)-2-methyl-1-azabicyclo[2.2.2]oct-3-yl] thieno[3,2-c]pyridine-2,6-dicarboxamide;

N-[(2S,3R)-2-methyl-1-azabicyclo[2.2.2]oct-3-yl]-2-(pyrrolidin-1-ylcarbonyl)thieno[3,2-c]pyridine-6-carboxamide;

N-[(2S,3R)-2-methyl-1-azabicyclo[2.2.2]oct-3-yl]-2-(piperidin-1-ylcarbonyl)thieno[3,2-c]pyridine-6-carboxamide;

N-[(2S,3R)-2-methyl-1-azabicyclo[2.2.2]oct-3-yl]-2-(piperazin-1-ylcarbonyl)thieno[3,2-c]pyridine-6-carboxamide;

N-[(2S,3R)-2-methyl-1-azabicyclo[2.2.2]oct-3-yl]-2-[(4-methylpiperazin-1-yl)carbonyl]thieno[3,2-c]pyridine-6-carboxamide;

N-[(2S,3R)-2-methyl-1-azabicyclo[2.2.2]oct-3-yl]-2-(morpholin-4-ylcarbonyl)thieno[3,2-c]pyridine-6-carboxamide;

N-[(2S,3R)-2-methyl-1-azabicyclo[2.2.2]oct-3-yl]-2-(thiomorpholin-4-ylcarbonyl)thieno[3,2-c]pyridine-6-carboxamide;

N-[(2S,3R)-2-methyl-1-azabicyclo[2.2.2]oct-3-yl]-2-(aziridin-1-ylcarbonyl)thieno[3,2-c]pyridine-6-carboxamide;

N-[(2S,3R)-2-methyl-1-azabicyclo[2.2.2]oct-3-yl]-2-(azetidin-1-ylcarbonyl)thieno[3,2-c]pyridine-6-carboxamide;

N-[(2S,3R)-2-methyl-1-azabicyclo[2.2.2]oct-3-yl]-2-formylthieno[3,2-c]pyridine-6-carboxamide;

2-acetyl-N-[(2S,3R)-2-methyl-1-azabicyclo[2.2.2]oct-3-yl]thieno[3,2-c]pyridine-6-carboxamide;

N-[(2S,3R)-2-methyl-1-azabicyclo[2.2.2]oct-3-yl]-2-(trifluoroacetyl)thieno[3,2-c]pyridine-6-carboxamide;

N-[(2S,3R)-2-methyl-1-azabicyclo[2.2.2]oct-3-yl]-2-[(phenyl)sulfonyl]1thieno[3,2-c]pyridine-6-carboxamide;

N-[(2S,3R)-2-methyl-1-azabicyclo[2.2.2]oct-3-yl]-2-(methylsulfonyl)thieno[3,2-c]pyridine-6-carboxamide;

6-{[(2S,3R)-2-methyl-1-azabicyclo[2.2.2]oct-3-ylamino]carbonyl}thieno[3,2-c]pyridine-2-carboxylic acid;

methyl 6-{[(2S,3R)-2-methyl-1-azabicyclo[2.2.2]oct-3-ylamino]carbonyl}thieno[3,2-c]pyridine-2-carboxylate;

isopropyl 6-{[(2S,3R)-2-methyl-1-azabicyclo[2.2.2]oct-3-ylamino]carbonyl}thieno[3,2-c]pyridine-2-carboxylate;

2,2,2-trifluoroethyl 6-{[(2S,3R)-2-methyl-1-azabicyclo[2.2.2]oct-3-ylamino]carbonyl}thieno[3,2-c]pyridine-2-carboxylate;

N-[(2S,3R)-2-methyl-1-azabicyclo[2.2.2]oct-3-yl]-3-vinylfuro[2,3-c]pyridine-5-carboxamide;

7-methyl-N-[(2S,3R)-2-methyl-1-azabicyclo[2.2.2]oct-3-yl]furo[2,3-c]pyridine-5-carboxamide;

7-methoxy-N-[(2S,3R)-2-methyl-1-azabicyclo[2.2.2]oct-3-yl]furo[2,3-c]pyridine-5-carboxamide;

N-[(2S,3R)-2-methyl-1-azabicyclo[2.2.2]oct-3-yl]-3-ethynylfuro[2,3-c]pyridine-5-carboxamide;

N-[(2S,3R)-2-methyl-1-azabicyclo[2.2.2]oct-3-yl]-3-prop-1-ynylfuro[2,3-c]pyridine-5-carboxamide;

N-[(2S,3R)-2-methyl-1-azabicyclo[2.2.2]oct-3-yl]-3-(3-hydroxyprop-1-ynyl)furo[2,3-c]pyridine-5-carboxamide;

methyl 3-(5-{[(2S,3R)-2-methyl-1-azabicyclo[2.2.2]oct-3-ylamino]carbonyl}furo[2,3-c]pyridin-3-yl)prop-2-ynoate;

3-(5-{[(2S,3R)-2-methyl-1-azabicyclo[2.2.2]oct-3-ylamino]carbonyl}furo[2,3-c]pyridin-3-yl)prop-2-ynoic acid;

3-(3-amino-3-oxoprop-1-ynyl)-N-[(2S,3R)-2-methyl-1-azabicyclo[2.2.2]oct-3-yl]furo[2,3-c]pyridine-5-carboxamide;

N-[(2S,3R)-2-methyl-1-azabicyclo[2.2.2]oct-3-yl]-3-cyanofuro[2,3-c]pyridine-5-carboxamide;

N-[(2S,3R)-2-methyl-1-azabicyclo[2.2.2]oct-3-yl]-3-fluorofuro[2,3-c]pyridine-5-carboxamide;

N-[(2S,3R)-2-methyl-1-azabicyclo[2.2.2]oct-3-yl]-3-chlorofuro[2,3-c]pyridine-5-carboxamide;

N-[(2S,3R)-2-methyl-1-azabicyclo[2.2.2]oct-3-yl]-3-bromofuro[2,3-c]pyridine-5-carboxamide;

N-[(2S,3R)-2-methyl-1-azabicyclo[2.2.2]oct-3-yl]-3-iodofuro[2,3-c]pyridine-5-carboxamide;
N-[(2S,3R)-2-methyl-1-azabicyclo[2.2.2]oct-3-yl]-3-trifluoromethylfuro[2,3-c]pyridine-5-carboxamide;
N-[(2S,3R)-2-methyl-1-azabicyclo[2.2.2]oct-3-yl]-3-mercaptofuro[2,3-c]pyridine-5-carboxamide;
N-[(2S,3R)-2-methyl-1-azabicyclo[2.2.2]oct-3-yl]-3-(methylthio)furo[2,3-c]pyridine-5-carboxamide;
N-[(2S,3R)-2-methyl-1-azabicyclo[2.2.2]oct-3-yl]-3-(methylamino)furo[2,3-c]pyridine-5-carboxamide;
N-[(2S,3R)-2-methyl-1-azabicyclo[2.2.2]oct-3-yl]-3-(formylamino)furo[2,3-c]pyridine-5-carboxamide;
N-[(2S,3R)-2-methyl-1-azabicyclo[2.2.2]oct-3-yl]-3-[formyl(methyl)amino]furo[2,3-c]pyridine-5-carboxamide;
3-(acetylamino)-N-[(2S,3R)-2-methyl-1-azabicyclo[2.2.2]oct-3-yl]furo[2,3-c]pyridine-5-carboxamide;
3-(acetyl(methyl)amino)-N-[(2S,3R)-2-methyl-1-azabicyclo[2.2.2]oct-3-yl]furo[2,3-c]pyridine-5-carboxamide;
N-[(2S,3R)-2-methyl-1-azabicyclo[2.2.2]oct-3-yl]-3-[(trifluoroacetyl)amino]furo[2,3-c]pyridine-5-carboxamide;
N-[(2S,3R)-2-methyl-1-azabicyclo[2.2.2]oct-3-yl]-3-(benzoylamino)furo[2,3-c]pyridine-5-carboxamide;
N-[(2S,3R)-2-methyl-1-azabicyclo[2.2.2]oct-3-yl]-3-(diethylamino)furo[2,3-c]pyridine-5-carboxamide;
N-[(2S,3R)-2-methyl-1-azabicyclo[2.2.2]oct-3-yl]-3-(diisopropylamino)furo[2,3-c]pyridine-5-carboxamide;
N-[(2S,3R)-2-methyl-1-azabicyclo[2.2.2]oct-3-yl]-3-(pyrrolidin-1-yl)furo[2,3-c]pyridine-5-carboxamide;
N-[(2S,3R)-2-methyl-1-azabicyclo[2.2.2]oct-3-yl]-3-(2-oxopyrrolidin-1yl)furo[2,3-c]pyridine-5-carboxamide;
N-[(2S,3R)-2-methyl-1-azabicyclo[2.2.2]oct-3-yl]-3-(piperidin-1-yl)furo[2,3-c]pyridine-5-carboxamide;
N-[(2S,3R)-2-methyl-1-azabicyclo[2.2.2]oct-3-yl]-3-(2-oxopiperidin-1yl)furo[2,3-c]pyridine-5-carboxamide;
N-[(2S,3R)-2-methyl-1-azabicyclo[2.2.2]oct-3-yl]-3-(morpholin-4-yl)furo[2,3-c]pyridine-5-carboxamide;
N-[(2S,3R)-2-methyl-1-azabicyclo[2.2.2]oct-3-yl]-3-(3-oxomorpholin-4yl)furo[2,3-c]pyridine-5-carboxamide;
N-[(2S,3R)-2-methyl-1-azabicyclo[2.2.2]oct-3-yl]-3-(thiomorpholin-4yl)furo[2,3-c]pyridine-5-carboxamide;
N-[(2S,3R)-2-methyl-1-azabicyclo[2.2.2]oct-3-yl]-3-(3-oxothiomorpholin-4yl)furo[2,3-c]pyridine-5-carboxamide;
N-[(2S,3R)-2-methyl-1-azabicyclo[2.2.2]oct-3-yl]-3-(piperazin-1-yl)furo[2,3-c]pyridine-5-carboxamide;
N-[(2S,3R)-2-methyl-1-azabicyclo[2.2.2]oct-3-yl]-3-(2-oxopiperazin-1yl)furo[2,3-c]pyridine-5-carboxamide;
N-[(2S,3R)-2-methyl-1-azabicyclo[2.2.2]oct-3-yl]-3-(4-methylpiperazin-1-yl)furo[2,3-c]pyridine-5-carboxamide;
N-[(2S,3R)-2-methyl-1-azabicyclo[2.2.2]oct-3-yl]-3-(4-methyl-2-oxopiperazin-1yl)furo[2,3-c]pyridine-5-carboxamide;
N-[(2S,3R)-2-methyl-1-azabicyclo[2.2.2]oct-3-yl]-3-(3-oxopiperazin-1yl)furo[2,3-c]pyridine-5-carboxamide;
N-[(2S,3R)-2-methyl-1-azabicyclo[2.2.2]oct-3-yl]-3-(4-methyl-3-oxopiperazin-1yl)furo[2,3-c]pyridine-5-carboxamide;
N-[(2S,3R)-2-methyl-1-azabicyclo[2.2.2]oct-3-yl]-3-(cyclopropylamino)furo[2,3-c]pyridine-5-carboxamide;
N-[(2S,3R)-2-methyl-1-azabicyclo[2.2.2]oct-3-yl]-3-[dimethylamino]furo[2,3-c]pyridine-5-carboxamide;
N-[(2S,3R)-2-methyl-1-azabicyclo[2.2.2]oct-3-yl]-3-(1H-pyrrole-1yl)furo[2,3-c]pyridine-5-carboxamide;
N-[(2S,3R)-2-methyl-1-azabicyclo[2.2.2]oct-3-yl]-3-(1H-imidazol-1-yl)furo[2,3-c]pyridine-5-carboxamide;
N-[(2S,3R)-2-methyl-1-azabicyclo[2.2.2]oct-3-yl]-3-(1H-1,2,4-triazol-1-yl)furo[2,3-c]pyridine-5-carboxamide;
N-[(2S,3R)-2-methyl-1-azabicyclo[2.2.2]oct-3-yl]-3-(1H-1,2,3-triazol-1-yl)furo[2,3-c]pyridine-5-carboxamide;
N-5-[(2S,3R)-2-methyl-1-azabicyclo[2.2.2]oct-3-yl]furo[2,3-c]pyridine-3,5-dicarboxamide;
N-[(2S,3R)-2-methyl-1-azabicyclo[2.2.2]oct-3-yl]-3-(pyrrolidin-1-ylcarbonyl)furo[2,3-c]pyridine-5-carboxamide;
N-[(2S,3R)-2-methyl-1-azabicyclo[2.2.2]oct-3-yl]-3-(piperidin-1-ylcarbonyl)furo[2,3-c]pyridine-5-carboxamide;
N-[(2S,3R)-2-methyl-1-azabicyclo[2.2.2]oct-3-yl]-3-(piperazin-1-ylcarbonyl)furo[2,3-c]pyridine-5-carboxamide;
N-[(2S,3R)-2-methyl-1-azabicyclo[2.2.2]oct-3-yl]-3-[(4-methylpiperazin-1-yl)carbonyl]furo[2,3-c]pyridine-5-carboxamide;
N-[(2S,3R)-2-methyl-1-azabicyclo[2.2.2]oct-3-yl]-3-(morpholin-4-ylcarbonyl)furo[2,3-c]pyridine-5-carboxamide;
N-[(2S,3R)-2-methyl-1-azabicyclo[2.2.2]oct-3-yl]-3-(thiomorpholin-4-ylcarbonyl)furo[2,3-c]pyridine-5-carboxamide;
N-[(2S,3R)-2-methyl-1-azabicyclo[2.2.2]oct-3-yl]-3-(aziridin-1-ylcarbonyl)furo[2,3-c]pyridine-5-carboxamide;
N-[(2S,3R)-2-methyl-1-azabicyclo[2.2.2]oct-3-yl]-3-(azetidin-1-ylcarbonyl)furo[2,3-c]pyridine-5-carboxamide;
N-[(2S,3R)-2-methyl-1-azabicyclo[2.2.2]oct-3-yl]-3-formylfuro[2,3-c]pyridine-5-carboxamide;
3-acetyl-N-[(2S,3R)-2-methyl-1-azabicyclo[2.2.2]oct-3-yl]furo[2,3-c]pyridine-5-carboxamide;
N-[(2S,3R)-2-methyl-1-azabicyclo[2.2.2]oct-3-yl]-3-(trifluoroacetyl)furo[2,3-c]pyridine-5-carboxamide;
N-[(2S,3R)-2-methyl-1-azabicyclo[2.2.2]oct-3-yl]-3-[(phenyl)sulfonyl]furo[2,3-c]pyridine-5-carboxamide;
N-[(2S,3R)-2-methyl-1-azabicyclo[2.2.2]oct-3-yl]-3-(methylsulfonyl)furo[2,3-c]pyridine-5-carboxamide;
5-{[(2S,3R)-2-methyl-1-azabicyclo[2.2.2]oct-3-ylamino]carbonyl}furo[2,3-c]pyridine-3-carboxylic acid;
methyl 5-{[(2S,3R)-2-methyl-1-azabicyclo[2.2.2]oct-3-ylamino]carbonyl}furo[2,3-c]pyridine-3-carboxylate;
isopropyl 5-{[(2S,3R)-2-methyl-1-azabicyclo[2.2.2]oct-3-ylamino]carbonyl}furo[2,3-c]pyridine-3-carboxylate;
2,2,2-trifluoroethyl 5-{[(2S,3R)-2-methyl-1-azabicyclo[2.2.2]oct-3-ylamino]carbonyl}furo[2,3-c]pyridine-3-carboxylate;
7-methyl-N-[(2S,3R)-2-methyl-1-azabicyclo[2.2.2]oct-3-yl]thieno[2,3-c]pyridine-5-carboxamide;
7-methylthio-N-[(2S,3R)-2-methyl-1-azabicyclo[2.2.2]oct-3-yl]thieno[2,3-c]pyridine-5-carboxamide;
7-methoxy-N-[(2S,3R)-2-methyl-1-azabicyclo[2.2.2]oct-3-yl]thieno[2,3-c]pyridine-5-carboxamide;
7-chloro-N-[(2S,3R)-2-methyl-1-azabicyclo[2.2.2]oct-3-yl]thieno[2,3-c]pyridine-5-carboxamide;
N-[(2S,3R)-2-methyl-1-azabicyclo[2.2.2]oct-3-yl]-3-vinylthieno[2,3-c]pyridine-5-carboxamide;

N-[(2S,3R)-2-methyl-1-azabicyclo[2.2.2]oct-3-yl]-3-ethynylthieno[2,3-c]pyridine-5-carboxamide;

N-[(2S,3R)-2-methyl-1-azabicyclo[2.2.2]oct-3-yl]-3-prop-1-ynylthieno[2,3-c]pyridine-5-carboxamide;

N-[(2S,3R)-2-methyl-1-azabicyclo[2.2.2]oct-3-yl]-3-(3-hydroxyprop-1-ynyl)thieno[2,3-c]pyridine-5-carboxamide;

methyl 3-(5-{[(2S,3R)-2-methyl-1-azabicyclo[2.2.2]oct-3-ylamino]carbonyl}thieno[2,3-c]pyridin-3-yl)prop-2-ynoate;

3-(5-{[(2S,3R)-2-methyl-1-azabicyclo[2.2.2]oct-3-ylamino]carbonyl}thieno[2,3-c]pyridin-3-yl)prop-2-ynoic acid;

3-(3-amino-3-oxoprop-1-ynyl)-N-[(2S,3R)-2-methyl-1-azabicyclo[2.2.2]oct-3-yl]thieno[2,3-c]pyridine-5-carboxamide;

N-[(2S,3R)-2-methyl-1-azabicyclo[2.2.2]oct-3-yl]-3-cyanothieno[2,3-c]pyridine-5-carboxamide;

N-[(2S,3R)-2-methyl-1-azabicyclo[2.2.2]oct-3-yl]-3-fluorothieno[2,3-c]pyridine-5-carboxamide;

N-[(2S,3R)-2-methyl-1-azabicyclo[2.2.2]oct-3-yl]-3-chlorothieno[2,3-c]pyridine-5-carboxamide;

N-[(2S,3R)-2-methyl-1-azabicyclo[2.2.2]oct-3-yl]-3-bromothieno[2,3-c]pyridine-5-carboxamide;

N-[(2S,3R)-2-methyl-1-azabicyclo[2.2.2]oct-3-yl]-3-iodothieno[2,3-c]pyridine-5-carboxamide;

N-[(2S,3R)-2-methyl-1-azabicyclo[2.2.2]oct-3-yl]-3-trifluoromethylthieno[2,3-c]pyridine-5-carboxamide;

N-[(2S,3R)-2-methyl-1-azabicyclo[2.2.2]oct-3-yl]-3-mercaptothieno[2,3-c]pyridine-5-carboxamide;

N-[(2S,3R)-2-methyl-1-azabicyclo[2.2.2]oct-3-yl]-3-(methylthio)thieno[2,3-c]pyridine-5-carboxamide;

N-[(2S,3R)-2-methyl-1-azabicyclo[2.2.2]oct-3-yl]-3-(methylamino)thieno[2,3-c]pyridine-5-carboxamide;

N-[(2S,3R)-2-methyl-1-azabicyclo[2.2.2]oct-3-yl]-3-(formylamino)thieno[2,3-c]pyridine-5-carboxamide;

N-[(2S,3R)-2-methyl-1-azabicyclo[2.2.2]oct-3-yl]-3-[formyl(methyl)amino]thieno[2,3-c]pyridine-5-carboxamide;

3-(acetylamino)-N-[(2S,3R)-2-methyl-1-azabicyclo[2.2.2]oct-3-yl]thieno[2,3-c]pyridine-5-carboxamide;

3-(acetyl(methyl)amino)-N-[(2S,3R)-2-methyl-1-azabicyclo[2.2.2]oct-3-yl]thieno[2,3-c]pyridine-5-carboxamide;

N-[(2S,3R)-2-methyl-1-azabicyclo[2.2.2]oct-3-yl]-3-[(trifluoroacetyl)amino]thieno[2,3-c]pyridine-5-carboxamide;

N-[(2S,3R)-2-methyl-1-azabicyclo[2.2.2]oct-3-yl]-3-(benzoylamino)thieno[2,3-c]pyridine-5-carboxamide;

N-[(2S,3R)-2-methyl-1-azabicyclo[2.2.2]oct-3-yl]-3-(diethylamino)thieno[2,3-c]pyridine-5-carboxamide;

N-[(2S,3R)-2-methyl-1-azabicyclo[2.2.2]oct-3-yl]-3-(diisopropylamino)thieno[2,3-c]pyridine-5-carboxamide;

N-[(2S,3R)-2-methyl-1-azabicyclo[2.2.2]oct-3-yl]-3-(pyrrolidin-1-yl)thieno[2,3-c]pyridine-5-carboxamide;

N-[(2S,3R)-2-methyl-1-azabicyclo[2.2.2]oct-3-yl]-3-(2-oxopyrrolidin-1yl)thieno[2,3-c]pyridine-5-carboxamide;

N-[(2S,3R)-2-methyl-1-azabicyclo[2.2.2]oct-3-yl]-3-(piperidin-1-yl)thieno[2,3-c]pyridine-5-carboxamide;

N-[(2S,3R)-2-methyl-1-azabicyclo[2.2.2]oct-3-yl]-3-(2-oxopiperidin-1yl)thieno[2,3-c]pyridine-5-carboxamide;

N-[(2S,3R)-2-methyl-1-azabicyclo[2.2.2]oct-3-yl]-3-(morpholin-4-yl)thieno[2,3-c]pyridine-5-carboxamide;

N-[(2S,3R)-2-methyl-1-azabicyclo[2.2.2]oct-3-yl]-3-(3-oxomorpholin-4yl)thieno[2,3-c]pyridine-5-carboxamide;

N-[(2S,3R)-2-methyl-1-azabicyclo[2.2.2]oct-3-yl]-3-(thiomorpholin-4yl)thieno[2,3-c]pyridine-5-carboxamide;

N-[(2S,3R)-2-methyl-1-azabicyclo[2.2.2]oct-3-yl]-3-(3-oxothiomorpholin-4yl)thieno[2,3-c]pyridine-5-carboxamide;

N-[(2S,3R)-2-methyl-1-azabicyclo[2.2.2]oct-3-yl]-3-(piperazin-1-yl)thieno[2,3-c]pyridine-5-carboxamide;

N-[(2S,3R)-2-methyl-1-azabicyclo[2.2.2]oct-3-yl]-3-(2-oxopiperazin-1yl)thieno[2,3-c]pyridine-5-carboxamide;

N-[(2S,3R)-2-methyl-1-azabicyclo[2.2.2]oct-3-yl]-3-(4-methylpiperazin-1-yl)thieno[2,3-c]pyridine-5-carboxamide;

N-[(2S,3R)-2-methyl-1-azabicyclo[2.2.2]oct-3-yl]-3-(4-methyl-2-oxopiperazin-1yl)thieno[2,3-c]pyridine-5-carboxamide;

N-[(2S,3R)-2-methyl-1-azabicyclo[2.2.2]oct-3-yl]-3-(3-oxopiperazin-1yl)thieno[2,3-c]pyridine-5-carboxamide;

N-[(2S,3R)-2-methyl-1-azabicyclo[2.2.2]oct-3-yl]-3-(4-methyl-3-oxopiperazin-1yl)thieno[2,3-c]pyridine-5-carboxamide;

N-[(2S,3R)-2-methyl-1-azabicyclo[2.2.2]oct-3-yl]-3-(cyclopropylamino)thieno[2,3-c]pyridine-5-carboxamide;

N-[(2S,3R)-2-methyl-1-azabicyclo[2.2.2]oct-3-yl]-3-[dimethylamino]thieno[2,3-c]pyridine-5-carboxamide;

N-[(2S,3R)-2-methyl-1-azabicyclo[2.2.2]oct-3-yl]-3-(1H-pyrrole-1yl)thieno[2,3-c]pyridine-5-carboxamide;

N-[(2S,3R)-2-methyl-1-azabicyclo[2.2.2]oct-3-yl]-3-(1H-imidazol-1-yl)thieno[2,3-c]pyridine-5-carboxamide;

N-[(2S,3R)-2-methyl-1-azabicyclo[2.2.2]oct-3-yl]-3-(1H-1,2,4-triazol-1-yl)thieno[2,3-c]pyridine-5-carboxamide;

N-[(2S,3R)-2-methyl-1-azabicyclo[2.2.2]oct-3-yl]-3-(1H-1,2,3-triazol-1-yl)thieno[2,3-c]pyridine-5-carboxamide;

N-5-[(2S,3R)-2-methyl-1-azabicyclo[2.2.2]oct-3-yl]thieno[2,3-c]pyridine-3,5-dicarboxamide;

N-[(2S,3R)-2-methyl-1-azabicyclo[2.2.2]oct-3-yl]-3-(pyrrolidin-1-ylcarbonyl)thieno[2,3-c]pyridine-5-carboxamide;

N-[(2S,3R)-2-methyl-1-azabicyclo[2.2.2]oct-3-yl]-3-(piperidin-1-ylcarbonyl)thieno[2,3-c]pyridine-5-carboxamide;

N-[(2S,3R)-2-methyl-1-azabicyclo[2.2.2]oct-3-yl]-3-(piperazin-1-ylcarbonyl)thieno[2,3-c]pyridine-5-carboxamide;

N-[(2S,3R)-2-methyl-1-azabicyclo[2.2.2]oct-3-yl]-3-[(4-methylpiperazin-1-yl)carbonyl]thieno[2,3-c]pyridine-5-carboxamide;

N-[(2S,3R)-2-methyl-1-azabicyclo[2.2.2]oct-3-yl]-3-(morpholin-4-ylcarbonyl)thieno[2,3-c]pyridine-5-carboxamide;

N-[(2S,3R)-2-methyl-1-azabicyclo[2.2.2]oct-3-yl]-3-(thiomorpholin-4-ylcarbonyl)thieno[2,3-c]pyridine-5-carboxamide;

N-[(2S,3R)-2-methyl-1-azabicyclo[2.2.2]oct-3-yl]-3-(aziridin-1-ylcarbonyl)thieno[2,3-c]pyridine-5-carboxamide;

N-[(2S,3R)-2-methyl-1-azabicyclo[2.2.2]oct-3-yl]-3-(azetidin-1-ylcarbonyl)thieno[2,3-c]pyridine-5-carboxamide;

N-[(2S,3R)-2-methyl-1-azabicyclo[2.2.2]oct-3-yl]-3-formylthieno[2,3-c]pyridine-5-carboxamide;
3-acetyl-N-[(2S,3R)-2-methyl-1-azabicyclo[2.2.2]oct-3-yl]thieno[2,3-c]pyridine-5-carboxamide;
N-[(2S,3R)-2-methyl-1-azabicyclo[2.2.2]oct-3-yl]-3-(trifluoroacetyl)thieno[2,3-c]pyridine-5-carboxamide;
N-[(2S,3R)-2-methyl-1-azabicyclo[2.2.2]oct-3-yl]-3[(phenyl)sulfonyl]thieno[2,3-c]pyridine-5-carboxamide;
N-[(2S,3R)-2-methyl-1-azabicyclo[2.2.2]oct-3-yl]-3-(methylsulfonyl)thieno[2,3-c]pyridine-5-carboxamide;
5-{[(2S,3R)-2-methyl-1-azabicyclo[2.2.2]oct-3-ylamino]carbonyl}thieno[2,3-c]pyridine-3-carboxylic acid;
methyl 5-{[(2S,3R)-2-methyl-1-azabicyclo[2.2.2]oct-3-ylamino]carbonyl}thieno[2,3-c]pyridine-3-carboxylate;
isopropyl 5-{[(2S,3R)-2-methyl-1-azabicyclo[2.2.2]oct-3-ylamino]carbonyl}thieno[2,3-c]pyridine-3-carboxylate;
2,2,2-trifluoroethyl 5-{[(2S,3R)-2-methyl-1-azabicyclo[2.2.2]oct-3-ylamino]carbonyl}thieno[2,3-c]pyridine-3-carboxylate;
N-[(2S,3R)-2-methyl-1-azabicyclo[2.2.2]oct-3-yl]-3-(phenylethynyl)furo[2,3-c]pyridine-5-carboxamide;
N-[(2S,3R)-2-methyl-1-azabicyclo[2.2.2]oct-3-yl]-3-(3,3,3-trifluoroprop-1-ynyl)furo[2,3-c]pyridine-5-carboxamide;
N-[(2S,3R)-2-methyl-1-azabicyclo[2.2.2]oct-3-yl]-3-(3,3-difluoroprop-1-ynyl)furo[2,3-c]pyridine-5-carboxamide;
N-[(2S,3R)-2-methyl-1-azabicyclo[2.2.2]oct-3-yl]-3-(3-pyrrolidin-1-ylprop-1-ynyl)furo[2,3-c]pyridine-5-carboxamide;
N-[(2S,3R)-2-methyl-1-azabicyclo[2.2.2]oct-3-yl]-3-(3-morpholin-4-ylprop-1-ynyl)furo[2,3-c]pyridine-5-carboxamide;
N-[(2S,3R)-2-methyl-1-azabicyclo[2.2.2]oct-3-yl]-3-(3-piperazin-1-ylprop-1-ynyl)furo[2,3-c]pyridine-5-carboxamide;
N-[(2S,3R)-2-methyl-1-azabicyclo[2.2.2]oct-3-yl]-3-[3-(4-methylpiperazin-1-yl)prop-1-ynyl]furo[2,3-c]pyridine-5-carboxamide;
N-[(2S,3R)-2-methyl-1-azabicyclo[2.2.2]oct-3-yl]-3-[3-(1H-pyrazol-1-yl)prop-1-ynyl]furo[2,3-c]pyridine-5-carboxamide;
N-[(2S,3R)-2-methyl-1-azabicyclo[2.2.2]oct-3yl]-2-(phenylethynyl)furo[3,2-c]pyridine-5-carboxamide;
N-[(2S,3R)-2-methyl-1-azabicyclo[2.2.2]oct-3yl]-2-(3,3,3-trifluoroprop-1-ynyl)furo[2,3-c]pyridine-5-carboxamide;
N-[(2S,3R)-2-methyl-1-azabicyclo[2.2.2]oct-3yl]-2-(3,3-difluoroprop-1-ynyl)furo[2,3-c]pyridine-5-carboxamide;
N-[(2S,3R)-2-methyl-1-azabicyclo[2.2.2]oct-3yl]-2-(3-pyrrolidin-1-ylprop-1-ynyl)furo[2,3-c]pyridine-5-carboxamide;
N-[(2S,3R)-2-methyl-1-azabicyclo[2.2.2]oct-3yl]-2-(3-morpholin-4-ylprop-1-ynyl)furo[2,3-c]pyridine-5-carboxamide;
N-[(2S,3R)-2-methyl-1-azabicyclo[2.2.2]oct-3yl]-2-(3-piperazin-1-ylprop-1-ynyl)furo[2,3-c]pyridine-5-carboxamide;
N-[(2S,3R)-2-methyl-1-azabicyclo[2.2.2]oct-3yl]-2-[3-(4-methylpiperazin-1-yl)prop-1-ynyl]furo[3,2-c]pyridine-5-carboxamide;
N-[(2S,3R)-2-methyl-1-azabicyclo[2.2.2]oct-3yl]-2-[3-(1H-pyrazol-1-yl)prop-1-ynyl]furo[3,2-c]pyridine-5-carboxamide;
N-[(2S,3R)-2-methyl-1-azabicyclo[2.2.2]oct-3-yl]-3-(phenylethynyl)thieno[2,3-c]pyridine-5-carboxamide;
N-[(2S,3R)-2-methyl-1-azabicyclo[2.2.2]oct-3-yl]-3-(3,3,3-trifluoroprop-1-ynyl)thieno[2,3-c]pyridine-5-carboxamide;
N-[(2S,3R)-2-methyl-1-azabicyclo[2.2.2]oct-3-yl]-3-(3,3-difluoroprop-1-ynyl)thieno[2,3-c]pyridine-5-carboxamide;
N-[(2S,3R)-2-methyl-1-azabicyclo[2.2.2]oct-3-yl]-3-(3-pyrrolidin-1-ylprop-1-ynyl)thieno[2,3-c]pyridine-5-carboxamide;
N-[(2S,3R)-2-methyl-1-azabicyclo[2.2.2]oct-3-yl]-3-(3-morpholin-4-ylprop-1-ynyl)thieno[2,3-c]pyridine-5-carboxamide;
N-[(2S,3R)-2-methyl-1-azabicyclo[2.2.2]oct-3-yl]-3-(3-piperazin-1-ylprop-1-ynyl)thieno[2,3-c]pyridine-5-carboxamide;
N-[(2S,3R)-2-methyl-1-azabicyclo[2.2.2]oct-3-yl]-3-[3-(4-methylpiperazin-1-yl)prop-1-ynyl]thieno[2,3-c]pyridine-5-carboxamide;
N-[(2S,3R)-2-methyl-1-azabicyclo[2.2.2]oct-3-yl]-3-[3-(1H-pyrazol-1-yl)prop-1-ynyl]thieno[2,3-c]pyridine-5-carboxamide;
N-[(2S,3R)-2-methyl-1-azabicyclo[2.2.2]oct-3yl]-2-(phenylethynyl)thieno[3,2-c]pyridine-5-carboxamide;
N-[(2S,3R)-2-methyl-1-azabicyclo[2.2.2]oct-3yl]-2-(3,3,3-trifluoroprop-1-ynyl)thieno[3,2-c]pyridine-5-carboxamide;
N-[(2S,3R)-2-methyl-1-azabicyclo[2.2.2]oct-3yl]-2-(3,3-difluoroprop-1-ynyl)thieno[3,2-c]pyridine-5-carboxamide;
N-[(2S,3R)-2-methyl-1-azabicyclo[2.2.2]oct-3yl]-2-(3-pyrrolidin-1-ylprop-1-ynyl)thieno[3,2-c]pyridine-5-carboxamide;
N-[(2S,3R)-2-methyl-1-azabicyclo[2.2.2]oct-3yl]-2-(3-morpholin-4-ylprop-1-ynyl)thieno[3,2-c]pyridine-5-carboxamide;
N-[(2S,3R)-2-methyl-1-azabicyclo[2.2.2]oct-3yl]-2-(3-piperazin-1-ylprop-1-ynyl)thieno[3,2-c]pyridine-5-carboxamide;
N-[(2S,3R)-2-methyl-1-azabicyclo[2.2.2]oct-3yl]-2-[3-(4-methylpiperazin-1-yl)prop-1-ynyl]thieno[3,2-c]pyridine-5-carboxamide;
N-[(2S,3R)-2-methyl-1-azabicyclo[2.2.2]oct-3yl]-2-[3-(1H-pyrazol-1-yl)prop-1-ynyl]thieno[3,2-c]pyridine-5-carboxamide; or a pharmaceutically acceptable salt thereof.

13. The compound according to claim 5, wherein $R_2$ is H.
14. The compound according to claim 13, wherein the compound of Formula I has the R stereochemistry at C3 of quinuclidine.
15. The compound according to claim 14, wherein the compound is
N-[(3R)-1-azabicyclo[2.2.2]oct-3-yl]-2,3-dihydrofuro[2,3-c]pyridine-5-carboxamide;
N-[(3R)-1-azabicyclo[2.2.2]oct-3-yl]furo[3,2-c]pyridine-2-carboxamide;
N-[(3R)-1-azabicyclo[2.2.2]oct-3-yl]-7-chlorofuro[2,3-c]pyridine-5-carboxamide;
N-[(3R)-1-azabicyclo[2.2.2]oct-3-yl]furo[2,3-c]pyridine-5-carboxamide;
N-[(3R)-1-azabicyclo[2.2.2]oct-3-yl]-3,3-dimethyl-2,3-dihydrofuro[2,3-c]pyridine-5-carboxamide;

N-[(3R)-1-azabicyclo[2.2.2]oct-3-yl]-2-methylfuro[2,3-c]pyridine-5-carboxamide;
N-[(3R)-1-azabicyclo[2.2.2]oct-3-yl]furo[2,3-c]pyridine-2-carboxamide;
N-[(3R)-1-azabicyclo[2.2.2]oct-3-yl]furo[2,3-b]pyridine-2-carboxamide;
N-[(3R)-1-azabicyclo[2.2.2]oct-3-yl]-3-methylfuro[2,3-c]pyridine-5-carboxamide;
N-[(3R)-1-azabicyclo[2.2.2]oct-3-yl]-3-ethylfuro[2,3-c]pyridine-5-carboxamide;
N-[(3R)-1-azabicyclo[2.2.2]oct-3-yl]-3-isopropylfuro[2,3-c]pyridine-5-carboxamide;
N-[(3R)-1-azabicyclo[2.2.2]oct-3-yl]-7-(methylsulfanyl)furo[2,3-c]pyridine-5-carboxamide;
N-((3R)-1-azabicyclo[2.2.2]oct-3-yl)thieno[2,3-b]pyridine-2-carboxamide;
N-[(3R)-1-azabicyclo[2.2.2]oct-3-yl]thieno[2,3-b]pyridine-5-carboxamide;
N-[(3R)-1-azabicyclo[2.2.2]oct-3-yl]thieno[2,3-b]pyridine-6-carboxamide;
N-[(3R)-1-azabicyclo[2.2.2]oct-3-yl]thieno[2,3-c]pyridine-2-carboxamide;
N-[(3R)-1-azabicyclo[2.2.2]oct-3-yl]thieno[3,2-b]pyridine-2-carboxamide;
N-[(3R)-1-azabicyclo[2.2.2]oct-3-yl]thieno[3,2-b]pyridine-5-carboxamide;
N-[(3R)-1-azabicyclo[2.2.2]oct-3-yl]thieno[3,2-b]pyridine-6-carboxamide;
N-[(3R)-1-azabicyclo[2.2.2]oct-3-yl]thieno[3,2-c]pyridine-2-carboxamide;
N-[(3R)-1-azabicyclo[2.2.2]oct-3-yl]thieno[2,3-c]pyridine-5-carboxamide;
N-[(3R)-1-azabicyclo[2.2.2]oct-3-yl]thieno[3,2-c]pyridine-6-carboxamide;
N-[(3R)-1-azabicyclo[2.2.2]oct-3-yl]-1H-pyrrolo[2,3-c]pyridine-5-carboxamide;
N-((3R)1-azabicyclo[2.2.2]oct-3-yl)-1-methyl-1H-pyrrolo[2,3-c]pyridine-5-carboxamide;
N-[(3R)-1-azabicyclo[2.2.2]oct-3-yl]-3-chlorofuro[2,3-c]pyridine-5-carboxamide;
N-[(3R)-1-azabicyclo[2.2.2]oct-3-yl]-3-bromofuro[2,3-c]pyridine-5-carboxamide;
N-[(3R)-1-azabicyclo[2.2.2]oct-3-yl]furo[3,2-c]pyridine-6-carboxamide;
N-[(3R)-1-azabicyclo[2.2.2]oct-3-yl]-3-bromothieno[2,3-c]pyridine-5-carboxamide;
N-[(3R)-1-azabicyclo[2.2.2]oct-3-yl]-3-ethynylfuro[2,3-c]pyridine-5-carboxamide;
or a pharmaceutically acceptable salt thereof.

16. The compound according to claim 14, wherein the compound is
N-[(3R)-1-azabicyclo[2.2.2]oct-3-yl]furo[3,2-c]pyridine-2-carboxamide;
N-[(3R)-1-azabicyclo[2.2.2]oct-3-yl]furo[3,2-c]pyridine-6-carboxamide;
or a pharmaceutically acceptable salt thereof.

17. The compound according to claim 14, wherein the compound is
N-[(3R)-1-azabicyclo[2.2.2]oct-3-yl]furo[2,3-c]pyridine-5-carboxamide;
N-[(3R)-1-azabicyclo[2.2.2]oct-3-yl]-2-methylfuro[2,3-c]pyridine-5-carboxamide;
N-[(3R)-1-azabicyclo[2.2.2]oct-3-yl]-3-methylfuro[2,3-c]pyridine-5-carboxamide;
N-[(3R)-1-azabicyclo[2.2.2]oct-3-yl]-3-ethylfuro[2,3-c]pyridine-5-carboxamide;
N-[(3R)-1-azabicyclo[2.2.2]oct-3-yl]-3-isopropylfuro[2,3-c]pyridine-5-carboxamide;
N-[(3R)-1-azabicyclo[2.2.2]oct-3-yl]-3-chlorofuro[2,3-c]pyridine-5-carboxamide;
N-[(3R)-1-azabicyclo[2.2.2]oct-3-yl]-3-bromofuro[2,3-c]pyridine-5-carboxamide;
N-[(3R)-1-azabicyclo[2.2.2]oct-3-yl]-3-ethynylfuro[2,3-c]pyridine-5-carboxamide;
or a pharmaceutically acceptable salt thereof.

18. The compound according to claim 14, wherein the compound is
N-[(3R)-1-azabicyclo[2.2.2]oct-3-yl]thieno[2,3-b]pyridine-6-carboxamide;
N-[(3R)-1-azabicyclo[2.2.2]oct-3-yl]thieno[2,3-c]pyridine-2-carboxamide;
N-[(3R)-1-azabicyclo[2.2.2]oct-3-yl]thieno[2,3-c]pyridine-5-carboxamide;
N-[(3R)-1-azabicyclo[2.2.2]oct-3-yl]thieno[3,2-c]pyridine-6-carboxamide;
N-[(3R)-1-azabicyclo[2.2.2]oct-3-yl]-3-bromothieno[2,3-c]pyridine-5-carboxamide;
or a pharmaceutically acceptable salt thereof.

19. The compound according to claim 14, wherein the compound is
N-[(3R)-1-azabicyclo[2.2.2]oct-3-yl]-2-vinylfuro[3,2-c]pyridine-6-carboxamide;
4-methyl-N-[(3R)-1-azabicyclo[2.2.2]oct-3-yl]furo[3,2-c]pyridine-6-carboxamide;
4-methylthio-N-[(3R)-1-azabicyclo[2.2.2]oct-3-yl]furo[3,2-c]pyridine-6-carboxamide;
4-methoxy-N-[(3R)-1-azabicyclo[2.2.2]oct-3-yl]furo[3,2-c]pyridine-6-carboxamide;
4-chloro-N-[(3R)-1-azabicyclo[2.2.2]oct-3-yl]furo[3,2-c]pyridine-6-carboxamide;
N-[(3R)-1-azabicyclo[2.2.2]oct-3-yl]-2-ethynylfuro[3,2-c]pyridine-6-carboxamide;
N-[(3R)-1-azabicyclo[2.2.2]oct-3-yl]-2-prop-1-ynylfuro[3,2-c]pyridine-6-carboxamide;
N-[(3R)-1-azabicyclo[2.2.2]oct-3-yl]-2-(3-hydroxyprop-1-ynyl)furo[3,2-c]pyridine-6-carboxamide;
methyl 3-(6-{[(3R)-1-azabicyclo[2.2.2]oct-3-ylamino]carbonyl}furo[3,2-c]pyridin-2-yl)prop-2-ynoate;
3-(6-{[(3R)-1-azabicyclo[2.2.2]oct-3-ylamino]carbonyl}furo[3,2-c]pyridin-2-yl)prop-2-ynoic acid;
2-(3-amino-3-oxoprop-1-ynyl)-N-[(3R)-1-azabicyclo[2.2.2]oct-3-yl]furo[3,2-c]pyridine-6-carboxamide;
N-[(3R)-1-azabicyclo[2.2.2]oct-3-yl]-2-cyanofuro[3,2-c]pyridine-6-carboxamide;
N-[(3R)-1-azabicyclo[2.2.2]oct-3-yl]-2-chlorofuro[3,2-c]pyridine-6-carboxamide;
N-[(3R)-1-azabicyclo[2.2.2]oct-3-yl]-2-fluorofuro[3,2-c]pyridine-6-carboxamide;
N-[(3R)-1-azabicyclo[2.2.2]oct-3-yl]-2-iodofuro[3,2-c]pyridine-6-carboxamide;
N-[(3R)-1-azabicyclo[2.2.2]oct-3-yl]-2-trifluoromethyl-furo[3,2-c]pyridine-6-carboxamide;
N-[(3R)-1-azabicyclo[2.2.2]oct-3-yl]-2-mercaptofuro[3,2-c]pyridine-6-carboxamide;
N-[(3R)-1-azabicyclo[2.2.2]oct-3-yl]-2-(methylthio)furo[3,2-c]pyridine-6-carboxamide;
N-[(3R)-1-azabicyclo[2.2.2]oct-3-yl]-2-(methylamino)furo[3,2-c]pyridine-6-carboxamide;
N-[(3R)-1-azabicyclo[2.2.2]oct-3-yl]-2-(formylamino)furo[3,2-c]pyridine-6-carboxamide;
N-[(3R)-1-azabicyclo[2.2.2]oct-3-yl]-2-[formyl(methyl)amino]furo[3,2-c]pyridine-6-carboxamide;

2-(acetylamino)-N-[(3R)-1-azabicyclo[2.2.2]oct-3-yl] furo[3,2-c]pyridine-6-carboxamide;
2-(acetyl(methyl)amino)-N-[(3R)-1-azabicyclo[2.2.2] oct-3-yl]furo[3,2-c]pyridine-6-carboxamide;
N-[(3R)-1-azabicyclo[2.2.2]oct-3-yl]-2-[(trifluoroacetyl) amino]furo[3,2-c]pyridine-6-carboxamide;
N-[(3R)-1-azabicyclo[2.2.2]oct-3-yl]-2-(benzoylamino) furo[3,2-c]pyridine-6-carboxamide;
N-[(3R)-1-azabicyclo[2.2.2]oct-3-yl]-2-(diethylamino) furo[3,2-c]pyridine-6-carboxamide;
N-[(3R)-1-azabicyclo[2.2.2]oct-3-yl]-2-(diisopropylamino)furo[3,2-c]pyridine-6-carboxamide;
N-[(3R)-1-azabicyclo[2.2.2]oct-3-yl]-2-(pyrrolidin-1-yl) furo[3,2-c]pyridine-6-carboxamide;
N-[(3R)-1-azabicyclo[2.2.2]oct-3-yl]-2-(2-oxopyrrolidin-1yl furo[3,2-c]pyridine-6-carboxamide;
N-[(3R)-1-azabicyclo[2.2.2]oct-3-yl]-2-(piperidin-1-yl) furo[3,2-c]pyridine-6-carboxamide;
N-[(3R)-1-azabicyclo[2.2.2]oct-3-yl]-2-(2-oxopiperidin-1yl)furo[3,2-c]pyridine-6-carboxamide;
N-[(3R)-1-azabicyclo[2.2.2]oct-3-yl]-2-(morpholin-4-yl) furo[3,2-c]pyridine-6-carboxamide;
N-[(3R)-1-azabicyclo[2.2.2]oct-3-yl]-2-(3-oxomorpholin-4yl)furo[3,2-c]pyridine-6-carboxamide;
N-[(3R)-1-azabicyclo[2.2.2]oct-3-yl]-2-(thiomorpholin-4yl)furo[3,2-c]pyridine-6-carboxamide;
N-[(3R)-1-azabicyclo[2.2.2]oct-3-yl]-2-(3-oxothiomorpholin-4yl)furo[3,2-c]pyridine-6-carboxamide;
N-[(3R)-1-azabicyclo[2.2.2]oct-3-yl]-2-(piperazin-1-yl) furo[3,2-c]pyridine-6-carboxamide;
N-[(3R)-1-azabicyclo[2.2.2]oct-3-yl]-2-(2-oxopiperazin-1yl)furo[3,2-c]pyridine-6-carboxamide;
N-[(3R)-1-azabicyclo[2.2.2]oct-3-yl]-2-(4-methylpiperazin-1-yl)furo[3,2-c]pyridine-6-carboxamide;
N-[(3R)-1-azabicyclo[2.2.2]oct-3-yl]-2-(4-methyl-2-oxopiperazin-1yl)furo[3,2-c]pyridine-6-carboxamide;
N-[(3R)-1-azabicyclo[2.2.2]oct-3-yl]-2-(3-oxopiperazin-1yl)furo[3,2-c]pyridine-6-carboxamide;
N-[(3R)-1-azabicyclo[2.2.2]oct-3-yl]-2-(4-methyl-3-oxopiperazin-1yl)furo[3,2-c]pyridine-6-carboxamide;
N-[(3R)-1-azabicyclo[2.2.2]oct-3-yl]-2-(cyclopropylamino)furo[3,2-c]pyridine-6-carboxamide;
N-[(3R)-1-azabicyclo[2.2.2]oct-3-yl]-2-[dimethylamino] furo[3,2-c]pyridine-6-carboxamide;
N-[(3R)-1-azabicyclo[2.2.2]oct-3-yl]-2-(1H-pyrrole-1yl) furo[3,2-c]pyridine-6-carboxamide;
N-[(3R)-1-azabicyclo[2.2.2]oct-3-yl]-2-(1H-imidazol-1-yl)furo[3,2-c]pyridine-6-carboxamide;
N-[(3R)-1-azabicyclo[2.2.2]oct-3-yl]-2-(1H-1,2,4-triazol-1-yl)furo[3,2-c]pyridine-6-carboxamide;
N-[(3R)-1-azabicyclo[2.2.2]oct-3-yl]-2-(1H-1,2,3-triazol-1-yl)furo[3,2-c]pyridine-6-carboxamide;
N-6-[(3R)-1-azabicyclo[2.2.2]oct-3-yl]furo[3,2-c]pyridine-2,6-dicarboxamide;
N-[(3R)-1-azabicyclo[2.2.2]oct-3-yl]-2-(pyrrolidin-1-ylcarbonyl)furo[3,2-c]pyridine-6-carboxamide;
N-[(3R)-1-azabicyclo[2.2.2]oct-3-yl]-2-(piperidin-1-ylcarbonyl)furo[3,2-c]pyridine-6-carboxamide;
N-[(3R)-1-azabicyclo[2.2.2]oct-3-yl]-2-(piperazin-1-ylcarbonyl)furo[3,2-c]pyridine-6-carboxamide;
N-[(3R)-1-azabicyclo[2.2.2]oct-3-yl]-2-[(4-methylpiperazin-1-yl)carbonyl]furo[3,2-c]pyridine-6-carboxamide;
N-[(3R)-1-azabicyclo[2.2.2]oct-3-yl]-2-(morpholin-4-ylcarbonyl)furo[3,2-c]pyridine-6-carboxamide;
N-[(3R)-1-azabicyclo[2.2.2]oct-3-yl]-2-(thiomorpholin-4-ylcarbonyl)furo[3,2-c]pyridine-6-carboxamide;
N-[(3R)-1-azabicyclo[2.2.2]oct-3-yl]-2-(aziridin-1-ylcarbonyl)furo[3,2-c]pyridine-6-carboxamide;
N-[(3R)-1-azabicyclo[2.2.2]oct-3-yl]-2-(azetidin-1-ylcarbonyl)furo[3,2-c]pyridine-6-carboxamide;
N-[(3R)-1-azabicyclo[2.2.2]oct-3-yl]-2-formylfuro[3,2-c]pyridine-6-carboxamide;
2-acetyl-N-[(3R)-1-azabicyclo[2.2.2]oct-3-yl]furo[3,2-c] pyridine-6-carboxamide;
N-[(3R)-1-azabicyclo[2.2.2]oct-3-yl]-2-(trifluoroacetyl) furo[3,2-c]pyridine-6-carboxamide;
N-[(3R)-1-azabicyclo[2.2.2]oct-3-yl]-2-[(phenyl)sulfonyl]furo[3,2-c]pyridine-6-carboxamide;
N-[(3R)-1-azabicyclo[2.2.2]oct-3-yl]-2-(methylsulfonyl) furo[3,2-c]pyridine-6-carboxamide;
6-{[(3R)-1-azabicyclo[2.2.2]oct-3-ylamino] carbonyl}furo[3,2-c]pyridine-2-carboxylic acid;
methyl 6-{[(3R)-1-azabicyclo[2.2.2]oct-3-ylamino] carbonyl}furo[3,2-c]pyridine-2-carboxylate;
isopropyl 6-{[(3R)-1-azabicyclo[2.2.2]oct-3-ylamino] carbonyl}furo[3,2-c]pyridine-2-carboxylate;
2,2,2-trifluoroethyl 6-{[(3R)-1-azabicyclo[2.2.2]oct-3-ylamino]carbonyl}furo[3,2-c]pyridine-2-carboxylate;
N-[(3R)-1-azabicyclo[2.2.2]oct-3-yl]-2-vinylthieno[3,2-c]pyridine-6-carboxamide;
4-methyl-N-[(3R)-1-azabicyclo[2.2.2]oct-3-yl]1thieno[3,2-c]pyridine-6-carboxamide;
4-methylthio-N-[(3R)-1-azabicyclo[2.2.2]oct-3-yl]thieno[3,2-c]pyridine-6-carboxamide;
4-methoxy-N-[(3R)-1-azabicyclo[2.2.2]oct-3-yl]thieno[3,2-c]pyridine-6-carboxamide;
4-chloro-N-[(3R)-1-azabicyclo[2.2.2]oct-3-yl]thieno[3,2-c]pyridine-6-carboxamide;
N-[(3R)-1-azabicyclo[2.2.2]oct-3-yl]-2-ethynylthieno[3,2-c]pyridine-6-carboxamide;
N-[(3R)-1-azabicyclo[2.2.2]oct-3-yl]-2-prop-1-ynylthieno[3,2-c]pyridine-6-carboxamide;
N-[(3R)-1-azabicyclo[2.2.2]oct-3-yl]-2-(3-hydroxyprop-1-ynyl)thieno[3,2-c]pyridine-6-carboxamide;
methyl 3-(6-{[(3R)-1-azabicyclo[2.2.2]oct-3-ylamino] carbonyl}thieno[3,2-c]pyridin-2-yl)prop-2-ynoate;
3-(6-{[(3R)-1-azabicyclo[2.2.2]oct-3-ylamino] carbonyl}thieno[3,2-c]pyridin-2-yl)prop-2-ynoic acid;
2-(3-amino-3-oxoprop-1-ynyl)-N-[(3R)-1-azabicyclo [2.2.2]oct-3-yl]thieno[3,2-c]pyridine-6-carboxamide;
N-[(3R)-1-azabicyclo[2.2.2]oct-3-yl]-2-cyanothieno[3,2-c]pyridine-6-carboxamide;
N-[(3R)-1-azabicyclo[2.2.2]oct-3-yl]-2-chlorothieno[3,2-c]pyridine-6-carboxamide;
N-[(3R)-1-azabicyclo[2.2.2]oct-3-yl]-2-fluorothieno[3,2-c]pyridine-6-carboxamide
N-[(3R)-1-azabicyclo[2.2.2]oct-3-yl]-2-iodothieno[3,2-c] pyridine-6-carboxamide;
N-[(3R)-1-azabicyclo[2.2.2]oct-3-yl]-2-trifluoromethylthieno[3,2-c]pyridine-6-carboxamide;
N-[(3R)-1-azabicyclo[2.2.2]oct-3-yl]-2-mercaptothieno [3,2-c]pyridine-6-carboxamide;
N-[(3R)-1-azabicyclo[2.2.2]oct-3-yl]-2-(methylthio) thieno[3,2-c]pyridine-6-carboxamide;
N-[(3R)-1-azabicyclo[2.2.2]oct-3-yl]-2-(methylamino) thieno[3,2-c]pyridine-6-carboxamide;
N-[(3R)-1-azabicyclo[2.2.2]oct-3-yl]-2-(fonylamino) thieno[3,2-c]pyridine-6-carboxamide;
N-[(3R)-1-azabicyclo[2.2.2]oct-3-yl]-2-[formyl(methyl) amino]thieno[3,2-c]pyridine-6-carboxamide;
2-(acetylamino)-N-[(3R)-1-azabicyclo[2.2.2]oct-3-yl] thieno[3,2-c]pyridine-6-carboxamide;

2-(acetyl(methyl)amino)-N-[(3R)-1-azabicyclo[2.2.2]oct-3-yl]thieno[3,2-c]pyridine-6-carboxamide;
N-[(3R)-1-azabicyclo[2.2.2]oct-3-yl]-2-[(trifluoroacetyl)amino]thieno[3,2-c]pyridine-6-carboxamide;
N-[(3R)-1-azabicyclo[2.2.2]oct-3-yl]-2-(benzoylamino)thieno[3,2-c]pyridine-6-carboxamide;
N-[(3R)-1-azabicyclo[2.2.2]oct-3-yl]-2-(diethylamino)thieno[3,2-c]pyridine-6-carboxamide;
N-[(3R)-1-azabicyclo[2.2.2]oct-3-yl]-2-(diisopropylamino)thieno[3,2-c]pyridine-6-carboxamide;
N-[(3R)-1-azabicyclo[2.2.2]oct-3-yl]-2-(pyrrolidin-1-yl)thieno[3,2-c]pyridine-6-carboxamide;
N-[(3R)-1-azabicyclo[2.2.2]oct-3-yl]-2-(2-oxopyrrolidin-1ylthieno[3,2-c]pyridine-6-carboxamide;
N-[(3R)-1-azabicyclo[2.2.2]oct-3-yl]-2-(piperidin-1-yl)thieno[3,2-c]pyridine-6-carboxamide;
N-[(3R)-1-azabicyclo[2.2.2]oct-3-yl]-2-(2-oxopiperidin-1yl)thieno[3,2-c]pyridine-6-carboxamide;
N-[(3R)-1-azabicyclo[2.2.2]oct-3-yl]-2-(morpholin-4-yl)thieno[3,2-c]pyridine-6-carboxamide;
N-[(3R)-1-azabicyclo[2.2.2]oct-3-yl]-2-(3-oxomorpholin-4yl)thieno[3,2-c]pyridine-6-carboxamide;
N-[(3R)-1-azabicyclo[2.2.2]oct-3-yl]-2-(thiomorpholin-4yl)thieno[3,2-c]pyridine-6-carboxamide;
N-[(3R)-1-azabicyclo[2.2.2]oct-3-yl]-2-(3-oxothiomorpholin-4yl)thieno[3,2-c]pyridine-6-carboxamide;
N-[(3R)-1-azabicyclo[2.2.2]oct-3-yl]-2-(piperazin-1-yl)thieno[3,2-c]pyridine-6-carboxamide;
N-[(3R)-1-azabicyclo[2.2.2]oct-3-yl]-2-(2-oxopiperazin-1yl)thieno[3,2-c]pyridine-6-carboxamide;
N-[(3R)-1-azabicyclo[2.2.2]oct-3-yl]-2-(4-methylpiperazin-1-yl)thieno[3,2-c]pyridine-6-carboxamide;
N-[(3R)-1-azabicyclo[2.2.2]oct-3-yl]-2-(4-methyl-2-oxopiperazin-1yl)thieno[3,2-c]pyridine-6-carboxamide;
N-[(3R)-1-azabicyclo[2.2.2]oct-3-yl]-2-(3-oxopiperazin-1yl)thieno[3,2-c]pyridine-6-carboxamide;
N-[(3R)-1-azabicyclo[2.2.2]oct-3-yl]-2-(4-methyl-3-oxopiperazin-1yl)thieno[3,2-c]pyridine-6-carboxamide;
N-[(3R)-1-azabicyclo[2.2.2]oct-3-yl]-2-(cyclopropylamino)thieno[3,2-c]pyridine-6-carboxamide; N-[(3R)-1-azabicyclo[2.2.2]oct-3-yl]-2-[dimethylamino]thieno[3,2-c]pyridine-6-carboxamide;
N-[(3R)-1-azabicyclo[2.2.2]oct-3-yl]-2-(1H-pyrrole-1yl)thieno[3,2-c]pyridine-6-carboxamide;
N-[(3R)-1-azabicyclo[2.2.2]oct-3-yl]-2-(1H-imidazol-1-yl)thieno[3,2-c]pyridine-6-carboxamide;
N-[(3R)-1-azabicyclo[2.2.2]oct-3-yl]-2-(1H-1,2,4-triazol-1-yl)thieno[3,2-c]pyridine-6-carboxamide;
N-[(3R)-1-azabicyclo[2.2.2]oct-3-yl]-2-(1H-1,2,3-triazol-1-yl)thieno[3,2-c]pyridine-6-carboxamide;
N-6-[(3R)-1-azabicyclo[2.2.2]oct-3-yl]thieno[3,2-c]pyridine-2,6-dicarboxamide;
N-[(3R)-1-azabicyclo[2.2.2]oct-3-yl]-2-(pyrrolidin-1-ylcarbonyl)thieno[3,2-c]pyridine-6-carboxamide;
N-[(3R)-1-azabicyclo[2.2.2]oct-3-yl]-2-(piperidin-1-ylcarbonyl)thieno[3,2-c]pyridine-6-carboxamide;
N-[(3R)-1-azabicyclo[2.2.2]oct-3-yl]-2-(piperazin-1-ylcarbonyl)thieno[3,2-c]pyridine-6-carboxamide;
N-[(3R)-1-azabicyclo[2.2.2]oct-3-yl]-2-[(4-methylpiperazin-1-yl)carbonyl]thieno[3,2-c]pyridine-6-carboxamide;
N-[(3R)-1-azabicyclo[2.2.2]oct-3-yl]-2-(morpholin-4-ylcarbonyl)thieno[3,2-c]pyridine-6-carboxamide;
N-[(3R)-1-azabicyclo[2.2.2]oct-3-yl]-2-(thiomorpholin-4-ylcarbonyl)thieno[3,2-c]pyridine-6-carboxamide;
N-[(3R)-1-azabicyclo[2.2.2]oct-3-yl]-2-(aziridin-1-ylcarbonyl)thieno[3,2-c]pyridine-6-carboxamide;
N-[(3R)-1-azabicyclo[2.2.2]oct-3-yl]-2-(azetidin-1-ylcarbonyl)thieno[3,2-c]pyridine-6-carboxamide;
N-[(3R)-1-azabicyclo[2.2.2]oct-3-yl]-2-formylthieno[3,2-c]pyridine-6-carboxamide;
2-acetyl-N-[(3R)-1-azabicyclo[2.2.2]oct-3-yl]thieno[3,2-c]pyridine-6-carboxamide;
N-[(3R)-1-azabicyclo[2.2.2]oct-3-yl]-2-(trifluoroacetyl)thieno[3,2-c]pyridine-6-carboxamide;
N-[(3R)-1-azabicyclo[2.2.2]oct-3-yl]-2-[(phenyl)sulfonyl]1thieno[3,2-c]pyridine-6-carboxamide;
N-[(3R)-1-azabicyclo[2.2.2]oct-3-yl]-2-(methylsulfonyl)thieno[3,2-c]pyridine-6-carboxamide;
6-{[(3R)-1-azabicyclo[2.2.2]oct-3-ylamino]carbonyl}thieno[3,2-c]pyridine-2-carboxylic acid;
methyl 6-{[(3R)-1-azabicyclo[2.2.2]oct-3-ylamino]carbonyl}thieno[3,2-c]pyridine-2-carboxylate;
isopropyl 6-{[(3R)-1-azabicyclo[2.2.2]oct-3-ylamino]carbonyl}thieno[3,2-c]pyridine-2-carboxylate;
2,2,2-trifluoroethyl 6-{[(3R)-1-azabicyclo[2.2.2]oct-3-ylamino]carbonyl}thieno[3,2-c]pyridine-2-carboxylate;
N-[(3R)-1-azabicyclo[2.2.2]oct-3-yl]-3-vinylfuro[2,3-c]pyridine-5-carboxamide;
7-methyl-N-[(3R)-1-azabicyclo[2.2.2]oct-3-yl]furo[2,3-c]pyridine-5-carboxamide;
7-methoxy-N-[(3R)-1-azabicyclo[2.2.2]oct-3-yl]furo[2,3-c]pyridine-5-carboxamide;
N-[(3R)-1-azabicyclo[2.2.2]oct-3-yl]-3-ethynylfuro[2,3-c]pyridine-5-carboxamide;
N-[(3R)-1-azabicyclo[2.2.2]oct-3-yl]-3-prop-1-ynylfuro[2,3c-]pyridine-5-carboxamide;
N-[(3R)-1-azabicyclo[2.2.2]oct-3-yl]-3-(3-hydroxyprop-1-ynyl)furo[2,3-c]pyridine-5-carboxamide;
methyl 3-(5-{[(3R)-1-azabicyclo[2.2.2]oct-3-ylamino]carbonyl}furo[2,3-c]pyridin-3-yl)prop-2-ynoate;
3-(5-{[(3R)-1-azabicyclo[2.2.2]oct-3-ylamino]carbonyl}furo[2,3-c]pyridin-3-yl)prop-2-ynoic acid;
3-(3-amino-3-oxoprop-1-ynyl)-N-[(3R)-1-azabicyclo[2.2.2]oct-3-yl]furo[2,3-c]pyridine-5-carboxamide;
N-[(3R)-1-azabicyclo[2.2.2]oct-3-yl]-3-cyanofuro[2,3-c]pyridine-5-carboxamide;
N-[(3R)-1-azabicyclo[2.2.2]oct-3-yl]-3-fluorofuro[2,3-c]pyridine-5-carboxamide;
N-[(3R)-1-azabicyclo[2.2.2]oct-3-yl]-3-iodofuro[2,3-c]pyridine-5-carboxamide;
N-[(3R)-1-azabicyclo[2.2.2]oct-3-yl]-3-trifluoromethyl-furo[2,3-c]pyridine-5-carboxamide;
N-[(3R)-1-azabicyclo[2.2.2]oct-3-yl]-3-mercaptofuro[2,3-c]pyridine-5-carboxamide;
N-[(3R)-1-azabicyclo[2.2.2]oct-3-yl]-3-(methylthio)furo[2,3-c]pyridine-5-carboxamide;
N-[(3R)-1-azabicyclo[2.2.2]oct-3-yl]-3-(methylamino)furo[2,3-c]pyridine-5-carboxamide;
N-[(3R)-1-azabicyclo[2.2.2]oct-3-yl]-3-(formylamino)furo[2,3-c]pyridine-5-carboxamide;
N-[(3R)-1-azabicyclo[2.2.2]oct-3-yl]-3-[formyl(methyl)amino]furo[2,3-c]pyridine-5-carboxamide;
3-(acetylamino)-N-[(3R)-1-azabicyclo[2.2.2]oct-3-yl]furo[2,3-c]pyridine-5-carboxamide;
3-(acetyl(methyl)amino)-N-[(3R)-1-azabicyclo[2.2.2]oct-3-yl]furo[2,3-c]pyridine-5-carboxamide;
N-[(3R)-1-azabicyclo[2.2.2]oct-3-yl]-3-[(trifluoroacetyl)amino]furo[2,3-c]pyridine-5-carboxamide;
N-[(3R)-1-azabicyclo[2.2.2]oct-3-yl]-3-(benzoylamino)furo[2,3-c]pyridine-5-carboxamide;
N-[(3R)-1-azabicyclo[2.2.2]oct-3-yl]-3-(diethylamino)furo[2,3-c]pyridine-5-carboxamide;

N-[(3R)-1-azabicyclo[2.2.2]oct-3-yl]-3-(diisopropylamino)furo[2,3-c]pyridine-5-carboxamide;
N-[(3R)-1-azabicyclo[2.2.2]oct-3-yl]-3-(pyrrolidin-1-yl)furo[2,3-c]pyridine-5-carboxamide;
N-[(3R)-1-azabicyclo[2.2.2]oct-3-yl]-3-(2-oxopyrrolidin-1yl)furo[2,3-c]pyridine-5-carboxamide;
N-[(3R)-1-azabicyclo[2.2.2]oct-3-yl]-3-(piperidin-1-yl)furo[2,3-c]pyridine-5-carboxamide;
N-[(3R)-1-azabicyclo[2.2.2]oct-3-yl]-3-(2-oxopiperidin-1yl)furo[2,3-c]pyridine-5-carboxamide;
N-[(3R)-1-azabicyclo[2.2.2]oct-3-yl]-3-(morpholin-4-yl)furo[2,3-c]pyridine-5-carboxamide;
N-[(3R)-1-azabicyclo[2.2.2]oct-3-yl]-3-(3-oxomorpholin-4yl)furo[2,3-c]pyridine-5-carboxamide;
N-[(3R)-1-azabicyclo[2.2.2]oct-3-yl]-3-(thiomorpholin-4yl)furo[2,3-c]pyridine-5-carboxamide;
N-[(3R)-1-azabicyclo[2.2.2]oct-3-yl]-3-(3-oxothiomorpholin-4yl)furo[2,3-c]pyridine-5-carboxamide;
N-[(3R)-1-azabicyclo[2.2.2]oct-3-yl]-3-(piperazin-1-yl)furo[2,3-c]pyridine-5-carboxamide;
N-[(3R)-1-azabicyclo[2.2.2]oct-3-yl]-3-(2-oxopiperazin-1yl)furo[2,3-c]pyridine-5-carboxamide;
N-[(3R)-1-azabicyclo[2.2.2]oct-3-yl]-3-(4-methylpiperazin-1-yl)furo[2,3-c]pyridine-5-carboxamide;
N-[(3R)-1-azabicyclo[2.2.2]oct-3-yl]-3-(4-methyl-2-oxopiperazin-1yl)furo[2,3-c]pyridine-5-carboxamide;
N-[(3R)-1-azabicyclo[2.2.2]oct-3-yl]-3-(3-oxopiperazin-1yl)furo[2,3-c]pyridine-5-carboxamide;
N-[(3R)-1-azabicyclo[2.2.2]oct-3-yl]-3-(4-methyl-3-oxopiperazin-1yl)furo[2,3-c]pyridine-5-carboxamide;
N-[(3R)-1-azabicyclo[2.2.2]oct-3-yl]-3-(cyclopropylamino)furo[2,3-c]pyridine-5-carboxamide;
N-[(3R)-1-azabicyclo[2.2.2]oct-3-yl]-3-[dimethylamino]furo[2,3-c]pyridine-5-carboxamide;
N-[(3R)-1-azabicyclo[2.2.2]oct-3-yl]-3-(1H-pyrrole-1yl)furo[2,3-c]pyridine-5-carboxamide;
N-[(3R)-1-azabicyclo[2.2.2]oct-3-yl]-3-(1H-imidazol-1-yl)furo[2,3-c]pyridine-5-carboxamide;
N-[(3R)-1-azabicyclo[2.2.2]oct-3-yl]-3-(1H-1,2,4-triazol-1-yl)furo[2,3-c]pyridine-5-carboxamide;
N-[(3R)-1-azabicyclo[2.2.2]oct-3-yl]-3-(1H-1,2,3-triazol-1-yl)furo[2,3-c]pyridine-5-carboxamide;
N-5-[(3R)-1-azabicyclo[2.2.2]oct-3-yl]furo[2,3-c]pyridine-3,5-dicarboxamide;
N-[(3R)-1-azabicyclo[2.2.2]oct-3-yl]-3-(pyrrolidin-1-ylcarbonyl)furo[2,3-c]pyridine-5-carboxamide;
N-[(3R)-1-azabicyclo[2.2.2]oct-3-yl]-3-(piperidin-1-ylcarbonyl)furo[2,3-c]pyridine-5-carboxamide;
N-[(3R)-1-azabicyclo[2.2.2]oct-3-yl]-3-piperazin-1-ylcarbonyl)furo[2,3-c]pyridine-5-carboxamide;
N-[(3R)-1-azabicyclo[2.2.2]oct-3-yl]-3-[(4-methylpiperazin-1-yl)carbonyl]furo[2,3-c]pyridine-5-carboxamide;
N-[(3R)-1-azabicyclo[2.2.2]oct-3-yl]-3-(morpholin-4-ylcarbonyl)furo[2,3-c]pyridine-5-carboxamide;
N-[(3R)-1-azabicyclo[2.2.2]oct-3-yl]-3-(thiomorpholin-4-ylcarbonyl)furo[2,3-c]pyridine-5-carboxamide;
N-[(3R)-1-azabicyclo[2.2.2]oct-3-yl]-3-(aziridin-1-ylcarbonyl)furo[2,3-c]pyridine-5-carboxamide;
N-[(3R)-1-azabicyclo[2.2.2]oct-3-yl]-3-(azetidin-1-ylcarbonyl)furo[2,3-c]pyridine-5-carboxamide;
N-[(3R)-1-azabicyclo[2.2.2]oct-3-yl]-3-formylfuro[2,3-c]pyridine-5-carboxamide;
3-acetyl-N-[(3R)-1-azabicyclo[2.2.2]oct-3-yl]furo[2,3-c]pyridine-5-carboxamide;
N-[(3R)-1-azabicyclo[2.2.2]oct-3-yl]-3-(trifluoroacetyl)furo[2,3-c]pyridine-5-carboxamide;
N-[(3R)-1-azabicyclo[2.2.2]oct-3-yl]-3-[(phenyl)sulfonyl]furo[2,3-c]pyridine-5-carboxamide;
N-[(3R)-1-azabicyclo[2.2.2]oct-3-yl]-3-(methylsulfonyl)furo[2,3-c]pyridine-5-carboxamide;
5-{[(3R)-1-azabicyclo[2.2.2]oct-3-ylamino]carbonyl}furo[2,3-c]pyridine-3-carboxylic acid;
methyl 5-{[(3R)-1-azabicyclo[2.2.2]oct-3-ylamino]carbonyl}furo[2,3-c]pyridine-3-carboxylate;
isopropyl 5-{[(3R)-1-azabicyclo[2.2.2]oct-3-ylamino]carbonyl}furo[2,3-c]pyridine-3-carboxylate;
2,2,2-trifluoroethyl 5-{[(3R)-1-azabicyclo[2.2.2]oct-3-ylamino]carbonyl}furo[2,3-c]pyridine-3-carboxylate;
7-methyl-N-[(3R)-1-azabicyclo[2.2.2]oct-3-yl]thieno[2,3-c]pyridine-5-carboxamide;
7-methylthio-N-[(3R)-1-azabicyclo[2.2.2]oct-3-yl]thieno[2,3-c]pyridine-5-carboxamide;
7-methoxy-N-[(3R)-1-azabicyclo[2.2.2]oct-3-yl]thieno[2,3-c]pyridine-5-carboxamide;
7-chloro-N-[(3R)-1-azabicyclo[2.2.2]oct-3-yl]thieno[2,3-c]pyridine-5-carboxamide;
N-[(3R)-1-azabicyclo[2.2.2]oct-3-yl]-3-vinylthieno[2,3-c]pyridine-5-carboxamide;
N-[(3R)-1-azabicyclo[2.2.2]oct-3-yl]-3-ethynylthieno[2,3-c]pyridine-5-carboxamide;
N-[(3R)-1-azabicyclo[2.2.2]oct-3-yl]-3-prop-1-ynylthieno[2,3-c]pyridine-5-carboxamide;
N-[(3R)-1-azabicyclo[2.2.2]oct-3-yl]-3-(3-hydroxyprop-1-ynyl)thieno[2,3-c]pyridine-5-carboxamide;
methyl 3-(5-{[(3R)-1-azabicyclo[2.2.2]oct-3-ylamino]carbonyl}thieno[2,3-c]pyridin-3-yl)prop-2-ynoate;
3-(5-{[(3R)-1-azabicyclo[2.2.2]oct-3-ylamino]carbonyl}thieno[2,3-c]pyridin-3-yl)prop-2-ynoic acid;
3-(3-amino-3-oxoprop-1-ynyl)-N-[(3R)-1-azabicyclo[2.2.2]oct-3-yl]thieno[2,3-c]pyridine-5-carboxamide;
N-[(3R)-1-azabicyclo[2.2.2]oct-3-yl]-3-cyanothieno[2,3-c]pyridine-5-carboxamide;
N-[(3R)-1-azabicyclo[2.2.2]oct-3-yl]-3-chlorothieno[2,3-c]pyridine-5-carboxamide;
N-[(3R)-1-azabicyclo[2.2.2]oct-3-yl]-3-fluorothieno[2,3-c]pyridine-5-carboxamide;
N-[(3R)-1-azabicyclo[2.2.2]oct-3-yl]-3-iodothieno[2,3-c]pyridine-5-carboxamide;
N-[(3R)-1-azabicyclo[2.2.2]oct-3-yl]-3-trifluoromethylthieno[2,3-c]pyridine-5-carboxamide;
N-[(3R)-1-azabicyclo[2.2.2]oct-3-yl]-3-mercaptothieno[2,3-c]pyridine-5-carboxamide;
N-[(3R)-1-azabicyclo[2.2.2]oct-3-yl]-3-(methylthio)thieno[2,3-c]pyridine-5-carboxamide;
N-[(3R)-1-azabicyclo[2.2.2]oct-3-yl]-3-(methylamino)thieno[2,3-c]pyridine-5-carboxamide;
N-[(3R)-1-azabicyclo[2.2.2]oct-3-yl]-3-(formylamino)thieno[2,3-c]pyridine-5-carboxamide;
N-[(3R)-1-azabicyclo[2.2.2]oct-3-yl]-3-[formyl(methyl)amino]thieno[2,3-c]pyridine-5-carboxamide;
3-(acetylamino)-N-[(3R)-1-azabicyclo[2.2.2]oct-3-yl]thieno[2,3-c]pyridine-5-carboxamide;
3-(acetyl(methyl)amino)-N-[(3R)-1-azabicyclo[2.2.2]oct-3-yl]thieno[2,3-c]pyridine-5-carboxamide;
N-[(3R)-1-azabicyclo[2.2.2]oct-3-yl]-3-[(trifluoroacetyl)amino]thieno[2,3-c]pyridine-5-carboxamide;
N-[(3R)-1-azabicyclo[2.2.2]oct-3-yl]-3-(benzoylamino)thieno[2,3-c]pyridine-5-carboxamide;
N-[(3R)-1-azabicyclo[2.2.2]oct-3-yl]-3-(diethylamino)thieno[2,3-c]pyridine-5-carboxamide;
N-[(3R)-1-azabicyclo[2.2.2]oct-3-yl]-3-(diisopropylamino)thieno[2,3-c]pyridine-5-carboxamide;

N-[(3R)-1-azabicyclo[2.2.2]oct-3-yl]-3-(pyrrolidin-1-yl)thieno[2,3-c]pyridine-5-carboxamide;
N-[(3R)-1-azabicyclo[2.2.2]oct-3-yl]-3-(2-oxopyrrolidin-1yl)thieno[2,3-c]pyridine-5-carboxamide;
N-[(3R)-1-azabicyclo[2.2.2]oct-3-yl]-3-(piperidin-1-yl)thieno[2,3-c]pyridine-5-carboxamide;
N-[(3R)-1-azabicyclo[2.2.2]oct-3-yl]-3-(2-oxopiperidin-1yl)thieno[2,3-c]pyridine-5-carboxamide;
N-[(3R)-1-azabicyclo[2.2.2]oct-3-yl]-3-(morpholin-4-yl)thieno[2,3-c]pyridine-5-carboxamide;
N-[(3R)-1-azabicyclo[2.2.2]oct-3-yl]-3-(3-oxomorpholin-4yl)thieno[2,3-c]pyridine-5-carboxamide;
N-[(3R)-1-azabicyclo[2.2.2]oct-3-yl]-3-(thiomorpholin-4yl)thieno[2,3-c]pyridine-5-carboxamide;
N-[(3R)-1-azabicyclo[2.2.2]oct-3-yl]-3-(3-oxothiomorpholin-4yl)thieno[2,3-c]pyridine-5-carboxamide;
N-[(3R)-1-azabicyclo[2.2.2]oct-3-yl]-3-(piperazin-1-yl)thieno[2,3-c]pyridine-5-carboxamide;
N-[(3R)-1-azabicyclo[2.2.2]oct-3-yl]-3-(2-oxopiperazin-1yl)thieno[2,3-c]pyridine-5-carboxamide;
N-[(3R)-1-azabicyclo[2.2.2]oct-3-yl]-3-(4-methylpiperazin-1-yl)thieno[2,3-c]pyridine-5-carboxamide;
N-[(3R)-1-azabicyclo[2.2.2]oct-3-yl]-3-(4-methyl-2-oxopiperazin-1yl)thieno[2,3-c]pyridine-5-carboxamide;
N-[(3R)-1-azabicyclo[2.2.2]oct-3-yl]-3-(3-oxopiperazin-1yl)thieno[2,3-c]pyridine-5-carboxamide;
N-[(3R)-1-azabicyclo[2.2.2]oct-3-yl]-3-(4-methyl-3-oxopiperazin-1yl)thieno[2,3-c]pyridine-5-carboxamide;
N-[(3R)-1-azabicyclo[2.2.2]oct-3-yl]-3-(cyclopropylamino)thieno[2,3-c]pyridine-5-carboxamide;
N-[(3R)-1-azabicyclo[2.2.2]oct-3-yl]-3-[dimethylamino]thieno[2,3-c]pyridine-5-carboxamide;
N-[(3R)-1-azabicyclo[2.2.2]oct-3-yl]-3-(1H-pyrrole-1yl)thieno[2,3-c]pyridine-5-carboxamide;
N-[(3R)-1-azabicyclo[2.2.2]oct-3-yl]-3-(1H-imidazol-1-yl)thieno[2,3-c]pyridine-5-carboxamide;
N-[(3R)-1-azabicyclo[2.2.2]oct-3-yl]-3-(1H-1,2,4-triazol-1-yl)thieno[2,3-c]pyridine-carboxamide;
N-[(3R)-1-azabicyclo[2.2.2]oct-3-yl]-3-(1H-1,2,3-triazol-1-yl)thieno[2,3-c]pyridine-carboxamide;
N-5-[(3R)-1-azabicyclo[2.2.2]oct-3-yl]thieno[2,3-c]pyridine-3,5-dicarboxamide;
N-[(3R)-1-azabicyclo[2.2.2]oct-3-yl]-3-(pyrrolidin-1-ylcarbonyl)thieno[2,3-c]pyridine-5-carboxamide;
N-[(3R)-1-azabicyclo[2.2.2]oct-3-yl]-3-(piperidin-1-ylcarbonyl)thieno[2,3-c]pyridine-5-carboxamide;
N-[(3R)-1-azabicyclo[2.2.2]oct-3-yl]-3-(piperazin-1-ylcarbonyl)thieno[2,3-c]pyridine-5-carboxamide;
N-[(3R)-1-azabicyclo[2.2.2]oct-3-yl]-3-[(4-methylpiperazin-1-yl)carbonyl]thieno[2,3-c]pyridine-5-carboxamide;
N-[(3R)-1-azabicyclo[2.2.2]oct-3-yl]-3-(morpholin-4-ylcarbonyl)thieno[2,3-c]pyridine-5-carboxamide;
N-[(3R)-1-azabicyclo[2.2.2]oct-3-yl]-3-(thiomorpholin-4-ylcarbonyl)thieno[2,3-c]pyridine-5-carboxamide;
N-[(3R)-1-azabicyclo[2.2.2]oct-3-yl]-3-(aziridin-1-ylcarbonyl)thieno[2,3-c]pyridine-5-carboxamide;
N-[(3R)-1-azabicyclo[2.2.2]oct-3-yl]-3-(azetidin-1-ylcarbonyl)thieno[2,3-c]pyridine-5-carboxamide;
N-[(3R)-1-azabicyclo[2.2.2]oct-3-yl]-3-formylthieno[2,3-c]pyridine-5-carboxamide;
3-acetyl-N-[(3R)-1-azabicyclo[2.2.2]oct-3-yl]thieno[2,3-c]pyridine-5-carboxamide;
N-[(3R)-1-azabicyclo[2.2.2]oct-3-yl]-3-(trifluoroacetyl)thieno[2,3-c]pyridine-5-carboxamide;
N-[(3R)-1-azabicyclo[2.2.2]oct-3-yl]-3-[(phenyl)sulfonyl]1thieno[2,3-c]pyridine-5-carboxamide;
N-[(3R)-1-azabicyclo[2.2.2]oct-3-yl]-3-(methylsulfonyl)thieno[2,3-c]pyridine-5-carboxamide;
5-{[(3R)-1-azabicyclo[2.2.2]oct-3-ylamino]carbonyl}thieno[2,3-c]pyridine-3-carboxylic acid;
methyl 5-{[(3R)-1-azabicyclo[2.2.2]oct-3-ylamino]carbonyl}thieno[2,3-c]pyridine-3-carboxylate;
isopropyl 5-{[(3R)-1-azabicyclo[2.2.2]oct-3-ylamino]carbonyl}thieno[2,3-c]pyridine-3-carboxylate;
2,2,2-trifluoroethyl 5-{[(3R)-1-azabicyclo[2.2.2]oct-3-ylamino]carbonyl}thieno[2,3-c]pyridine-3-carboxylate;
N-[(3R)-1-azabicyclo[2.2.2]oct-3-yl]-3-(phenylethynyl)furo[2,3-c]pyridine-5-carboxamide;
N-[(3R)-1-azabicyclo[2.2.2]oct-3-yl]-3-(3,3,3-trifluoroprop-1-ynyl)furo[2,3-c]pyridine-5-carboxamide;
N-[(3R)-1-azabicyclo[2.2.2]oct-3-yl]-3-(3,3-difluoroprop-1-ynyl)furo[2,3-c]pyridine-5-carboxamide;
N-[(3R)-1-azabicyclo[2.2.2]oct-3-yl]-3-(3-pyrrolidin-1-ylprop-1-ynyl)furo[2,3-c]pyridine-5-carboxamide;
N-[(3R)-1-azabicyclo[2.2.2]oct-3-yl]-3-(3-morpholin-4-ylprop-1-ynyl)furo[2,3-c]pyridine-5-carboxamide;
N-[(3R)-1-azabicyclo[2.2.2]oct-3-yl]-3-(3-piperazin-1-ylprop-1-ynyl)furo[2,3-c]pyridine-5-carboxamide;
N-[(3R)-1-azabicyclo[2.2.2]oct-3-yl]-3-[3-(4-methylpiperazin-1-yl)prop-1-ynyl]furo[2,3-c]pyridine-5-carboxamide;
N-[(3R)-1-azabicyclo[2.2.2]oct-3-yl]-3-[3-(1H-pyrazol-1-yl)prop-1-ynyl]furo[2,3-c]pyridine-5-carboxamide;
N-[(3R)-1-azabicyclo[2.2.2]oct-3yl]-2-(phenylethynyl)furo[3,2-c]pyridine-5-carboxamide;
N-[(3R)-1-azabicyclo[2.2.2]oct-3yl]-2-(3,3,3-trifluoroprop-1-ynyl)furo[3,2-c]pyridine-5-carboxamide;
N-[(3R)-1-azabicyclo[2.2.2]oct-3yl]-2-(3,3-difluoroprop-1-ynyl)furo[3,2-c]pyridine-5-carboxamide;
N-[(3R)-1-azabicyclo[2.2.2]oct-3yl]-2-(3-pyrrolidin-1-ylprop-1-ynyl)furo[2,3-c]pyridine-5-carboxamide;
N-[(3R)-1-azabicyclo[2.2.2]oct-3yl]-2-(3-morpholin-4-ylprop-1-ynyl)furo[3,2-c]pyridine-5-carboxamide;
N-[(3R)-1-azabicyclo[2.2.2]oct-3yl]-2-(3-piperazin-1-ylprop-1-ynyl)furo[2,3-c]pyridine-5-carboxamide;
N-[(3R)-1-azabicyclo[2.2.2]oct-3yl]-2-[3-(4-methylpiperazin-1-yl)prop-1-ynyl]furo[2,3-c]pyridine-5-carboxamide;
N-[(3R)-1-azabicyclo[2.2.2]oct-3yl]-3-[3-(1H-pyrazol-1-yl)prop-1-ynyl]furo[2,3-c]pyridine-5-carboxamide;
N-[(3R)-1-azabicyclo[2.2.2]oct-3-yl]-3-(phenylethynyl)thieno[2,3-c]pyridine-5-carboxamide;
N-[(3R)-1-azabicyclo[2.2.2]oct-3-yl]-3-(3,3,3-trifluoroprop-1-ynyl)thieno[2,3-c]pyridine-5-carboxamide;
N-[(3R)-1-azabicyclo[2.2.2]oct-3-yl]-3-(3,3-difluoroprop-1-ynyl)thieno[2,3-c]pyridine-5-carboxamide;
N-[(3R)-1-azabicyclo[2.2.2]oct-3-yl]-3-(3-pyrrolidin-1-ylprop-1-ynyl)thieno[2,3-c]pyridine-5-carboxamide;
N-[(3R)-1-azabicyclo[2.2.2]oct-3-yl]-3-(3-morpholin-4-ylprop-1-ynyl)thieno[2,3-c]pyridine-5-carboxamide;
N-[(3R)-1-azabicyclo[2.2.2]oct-3-yl]-3-(3-piperazin-1-ylprop-1-ynyl)thieno[2,3-c]pyridine-5-carboxamide;
N-[(3R)-1-azabicyclo[2.2.2]oct-3-yl]-3-[3-(4-methylpiperazin-1-yl)prop-1-ynyl]thienyl[2,3-c]pyridine-5-carboxamide;
N-[(3R)-1-azabicyclo[2.2.2]oct-3-yl]-3-[3-(1H-pyrazol-1-yl)prop-1-ynyl]thieno[2,3-c]pyridine-5-carboxamide;
N-[(3R)-1-azabicyclo[2.2.2]oct-3yl]-2-(phenylethynyl)thieno[3,2-c]pyridine-5-carboxamide;
N-[(3R)-1-azabicyclo[2.2.2]oct-3yl]-2-(3,3,3-trifluoroprop-1-ynyl)thieno[3,2-c]pyridine-5-carboxamide;

N-[(3R)-1-azabicyclo[2.2.2]oct-3yl]-2-(3,3-difluoroprop-1-ynyl)thieno[3,2-c]pyridine-5-carboxamide;
N-[(3R)-1-azabicyclo[2.2.2]oct-3yl]-2-(3-pyrrolidin-1-ylprop-1-ynyl)thieno[2,3-c]pyridine-5-carboxamide;
N-[(3R)-1-azabicyclo[2.2.2]oct-3yl]-2-(3-morpholin-4-ylprop-1-ynyl)thieno[2,3-c]pyridine-5-carboxamide;
N-[(3R)-1-azabicyclo[2.2.2]oct-3yl]-2-(3-piperazin-1-yl-prop-1-ynyl)thieno[2,3-c]pyridine-5-carboxamide;
N-[(3R)-1-azabicyclo[2.2.2]oct-3yl]-2-[3-(4-methylpiperazin-1-yl)prop-1-ynyl]thieno[2,3-c]pyridine-5-carboxamide;
N-[(3R)-1-azabicyclo[2.2.2]oct-3yl]-2-[3-(1H-pyrazol-1-yl)prop-1-ynyl]thieno[2,3-c]pyridine-5-carboxamide;
or a pharmaceutically acceptable salt thereof.

20. The compound according to claim 13, wherein the compound of Formula I has the S stereochemistry at C3 of quinuclidine.

21. The compound according to claim 20, wherein the compound is
N-[(3S)-1-azabicyclo[2.2.2]oct-3-yl]-2,3-dihydrofuro[2,3-c]pyridine-5-carboxamide;
N-[(3S)-1-azabicyclo[2.2.2]oct-3-yl]furo[3,2-c]pyridine-2-carboxamide;
N-[(3S)-1-azabicyclo[2.2.2]oct-3-yl]-7-chlorofuro[2,3-c]pyridine-5-carboxamide;
N-[(3S)-1-azabicyclo[2.2.2]oct-3-yl]furo[2,3-c]pyridine-5-carboxamide;
N-[(3S)-1-azabicyclo[2.2.2]oct-3-yl]-3,3-dimethyl-2,3-dihydrofuro[2,3-c]pyridine-5-carboxamide;
N-[(3S)-1-azabicyclo[2.2.2]oct-3-yl]-2-methylfuro[2,3-c]pyridine-5-carboxamide;
N-[(3S)-1-azabicyclo[2.2.2]oct-3-yl]furo[2,3-c]pyridine-2-carboxamide;
N-[(3S)-1-azabicyclo[2.2.2]oct-3-yl]furo[2,3-b]pyridine-2-carboxamide;
N-[(3S)-1-azabicyclo[2.2.2]oct-3-yl]-3-methylfuro[2,3-c]pyridine-5-carboxamide;
N-[(3S)-1-azabicyclo[2.2.2]oct-3-yl]-3-ethylfuro[2,3-c]pyridine-5-carboxamide;
N-[(3S)-1-azabicyclo[2.2.2]oct-3-yl]-3-isopropylfuro[2,3-c]pyridine-5-carboxamide;
N-[(3S)-1-azabicyclo[2.2.2]oct-3-yl]-7-(methylsulfanyl)furo[2,3-c]pyridine-5-carboxamide;
N-((3S)-1-azabicyclo[2.2.2]oct-3-yl)thieno[2,3-b]pyridine-2-carboxamide;
N-[(3S)-1-azabicyclo[2.2.2]oct-3-yl]thieno[2,3-b]pyridine-5-carboxamide;
N-[(3S)-1-azabicyclo[2.2.2]oct-3-yl]thieno[2,3-b]pyridine-6-carboxamide;
N-[(3S)-1-azabicyclo[2.2.2]oct-3-yl]thieno[2,3-c]pyridine-2-carboxamide;
N-[(3S)-1-azabicyclo[2.2.2]oct-3-yl]thieno[3,2-b]pyridine-2-carboxamide;
N-[(3S)-1-azabicyclo[2.2.2]oct-3-yl]thieno[3,2-b]pyridine-5-carboxamide;
N-[(3S)-1-azabicyclo[2.2.2]oct-3-yl]thieno[3,2-b]pyridine-6-carboxamide;
N-[(3S)-1-azabicyclo[2.2.2]oct-3-yl]thieno[3,2-c]pyridine-2-carboxamide;
N-[(3S)-1-azabicyclo[2.2.2]oct-3-yl]thieno[2,3-c]pyridine-5-carboxamide;
N-[(3S)-1-azabicyclo[2.2.2]oct-3-yl]thieno[3,2-c]pyridine-6-carboxamide;
N-[(3S)-1-azabicyclo[2.2.2]oct-3-yl]-1H-pyrrolo[2,3-c]pyridine-5-carboxamide;
N-((3S)1-azabicyclo[2.2.2]oct-3-yl)-1-methyl-1H-pyrrolo[2,3-c]pyridine-5-carboxamide;
N-[(3S)-1-azabicyclo[2.2.2]oct-3-yl]-3-chlorofuro[2,3-c]pyridine-5-carboxamide;
N-[(3S)-1-azabicyclo[2.2.2]oct-3-yl]-3-bromofuro[2,3-c]pyridine-5-carboxamide;
N-[(3S)-1-azabicyclo[2.2.2]oct-3-yl]furo[3,2-c]pyridine-6-carboxamide;
N-[(3S)-1-azabicyclo[2.2.2]oct-3-yl]-3-bromothieno[2,3-c]pyridine-5-carboxamide;
N-[(3S)-1-azabicyclo[2.2.2]oct-3-yl]-3-ethynylfuro[2,3-c]pyridine-5-carboxamide;
or a pharmaceutically acceptable salt thereof.

22. The compound according to claim 20, wherein the compound is
N-[(3S)-1-azabicyclo[2.2.2]oct-3-yl]furo[3,2-c]pyridine-2-carboxamide;
N-[(3S)-1-azabicyclo[2.2.2]oct-3-yl]furo[2,3-c]pyridine-5-carboxamide;
N-[(3S)-1-azabicyclo[2.2.2]oct-3-yl]-2-methylfuro[2,3-c]pyridine-5-carboxamide;
N-[(3S)-1-azabicyclo[2.2.2]oct-3-yl]-3-methylfuro[2,3-c]pyridine-5-carboxamide;
N-[(3S)-1-azabicyclo[2.2.2]oct-3-yl]-3-ethylfuro[2,3-c]pyridine-5-carboxamide;
N-[(3S)-1-azabicyclo[2.2.2]oct-3-yl]-3-isopropylfuro[2,3-c]pyridine-5-carboxamide;
N-[(3S)-1-azabicyclo[2.2.2]oct-3-yl]thieno[2,3-b]pyridine-6-carboxamide;
N-[(3S)-1-azabicyclo[2.2.2]oct-3-yl]thieno[2,3-c]pyridine-2-carboxamide;
N-[(3S)-1-azabicyclo[2.2.2]oct-3-yl]thieno[2,3-c]pyridine-5-carboxamide;
N-[(3S)-1-azabicyclo[2.2.2]oct-3-yl]thieno[3,2-c]pyridine-6-carboxamide;
N-[(3S)-1-azabicyclo[2.2.2]oct-3-yl]-3-chlorofuro[2,3-c]pyridine-5-carboxamide;
N-[(3S)-1-azabicyclo[2.2.2]oct-3-yl]-3-bromofuro[2,3-c]pyridine-5-carboxamide;
N-[(3S)-1-azabicyclo[2.2.2]oct-3-yl]furo[3,2-c]pyridine-6-carboxamide;
N-[(3S)-1-azabicyclo[2.2.2]oct-3-yl]-3-bromothieno[2,3-c]pyridine-5-carboxamide;
N-[(3S)-1-azabicyclo[2.2.2]oct-3-yl]-3-ethynylfuro[2,3-c]pyridine-5-carboxamide;
or a pharmaceutically acceptable salt thereof.

23. The compound according to claim 3, wherein W is

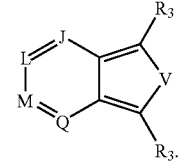

24. The compound according to claim 23, wherein W is thieno[3,4-c]pyridin-6-yl, optionally substituted with F, Br, Cl, —CN, —NO$_2$, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, halogenated heterocycloalkyl, lactam heterocycloalkyl, —OR$_1$, —NR$_1$COR$_{16}$, —N(R$_{10}$)$_2$, —SR$_1$, or aryl.

25. The compound according to claim 24, wherein R$_2$ is alkyl, halogenated alkyl, or substituted alkyl.

26. The compound according to claim 25, wherein R$_2$ is alkyl.

27. The compound according to claim 26, wherein $R_2$ is $CH_3$.

28. The compound according to claim 27, wherein the compound of Formula I has the R stereochemistry at C3 of quinuclidine.

29. The compound according to claim 28, wherein the compound is
N-[(2S,3R)-2-methyl-1-azabicyclo[2.2.2]oct-3-yl]thieno[3,4-c]pyridine-6-carboxamide; or a pharmaceutically acceptable salt thereof.

30. The compound according to claim 24, wherein $R_2$ is H.

31. The compound according to claim 30, wherein the compound of Formula I has the R stereochemistry at C3 of quinuclidine.

32. The compound according to claim 31, wherein the compound is
N-[(3R)-1-azabicyclo[2.2.2]oct-3-yl]thieno[3,4-c]pyridine-6-carboxamide;
or a pharmaceutically acceptable salt thereof.

33. The compound according to claim 30, wherein the compound of Formula I has the S stereochemistry at C3 of quinuclidine.

34. The compound according to claim 33, wherein the compound is
N-[(3S)-1-azabicyclo[2.2.2]oct-3-yl]thieno[3,4-c]pyridine-6-carboxamide; or a pharmaceutically acceptable salt thereof.

35. The compound according to claim 3, wherein W is

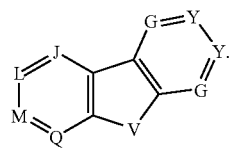

36. The compound according to claim 35, wherein W is benzothieno[2,3-c]pyridin-3-yl, benzothieno[3,2-c]pyridin-3-yl, or benzofuro[3,2-c]pyridin-3-yl, any of which is optionally substituted with F, Br, Cl, —CN, —NO$_2$, alkyl, substituted alkyl, halogenated alkyl, alkenyl, substituted alkenyl, halogenated alkenyl, alkynyl, substituted alkynyl, halogenated alkynyl, heterocycloalkyl, substituted heterocycloalkyl, halogenated heterocycloalkyl, lactam heterocycloalkyl, —OR$_1$, —NR$_1$COR$_{16}$, —N(R$_{10}$)$_2$, —SR$_1$, or aryl.

37. The compound according to claim 36, wherein $R_2$ is alkyl, halogenated alkyl, or substituted alkyl.

38. The compound according to claim 37, wherein $R_2$ is alkyl.

39. The compound according to claim 38, wherein $R_2$ is $CH_3$.

40. The compound according to claim 39, wherein the compound of Formula I has the R stereochemistry at C3 of quinuclidine.

41. The compound according to claim 40, wherein the compound is
N-[(2S,3R)-2-methyl-1-azabicyclo[2.2.2]oct-3-yl]benzothieno[2,3-c]pyridine-3-carboxamide;
N-[(2S,3R)-2-methyl-1-azabicyclo[2.2.2]oct-3-yl]benzothieno[3,2-c]pyridine-3-carboxamide;
N-[(2S,3R)-2-methyl-1-azabicyclo[2.2.2]oct-3-yl]benzofuro[3,2-c]pyridine-3-carboxamide;
or a pharmaceutically acceptable salt thereof.

42. The compound according to claim 36, wherein $R_2$ is H.

43. The compound according to claim 42, wherein the compound of Formula I has the R stereochemistry at C3 of quinuclidine.

44. The compound according to claim 43, wherein the compound is
N-[(3R)-1-azabicyclo[2.2.2]oct-3-yl]benzothieno[2,3-c]pyridine-3-carboxamide;
N-[(3R)-1-azabicyclo[2.2.2]oct-3-yl]benzothieno[3,2-c]pyridine-3-carboxamide;
N-[(3R)-1-azabicyclo[2.2.2]oct-3-yl]benzofuro[3,2-c]pyridine-3-carboxamide;
or a pharmaceutically acceptable salt thereof.

45. The compound according to claim 42, wherein the compound of Formula I has the S stereochemistry at C3 of quinuclidine.

46. The compound according to claim 45, wherein the compound is
N-[(3S)-1-azabicyclo[2.2.2]oct-3-yl]benzothieno[2,3-c]pyridine-3-carboxamide;
N-[(3S)-1-azabicyclo[2.2.2]oct-3-yl]benzothieno[3,2-c]pyridine-3-carboxamide;
N-[(3S)-1-azabicyclo[2.2.2]oct-3-yl]benzofuro[3,2-c]pyridine-3-carboxamide;
or a pharmaceutically acceptable salt thereof.

47. The compound according to claim 3, wherein the compound is:
N-[(2S,3R)-2-methyl-1-azabicyclo[2.2.2]oct-3-yl]furo[3,4-c]pyridine-6-carboxamide;
N-[(3R)-1-azabicyclo[2.2.2]oct-3-yl]furo[3,4-c]pyridine-6-carboxamide;
N-[(2S,3R)-2-methyl-1-azabicyclo[2.2.2]oct-3-yl][1]benzofuro[2,3-c]pyridine-3-carboxamide;
N-[(3R)-1-azabicyclo[2.2.2]oct-3-yl][1]benzofuro[2,3-c]pyridine-3-carboxamide;
or a pharmaceutically acceptable salt thereof.

48. The compound of claim 5, wherein each $R_1$ is alkyl, cycloalkyl, halogenated alkyl, substituted phenyl, or substituted naphthyl.

49. A pharmaceutical composition comprising a compound according to claim 1 and a pharmaceutically acceptable excipient.

50. The pharmaceutical composition according to claim 49, wherein said compound is administered rectally, topically, orally, sublingually, or parenterally for a therapeutically effective interval.

51. The pharmaceutical composition according to claim 49, wherein said compound is administered in an amount of from about 0.001 to about 100 mg/kg of body weight of said mammal per day.

52. The pharmaceutical composition according to claim 49, wherein said compound is administered in an amount of from about 0.1 to about 50 mg/kg of body weight of said mammal per day.

53. A pharmaceutical composition comprising a compound according to claim 1, and an anti-psychotic agent.

54. The pharmaceutical composition according to claim 53, wherein said compound and said agent are to be independently administered rectally, topically, orally, sublingually, or parenterally for a therapeutically effective interval.

55. The pharmaceutical composition according to claim 53, wherein said compound is administered in an amount of from about 0.001 to about 100 mg/kg of body weight of said mammal per day.

56. The pharmaceutical composition according to claim 53, wherein said compound is administered in an amount of from about 0.1 to about 50 mg/kg of body weight of said mammal per day.

57. A method for treating a disease or condition in a mammal in need thereof, wherein the α7 nicotinic acetylcholine receptor is implicated comprising administering to the mammal a therapeutically effective amount of a compound according to claim 1, wherein the disease or condition is attention deficit disorder, attention deficit hyperactivity disorder, mood and affective disorders, amyotrophic lateral sclerosis, borderline personality disorder, traumatic brain injury, behavioral and cognitive problems associated with brain tumors, AIDS dementia complex, dementia associated with Down's syndrome, dementia associated with Lewy Bodies, Huntington's disease, depression, general anxiety disorder, age-related macular degeneration, Parkinson's disease, tardive dyskinesia, Pick's disease, post traumatic stress disorder, dysregulation of food intake, withdrawal symptoms associated with smoking cessation and dependant drug cessation, Gilles de la Tourette's Syndrome, glaucoma, neurodegeneration associated with glaucoma, or symptoms associated with pain.

58. The method according to claim 57, wherein the disease or condition is attention deficit disorder, attention deficit hyperactivity disorder.

59. The method according to claim 57, wherein the disease or condition is depression, general anxiety disorder, or post traumatic stress disorder.

60. A method for treating a disease or condition in a mammal in need thereof, wherein the disease or condition is cognitive and attention deficit symptoms of Alzheimer's, and neurodegeneration comprising administering to the mammal a therapeutically effective amount of a compound according to claim 1.

61. A method for treating schizophrenia or psychosis in a mammal in need thereof comprising administering to the mammal a therapeutically effective amount of compound according to claim 1.

62. The method of claim 61, wherein the mammal would receive symptomatic relief from the administration of a therapeutically effective amount of α7 nicotinic acetylcholine receptor agonist and an anti-psychotic agent for a therapeutically effective interval.

63. The method according to claim 57, wherein the dysregulation of food intake is bulemia or anorexia nervosa.

64. The method according to claim 60, wherein the neurodegeneration is associated with Alzheimer's disease, pre-senile dementia (mild cognitive impairment), or senile dementia.

* * * * *